US010351915B2

(12) United States Patent
Narain et al.

(10) Patent No.: US 10,351,915 B2
(45) Date of Patent: Jul. 16, 2019

(54) METHODS FOR TREATMENT OF ONCOLOGICAL DISORDERS USING AN EPIMETABOLIC SHIFTER (COENZYME Q10)

(71) Applicant: Berg LLC, Framingham, MA (US)

(72) Inventors: Niven Rajin Narain, Cambridge, MA (US); John Patrick McCook, Frisco, TX (US)

(*) Notice: Subject to any disclaimer, the term of this patent is extended or adjusted under 35 U.S.C. 154(b) by 0 days.

(21) Appl. No.: 15/862,856

(22) Filed: Jan. 5, 2018

(65) Prior Publication Data

US 2018/0355435 A1   Dec. 13, 2018

Related U.S. Application Data

(63) Continuation of application No. 14/171,419, filed on Feb. 3, 2014, now Pat. No. 9,896,731, which is a continuation of application No. 12/778,094, filed on May 11, 2010.

(60) Provisional application No. 61/177,245, filed on May 11, 2019, provisional application No. 61/177,246, filed on May 11, 2009, provisional application No. 61/177,244, filed on May 11, 2009, provisional application No. 61/177,243, filed on May 11, 2009,
(Continued)

(51) Int. Cl.
| | |
|---|---|
| *C12Q 1/6886* | (2018.01) |
| *A61K 31/00* | (2006.01) |
| *A61K 31/122* | (2006.01) |
| *C12Q 1/6883* | (2018.01) |
| *G01N 33/573* | (2006.01) |
| *G01N 33/574* | (2006.01) |

(52) U.S. Cl.
CPC .......... *C12Q 1/6886* (2013.01); *A61K 31/00* (2013.01); *A61K 31/122* (2013.01); *C12Q 1/6883* (2013.01); *G01N 33/5735* (2013.01); *G01N 33/57484* (2013.01); *C12Q 2600/106* (2013.01); *C12Q 2600/112* (2013.01); *C12Q 2600/136* (2013.01); *C12Q 2600/158* (2013.01); *C12Q 2600/16* (2013.01); *G01N 2570/00* (2013.01); *G01N 2800/042* (2013.01); *G01N 2800/52* (2013.01)

(58) Field of Classification Search
CPC .............................. A61K 31/00; A61K 31/122
See application file for complete search history.

(56) References Cited

U.S. PATENT DOCUMENTS

| | | | |
|---|---|---|---|
| 4,483,873 | A | 11/1984 | Ohashi et al. |
| 4,515,736 | A | 5/1985 | Deamer |
| (Continued) | | | |

FOREIGN PATENT DOCUMENTS

| | | |
|---|---|---|
| CA | 2553690 A1 | 8/2005 |
| CA | 2680825 A1 | 9/2008 |
| (Continued) | | |

OTHER PUBLICATIONS

Abe et al., Effect of coenzyme Q10 in patients with mitochondrial myopathy, encephalopathy, lactic acidosis, and stroke-like episodes (MELAS): evaluation by noninvasive tissue oximetry. J Neurol Sci. Jan. 1, 1999;162(1):65-8.

(Continued)

*Primary Examiner* — Savitha M Rao
(74) *Attorney, Agent, or Firm* — McCarter & English, LLP; Jill Mello

(57) ABSTRACT

Methods and formulations for treating onocological disorders in humans using Coenzyme Q10 are described.

9 Claims, 33 Drawing Sheets

Related U.S. Application Data provisional application No. 61/177,241, filed on May 11, 2009.

(56) References Cited

U.S. PATENT DOCUMENTS

| | | |
|---|---|---|
| 4,525,350 A | 6/1985 | Casey et al. |
| 4,636,381 A | 1/1987 | Takada et al. |
| 4,654,373 A | 3/1987 | Bertelli |
| 4,824,669 A | 4/1989 | Folkers et al. |
| 4,833,128 A | 5/1989 | Solomon et al. |
| 4,895,727 A | 1/1990 | Allen |
| 5,015,483 A | 5/1991 | Haynes et al. |
| 5,045,559 A | 9/1991 | Scott |
| 5,362,494 A | 11/1994 | Zysman et al. |
| 5,378,461 A | 1/1995 | Neigut |
| 5,527,789 A | 6/1996 | Nyce |
| 5,602,184 A | 2/1997 | Myers et al. |
| 5,603,958 A | 2/1997 | Morein et al. |
| 5,605,930 A | 2/1997 | Samid |
| 5,651,991 A | 7/1997 | Sugiyama et al. |
| 5,700,482 A | 12/1997 | Frederiksen et al. |
| 5,719,303 A | 2/1998 | Yoshida et al. |
| 5,770,222 A | 6/1998 | Unger et al. |
| 5,876,737 A | 3/1999 | Schonrock et al. |
| 5,889,062 A | 3/1999 | Hoppe et al. |
| 5,891,465 A | 4/1999 | Keller et al. |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,886 A | 4/2000 | Neigut |
| 6,063,820 A | 5/2000 | Cavazza |
| 6,071,495 A | 6/2000 | Unger et al. |
| 6,093,706 A | 7/2000 | Zeligs |
| 6,093,743 A | 7/2000 | Lai et al. |
| 6,184,353 B1 | 2/2001 | Evans et al. |
| 6,228,891 B1 | 5/2001 | Enzmann et al. |
| 6,261,575 B1 | 7/2001 | Hoppe et al. |
| 6,348,506 B2 | 2/2002 | Sneed |
| 6,372,234 B1 | 4/2002 | Deckers et al. |
| 6,403,116 B1 | 6/2002 | Anderson et al. |
| 6,416,957 B1 | 7/2002 | Evans et al. |
| 6,417,233 B1 | 7/2002 | Sears et al. |
| 6,441,050 B1 | 8/2002 | Chopra |
| 6,461,593 B1 | 10/2002 | Hanioka et al. |
| 6,465,517 B1 | 10/2002 | Van Der Zee |
| 6,468,552 B1 | 10/2002 | Stahl et al. |
| 6,469,061 B1 | 10/2002 | Flescher et al. |
| 6,482,943 B1 | 11/2002 | Blokhin et al. |
| 6,503,506 B1 | 1/2003 | Germano |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |
| 6,569,463 B2 | 5/2003 | Patel et al. |
| 6,573,284 B1 | 6/2003 | Riley et al. |
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 7/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,632,443 B2 | 10/2003 | Borowy-Borowski et al. |
| 6,652,891 B2 | 11/2003 | Selzer |
| 6,682,763 B2 | 1/2004 | Kuno et al. |
| 6,686,485 B2 | 2/2004 | West |
| 6,696,484 B2 | 2/2004 | Liao et al. |
| 6,726,924 B2 | 4/2004 | Keller |
| 6,727,234 B2 | 4/2004 | Wiemer et al. |
| 6,733,790 B1 | 5/2004 | Garces Garces |
| 6,753,325 B2 | 6/2004 | Rosenbloom |
| 6,803,193 B1 | 10/2004 | Hopper et al. |
| 6,806,069 B2 | 10/2004 | Chokshi |
| 6,809,176 B2 | 10/2004 | Blokhin et al. |
| 6,866,864 B2 | 3/2005 | Mousa |
| 6,867,024 B2 | 3/2005 | Chokshi |
| 6,906,106 B2 | 6/2005 | Chevalier |
| 6,923,988 B2 | 8/2005 | Patel et al. |
| 7,005,274 B1 | 2/2006 | Terkeltaub et al. |
| 7,060,733 B2 | 6/2006 | Pandol et al. |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,182,950 B2 | 2/2007 | Garti et al. |
| 7,198,801 B2 | 4/2007 | Carrara et al. |
| 7,208,298 B2 | 4/2007 | Miyake et al. |
| 7,247,714 B2 | 7/2007 | Kunsch et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay et al. |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 7,456,161 B2 | 11/2008 | Nyce |
| 7,635,722 B1 | 12/2009 | Bachynsky et al. |
| 7,776,894 B2 | 8/2010 | Ronai et al. |
| 7,824,673 B2 | 11/2010 | Wegman et al. |
| 7,858,659 B2 | 12/2010 | Hoffman et al. |
| 7,879,823 B2 | 2/2011 | Seiberg et al. |
| 7,906,140 B2 | 3/2011 | Bromley et al. |
| 8,147,825 B2 | 4/2012 | Hsia et al. |
| 8,293,227 B2 | 10/2012 | Hsia et al. |
| 8,562,976 B2 | 10/2013 | Hsia et al. |
| 8,586,030 B2 | 11/2013 | Hsia et al. |
| 8,746,515 B2 | 6/2014 | Fatherazi et al. |
| 8,771,680 B2 | 7/2014 | Hsia et al. |
| 9,205,064 B2 | 12/2015 | Narain et al. |
| 9,896,731 B2 | 2/2018 | Narain et al. |
| 9,901,542 B2 | 2/2018 | Narain et al. |
| 9,926,580 B2 | 3/2018 | Yajima et al. |
| 2001/0022965 A1 | 9/2001 | Heger et al. |
| 2001/0043909 A1 | 11/2001 | SaNogueira et al. |
| 2001/0053356 A1 | 12/2001 | Mousa |
| 2002/0039595 A1 | 4/2002 | Keller |
| 2002/0044913 A1 | 4/2002 | Hamilton |
| 2002/0045230 A1 | 4/2002 | Rosen et al. |
| 2002/0048559 A1 | 4/2002 | Shinoda et al. |
| 2002/0048798 A1 | 4/2002 | Avery et al. |
| 2002/0049176 A1 | 4/2002 | Anderson et al. |
| 2002/0049253 A1 | 4/2002 | Kaddurah-Daouk |
| 2002/0049422 A1 | 4/2002 | Brewitt |
| 2002/0058712 A1 | 5/2002 | Sneed |
| 2002/0071852 A1 | 6/2002 | Deckers et al. |
| 2002/0091288 A1 | 7/2002 | Wilbur et al. |
| 2002/0098169 A1 | 7/2002 | Smith |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0136711 A1 | 9/2002 | Cochran |
| 2002/0146463 A1 | 10/2002 | Clayton |
| 2002/0155151 A1 | 10/2002 | Enzmann et al. |
| 2002/0156302 A1 | 10/2002 | West |
| 2002/0164317 A1 | 11/2002 | Gorsek |
| 2002/0182199 A1 | 12/2002 | Hoppe et al. |
| 2002/0198177 A1 | 12/2002 | Horrobin |
| 2003/0012762 A1 | 1/2003 | Zulli et al. |
| 2003/0012779 A1 | 1/2003 | Grieb et al. |
| 2003/0012825 A1 | 1/2003 | Kapper |
| 2003/0031688 A1 | 2/2003 | Ghosh et al. |
| 2003/0044441 A1 | 3/2003 | Schmid et al. |
| 2003/0077297 A1 | 4/2003 | Chen et al. |
| 2003/0077335 A1 | 4/2003 | Richardson et al. |
| 2003/0087331 A1 | 5/2003 | Pettit et al. |

(56) References Cited

U.S. PATENT DOCUMENTS

| | | |
|---|---|---|
| 2003/0091518 A1 | 5/2003 | Pauly et al. |
| 2003/0103954 A1 | 6/2003 | Rosenbloom |
| 2003/0104048 A1 | 6/2003 | Patel et al. |
| 2003/0104080 A1 | 6/2003 | Singh et al. |
| 2003/0105027 A1 | 6/2003 | Rosenbloom |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118525 A1 | 6/2003 | Grigg |
| 2003/0118536 A1 | 6/2003 | Rosenbloom |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0138792 A1 | 7/2003 | Schlegel et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0207834 A1 | 11/2003 | Dale et al. |
| 2003/0212114 A1 | 11/2003 | Sato |
| 2003/0215406 A1 | 11/2003 | Schreiner et al. |
| 2003/0219472 A1 | 11/2003 | Pauletti et al. |
| 2003/0235812 A1 | 12/2003 | Anderson et al. |
| 2004/0028614 A1 | 2/2004 | Corbella et al. |
| 2004/0028668 A1 | 2/2004 | Gaetani |
| 2004/0034107 A1 | 2/2004 | Enzmann |
| 2004/0043045 A1 | 3/2004 | Seipel et al. |
| 2004/0047896 A1 | 3/2004 | Malnoe et al. |
| 2004/0049022 A1 | 3/2004 | Nyce et al. |
| 2004/0063648 A1 | 4/2004 | Pandol et al. |
| 2004/0063661 A1 | 4/2004 | Linnane |
| 2004/0067260 A1 | 4/2004 | Milley et al. |
| 2004/0082522 A1 | 4/2004 | Nyce |
| 2004/0086538 A1 | 5/2004 | Sauermann et al. |
| 2004/0101874 A1 | 5/2004 | Ghosh et al. |
| 2004/0109880 A1 | 6/2004 | Pauly et al. |
| 2004/0110848 A1 | 6/2004 | Peffley et al. |
| 2004/0115181 A1 | 6/2004 | Fujii et al. |
| 2004/0122109 A1 | 6/2004 | Fujii et al. |
| 2004/0126367 A1 | 7/2004 | Fujii et al. |
| 2004/0133352 A1 | 7/2004 | Bevilacqua et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0151711 A1 | 8/2004 | West |
| 2004/0170560 A1 | 9/2004 | Fossheim et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0202740 A1 | 10/2004 | Tan |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0253323 A1 | 12/2004 | Giles |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019268 A1 | 1/2005 | Enzmann |
| 2005/0019278 A1 | 1/2005 | Berg-Schultz |
| 2005/0019353 A1 | 1/2005 | Prinz et al. |
| 2005/0025756 A1 | 2/2005 | Erwin |
| 2005/0026848 A1 | 2/2005 | Robinson et al. |
| 2005/0026850 A1 | 2/2005 | Robinson et al. |
| 2005/0036976 A1 | 2/2005 | Rubin et al. |
| 2005/0037036 A1 | 2/2005 | Nielsen et al. |
| 2005/0037102 A1 | 2/2005 | Tan et al. |
| 2005/0042678 A1 | 2/2005 | Epstein et al. |
| 2005/0043336 A1 | 2/2005 | Hennequin et al. |
| 2005/0058610 A1 | 3/2005 | Baschong et al. |
| 2005/0069582 A1 | 3/2005 | Fantuzzi |
| 2005/0070610 A1 | 3/2005 | Fujii et al. |
| 2005/0070611 A1 | 3/2005 | Fantuzzi |
| 2005/0079164 A1 | 4/2005 | Fantuzzi et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118151 A1 | 6/2005 | Larsen et al. |
| 2005/0118209 A1 | 6/2005 | Jentszch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0147598 A1 | 7/2005 | Ueda et al. |
| 2005/0148603 A1 | 7/2005 | Jimenez et al. |
| 2005/0152856 A2 | 7/2005 | Andersson et al. |
| 2005/0184275 A1 | 8/2005 | Mora-Gutierrez et al. |
| 2005/0202521 A1 | 9/2005 | Crum |
| 2005/0214333 A1 | 9/2005 | Lanzendoerfer et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0239721 A1 | 10/2005 | Rosenbloom |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288333 A1 | 12/2005 | Kern |
| 2005/0288378 A1 | 12/2005 | Yan et al. |
| 2006/0002911 A1 | 1/2006 | Casteilla et al. |
| 2006/0002964 A9 | 1/2006 | Schreiber et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0041017 A1 | 2/2006 | Chopra |
| 2006/0051462 A1 | 3/2006 | Wang |
| 2006/0052438 A1 | 3/2006 | Ho et al. |
| 2006/0057081 A1 | 3/2006 | Boxrud |
| 2006/0062755 A1 | 3/2006 | Woodward |
| 2006/0069068 A1 | 3/2006 | Kajander et al. |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0099244 A1 | 5/2006 | Guilford |
| 2006/0110415 A1 | 5/2006 | Gupta |
| 2006/0120997 A1 | 6/2006 | Lipton |
| 2006/0121016 A1 | 6/2006 | Lee |
| 2006/0127384 A1 | 6/2006 | Capaccioli et al. |
| 2006/0127928 A1 | 6/2006 | Bacus et al. |
| 2006/0128643 A1 | 6/2006 | Kaddurah-Daouk et al. |
| 2006/0153783 A1 | 7/2006 | Ehlis et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0205771 A1 | 9/2006 | Noble et al. |
| 2006/0251690 A1 | 11/2006 | Lipshutz et al. |
| 2006/0251708 A1 | 11/2006 | Chen et al. |
| 2006/0252042 A1 | 11/2006 | Molero |
| 2006/0286046 A1 | 12/2006 | Haber |
| 2006/0292220 A1 | 12/2006 | Giordano et al. |
| 2007/0021360 A1 | 1/2007 | Nyce et al. |
| 2007/0026072 A1 | 2/2007 | Olsen et al. |
| 2007/0053985 A1 | 3/2007 | Ueda et al. |
| 2007/0054282 A1 | 3/2007 | Liew |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |

(56) References Cited

U.S. PATENT DOCUMENTS

| | | |
|---|---|---|
| 2007/0110731 A1 | 5/2007 | Riley |
| 2007/0129428 A1 | 6/2007 | Richelle et al. |
| 2007/0149618 A1 | 6/2007 | Cuevas Sanchez et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0202496 A1 | 8/2007 | Beretta |
| 2007/0203091 A1 | 8/2007 | Rapaport |
| 2007/0218042 A1 | 9/2007 | Khaled |
| 2007/0225255 A1 | 9/2007 | Frohlich et al. |
| 2007/0243180 A1 | 10/2007 | Tanaka et al. |
| 2007/0248590 A1 | 10/2007 | Milne et al. |
| 2007/0248693 A1 | 10/2007 | Mazzio et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0259009 A1 | 11/2007 | Linder |
| 2007/0275021 A1 | 11/2007 | Lee et al. |
| 2008/0014187 A1 | 1/2008 | Villeponteau |
| 2008/0020018 A1 | 1/2008 | Moodley et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0038736 A1 | 2/2008 | Llovet et al. |
| 2008/0057116 A1 | 3/2008 | Pleva |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0102313 A1 | 5/2008 | Nilsen et al. |
| 2008/0138326 A1 | 6/2008 | Fujii et al. |
| 2008/0233183 A1 | 9/2008 | McCook et al. |
| 2008/0260878 A1 | 10/2008 | Harano et al. |
| 2008/0287541 A1 | 11/2008 | Hoffman et al. |
| 2008/0299100 A1 | 12/2008 | Hsia et al. |
| 2009/0005398 A1 | 1/2009 | Dar |
| 2009/0010917 A1 | 1/2009 | Rosenblum et al. |
| 2009/0036516 A1 | 2/2009 | Scherrer et al. |
| 2009/0060891 A1 | 3/2009 | Harris et al. |
| 2009/0068281 A1 | 3/2009 | Toyomura et al. |
| 2009/0137556 A1 | 5/2009 | Bonnichsen |
| 2009/0280987 A1 | 11/2009 | Strobel |
| 2010/0062048 A1 | 3/2010 | Hsia et al. |
| 2010/0150894 A1 | 6/2010 | Wakabayashi et al. |
| 2010/0209388 A1 | 8/2010 | Mazzio et al. |
| 2010/0239652 A1 | 9/2010 | Rochlitz et al. |
| 2011/0020312 A1 | 1/2011 | Narain et al. |
| 2011/0027247 A1 | 2/2011 | Narain et al. |
| 2011/0064747 A1 | 3/2011 | Sarangarajan et al. |
| 2011/0110914 A1 | 5/2011 | Narain et al. |
| 2011/0129503 A1 | 6/2011 | Strober et al. |
| 2011/0136231 A1 | 6/2011 | Narain et al. |
| 2011/0142914 A1 | 6/2011 | Persaud et al. |
| 2011/0229554 A1 | 9/2011 | Narain et al. |
| 2012/0164215 A1 | 6/2012 | Hsia et al. |
| 2012/0183621 A1 | 7/2012 | Sinko et al. |
| 2012/0201801 A1 | 8/2012 | Hsia et al. |
| 2012/0269867 A1 | 10/2012 | Jimenez et al. |
| 2012/0309086 A1 | 12/2012 | Narain et al. |
| 2013/0203853 A1 | 8/2013 | Jacobson |
| 2014/0017317 A1 | 1/2014 | Narain et al. |
| 2014/0255372 A1 | 9/2014 | Hsia et al. |
| 2014/0302014 A1 | 10/2014 | Narain et al. |
| 2015/0023940 A1 | 1/2015 | Narain et al. |
| 2015/0157559 A1 | 6/2015 | Narain et al. |
| 2017/0189350 A1 | 7/2017 | Narain et al. |
| 2017/0216223 A1 | 8/2017 | Narain et al. |
| 2017/0246125 A1 | 8/2017 | Jimenez et al. |
| 2018/0353425 A1 | 12/2018 | Narain et al. |

FOREIGN PATENT DOCUMENTS

| | | |
|---|---|---|
| CN | 1535605 A | 10/2004 |
| CN | 1853507 A | 11/2006 |
| CN | 1928556 A | 3/2007 |
| CN | 1953743 A | 4/2007 |
| CN | 101102768 A | 1/2008 |
| CN | 101365806 A | 2/2009 |
| EP | 1473043 A1 | 11/2004 |
| EP | 1493437 A1 | 1/2005 |
| EP | 1908459 A1 | 4/2008 |
| EP | 2371363 A1 | 10/2011 |
| EP | 2429512 A2 | 3/2012 |
| EP | 2854528 A1 | 4/2015 |
| JP | S57-075916 | 5/1982 |
| JP | S62-123113 A | 6/1987 |
| JP | H01-143826 A | 6/1989 |
| JP | H02-273619 A | 11/1990 |
| JP | 2001-514209 A | 9/2001 |
| JP | 2004-345988 A | 12/2004 |
| JP | 2007-001922 A | 1/2007 |
| JP | 2007-176804 A | 7/2007 |
| JP | 2007-518805 A | 7/2007 |
| JP | 2009-050168 A | 3/2009 |
| JP | 2009-096757 A | 5/2009 |
| JP | 2015151900 A | 8/2015 |
| RU | 2307666 C2 | 10/2007 |
| WO | WO-1988/04173 A1 | 6/1988 |
| WO | WO-1993/16704 A1 | 9/1993 |
| WO | WO-1994/11547 A1 | 5/1994 |
| WO | WO-1995/05164 A1 | 2/1995 |
| WO | WO-1995/10271 A2 | 4/1995 |
| WO | WO-1996/17626 A2 | 6/1996 |
| WO | WO-1998/35660 A1 | 8/1998 |
| WO | WO-1999/11242 A1 | 3/1999 |
| WO | WO-1999/65469 A2 | 12/1999 |
| WO | WO-2000/007607 A1 | 2/2000 |
| WO | WO-2002/40012 A1 | 5/2002 |
| WO | WO-2002/060484 A1 | 8/2002 |
| WO | WO-2002/062329 A1 | 8/2002 |
| WO | WO-2002/062338 A1 | 8/2002 |
| WO | WO-2002/078727 A1 | 10/2002 |
| WO | WO-2002/085297 A2 | 10/2002 |
| WO | WO-2003/008405 A1 | 1/2003 |
| WO | WO-2003/077895 A1 | 9/2003 |
| WO | WO-2003/078456 A1 | 9/2003 |
| WO | WO-2004/003564 A2 | 1/2004 |
| WO | WO-2004/059293 A2 | 7/2004 |
| WO | WO-2004/060316 A2 | 7/2004 |
| WO | WO-2005/055738 A1 | 6/2005 |
| WO | WO-2005/069916 A2 | 8/2005 |
| WO | WO-2006/017494 A2 | 2/2006 |
| WO | WO-2006/063402 A1 | 6/2006 |
| WO | WO-2007/039184 A2 | 4/2007 |
| WO | WO-2007/095186 A2 | 8/2007 |
| WO | WO-2007/131047 A2 | 11/2007 |
| WO | WO-2008/049330 A1 | 5/2008 |
| WO | WO-2008/116135 A2 | 9/2008 |
| WO | WO-2008/156654 A2 | 12/2008 |
| WO | WO-2009/005215 A1 | 1/2009 |
| WO | WO-2009/006366 A2 | 1/2009 |
| WO | WO-2009/012718 A1 | 1/2009 |
| WO | WO-2009/014639 A2 | 1/2009 |
| WO | WO-2009/073843 A1 | 6/2009 |
| WO | WO-2009/126764 A1 | 10/2009 |
| WO | 2010/065601 A1 | 6/2010 |
| WO | WO-2010/132440 A2 | 11/2010 |
| WO | WO-2010/132507 A2 | 11/2010 |
| WO | WO-2011/031503 A2 | 3/2011 |
| WO | WO-2011/112900 A2 | 9/2011 |
| WO | 2012/012347 A2 | 1/2012 |

(56) References Cited

FOREIGN PATENT DOCUMENTS

WO   WO-2012/138765 A1   10/2012
WO   WO-2013/181639 A1   12/2013

OTHER PUBLICATIONS

Abe et al., Marked reduction in CSF lactate and pyruvate levels after CoQ therapy in a patient with mitochondrial myopathy, encephalopathy, lactic acidosis and stroke-like episodes (MELAS). Acta Neurol Scand. Jun. 1991;83(6):356-9.
American Cancer Society, Brain and Spinal Cord Tumors in Adults. Retrieved online at: http://www.cancer.org/cancer/braincnstumorsinadults/detailedguide/brain-and-spinal-cord-tumors-in-adults-what-are-brain-spinal-tumors. Nov. 12, 2009. 4 pages.
American Cancer Society, Colorectal Cancer. Retrieved online at: http:www.cancer.org/acs/groups/cid/documents/webcontent/003096-pdf.pdf. 122 pages, (2016).
Ansell et al., Brain tumor signs and symptoms: analysis of primary health care records from the UKCCS. Pediatrics. Jan. 2010;125(1):112-9.
Aris et al., Noise filtering and nonparametric analysis of microarray data underscores discriminating markers of oral, prostate, lung, ovarian and breast cancer. BMC Bioinformatics. Nov. 29, 2004;5(185):1-9.
Bjarnason, Chronobiology. Implications for cancer chemotherapy. Acta Oncol. 1995;34(5):615-24.
Bliznakov et al., Coenzymes Q: stimulants of the phagocytic activity in rats and immune response in mice. Experientia. Sep. 26, 1970;26(9):953-4.
Bliznakov, Effect of stimulation of the host defense system by coenzyme Q 0 on dibenzpyrene-induced tumors and infection with Friend leukemia virus in mice. Proc Natl Acad Sci U S A. Feb. 1973;70(2):390-4.
Blom et al., The risk of a venous thrombotic event in lung cancer patients: higher risk for adenocarcinoma than squamous cell carcinoma. J Thromb Haemost. Oct. 2004;2(10):1760-5.
Carmona et al., Coadministration of coenzyme Q prevents rosiglitazone-induced adipogenesis in ob/ob mice. Int J Obes (Lond). Feb. 2009;33(2):204-11.
Chan et al., Metabolic changes in patients with mitochondrial myopathies and effects of coenzyme Q10 therapy. J Neurol. Oct. 1998;245(10):681-5.
Cheung et al., Novel markers of subclinical disease for Ewing family tumors from gene expression profiling. Clin Cancer Res. Dec. 1, 2007;13(23):6978-83.
Chew et al., Coenzyme Q10 and diabetic endotheliopathy: oxidative stress and the 'recoupling hypothesis'. QJM. Aug. 2004;97(8):537-48.
Colman et al., Hemostasis and Thrombosis. Basic Principles and Clinical Practice, 5th Edition, Lippincott Williams & Wilkins, p. 1161 (2006).
Colon cancer: Tests and diagnosis—MayoClinic.com. Retrieved online at: http://www.mayoclinic.com/health/colon-cancer/ds00035/dsection=tests-and-diagnosis. 3 pages, Aug. 13, 2011.
Conklin, Cancer chemotherapy and antioxidants. J Nutr. Nov. 2004;134(11):32015-32045.
Conklin, Coenzyme q10 for prevention of anthracycline-induced cardiotoxicity. Integr Cancer Ther. Jun. 2005;4(2):110-30.
Crane, New Functions for Coenzyme Q. Protoplasma. 2000;213:127-133.
Crawford et al., Multiplex standardized RT-PCR for expression analysis of many genes in small samples. Biochem Biophys Res Commun. Apr. 26, 2002;293(1):509-16.
De Oliveria, A Nutritious Cocktail for the Treatment of Melanoma: A Case Report. The Journal of Orthomolecular Medicine. 1998;13(3)13, 2 pages.
Deeb et al., Vitamin D signalling pathways in cancer: potential for anticancer therapeutics. Nat Rev Cancer. Sep. 2007;7(9):684-700.
Eisenhauer et al., New response evaluation criteria in solid tumours: Revised RECIST guideline (version 1.1). European Journal of Cancer. 2009;45:228-247.
Family Caregiver Alliance, Fact Sheet: Brain Tumor. Los Angeles Caregiver Resource Center. Retrieved online at: http://lacrc.usc.edu/forms/brain tumor.pdf. 12 pages (2004).
Fang et al., Expression of ectonucleotide pyrophosphatase/phosphodiesterase 1 in human ovary and its relationship with polycystic ovary syndrome. ACTA Anatomica Sinica. 2008;39(4):552-556.
Fernández-Ayala et al., Coenzyme Q protects cells against serum withdrawal-induced apoptosis by inhibition of ceramide release and caspase-3 activation. Antioxid Redox Signal. 2000 Summer;2(2):263-75.
Ferrara et al., Protective role of chronic ubiquinone administration on acute cardiac oxidative stress. J Pharmacol Exp Ther. Aug. 1995;274(2):858-65.
Folkers et al., Survival of cancer patients on therapy with coenzyme Q10. Biochem Biophys Res Commun. Apr. 15, 1993;192(1):241-5.
Folkers, Relevance of the biosynthesis of coenzyme Q10 and of the four bases of DNA as a rationale for the molecular causes of cancer and a therapy. Biochem Biophys Res Commun. Jul. 16, 1996;224(2):358-61.
Gaby, The Role of Coenzyme Q10 in Clinical Medicine: Part I. Alt Med Rev. 1996;1:11-17.
Galili et al., Clinical response of myelodysplastic syndromes patients to treatment with coenzyme Q10. Leuk Res. Jan. 2007;31(1):19-26.
Gersten, Brain Cancer Overview. The New York Times. Retrieved online at: http://health.nytimes.com/health/guides/disease/brain-tumor-adults. 3 pages.
Golay et al., Link between obesity and type 2 diabetes. Best Pract Res Clin Endocrinol Metab. Dec. 2005;19(4):649-63.
Gorelick et al., Coenzyme Q10 and lipid-related gene induction in HeLa cells. Am J Obstet Gynecol. May 2004;190(5):1432-4.
Haider et al., Effects of etanercept are distinct from infliximab in modulating proinflammatory genes in activated human leukocytes. J Investig Dermatol Symp Proc. May 2007;12(1):9-15.
Higdon et al., Obesity and oxidative stress: a direct link to CVD? Arterioscler Thromb Vasc Biol. Mar. 1, 2003;23(3):365-7.
Hill et al., Pharmacokinetics of drug infusions. Continuing Education in Anaesthesia. 2004. 4(3):76-80.
Hodges et al., CoQ10: could it have a role in cancer management? Biofactors. 1999;9(24):365-70.
Hodgson et al., Coenzyme Q10 improves blood pressure and glycaemic control: a controlled trial in subjects with type 2 diabetes. Eur J Clin Nutr. Nov. 2002;56(11):1137-42.
Huang et al., Treatment of refractory recurrent malignant glioma with adoptive cellular immunotherapy: a case report. Critical Reviews in Oncology/Hematology. 2001;57:17-23.
Hudson et al., Characterization of potentially chemopreventive phenols in extracts of brown rice that inhibit the growth of human breast and colon cancer cells. Cancer Epidemiol Biomarkers Prev. Nov. 2000;9(11):1163-70.
Iarussi et al., Protective effect of coenzyme Q10 on anthracyclines cardiotoxicity: control study in children with acute lymphoblastic leukemia and non-Hodgkin lymphoma. Mol Aspects Med. 1994;15 Suppl:s207-12.
Izyumov, Programmed Death of Cells and Oxidative Stress Caused by Inhibitors of Mitochondrial Functions. (synopsis of Ph.D. thesis), Moscow, 2005, pp. 17-20: URL: <http://www.lib.ua.net/diss/cont/151000.html>.
Judy et al., Coenzyme Q10 Facts or Fiction. Natural Products Insider. 3 pages. Oct. 22, 2007.
Kawase et al., Enhancing effect of coenzyme, Q10 on immunorestoration with Mycobacterium bovis BCG in tumor-bearing mice. Gan. Aug. 1978;69(4):493-7.
Khan et al., Prolongation of Survival of Mice Bearing Leukemia 1210; Treated with Adriamycin and Coenzyme Q10. Proceedings of the American Association for Cancer Research. 1990;31:388, Poster 2303.
Kokawa et al., [Coenzyme Q10 in cancer chemotherapy—experimental studies on augmentation of the effects of masked compounds, especially in the combined chemotherapy with immunopotentiators]. Gan to Kagaku Ryoho. Mar. 1983;10(3):768-74. (Abstract only).

(56) References Cited

OTHER PUBLICATIONS

Kunitomo et al., Beneficial effect of coenzyme Q10 on increased oxidative and nitrative stress and inflammation and individual metabolic components developing in a rat model of metabolic syndrome. J Pharmacol Sci. Jun. 2008;107(2):128-37.
Lamson et al., Antioxidants in cancer therapy; their actions and interactions with oncologic therapies. Altern Med Rev. Oct. 1999;4(5):304-29.
Langham et al., Increased renal gene transcription of protein kinase C-beta in human diabetic nephropathy: relationship to long-term glycaemic control. Diabetologia. Apr. 2008;51(4):668-74.
Langsjoen, Alleviating Congestive Heart Failure with Coenzyme Q10. LifeExtension. http://www.lef.org/. Feb. 2008. 7 pages.
Larsson, Effects of isoprenoids on growth of normal human mammary epithelial cells and breast cancer cells in vitro. Anticancer Res. Jan.-Feb. 1994;14(1A):123-8.
Lassman, Molecular Biology of Gliomas. Current Neurology and Neuroscience Reports. 2004;4:228-233.
Li et al., Protective Effect of Coenzyme Q10 against the Adverse Reaction of Mytomycin G in Mouse Liver. Acta Histochemica et Cytochemica. 1987;20(4):455-467.
Littman et al., Effect of Cholesterol-Free, Fat-Free Diet and Hypocholesteremic Agents on Growth of Transplantable Animal Tumors. Cancer Chemotherapy Reports. Jan.-Feb. 1966;50(1 and 2):25-45.
Lockwood et al., Apparent partial remission of breast cancer in 'high risk' patients supplemented with nutritional antioxidants, essential fatty acids and coenzyme Q10. Mol Aspects Med. 1994;15 Suppl:s231-40.
Lockwood et al., Partial and complete regression of breast cancer in patients in relation to dosage of coenzyme Q10. Biochem Biophys Res Commun. Mar. 30, 1994;199(3):1504-8.
Lockwood et al., Progress on therapy of breast cancer with vitamin Q10 and the regression of metastases. Biochem Biophys Res Commun. Jul. 6, 1995;212(1):172-7.
Mazoff, Bleeding Disorders & Hepatitis C. HCV Advocate, HCSP Fact Sheet. www.hcvadvocate.org. HCSP, Version 3, 5 pages. Dec. 2014.
Mazzio et al., Effects of enhancing mitochondrial oxidative phosphorylation with reducing equivalents and ubiquinone on 1-methyl-4-phenylpyridinium toxicity and complex I-IV damage in neuroblastoma cells. Biochem Pharmacol. Mar. 15, 2004;67(6):1167-84.
Merck Manual Japanese Edition, 17th ed., pp. 59-63 (2002).
Modi et al., Effect of coenzyme Q10 on catalase activity and other antioxidant parameters in streptozotocin-induced diabetic rats. Biol Trace Elem Res. Jan. 2006;109(1):25-34.
Mousa, Antithrombotic Effects of Naturally Derived Products on Coagulation and Platelet Function. Anticoagulants, Antiplatelets, and Thrombolytics, 2nd Edition. Humana Press, 2010, Chapter 9, pp. 229-240.
Mura et al., Evaluation of transcutol as a clonazepam transdermal permeation enhancer from hydrophilic gel formulations. Eur J Pharm Sci. Feb. 2000;9(4):365-72.
NIH, National Cancer Institute, Drugs Approved for Different Types of Cancer. 7 pages, Jan. 16, 2015.
Nissim, A Gentle Cancer Killer. University of Miami MedicineOnline. Retrieved online at: http://www6.miami.edu/ummedicine-magazine/fall2005/fstory4.html. 3 pages. 2005.
Ohira et al., Expression profiling and characterization of 4200 genes cloned from primary neuroblastomas: identification of 305 genes differentially expressed between favorable and unfavorable subsets. Oncogene. Aug. 21, 2003;22(35):5525-36.
Olson, Karl Aug. Folkers (1906-1997). American Society for Nutritional Sciences, J. Nutr. 2001;131:2227-2230.
Palan et al., Plasma concentrations of coenzyme Q10 and tocopherols in cervical intraepithelial neoplasia and cervical cancer. Eur J Cancer Prev. Aug. 2003;12(4):321-6.
Panwar et al., Preparation, characterization, and in vitro release study of albendazole-encapsulated nanosize liposomes. Int J Nanomedicine. Mar. 9, 201;5:101-8.
Persaud et al., Apoptotic affect of Ubiquinone precursors in melanoma. Cancer Research. Cellular and Molecular Biology. AACR Annual Meeting. 2 pages. Abstract 3281. May 1, 2009.
Perumal et al., Therapeutic effect of tamoxifen and energy-modulating vitamins on carbohydrate-metabolizing enzymes in breast cancer. Cancer Chemother Pharmacol. 2005 u1;56(1):105-14.
Pfaffl et al., Real-time RT-PCR quantification of insulin-like growth factor (IGF)-1, IGF-1 receptor, IGF-2, IGF-2 receptor, insulin receptor, growth hormone receptor, IGF-binding proteins 1, 2 and 3 in the bovine species. Domest Anim Endocrinol. Apr. 2002;22(2):91-102.
Prostate-Specific Antigen (PSA) Test. Retrieved online at: http://www.cancer.gov/cancertopics/factsheet/detection /PSA. Mar. 18, 2009.
Rastogi, Analytical control of preservative labelling on skin creams. Contact Dermatitis. Dec. 2000;43(6):339-43. (Abstract only).
Roffe et al., Efficacy of coenzyme Q10 for improved tolerability of cancer treatments: a systematic review. J Clin Oncol. Nov. 1, 2004;22(21):4418-24.
Sander et al., Vesicle associated membrane protein (VAMP)-7 and VAMP-8, but not VAMP-2 or VAMP-3, are required for activation-induced degranulation of mature human mast cells. Eur J Immunol. Mar. 2008;38(3):855-63.
Scotton et al., Analysis of CC chemokine and chemokine receptor expression in solid ovarian tumours. Br J Cancer. Sep. 14, 2001;85(6):891-7.
Seifried et al., The antioxidant conundrum in cancer. Cancer Res. Aug. 1, 2003;63(15):4295-8.
Shaoqiong et al., Related gene expressions in anti-keratinocyte aging induced by Ganoderma lucidum polysaccharides. J of Medical Colleges of PLA. 2008;23:167-175.
Shekelle et al., Effect of the supplemental use of antioxidants vitamin C, vitamin E, and coenzyme Q10 for the prevention and treatment of cancer. Evid Rep Technol Assess (Summ). Oct. 2003;(75):1-3.
Shen et al., Bioactive Components from the Mycelium of Antrodia salmonea. Journal of the Chinese Chemical Society. 2008;55:854-857.
Shimada et al., Effect of high dose of pyridoxine on mammary tumorigenesis. Nutr Cancer. 2005;53(2):202-7.
Shimizu, Paclitaxel Pirarubicin Weekly. Japan J. Cancer and Chemotherapy, Jan. 2003;30:105-109.
Sieben et al., Differential Gene Expressionin Ovarian Tumors Reveals Dusp 4 and Serpina 5 As Key Regulators for Benign Behavior of Serous Borderline Tumors. J Clinical Oncology. Oct. 1, 2005;23(29):7275-7264.
Small Cell Lung Cancer Treatment (PDQ®)—National Cancer Institute. Retrieved online at: http://www.cancer.gov/cancertopics/pdq/treatment/small-cell-lung/healthprofessional. Jan. 20, 2012.
Soule et al., A human cell line from a pleural effusion derived from a breast carcinoma. J Natl Cancer Inst. Nov. 1973;51(5):1409-16.
The National Cancer Institute, Coenzyme Q10 (PDQ.RTM.) Patient Version. 13 pages. Retrieved online at: http://www.cancer.gov/cancertopics/pdq/cam/coenzymeQ10/patient/allpages; Jul. 10, 2009.
Thibault et al., Phase I Study of Lovastatin, an Inhibitor of the Mevalonate Pathway, in Patients with Cancer. Clinical Cancer Research. Mar. 1996;2:483-491.
Todaro et al., Apoptosis resistance in epithelial tumors is mediated by tumor-cell-derived interleukin-4. Cell Death Differ. Apr. 2008;15(4):762-72.
Tsubaki et al., [Investigation of the preventive effect of CoQ10 against the side-effects of anthracycline antineoplastic agents]. Gan to Kagaku Ryoho. Jul. 1984;11(7):1420-7.
Tsuneki et al., Coenzyme Q10 prevents high glucose-induced oxidative stress in human umbilical vein endothelial cells. Eur J Pharmacol. Jul. 2, 2007;566(1-3):1-10.
Women's Health Update: Coenzyme Q10 and Breast Cancer. Retrieved online at: http://www.encognitive.com/node/13574 on Dec. 26, 2012. 4 pages.
Yang et al., Efficiency Observations of 116 cases on Coenzyme Q10 as an Auxiliary Therapy for Treating Diabetes Combined with Coronary Heart Disease. Journal of Chinese Physician. Oct. 2002;4(10):1148-1149. (with English translation).

(56) References Cited

OTHER PUBLICATIONS

Yunis et al., Human pancreatic carcinoma (MIA PaCa-2) in continuous culture: sensitivity to asparaginase. Int J Cancer. Jan. 1977;19(1):128-35.

Zhang et al., Preparation and Physico-chemical Property of Coenzyme Q10 Submicroemulsion. China Pharmacy. 2007;18(19):1476-1478.

Zhao et al., The Clinical Application of Coenzyme Q10. Shandong Medical Journal. Jan. 31, 1996;36(1):52, (with English translation).

Zucher et al., Liposome drugs' loading efficiency: a working model based on loading conditions and drug's physicochemical properties. J Control Release. Oct. 1, 2009;139(1):73-80.

International Search Report for Application No. PCT/US2010/034453, dated Jan. 31, 2011.

Groneberg et al., Coenzyme Q10 affects expression of genes involved in cell signaling, metabolism and transport in human CaCo-2 cells. The International Journal of Biochemistry and Cell Biology. 2005;37:1208-1218.

Peddinghaus et al., Evaluation of the Usage Pattern and Safety Profile of a Frozen Plasma Transfusion Protocol. Transfusion. 2009;49:159A, Abstract SP285.

METHODS FOR TREATMENT OF ONCOLOGICAL DISORDERS USING AN EPIMETABOLIC SHIFTER (COENZYME Q10)

RELATED APPLICATIONS

This application is a continuation application of U.S. patent application Ser. No. 14/171,419, filed Feb. 3, 2014 which, in turn, is a continuation application of U.S. patent application Ser. No. 12/778,094, filed May 11, 2010, entitled "Methods for Treatment of Oncological Disorders Using an Epimetabolic Shifter (Coenzyme Q10)"; which in turn claims priority to U.S. Provisional Application Ser. No. 61/177,241, filed May 11, 2009, entitled "Methods for Treatment of Oncological Disorders Using an Epimetabolic Shifter (Coenzyme Q10)"; U.S. Provisional Application Ser. No. 61/177,243, filed May 11, 2009, entitled "Methods for Treatment of Oncological Disorders Using Epimetabolic Shifters, Multidimensional Intracellular Molecules or Environmental Influencers"; U.S. Provisional Application Ser. No. 61/177,244, filed May 11, 2009, entitled "Methods for the Diagnosis of Oncological Disorders Using Epimetabolic Shifters, Multidimensional Intracellular Molecules or Environmental Influencers"; U.S. Provisional Application Ser. No. 61/177,245, filed May 11, 2009, entitled "Methods for Treatment of Metabolic Disorders Using Epimetabolic Shifters, Multidimensional Intracellular Molecules or Environmental Influencers"; and U.S. Provisional Application Ser. No. 61/177,246, filed May 11, 2009, entitled "Methods for the Diagnosis of Metabolic Disorders Using Epimetabolic Shifters, Multidimensional Intracellular Molecules or Environmental Influencers". The entire contents of each of the foregoing applications are hereby incorporated herein by reference.

BACKGROUND OF THE INVENTION

Cancer is presently one of the leading causes of death in developed nations and is a serious threat to modern society. Cancer can develop in any tissue of any organ at any age. Worldwide, more than 10 million people are diagnosed with cancer every year and it is estimated that this number will grow to 15 million new cases every year by 2020. It is believed that cancer causes six million deaths every year or 12% of the deaths worldwide.

The etiology of cancer is not clearly understood. Cancer has been linked to or associated with many factors over the many years of ongoing research including genetic susceptibility, chromosome breakage disorders, viruses, environmental factors and immunologic disorders. Cancer encompasses a large category of medical conditions. Cancer cells can arise in almost any organ and/or tissue of the body. Cancer develops when cells in a part of the body begin to grow or differentiate out of control.

Although recent research has vastly increased our understanding of many of the molecular mechanisms of tumorigenesis and has provided numerous new avenues for the treatment of cancer, standard treatments for most malignancies remain gross resection, chemotherapy, and radiotherapy. While increasingly successful, each of these treatments may cause numerous undesired side effects. For example, surgery may result in pain, traumatic injury to healthy tissue, and scarring. Radiation therapy has the advantage of killing cancer cells but it also damages non-cancerous tissue at the same time. Chemotherapy involves the administration of various anti-cancer drugs to a patient. These standard treatments often are accompanied by adverse side effects, e.g., nausea, immune suppression, gastric ulceration and secondary tumorigenesis.

Over the years, many individuals and companies have conducted extensive research searching for improvements in the treatments for the wide array of cancers. Companies are developing bioactive agents including chemical entities, e.g., small molecules, and biologics, e.g., antibodies, with the desire of providing more beneficial therapies for cancer. Some of the bioactive agents tested have worked and provided beneficial therapeutic effects in some individuals or cancer types and others have failed or had minimal therapeutic effects in their testing protocols. Other bioactive agents studied to date have mechanisms of action that are not entirely understood.

Coenzyme Q10, also referred to herein as CoQ10, Q10, ubiquinone, or ubidecarenone, is a popular nutritional supplement and can be found in capsule form in nutritional stores, health food stores, pharmacies, and the like, as a vitamin-like supplement to help protect the immune system through the antioxidant properties of ubiquinol, the reduced form of CoQ10. CoQ10 is art-recognized and further described in International Publication No. WO 2005/069916, the entire disclosure of which is incorporated by reference herein.

CoQ10 is found throughout most tissues of the human body and the tissues of other mammals. The tissue distribution and redox state of CoQ10 in humans has been reviewed in a review article by Bhagavan H N, et al., *Coenzyme Q10: Absorption, tissue uptake, metabolism and pharmacokinetic*, Free Radical Research 40(5), 445-453 (2006) (hereinafter, Bhagavan, et al.). The authors report that "as a general rule, tissues with high-energy requirements or metabolic activity such as the heart, kidney, liver and muscle contain relatively high concentrations of CoQ10." The authors further report that "[a] major portion of CoQ10 in tissues is in the reduced form as the hydroquinone or ubiquinol, with the exception of brain and lungs," which "appears to be a reflection of increased oxidative stress in these two tissues." In particular, Bhagavan et al. reports that in heart, kidney, liver, muscle, intestine and blood (plasma), about 61%, 75%, 95%, 65%, 95% and 96%, respectively, of CoQ10 is in the reduced form. Similarly, Ruiz-Jiminez, et al., *Determination of the ubiquinol-10 and ubiquinone-10 (coenzyme Q10) in human serum by liquid chromatography tandem mass spectrometry to evaluate the oxidative stress*, J. Chroma A 1175(2), 242-248 (2007) (hereinafter Ruiz-Jiminez, et al.) reports that when human plasma was evaluated for Q10 and the reduced form of Q10 (Q10H2), the majority (90%) of the molecule was found in the reduced form.

CoQ10 is very lipophilic and, for the most part, insoluble in water. Due to its insolubility in water, limited solubility in lipids, and relatively large molecular weight, the efficiency of absorption of orally administered CoQ10 is poor. Bhagavan, et al. reports that "in one study with rats it was reported that only about 2-3% of orally-administered CoQ10 was absorbed." Bhagavan, et al. further reports that "[d]ata from rat studies indicate that CoQ10 is reduced to ubiquinol either during or following absorption in the intestine."

CoQ10 has been associated with cancer in the literature for many years. Described below are some representative but not all inclusive examples of the reported associations in the literature. Karl Folkers, et al., *Survival of Cancer Patients on Therapy with Coenzyme Q10*, Biochemical and Biophysical Research Communication 192, 241-245 (1993) (herein after "Folkers, et al.") describes eight case histories of cancer patients "on therapy with CoQ10" and their stories of survival . . . "for periods of 5-15 years." CoQ10 was orally administered to eight patients having different types of cancer, including pancreatic carcinoma, adenocarcinoma, laryngeal carcinoma, breast, colon, lung and prostate cancer. Folkers, et al. sets forth that "these results now justify systemic protocols." Lockwood, et al., *Progress on Therapy of Breast Cancer with Vitamin Q10 and the Regression of Metastases, Biochemical and Biophysical Research Communication* 212, 172-177 (1995) (hereinafter "Lockwood, et al.") is another review article that reports on the "[p]rogress on therapy of breast cancer with Vitamin Q10". Lockwood, et al. refers to Folkers, et al., which "covers 35 years of international research on animals and humans which revealed variable levels of vitamin Q10 in non-tumor and tumor tissues and includes data on vitamin Q10 which are intrinsic to the host defense system as based on increased survivors of treated mice with tumors".

Lockwood, et al. further sets forth that "[t]he potential of vitamin Q10 therapy of human cancer became evident in 1961" relying on a study that determined the blood levels of CoQ10 in 199 Swedish and American cancer patients that revealed variable levels of deficiencies in cases of breast cancer. U.S. Pat. No. 6,417,233, issued Jul. 9, 2002 (hereinafter Sears, et al.) describes compositions containing lipid-soluble benzoquinones, e.g., coenzyme Q10, for the prevention and/or treatment of mitochondriopathies. Sears, et al. sets forth that "CoQ10 treatment has been reported to provide some benefits in cancer patients (see column 2, lines 30-31)."

As of the date of filing of this application, the National Cancer Institute reports that no well-designed clinical trials involving large numbers of patients of CoQ10 in cancer treatment have been conducted since "the way the studies were done and the amount of information reported made it unclear if the benefits were caused by the coenzyme Q10 or by something else." See The National Cancer Institute (NCI), available at www.cancer.gov/cancertopics/pdq/cam/coenzymeQ10/patient/allpages (Sep. 29, 2008). In particular, the NCI cites three small studies on the use of CoQ10 as an adjuvant therapy after standard treatment in breast cancer patients, in which some patients appeared to be helped by the treatment, and reiterates that "weaknesses in study design and reporting, however, made it unclear if benefits were caused by the coenzyme Q10 or by something else." The NCI specifies that "these studies had the following weaknesses: the studies were not randomized or controlled; the patients used other supplements in addition to coenzyme Q10; the patients received standard treatments before or during the coenzyme Q10 therapy; and details were not reported for all patients in the studies." The NCI further reports on "anecdotal reports that coenzyme Q10 has helped some cancer patients live longer, including patients with cancers of the pancreas, lung, colon, rectum and prostate," but states that "the patients described in these reports, however, also received treatments other than coenzyme Q10 including chemotherapy, radiation therapy and surgery."

US Patent Application Publication 2006/0035981, published Feb. 16, 2006 (hereinafter "Mazzio 2006") describes methods and formulations for treating or preventing human and animal cancers using compositions that exploit the vulnerability of cancers with regards to its anaerobic requirement for non-oxidative phosphorylation of glucose to derive energy, which is opposite to the host. The formulations of Mazzio 2006 contain one or more compounds that synergistically promote oxidative metabolism and/or impede lactic acid dehydrogenase or anaerobic glucose metabolism and more particularly are described as containing "2,3-dimethoxy-5-methyl-1,4-benzoquinone (herein also termed "DMBQ") (quinoid base) and options for the entire ubiquinone series including corresponding hydroquinones, ubichromenols, ubichromanols or synthesized/natural derivatives and analogues. See Mazzio 2006 at page 3, paragraph 0010. Mazzio 2006 establishes "the short chain ubiquinones (CoQ<3) as anti-cancer agents and even further establishes that "2,3-dimethoxy-5-methyl-1,4-benzoquinone (DMBQ) is in excess of 1000 times more potent than CoQ10 as an anti-cancer agent." See Mazzio 2006 at page 3, paragraph 0011. Mazzio 2006 further set forth that the study "did not find CoQ10 to be as lethal as expected" and like "previous studies that have employed CoQ10 against cancer have been somewhat contradictory". See Mazzio 2006 at pages 3-4 for an extensive list of citations supporting this statement.

US Patent Application Publication 2007/0248693, published Oct. 25, 2007 (herein after "Mazzio 2007") also describes nutraceutical compositions and their use for treating or preventing cancer. Again, this published patent application focuses on the short chain ubiquinones and specifically sets forth that CoQ10 is not a critical component of this invention. According to Mazzio 2007 "while CoQ10 can increase the Vmax of mitochondrial complex II activity in cancer cells (Mazzio and Soliman, Biochem Pharmacol. 67:1167-84, 2004), this did not control the rate of mitochondrial respiration or 02 utilization through complex IV. And, CoQ10 was not as lethal as expected. Likewise, results of CoQ10 against cancer have been contradictory." See Mazzio 2007 at page 5, paragraph 0019.

SUMMARY OF THE INVENTION

Applicants have previously described topical formulations of CoQ10 and methods for reducing the rate of tumor growth in animal subjects (Hsia et al., WO 2005/069916 published Aug. 4, 2005). In the experiments described in Hsia et al., CoQ10 was shown to increase the rate of apoptosis in a culture of skin cancer cells but not normal cells. Moreover, treatment of tumor-bearing animals with a topical formulation of CoQ10 was shown to dramatically reduce the rate of tumor growth in the animals. The present invention is based, at least in part, upon a more complete understanding of the role of CoQ10 within a human and/or cell. In particular, the methods and formulations of the present invention are based, at least in part, upon the knowledge gained about the therapeutic activity of CoQ10 for oncological disorders learned by designing and implementing human clinical trials and/or by administering CoQ10 to human subjects and observing the surprising and unexpected results that occur during these trials and/or treatment regimens. The methods and formulations of the present invention are further based, at least in part, upon insight gained into the therapeutic mechanism of CoQ10 from extensive studies of CoQ10 treatment of cells in vitro.

Specifically, in at least one embodiment, the methods and formulations of the present invention are based, at least in part, on the surprising discovery that application of Coenzyme Q10 (also referred to as CoQ10 or Q10 herein) to cells results in selective induction of an apoptotic response in cancer cells, with no effect or, in some cases, a positive effect on growth of normal cells. Moreover, in at least one additional embodiment, it was unexpectedly found that cell lines derived from aggressive cancers were more sensitive to CoQ10 (e.g., required lower concentrations and/or treatment time of CoQ10 for cytotoxicity and/or induction of apoptosis) as compared to cell lines derived from less aggressive or non-aggressive cancers. A time and dose response of mitochondrial Q10 levels was observed, wherein after 48 hours, the level of Q10 in cell mitochondria was increased by six fold. In at least one additional embodiment, the invention is further based on the surprising and unexpected discovery that the Q10 is maintained in the supplied oxidized form (pro-oxidant) and not converted to the reduced (anti-oxidant) form of Q10H2 in any significant amounts. In another embodiment, the invention is still further based on the discovery that the expression of a significant number of genes are modulated in cells treated with the oxidized from of Q10. These modulated proteins were found to be clustered into several cellular pathways, including apoptosis, cancer biology and cell growth, glycolysis and metabolism, molecular transport, and cellular signaling.

Taken together, the results described herein have provided insight into the therapeutic mechanism of Q10. For example, while not wishing to be bound by theory, Applicants' discoveries indicate that Q10 and, in particular, the oxidized form of Q10, induces a metabolic shift to the cell microenvironment. Differential metabolism is known to occur in cancer cells (the Warburg effect), whereby most cancer cells predominantly produce energy by glycolysis followed by lactic acid fermentation in the cytosol, rather than by oxidative phosphorylation (oxidation of pyruvate) in the mitochondria. Applicants' discoveries indicate that Q10 is capable of shifting the metabolic state of cancer cells from anaerobic use of glucose to mitochondrial oxidative phosphorylation.

Accordingly, the present invention provides, in one aspect, methods for treating or preventing oncological disorders in humans by topically administering Coenzyme Q10 to the human such that treatment or prevention occurs. In some embodiments, the CoQ10 induces apoptosis or cell death mechanism in a cancerous cell of the oncological disorder. In other embodiments, the CoQ10 inhibits angiogenesis in a cancerous cell of the oncological disorder. In certain other embodiments, the CoQ10 induces a modulation of the immune-related elements within the microenvironment in a cancerous cell of the oncological disorder while in other embodiments, the CoQ10 induces a change in cell cycle control in a cancerous cell of the oncological disorder. In an embodiment, the topical administration is via a dose selected for providing efficacy in humans for the particular disorder being treated. In certain embodiments, treatment or prevention of the disorder occurs by the administration of the oxidized form of Coenzyme Q10.

In one embodiment, a population of humans are treated and at least 25% of the population had a dimishment of symptoms as measured by art-recognized endpoints including tissue pathology, clinical observations, photographic analyses, CT-scan, MRI imaging, blood, serum or plasma markers of cancer. In one embodiment, a population of humans are treated and at least 50% of the population had a dimishment of symptoms as measured by art-recognized endpoints including tissue pathology, clinical observations, photographic analyses, CT-scan, MRI imaging, blood, serum or plasma markers of cancer, and physical measurement of the treated site before and after treatment. In other embodiments, a population of humans are treated and at least 5%, 10%, 15%, 20%, 25%, 30%, 35%, 40%, 45%, 50%, 55%, 60%, 65%, 70%, 75%, 80%, 85%, 90%, 95%, 98% or more of the population had a dimishment of symptoms as measured by art-recognized endpoints including tissue pathology, clinical observations, photographic analyses, CT-scan, MRI imaging, blood, serum or plasma markers of cancer. It should be understood that ranges having any one of these values as the upper or lower limits are also intended to be part of this invention, e.g., 10% to 25%, 15% to 35%, 25% to 50%, 35% to 60%, 40% to 70%, 50% to 75%, 60% to 85% or 70% to 90%.

In various embodiments, the population of humans treated may be about 3 patients, about 5 patients, about 10 patients, about 15 patients, about 20 patients, about patients, about 30 patients, about 35 patients, about 40 patients, about 50 patients, about 60 patients, about 70 patients, about 80 patients, about 90 patients, about 100 patients, about 125 patients, about 150 patients, about 160 patients, about 175 patients, about 200 patients, about 250 patients, about 300 patients, about 400 patients or more. In one embodiment, the population of humans treated is It should be understood that ranges having any one of these values as the upper or lower limits are also intended to be part of this invention, e.g., about 10 to about 25, about 15 to about 35, about 25 to about 50, or about 20 to about 160 patients.

It will be understood that a skilled artisan would be able, upon examination of one or more art-recognized endpoints, to recognize a patient that had a diminishment of symptoms based upon common knowledge in the art. For example, a skilled artisan would be able to examine and compare photographs of a skin cancer lesion, such as in situ cutaneous squamous cell carcinoma, before and after treatment (e.g., such as the photographs provided herein in the Examples) and be able to recognize a diminishment of symptoms based upon, for example, a diminishment in size of the lesion, color of the lesion, or any other visual characteristic of the lesion typically indicative of the cancer. In another example, a skilled artisan would be able to examine and compare the tissue pathology of, e.g., a skin cancer, before and after treatment and be able to recognize a diminishment of symptoms based upon a change in tissue pathology indicating, e.g., a diminishment in oncogenicity or in severity of the cancer. In another example, a skilled artisan would be able to examine and compare a CT-scan or MRI image of a tumor or sites of metastatic lesions before and after treatment, and be able to recognize a dimishment of symptoms based upon, for example, a diminishment in size of a primary tumor or a diminishment in size or number of metastatic lesions.

In one embodiment, a population of human patients (e.g., about 160 patients) with superficial basal cell carcinoma are treated with placebo cream (0% CoQ10), placebo plus 1.5% by weight CoQ10 in a topical cream base, 1.5% CoQ10 cream plus 3% by weight CoQ10 cream, or 3% by weight CoQ10 cream alone and at least 25% of the total patient population had a diminishment of symptoms as measured by art-recognized endpoints including tissue pathology, clinical observations by trained experts, photographic analyses, CT-scan, MRI imaging, blood, serum or plasma markers of cancer, physical measurement of the treated site before and after treatment, pathological examination for sBCC before and after treatment, and digital high-resolution clinical photography.

In one embodiment, a population of human patients (e.g., about 25 patients) with squamous cell carcinoma in situ (SCCIS) are treated for a relatively short treatment course (six weeks vs. standard treatment of 16-20 weeks) with a cream containing 3% by weight Coenzyme Q10 and at least 50% of the population had a diminishment of symptoms as measured by art-recognized endpoints including tissue pathology, clinical observations by trained experts, photographic analyses, CT-scan, MRI imaging, blood, serum or plasma markers of cancer, physical measurement of the treated site before and after treatment, pathological examination for SCCIS before and after treatment, and digital high-resolution clinical photography.

In one embodiment, a population of humans are treated and at least 25% of the population had a systemic Coenzyme Q10 level that was therapeutic for the disorder being treated. In other embodiments, a population of humans are treated and at least 5%, 10%, 15%, 20%, 25%, 30%, 35%, 40%, 45%, 50%, 55%, 60%, 65%, 70%, 75%, 80%, 85%, 90%, 95% or more of the population had a systemic Coenzyme Q10 level that was therapeutic for the disorder being treated. It should be understood that ranges having any one of these values as the upper or lower limits are also intended to be part of this invention, e.g., 10% to 25%, 15% to 35%, 25% to 50%, 35% to 60%, 40% to 70%, 50% to 75%, 60% to 85% or 70% to 90%.

In certain embodiments, the oncological disorder being treated or prevented is not a disorder that is typically treated or prevented by topical administration with the expectation of systemic delivery of an active agent in therapeutically effective levels.

In some embodiments, the concentration of Coenzyme Q10 in the tissues of the humans being treated is different that that of a control standard of human tissue representative of a healthy or normal state.

In certain other embodiments of the invention, the form of Coenzyme Q10 that is administered to the human is different than the predominant form found in systemic circulation within the human.

In certain embodiments of the invention, methods are provided for treating or preventing an oncological disorder in a human by topically administering Coenzyme Q10 to the human such that treatment or prevention occurs, wherein the human is administered a topical dose of Coenzyme Q10 in a topical vehicle where Coenzyme Q10 is applied to the target tissue in the range of about 0.01 to about 0.5 milligrams of coenzyme Q10 per square centimeter of skin. In one embodiment, Coenzyme Q10 is applied to the target tissue in the range of about 0.09 to about 0.15 mg CoQ10 per square centimeter of skin. In various embodiments, Coenzyme Q10 is applied to the target tissue in the range of about 0.001 to about 5.0, about 0.005 to about 1.0, about 0.005 to about 0.5, about 0.01 to about 0.5, about 0.025 to about 0.5, about 0.05 to about 0.4, about 0.05 to about 0.30, about 0.10 to about 0.25, or about 0.10 to 0.20 mg CoQ10 per square centimeter of skin. In other embodiments, Coenzyme Q10 is applied to the target tissue at a dose of about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49 or 0.5 mg CoQ10 per square centimeter of skin. In one embodiment, Coenzyme Q10 is applied to the target tissue at a dose of about 0.12 mg CoQ10 per square centimeter of skin It should be understood that ranges having any one of these values as the upper or lower limits are also intended to be part of this invention, e.g., about 0.03 to about 0.12, about 0.05 to about 0.15, about 0.1 to about 0.20, or about 0.32 to about 0.49 mg CoQ10 per square centimeter of skin.

In another embodiment of the invention, the Coenzyme Q10 is administered in the form of a CoQ10 cream at a dosage of between 0.5 and 10 milligrams of the CoQ10 cream per square centimeter of skin, wherein the CoQ10 cream comprises between 1 and 5% of Coenzyme Q10. In one embodiment, the CoQ10 cream comprises about 3% of Coenzyme Q10. In other embodiments, the CoQ10 cream comprises about 1%, 1.5%, 2%, 2.5%, 3%, 3.5%, 4%, 4.5% or 5% of Coenzyme Q10. In various embodiments, the CoQ10 cream is administered at a dosage of about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10 milligrams of CoQ10 cream per square centimeter of skin. It should be understood that ranges having any one of these values as the upper or lower limits are also intended to be part of this invention, e.g., between about 0.5 and about 5.0, about 1.5 and 2.5, or about 2.5 and 5.5 mg CoQ10 cream per square centimeter of skin.

In another embodiment, the Coenzyme Q10 is administered in the form of a CoQ10 cream at a dosage of between 3 and 5 milligrams of the CoQ10 cream per square centimeter of skin, wherein the CoQ10 cream comprises between 1 and 5% of Coenzyme Q10. In one embodiment, the CoQ10 cream comprises about 3% of Coenzyme Q10. In other embodiments, the CoQ10 cream comprises about 1%, 1.5%, 2%, 2.5%, 3%, 3.5%, 4%, 4.5% or 5% of Coenzyme Q10. In various embodiments, the CoQ10 cream is administered at a dosage of about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 milligrams of CoQ10 cream per square centimeter of skin. It should be understood that ranges having any one of these values as the upper or lower limits are also intended to be part of this invention, e.g., between about 3.0 and about 4.0, about 3.3 and 5.3, or about 4.5 and 4.9 mg CoQ10 cream per square centimeter of skin.

In certain embodiments of the invention, the oncological disorder being treated or prevented is Squamous Cell Carcinoma. In certain other embodiments, the oncological disorder being treated or prevented is Basal Cell Carcinoma. Other embodiments of the invention, the oncological disorder being prevented is SCC, and the method prevents the pre-cancerous lesion actinic keratosis from progressing into SCC. In other embodiments, the oncological disorder being treated or prevented is melanoma.

Certain aspects of the invention provide methods for treating or preventing an oncological disorder in a human by topically administering Coenzyme Q10 to the human such that treatment or prevention occurs, wherein the Coenzyme Q10 is topically applied one or more times per 24 hours for six weeks or more.

The invention also provides, in another aspect, methods for treating or preventing aggressive oncological disorders in humans. These methods include administering Coenzyme Q10 to the human at a selected lower dosage than a dosage regimen used or selected for less aggressive or non-aggressive oncological disorder, so that treatment or prevention of the aggressive oncological disorder occurs. In certain embodiments the aggressive oncological disorder includes pancreatic carcinoma, hepatocellular carcinoma, Ewing's sarcoma, metastatic breast cancer, metastatic melanoma, brain cancer (astrocytoma, glioblastoma), neuroendocrine cancer, colon cancer, lung cancer, osteosarcoma, androgen-independent prostate cancer, ovarian cancer and non-Hodgkin's Lymphoma. In a related aspect, the invention provides a method for treating or preventing a non-aggressive oncological disorder in a human which includes administering Coenzyme Q10 to the human at a selected higher dosage over a dosage regimen used or selected for aggressive oncological disorders so that treatment or prevention of the non-aggressive oncological disorder occurs. In certain embodiments, the non-aggressive oncological disorder includes non-metastatic breast cancer, androgen-dependent prostate cancer, small cell lung cancer and acute lymphocytic leukemia. In certain embodiments, the intermediate comprises: (a) benzoquinone or at least one molecule that facilitates the biosynthesis of the benzoquinone ring, and (b) at least one molecule that facilitates the synthesis of and/or attachment of isoprenoid units to the benzoquinone ring. In other embodiments, said at least one molecule which facilitates the biosynthesis of the benzoquinone ring comprises: L-Phenylalanine, DL-Phenylalanine, D-Phenylalanine, L-Tyrosine, DL-Tyrosine, D-Tyrosine, 4-hydroxy-phenylpyruvate, 3-methoxy-4-hydroxymandelate (vanillylmandelate or VMA), vanillic acid, pyridoxine, or panthenol. In other embodiments, said at least one molecule which facilitates the synthesis of and/or attachment of isoprenoid units to the benzoquinone ring comprises: phenylacetate, 4-hydroxy-benzoate, mevalonic acid, acetylglycine, acetyl-CoA, or farnesyl. In other embodiments, the intermediate comprises: (a) one or more of L-Phenylalanine, L-Tyrosine, and 4-hydroxyphenylpyruvate; and, (b) one or more of 4-hydroxy benzoate, phenylacetate, and benzoquinone. In other embodiments, the intermediate: (a) inhibits Bcl-2 expression and/or promotes Caspase-3 expression; and/or, (b) inhibits cell proliferation. It was unexpected that these lower dosages were therapeutic for the aggressive oncological disorders and the higher dosages were therapeutic for the non-aggressive oncological disorders.

A selected lower dosage of CoQ10 for the treatment of aggressive oncological disorders is intended to include a dosage that is lower than a dosage regimen that is typically used or selected for less aggressive or non-aggressive oncological disorders. In various embodiments, the selected lower dosage of CoQ10 is about 1.5-fold lower, about 2 fold lower, about 3-fold lower, about 4-fold lower, about 5-fold lower or about 10-fold lower than a dosage regimen that is typically used or selected for less aggressive or non-aggressive oncological disorders. It will be understood that a selected lower dosage of CoQ10 also includes a shorter treatment time (e.g., 1.5 fold, 2 fold, 3 fold, 4 fold, 5 fold or 10 fold shorter treatment time) of CoQ10 or less frequent administration (e.g., half as frequent, 3 fold, 4 fold, 5 fold, 10 fold, 20 fold or 24 fold less frequent) of CoQ10 as compared to the treatment time or administration protocol typically used or selected for less aggressive or on-aggressive oncological disorders. In various embodiments, the selected lower dosage of coenzyme Q10 for the treatment of aggressive oncological disorders includes about 0.0001 to about 5.0, about 0.001 to about 1.0, about 0.001 to about 0.5, about 0.001 to about 0.4, about 0.001 to about 0.30, about 0.001 to about 0.25, about 0.001 to about 0.20, about 0.001 to about 0.12, or about 0.001 to about 0.09 mg CoQ10 per square centimeter of skin. In other embodiments, Coenzyme Q10 is applied to the target tissue at a dose of about 0.0001, 0.001, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49 or 0.5 mg CoQ10 per square centimeter of skin. It should be understood that ranges having any one of these values as the upper or lower limits are also intended to be part of this invention, e.g., about 0.005 to about 0.09 mg CoQ10 per square centimeter of skin.

A selected higher dosage of CoQ10 for the treatment of non-aggressive oncological disorders is intended to include a dosage that is higher than a dosage regimen that is typically used or selected for aggressive oncological disorders. In various embodiments, the selected higher dosage of CoQ10 is about 1.5-fold, about 2 fold, about 3-fold, about 4-fold, about 5-fold or about 10-fold higher than a dosage regimen that is typically used or selected for aggressive oncological disorders. It will be understood that a selected lower dosage of CoQ10 also includes a longer treatment time (e.g., 1.5 fold, 2 fold, 3 fold, 4 fold, 5 fold or 10 fold longer treatment time) of CoQ10 or more frequent administration (e.g., 1.5 fold, 2 fold, 3 fold, 4 fold, 5 fold, 10 fold, 20 fold or 24 fold more frequent) of CoQ10 as compared to the treatment time or administration protocol typically used or selected for aggressive oncological disorders. In various embodiments, the selected higher dosage of coenzyme Q10 for the treatment of aggressive oncological disorders includes about 0.001 to about 10.0, about 0.005 to about 10.0, about 0.01 to about 10.0, about 0.05 to about 5.0, about 0.05 to about 2.0, about 0.05 to about 1.0, about 0.05 to about 0.7, about 0.10 to about 0.50, or about 0.12 to 0.5 mg CoQ10 per square centimeter of skin In other embodiments, Coenzyme Q10 is applied to the target tissue at a dose of about 0.001, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.5 mg, 0.6 mg, 0.7 mg., 0.8 mg., 0.9 mg or 1.0 mg CoQ10 per square centimeter of skin. It should be understood that ranges having any one of these values as the upper or lower limits are also intended to be part of this invention, e.g., about 0.15 to about 0.5 mg CoQ10 per square centimeter of skin.

In another aspect, the invention provides a method for treating or preventing an oncological disorder in a human, comprising administering Coenzyme Q10 to the human such that it is maintained in its oxidized form during treatment of the oncological disorder. In one embodiment, the oncological disorder being treated is not a disorder typically treated via topical administration, e.g., breast or prostate cancer, with the expectation of systemic delivery of an active agent at therapeutically effective levels.

The present invention provides, in yet another aspect, methods for blocking anaerobic use of glucose and augmenting mitochondrial oxidative phosphorylation in a human. These methods include selecting or treating a human subject suffering from an oncological disorder and administering to said human a therapeutically effective amount of coenzyme Q10 or an intermediate in the coenzyme Q10 biosynthesis pathway thereby blocking anaerobic use of glucose and augmenting mitochondrial oxidative phosphorylation. In some embodiments, the method further includes upregulating the expression of one or more genes selected from the group consisting of HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II and any one or more of genes listed in Tables 2-4 & 6-28 and/or downregulating the expression of one or more genes selected from the group consisting of HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II, thereby blocking anaerobic use of glucose and augmenting mitochondrial oxidative phosphorylation.

The present invention provides, in a related aspect, methods for blocking anaerobic use of glucose and augmenting mitochondrial oxidative phosphorylation in a human, involving selecting a human subject suffering from an aggressive oncological disorder and administering to said human a therapeutically effective amount of Coenzyme Q10 or an intermediate in the Coenzyme Q10 biosynthesis pathway thereby blocking anaerobic use of glucose and augmenting mitochondrial oxidative phosphorylation. In some embodiments, the oncological disorder is selected from the group consisting of pancreatic carcinoma, hepatocellular carcinoma, Ewing's sarcoma, metastatic breast cancer, metastatic melanoma, brain cancer (astrocytoma, glioblastoma), neuroendocrine cancer, colon cancer, lung cancer, osteosarcoma, androgen-independent prostate cancer, ovarian cancer and non-Hodgkin's Lymphoma.

The present invention provides, in a related aspect, methods for blocking anaerobic use of glucose and augmenting mitochondrial oxidative phosphorylation in a human. These methods include selecting a human subject suffering from a non-aggressive oncological disorder and administering to said human a therapeutically effective amount of Coenzyme Q10 or an intermediate in the Coenzyme Q10 biosynthesis pathway thereby blocking anaerobic use of glucose and augmenting mitochondrial oxidative phosphorylation. In some embodiments, the oncological disorder is selected from the group consisting of non-metastatic breast cancer, androgen-dependent prostate cancer, small cell lung cancer and acute lymphocytic leukemia.

In another aspect, the invention provides a method for treating an oncological disorder in a human. This process includes administering Coenzyme Q10 to a human in need thereof in a dosing regimen such that the permeability of the cell membranes of the human is modulated and treatment occurs.

In some embodiments of the invention, the treatment or prevention of the oncological disorder occurs via an interaction of CoQ10 with a protein selected from the group consisting of HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II and any one or more of genes listed in Tables 2-4 & 6-28. In some embodiments the oncological disorder is selected from the group consisting of leukemia, a lymphoma, a melanoma, a carcinoma or a sarcoma.

In certain embodiments of the invention, the oncological disorder is selected from the group consisting of a leukemia, a lymphoma, a melanoma, a carcinoma and a sarcoma.

In certain embodiments of the invention, the methods further include a treatment regimen which includes any one of or a combination of surgery, radiation, hormone therapy, antibody therapy, therapy with growth factors, cytokines, and chemotherapy.

Certain aspects of the invention provide methods for the preparation of a Coenzyme Q10 cream 3% which includes the steps of preparing a Phase A, B, C, D and E and combining all the phases such that an oil-in-water emulsion of 3% CoQ10 cream is formed.

In some embodiments, the Phase A ingredients include Alkyl $C_{12-15}$ benzoate NF at 4.00% w/w, cetyl alcohol NF at 2.00% w/w, glyceryl stearate/PEG-100 at 4.5% w/w and stearyl alcohol NF at 1.50% w/w while the Phase B ingredients include diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion 2% at 40.00% w/w and the Phase C ingredients include lactic acid USP at 0.50% w/w, sodium lactate solution USP at 2.00% w/w, trolamine NF at 1.30% w/w, and purified water USP at 2.50% w/w. Furthermore in these embodiments the Phase D ingredients include titanium dioxide USP at 1.00% w/w while the Phase E ingredients include CoQ10 21% concentrate at 15% w/w.

In certain other embodiments, the Phase A ingredients include capric/caprylic triglyceride at 4.00% w/w, cetyl alcohol NF at 2.00% w/w, glyceril stearate/PEG-100 at 4.5% and stearyl alcohol NF at 1.5% w/w while the Phase B ingredients include diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion 2% at 40.00% w/w and the Phase C ingredients include lactic acid USP at 0.50% w/w, sodium lactate solution USP at 2.00% w/w, trolamine NF at 1.30% w/w, and purified water USP at 2.50% w/w. Furthermore in these embodiments the Phase D ingredients include titanium dioxide USP at 1.00% w/w while the Phase E ingredients include CoQ10 21% concentrate at 15% w/w.

In certain embodiments of the invention, methods are provided for the preparation of a Coenzyme Q10 cream 3% which include the steps of (1) adding the Phase A ingredients to a suitable container and heating to 70-80 degrees C. in a water bath; (2) adding the Phase B ingredients, excluding the Carbomer Dispersion, to a suitable container and mixing to form a mixed Phase B; (3) placing the Phase E ingredients into a suitable container and melting them at 50-60 degrees C. using a water bath to form a melted Phase E; (4) adding the Carbomer Dispersion to a Mix Tank and heating to 70-80 degrees C. while mixing; (5) adding the mixed Phase B to the Mix Tank while maintaining the temperature at 70-80 degrees C.; (6) adding the Phase C ingredients to the Mix Tank while maintaining the temperature at 70-80 degrees C.; (7) adding the Phase D ingredients to the Mix Tank and then continue mixing and homogenizing the contents of the Mix Tank; then (8) stopping the homogenization and cooling the contents of the Mix Tank to 50-60 degrees C.; then (9) discontinuing the mixing and adding the melted Phase E to the Mix Tank to form a dispersion; (10) mixing is then resumed until the dispersion is smooth and uniform; then (11) cooling the contents of the Mix Tank to 45-50 degrees C.

In some other embodiments of the invention, a pharmaceutical composition comprising CoQ10 cream 3% is provided. The cream includes a phase A having $C_{12-15}$ alkyl benzoate at 4.00% w/w of the composition, cetyl alcohol at 2.00% w/w of the composition, stearyl alcohol at 1.5% w/w, glyceryl stearate and PEG-100 at 4.5% w/w; a phase B having glycerin at 2.00% w/w, propylene glycol at 1.5% w/w, ethoxydiglycol at 5.0% w/w, phenoxyethanol at 0.475% w/w, a carbomer dispersion at 40.00% w/w, purified water at 16.725% w/w; a phase C having triethanolamine at 1.300% w/w, lactic acid at 0.500% w/w, sodium lactate solution at 2.000% w/w, water at 2.5% w/w; a phase D having titanium dioxide at 1.000% w/w; and a phase E having CoQ10 21% concentrate at 15.000% w/w. In some embodiments the Carbomer Dispersion includes water, phenoxyethanol, propylene glycol and Carbomer 940.

In some other embodiments of the invention, a pharmaceutical composition comprising CoQ10 cream 3% is provided. The cream includes a phase A having Capric/Caprylic triglyceride at 4.00% w/w of the composition, cetyl alcohol at 2.00% w/w of the composition, stearyl alcohol at 1.5% w/w, glyceryl stearate and PEG-100 at 4.5% w/w; a phase B having glycerin at 2.00% w/w, propylene glycol at 1.5% w/w, ethoxydiglycol at 5.0% w/w, phenoxyethanol at 0.475% w/w, a carbomer dispersion at 40.00% w/w, purified water at 16.725% w/w; a phase C having triethanolamine at 1.300% w/w, lactic acid at 0.500% w/w, sodium lactate solution at 2.000% w/w, water at 2.5% w/w; a phase D having titanium dioxide at 1.000% w/w; and a phase E having CoQ10 21% concentrate at 15.000% w/w. In some embodiments the Carbomer Dispersion includes water, phenoxyethanol, propylene glycol and Carbomer 940.

In some other embodiments of the invention, a pharmaceutical composition comprising CoQ10 cream 1.5% is provided. The cream includes a phase A having $C_{12-15}$ alkyl benzoate at 5.000% w/w, cetyl alcohol at 2.000% w/w, stearyl alcohol at 1.5% w/w, glyceryl stearate and PEG-100 stearate at 4.500% w/w; a phase B having glycerin at 2.000% w/w, propylene at 1.750% w/w, ethoxydiglycol at 5.000% w/w, phenoxyethanol at 0.463% w/w, a carbomer dispersion at 50% w/w, and purified water at 11.377% w/w; a phase C having triethanolamine at 1.3% w/w, lactic acid at 0.400% w/w, sodium lactate solution at 2.000% w/w, and water at 4.210% w/w; a phase D having titanium dioxide at 1.000% w/w; and a phase E having CoQ10 21% concentrate at 7.500% w/w.

In some other embodiments of the invention, a pharmaceutical composition comprising CoQ10 cream 1.5% is provided. The cream includes a phase A having Capric/Caprylic triglyceride at 5.000% w/w, cetyl alcohol at 2.000% w/w, stearyl alcohol at 1.5% w/w, glyceryl stearate and PEG-100 stearate at 4.500% w/w; a phase B having glycerin at 2.000% w/w, propylene at 1.750% w/w, ethoxydiglycol at 5.000% w/w, phenoxyethanol at 0.463% w/w, a carbomer dispersion at 50% w/w, and purified water at 11.377% w/w; a phase C having triethanolamine at 1.3% w/w, lactic acid at 0.400% w/w, sodium lactate solution at 2.000% w/w, and water at 4.210% w/w; a phase D having titanium dioxide at 1.000% w/w; and a phase E having CoQ10 21% concentrate at 7.500% w/w. In some embodiments the Carbomer Dispersion includes water, phenoxyethanol and propylene glycol.

In certain embodiments, methods are provided for treating or preventing CoQ10 responsive disorder in a human, comprising: topically administering Coenzyme Q10 (CoQ10) to the human such that treatment or prevention occurs. In certain other embodiments, the CoQ10 responsive disorder is an oncological disorder.

BRIEF DESCRIPTION OF THE DRAWINGS

Various embodiments of the present disclosure will be described herein below with reference to the figures wherein.

DETAILED DESCRIPTION OF THE INVENTION

I. Definitions

Figure 1:
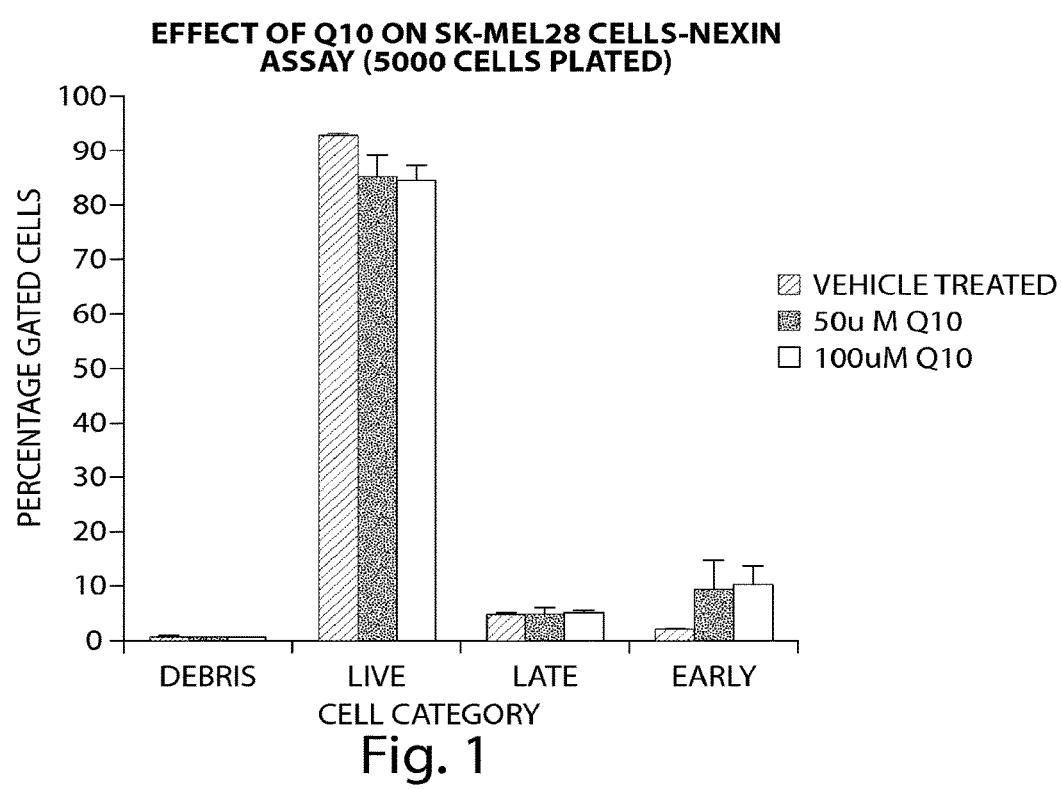
FIG. 1: Sensitivity of SK-MEL-28 to 24 hours of Q10 treatment measured by the amount of early and late apoptotic cells.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

A "patient" or "subject" to be treated by the method of the invention can mean either a human or non-human animal, preferably a mammal. It should be noted that clinical observations described herein were made with human subjects and, in at least some embodiments, the subjects are human.

"Therapeutically effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" will vary depending on the compound, the disease and its severity and the age, weight, etc., of the patient to be treated.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

The term "prophylactic" or "therapeutic" treatment refers to administration to the subject of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

By "patient" is meant any animal (e.g., a human), including horses, dogs, cats, pigs, goats, rabbits, hamsters, monkeys, guinea pigs, rats, mice, lizards, snakes, sheep, cattle, fish, and birds "Metabolic pathway" refers to a sequence of enzyme-mediated reactions that transform one compound to another and provide intermediates and energy for cellular functions. The metabolic pathway can be linear or cyclic.

"Metabolic state" refers to the molecular content of a particular cellular, multicellular or tissue environment at a given point in time as measured by various chemical and biological indicators as they relate to a state of health or disease.

The term "microarray" refers to an array of distinct polynucleotides, oligonucleotides, polypeptides (e.g., antibodies) or peptides synthesized on a substrate, such as paper, nylon or other type of membrane, filter, chip, glass slide, or any other suitable solid support.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

The term "modulation" refers to upregulation (i.e., activation or stimulation), downregulation (i.e., inhibition or suppression) of a response, or the two in combination or apart. A "modulator" is a compound or molecule that modulates, and may be, e.g., an agonist, antagonist, activator, stimulator, suppressor, or inhibitor.

The term "Trolamine," as used herein, refers to Trolamine NF, Triethanolamine, TEAlan®, TEAlan 99%, Triethanolamine, 99%, Triethanolamine, NF or Triethanolamine, 99%, NF. These terms may be used interchangeably herein.

The term "intermediate of the coenzyme biosynthesis pathway" as used herein, characterizes those compounds that are formed between the chemical/biological conversion of tyrosine and Acetyl-CoA to ubiquinone. Intermediates of the coenzyme biosynthesis pathway include 3-hexaprenyl-4-hydroxybenzoate, 3-hexaprenyl-4,5-dihydroxybenzoate, 3-hexaprenyl-4-hydroxy-5-methoxybenzoate, 2-hexaprenyl-6-methoxy-1,4-benzoquinone, 2-hexaprenyl-3-methyl-6-methoxy-1,4-benzoquinone, 2-hexaprenyl-3-methyl-5-hydroxy-6-methoxy-1,4-benzoquinone, 3-Octaprenyl-4-hydroxybenzoate, 2-octaprenylphenol, 2-octaprenyl-6-metholxyphenol, 2-octaprenyl-3-methyl-6-methoxy-1,4-benzoquinone, 2-octaprenyl-3-methyl-5-hydroxy-6-methoxy-1,4-benzoquinone, 2-decaprenyl-3-methyl-5-hydroxy-6-methoxy-1,4-benzoquinone, 2-decaprenyl-3-methyl-6-methoxy-1,4-benzoquinone, 2-decaprenyl-6-methoxy-1,4-benzoquinone, 2-decaprenyl-6-methoxyphenol, 3-decaprenyl-4-hydroxy-5-methoxybenzoate, 3-decaprenyl-4,5-dihydroxybenzoate, 3-decaprenyl-4-hydroxybenzoate, 4-hydroxy phenylpyruvate, 4-hydroxyphenyllactate, 4-hydroxy-benzoate, 4-hydroxycinnamate and hexaprenydiphosphate.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

II. Environmental Influencers

The present invention provides methods of treating oncological disorders by administration of an Environmental influencer. "Environmental influencers" (Env-influencers) are molecules that influence or modulate the disease environment of a human in a beneficial manner allowing the human's disease environment to shift, reestablish back to or maintain a normal or healthy environment leading to a normal state. Env-influencers include both Multidimensional Intracellular Molecules (MIMs) and Epimetabolic shifters (Epi-shifters) as defined below.

As used herein, "oncological disorder" refers to all types of cancer or neoplasm or malignant tumors found in humans, including, but not limited to: leukemias, lymphomas, melanomas, carcinomas and sarcomas. As used herein, the terms or language "oncological disorder", "cancer," "neoplasm," and "tumor," are used interchangeably and in either the singular or plural form, refer to cells that have undergone a malignant transformation that makes them pathological to the host organism. In some embodiments the oncological disorder is a Coenzyme Q10 responsive state.

In some embodiments, the oncological disorder or cancer is characterized by a lack of apoptosis. In other embodiments, the oncological disorder or cancer is characterized by increased angiogenesis. In other embodiments, the oncological disorder or cancer is characterized by extracellular matrix (ECM) degradation. In yet other embodiments, the oncological disorder or cancer is characterized by loss of cell cycle control. In still other embodiments, the oncological disorder or cancer is characterized by a shift in metabolic governance from mitochondrial oxidative phosphorylation to increased utilization and/or dependency on lactate and glycolytic flux. In further embodiments, the oncological disorder or cancer is characterized by adapted immunomodulatory mechanisms that have evaded immunosurveillance. In one embodiment, the oncological disorder or cancer is characterized by at least two of the above features, e.g., increased angiogenesis and ECM degradation. In one embodiment, the oncological disorder or cancer is characterized by at least three of the above features. In one embodiment, the oncological disorder or cancer is characterized by at least four of the above features. In one embodiment, the oncological disorder or cancer is characterized by at least five of the above features. In one embodiment, the oncological disorder or cancer is characterized by all six of the above features.

Accordingly, in some embodiments, the compounds of the present invention function by restoring the capacity for apoptosis or inducing apoptosis. In other embodiments, the compounds of the present invention function by reducing, decreasing or inhibiting angiogenesis. In still other embodiments, the compounds of the present invention function by restoring re-establishing extracellular matrix. In other embodiments, the compounds of the present invention function by restoring cell cycle control. In still other embodiments, the compounds of the present invention function by shifting metabolic governance back from glycolysis to mitochondrial oxidative phosphorylation. In further embodiments, the compounds of the present invention function by restoring immunosurveilance or restoring the body's ability to recognize the cancer cell as foreign.

Without wishing to be bound by any particular theory, it is believed that there is typically a coordinated cascade of events that aggregate to develop into cancer. That is, in some embodiments, cancer is not singularly dependent on a 1 gene-1 protein-root causality. In some embodiments, cancer is a physiologic disease state that manifests into tissue changes and alterations that become tumors, altered tissue states, e.g., energetics, compromised extracellular matrix integrity that allows for metastatic potential, lack of immunosurveilance and/or altered state of angiogenesis.

Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

1. Multidimensional Intracellular Molecule (MIM)

The term "Multidimensional Intracellular Molecule (MIM)", is an isolated version or synthetically produced version of an endogenous molecule that is naturally produced by the body and/or is present in at least one cell of a human. A MIM is characterized by one or more, two or more, three or more, or all of the following functions. MIMs are capable of entering a cell, and the entry into the cell includes complete or partial entry into the cell, as long as the biologically active portion of the molecule wholly enters the cell. MIMs are capable of inducing a signal transduction and/or gene expression mechanism within a cell. MIMs are multidimensional in that the molecules have both a therapeutic and a carrier, e.g., drug delivery, effect. MIMs also are multidimensional in that the molecules act one way in a disease state and a different way in a normal state. For example, in the case of CoQ-10, administration of CoQ-10 to a melanoma cell in the presence of VEGF leads to a decreased level of Bcl2 which, in turn, leads to a decreased oncogenic potential for the melanoma cell. In contrast, in a normal fibroblast, co-administration of CoQ-10 and VEFG has no effect on the levels of Bcl2. Preferably, MIMs selectively act in cells of a disease state, and have substantially no effect in (matching) cells of a normal state. Preferably, MIMs selectively renders cells of a disease state closer in phenotype, metabolic state, genotype, mRNA/protein expression level, etc. to (matching) cells of a normal state.

In one embodiment, a MIM is also an epi-shifter. In another embodiment, a MIM is not an epi-shifter. The skilled artisan will appreciate that a MIM of the invention is also intended to encompass a mixture of two or more endogenous molecules, wherein the mixture is characterized by one or more of the foregoing functions. The endogenous molecules in the mixture are present at a ratio such that the mixture functions as a MIM.

MIMs can be lipid based or non-lipid based molecules. Examples of MIMs include, but are not limited to, CoQ10, acetyl Co-A, palmityl Co-A, L-carnitine, amino acids such as, for example, tyrosine, phenylalanine, and cysteine. In one embodiment, the MIM is a small molecule. In one embodiment of the invention, the MIM is not CoQ10. MIMs can be routinely identified by one of skill in the art using any of the assays described in detail herein.

In some embodiments, MIMs include compounds in the Vitamin B family, or nucleosides, mononucleotides or dinucleotides that comprise a compound in the Vitamin B family. Compounds in the vitamin B family include, for example, thiamine (vitamin B1), niacin (also known as nicotinic acid or Vitamin B3), or pyridoxine (vitamin B6) as well as provitamins such as panthenol (provitamin B5). In some embodiments, the MIM is selected from thiamine, niacin and pyridoxine. Nucleosides, mononucleotides or dinucleotides that comprise a compound in the vitamin B family include, for example, nucleosides, mononucleotides or dinucleotides which include an adenine or a niacin (nicotinic acid) molecule. In some embodiments, the MIM is selected from adenosine, adenosine diphosphate (ADP), flavin adenosine dinucleotide (FAD, which comprises parts of vitamin B2 and ADP) and nicotinic acid dinucleotide.

In other embodiments, the MIMs include amino acids. Examples of amino acids include, for example, tyrosine (e.g., L-tyrosine), cysteine, phenylalanine (e.g., L-phenylalanine) and alanine. In some embodiments, the amino acid is phenylalanine or alanine. In some embodiments, the MIMs include amino acid derivatives such as 4-hydroxyphenylpyruvate or acetylglycine.

In some embodiment, the MIM is a glucose analog, e.g., a glucose molecule wherein one —OH or —CH2OH substituent has been replaced with a —COOH, a —COO— or an —NH2 substituent. Examples of glucose analogs include glucosamine, glucoronic acid, glucoronide and glucoronate.

In some embodiments, the MIM is selected from compounds of formula (I):

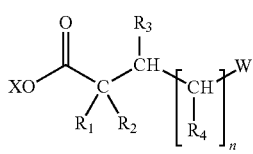

(I)

wherein
n is an integer of 0 or 1;
R1, R2, R3 and R4, when present, are each independently selected from hydrogen and hydroxyl or R1 and R2 are taken together with the carbon on which they are attached to form a carbonyl (C=O) group;
W is —COOH or —N(CH3)3+; and
X is hydrogen, a negative charge or a alkali metal cation, such as Na+ or.

It is to be understood that when n is 0, the CHR3 group is bonded to the W substituent.

In some embodiments, W is —N(CH3)3+. In some embodiments, the MIM is a carnitine, such as L-carnitine.

In some embodiments, the MIM is a dicarboxylic acid. In some embodiments, W is —COOH. In some embodiments, R3 is hydrogen. In some embodiments, n is 0. In some embodiments, R1 and R2 are each independently hydrogen. In some embodiments, W is —COOH, R3 is hydrogen, n is 0 and R1 and R2 are each independently hydrogen. In some embodiments, n is 1. In some embodiments R1 and R2 are taken together with the carbon on which they are attached to form a carbonyl (C=O) group. In some embodiments, R4 is hydrogen. In some embodiments, R4 is hydroxyl. In some embodiments, W is —COOH, R3 is hydrogen, n is 1 and R1 and R2 are taken together with the carbon on which they are attached to form a carbonyl (C=O) group.

In some embodiments, the MIM is an intermediate of the Krebs Cycle, the excess of which drives the Krebs Cycle towards productive oxidative phosphorylation. Exemplary Krebs Cycle intermediates that are MIMs include succinic acid or succinate, malic acid or malate, and α-ketoglutaric acid or α-ketoglutarate.

In some embodiments, the MIM is a building block of CoQ10, which has the following structure:

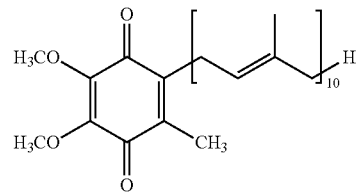

Thus, building blocks of CoQ10 include, but are not limited to, phenylalanine, tyrosine, 4-hydroxyphenylpyruvate, phenylacetate, 3-methoxy-4-hydroxymandelate, vanillic acid, 4-hydroxybenzoate, mevalonic acid, farnesyl, 2,3-dimethoxy-5-methyl-p-benzoquinone, as well as the corresponding acids or ions thereof. In some embodiments, the MIM is selected from phenylalanine, tyrosine, 4-hydroxyphenylpyruvate, phenylacetate and 4-hydroxybenzoate.

2. Epimetabolic Shifters (Epi-shifters)

As used herein, an "epimetabolic shifter" (epi-shifter) is a molecule (endogenous or exogenous) that modulates the metabolic shift from a healthy (or normal) state to a disease state and vice versa, thereby maintaining or reestablishing cellular, tissue, organ, system and/or host health in a human. Epi-shifters are capable of effectuating normalization in a tissue microenvironment. For example, an epi-shifter includes any molecule which is capable, when added to or depleted from a cell, of affecting the microenvironment (e.g., the metabolic state) of a cell. The skilled artisan will appreciate that an epi-shifter of the invention is also intended to encompass a mixture of two or more molecules, wherein the mixture is characterized by one or more of the foregoing functions. The molecules in the mixture are present at a ratio such that the mixture functions as an epi-shifter. Examples of epi-shifters include, but are not limited to, CoQ-10; vitamin D3; ECM components such as fibronectin; immunomodulators, such as TNFa or any of the interleukins, e.g., IL-5, IL-12, IL-23; angiogenic factors; and apoptotic factors.

In some embodiments, the epi-shifter is an enzyme, such as an enzyme that either directly participates in catalyzing one or more reactions in the Krebs Cycle, or produces a Krebs Cycle intermediate, the excess of which drive the Krebs Cycle. In some embodiments, the enzyme is an enzyme of the non-oxidative phase of the pentose phosphate pathway, such as transaldolase, or transketolase. In other embodiments, the enzyme is a component enzyme or enzyme complex that facilitates the Krebs Cycle, such as a synthase or a ligase. Exemplary enzymes include succinyl CoA synthase (Krebs Cycle enzyme) or pyruvate carboxylase (a ligase that catalyzes the reversible carboxylation of pyruvate to form oxaloacetate (OAA), a Krebs Cycle intermediate).

In some embodiments, the epi-shifter is a building block of CoQ10. Building blocks of CoQ10 include, but are not limited to, phenylalanine, tyrosine, 4-hydroxyphenylpyruvate, phenylacetate, 3-methoxy-4-hydroxymandelate, vanillic acid, 4-hydroxybenzoate, mevalonic acid, farnesyl, 2,3-dimethoxy-5-methyl-p-benzoquinone, as well as the corresponding acids or ions thereof. In some embodiments, the epi-shifter is selected from phenylalanine, tyrosine, 4-hydroxyphenylpyruvate, phenylacetate and 4-hydroxybenzoate.

In some embodiments, the epi-shifter is a compound in the Vitamin B family. Compounds in the vitamin B family include, for example, riboflavin (vitamin B2), or analogs thereof. Epi-shifters also include any analogs or pro-drugs that may be metabolized in vivo to any of the endogenous MIMs, such as those described herein.

In one embodiment, the epi-shifter also is a MIM. In one embodiment, the epi-shifter is not CoQ10. Epi-shifters can be routinely identified by one of skill in the art using any of the assays described in detail herein.

In some embodiments, the compounds of the present invention, e.g., the MIMs or epi-shifters described herein, may be used to treat a Coenzyme Q10 responsive state in a subject in need thereof. The language "Coenzyme Q10 responsive state," or "CoQ10 responsive state," includes diseases, disorders, states and/or conditions which can be treated, prevented, or otherwise ameliorated by the administration of Coenzyme Q10. Without wishing to be bound by any particular theory, and as described further herein, it is believed that CoQ10 functions, at least partially, by inducing a metabolic shift to the cell microenvironment, such as a shift towards the type and/or level of oxidative phosphorylation in normal state cells. Accordingly, in some embodiments, CoQ10 responsive states are states that arise from an altered metabolism of cell microenvironment. Coenzyme Q10 responsive states include, for example, oncological disorders, which, for example, may be biased towards glycolysis and lactate biosynthesis. In some embodiments, CoQ10 responsive oncological disorders include liver cancer, pancreatic cancer, breast cancer, prostate cancer, liver cancer, or bone cancer, squamous cell carcinomas, basal cell carcinomas, melanomas, and actinic keratosis, among others. Coenzyme Q10 responsive states further include other oncological disorders as described herein.

Coenzyme Q10 responsive states also include, for example, metabolic disorders such as obesity, diabetes, pre-diabetes, Metabolic Syndrome, satiety, and endocrine abnormalities. Coenzyme Q10 responsive states further include other metabolic disorders as described herein.

In some embodiments, the compounds of the present invention, e.g., the MIMs or epi-shifters described herein, share a common activity with Coenzyme Q10. As used herein, the phrase "share a common activity with Coenzyme Q10" refers to the ability of a compound to exhibit at least a portion of the same or similar activity as Coenzyme Q10. In some embodiments, the compounds of the present invention exhibit 25% or more of the activity of Coenzyme Q10. In some embodiments, the compounds of the present invention exhibit up to and including about 130% of the activity of Coenzyme Q10. In some embodiments, the compounds of the present invention exhibit about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, or 130% of the activity of Coenzyme Q10. It is to be understood that each of the values listed in this paragraph may be modified by the term "about." Additionally, it is to be understood that any range which is defined by any two values listed in this paragraph is meant to be encompassed by the present invention. For example, in some embodiments, the compounds of the present invention exhibit between about 50% and about 100% of the activity of Coenzyme Q10. In some embodiments, the activity shared by Coenzyme Q10 and the compounds of the present invention is the ability to induce a shift in cellular metabolism. In certain embodiments, the activity shared by of CoQ10 and the compounds of the present invention is measured by OCR (Oxigen Consumption Rate) and/or ECAR (ExtraCellular Acidification Rate).

III. Assays Useful for Identifying MIMs/Epi-shifters

Techniques and methods of the present invention employed to separate and identify molecules and compounds of interest include but are not limited to: liquid chromatography (LC), high-pressure liquid chromatography (HPLC), mass spectroscopy (MS), gas chromatography (GC), liquid chromatography/mass spectroscopy (LC-MS), gas chromatography/mass spectroscopy (GC-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS) and matrix-assisted laser desorption/ionization time-of-flight mass spectrometry (MALDI-TOF MS).

Quantification of Bioenergetic Molecule Levels:

Environmental influencers (e.g., MIMs or Epi-shifters) may be identified by changes in cellular bioenergetic molecule levels (e.g., ATP, pyruvate, ADP, NADH, NAD, NADPH, NADP, acetylCoA, FADH2) of cells to which a candidate epi-shifter has been applied. Exemplary assays of bioenergetic molecule levels use colorometric, fluorescence, and/or bioluminescent-based methods. Examples of such assays are provided below.

Levels of ATP within cells can be measured with a number of assays and systems known in the art. For example, in one system, cytoplasmic ATP released from lysed cells reacts with luciferin and the enzyme luciferase to produce light. This bioluminescence is measured by a bioluminometer and the intracellular ATP concentration of the lysed cells can be calculated (EnzyLight™ ATP Assay Kit (EATP-100), BioAssay Systems, Hayward, Calif.). In another system, for example, both ATP and its dephosphorylated form, ADP, are calculated via bioluminescence; after ATP levels are calculated, ADP is transformed into ATP and then detected and calculated using the same luciferase system (ApoSENSOR™ ADP/ATP Ratio Assay Kit, BioVision Inc., Mountain View, Calif.).

Pyruvate is an important intermediate in cellular metabolic pathways. Pyruvate may be converted into carbohydrate via gluconeogenesis, converted into fatty acid or metabolized via acetyl CoA, or converted into alanine or ethanol, depending upon the metabolic state of a cell. Thus detection of pyruvate levels provides a measure of the metabolic activity and state of a cell sample. One assay to detect pyruvate, for example, uses both a colorimetric and fluorimetric to detect pyruvate concentrations within different ranges (EnzyChrom™ Pyruvate Assay Kit (Cat# EPYR-100), BioAssay Systems, Hayward, Calif.).

Environmental influencers (e.g., MIMs or Epi-shifters) may influence the process of oxidative phosphorylation carried out by mitochondria in cells, which are involved in the generation and maintenance of bioenergetic molecules in cells. In addition to assays that detect changes in cellular energetics in cell cultures and samples directly (described below), assays exist that detect and quantify the effects of compounds on discrete enzymes and complexes of mitochondria in cells. For example, the MT-OXC MitoTox™ Complete OXPHOS Activity Assay (MitoSciences Inc., Eugene, Oreg.) can detect and quantify the effects of compounds applied directly to complexes I to V extracted from mitochondria. Assays for the detection and quantification of effects on individual mitochondrial complexes such as NADH dehydrogenase (Complex I), cytochrome c oxidase (Complex IV) and ATP synthase (Complex V) are also available (MitoSciences Inc., Eugene, Oreg.).

Measurement of Cellular Energetics:

Environmental influencers (e.g., MIMs or Epi-shifters) may also be identified by changes in cellular energetics. One example of the measurement of cellular energetics are the real-time measures of the consumption of molecular oxygen and/or the change in pH of the media of a cell culture. For example, the ability of a potential epi-shifter to modulate the metabolic state of a cell may be analyzed using, for example, the XF24 Analyzer (Seahorse, Inc.). This technology allows for real time detection of oxygen and pH changes in a monolayer of cells in order to evaluate the bioenergetics of a cell microenvironment. The XF24 Analyzer measures and compares the rates of oxygen consumption (OCR), which is a measure of aerobic metabolism, and extracellular acidification (ECAR), which is a measure of glycolysis, both key indicators of cellular energetics.

Measurement of Oxidative Phosphorylation and Mitochondrial Function

Oxidative Phosphorylation is a process by which ATP is generated via the oxidation of nutrient compounds, carried out in eukaryotes via protein complexes embedded in the membranes of mitochondria. As the primary source of ATP in the cells of most organisms, changes in oxidative phosphorylation activity can strongly alter metabolism and energy balance within a cell. In some embodiments of the invention, environmental influencers (e.g., MIMs or Epi-shifters) may be detected and/or identified by their effects on oxidative phosphorylation. In some embodiments, environmental influencers (e.g., MIMs or Epi-shifters) may be detected and/or identified by their effects on specific aspects of oxidative phosphorylation, including, but not limited to, the electron transport chain and ATP synthesis.

The membrane-embedded protein complexes of the mitochondria that carry out processes involved in oxidative phosphorylation perform specific tasks and are numbered I, II, III and IV. These complexes, along with the trans-inner membrane ATP synthase (also known as Complex V), are the key entities involved in the oxidative phosphorylation process. In addition to assays that can examine the effects of environmental influencers (e.g., MIMs or Epi-shifters) on mitochondrial function in general and the oxidative phosphorylation process in particular, assays are available that can be used to examine the effects of an epi-shifter on an individual complex separately from other complexes.

Complex I, also known as NADH-coenzyme Q oxidoreductase or NADH dehydrogenase, is the first protein in the electron transport chain. In some embodiments, the detection and quantification of the effect of an epi-shifter on the production of $NAD^+$ by Complex I may be performed. For example, the complex can be immunocaptured from a sample in a 96-well plate; the oxidation of NADH to $NAD^+$ takes place concurrently with the reduction of a dye molecule which has an increased absorbance at 450 nM (Complex I Enzyme Activity Microplate Assay Kit, MitoSciences Inc., Eugene, Oreg.).

Complex IV, also known as cytochrome c oxidase (COX), is the last protein in the electron transport chain. In some embodiments, the detection and quantification of the effect of an epi-shifter on the oxidation of cytochrome c and the reduction of oxygen to water by Complex IV may be performed. For example, COX can be immunocaptured in a microwell plate and the oxidation of COX measured with a colorimetric assay (Complex IV Enzyme Activity Microplate Assay Kit, MitoSciences Inc., Eugene, Oreg.).

The final enzyme in the oxidative phosphorylation process is ATP synthase (Complex V), which uses the proton gradient created by the other complexes to power the synthesis of ATP from ADP. In some embodiments, the detection and quantification of the effect of an epi-shifter on the activity of ATP synthase may be performed. For example, both the activity of ATP synthase and the amount of ATP synthase in a sample may be measured for ATP synthase that has been immunocaptured in a microwell plate well. The enzyme can also function as an ATPase under certain conditions, thus in this assay for ATP synthase activity, the rate at which ATP is reduced to ADP is measured by detecting the simultaneous oxidation of NADH to $NAD^+$. The amount of ATP is calculated using a labeled antibody to ATPase (ATP synthase Duplexing (Activity+Quantity) Microplate Assay Kit, MitoSciences Inc., Eugene, Oreg.). Additional assays for oxidative phosphorylation include assays that test for effects on the activity of Complexes II and III. For example, the MT-OXC MitoTox™ Complete OXPHOS System (MitoSciences Inc., Eugene, Oreg.) can be used to evaluate effects of a compound on Complex II and III as well as Complex I, IV and V, to provide data on the effects of a compound on the entire oxidative phosphorylation system.

As noted above, real-time observation of intact cell samples can be made using probes for changes in oxygen consumption and pH in cell culture media. These assays of cell energetics provide a broad overview of mitochondrial function and the effects of potential environmental influencers (e.g., MIMs or Epi-shifters) on the activity of mitochondria within the cells of the sample.

Environmental influencers (e.g., MIMs or Epi-shifters) may also affect mitochondrial permeability transition (MPT), a phenomena in which the mitochondrial membranes experience an increase in permeability due to the formation of mitochondrial permeability transition pores (MPTP). An increase in mitochondrial permeability can lead to mitochondrial swelling, an inability to conduct oxidative phosphorylation and ATP generation and cell death. MPT may be involved with induction of apoptosis. (See, for example, Halestrap, A. P., Biochem. Soc. Trans. 34:232-237 (2006) and Lena, A. et al. Journal of Translational Med. 7:13-26 (2009), hereby incorporated by reference in their entirety.)

In some embodiments, the detection and quantification of the effect of an environmental influencer (e.g., MIM or epi-shifter) on the formation, discontinuation and/or effects of MPT and MPTPs are measured. For example, assays can detect MPT through the use of specialized dye molecules (calcein) that are localized within the inner membranes of mitochondria and other cytosolic compartments. The application of another molecule, $CoCl_2$, serves to squelch the fluorescence of the calcein dye in the cytosol. $CoCl_2$ cannot access, however, the interior of the mitochondria, thus the calcein fluorescence in the mitochondria is not squelched unless MPT has occurred and $CoCl_2$ can access the interior of the mitochondria via MPTPs. Loss of mitochondrial-specific fluorescence signals that MPT has occurred. Flow cytometry can be used to evaluate cellular and organelle fluorescence (MitoProbe™ Transition Pore Assay Kit, Molecular Probes, Eugene, Oreg.). Additional assays utilize a fluorescence microscope for evaluating experimental results (Image-iT™ LIVE Mitochondrial Transition Pore Assay Kit, Molecular Probes, Eugene, Oreg.).

Measurement of Cellular Proliferation and Inflammation

In some embodiments of the invention, environmental influencers (e.g., MIMs or Epi-shifters) may be identified and evaluated by their effects on the production or activity of molecules associated with cellular proliferation and/or inflammation. These molecules include, but are not limited to, cytokines, growth factors, hormones, components of the extra-cellular matrix, chemokines, neuropeptides, neurotransmitters, neurotrophins and other molecules involved in cellular signaling, as well as intracellular molecules, such as those involved in signal transduction.

Vascular endothelial growth factor (VEGF) is a growth factor with potent angiogenic, vasculogenic and mitogenic properties. VEGF stimulates endothelial permeability and swelling and VEGF activity is implicated in numerous diseases and disorders, including rheumatoid arthritis, metastatic cancer, age-related macular degeneration and diabetic retinopathy.

In some embodiments of the invention, an environmental influencer (e.g., MIM or Epi-shifter) may be identified and characterized by its effects on the production of VEGF. For example, cells maintained in hypoxic conditions or in conditions mimicking acidosis will exhibit increased VEGF production. VEGF secreted into media can be assayed using an ELISA or other antibody-based assays, using available anti-VEGF antibodies (R&D Systems, Minneapolis, Minn.). In some embodiments of the invention, an Epi-shifter may be identified and/or characterized based on its effect(s) on the responsiveness of cells to VEGF and/or based on its effect(s) on the expression or activity of the VEGF receptor.

Implicated in both healthy immune system function as well as in autoimmune diseases, tumor necrosis factor (TNF) is a key mediator of inflammation and immune system activation. In some embodiments of the invention, an Epi-shifter may be identified and characterized by its effects on the production or the activity of TNF. For example, TNF produced by cultured cells and secreted into media can be quantified via ELISA and other antibody-based assays known in the art. Furthermore, in some embodiments an environmental influencer may be identified and characterized by its effect(s) on the expression of receptors for TNF (Human TNF RI Duoset, R&D Systems, Minneapolis, Minn.).

The components of the extracellular matrix (ECM) play roles in both the structure of cells and tissues and in signaling processes. For example, latent transforming growth factor beta binding proteins are ECM components that create a reservoir of transforming growth factor beta (TGFβ) within the ECM. Matrix-bound TGFβ can be released later during the process of matrix remodeling and can exert growth factor effects on nearby cells (Dallas, S. Methods in Mol. Biol. 139:231-243 (2000)).

In some embodiments, an environmental influencer (e.g., MIM or Epi-shifter) may be identified or characterized by its effect(s) on the creation of ECM by cultured cells. Researchers have developed techniques with which the creation of ECM by cells, as well as the composition of the ECM, can be studied and quantified. For example, the synthesis of ECM by cells can be evaluated by embedding the cells in a hydrogel before incubation. Biochemical and other analyses are performed on the ECM generated by the cells after cell harvest and digestion of the hydrogel (Strehin, I. and Elisseeff, J. Methods in Mol. Bio. 522:349-362 (2009)).

In some embodiments, the effect of environmental influencer (e.g., MIM or epi-shifter) on the production, status of or lack of ECM or one of its components in an organism may be identified or characterized. Techniques for creating conditional knock-out (KO) mice have been developed that allow for the knockout of particular ECM genes only in discrete types of cells or at certain stages of development (Brancaccio, M. et al. *Methods in Mol Bio.* 522:15-50 (2009)). The effect of the application or administration of an epi-shifter or potential epi-shifter on the activity or absence of a particular ECM component in a particular tissue or at a particular stage of development may thus be evaluated.

Measurement of Plasma Membrane Integrity and Cell Death

Environmental influencers (e.g., MIMs or Epi-shifters) may be identified by changes in the plasma membrane integrity of a cell sample and/or by changes in the number or percentage of cells that undergo apoptosis, necrosis or cellular changes that demonstrate an increased or reduced likelihood of cell death.

An assay for lactate dehydrogenase (LDH) can provide a measurement of cellular status and damage levels. LDH is a stable and relatively abundant cytoplasmic enzyme. When plasma membranes lose physical integrity, LDH escapes to the extracellular compartment. Higher concentrations of LDH correlate with higher levels of plasma membrane damage and cell death. Examples of LDH assays include assays that use a colorimetric system to detect and quantify levels of LDH in a sample, wherein the reduced form of a tetrazolium salt is produced via the activity of the LDH enzyme (QuantiChrom™ Lactate Dehydrogenase Kit (DLDH-100), BioAssay Systems, Hayward, Calif.; LDH Cytotoxicity Detection Kit, Clontech, Mountain View, Calif.).

Apoptosis is a process of programmed cell death that may have a variety of different initiating events. A number of assays can detect changes in the rate and/or number of cells that undergo apoptosis. One type of assay that is used to detect and quantify apoptosis is a capase assay. Capases are aspartic acid-specific cysteine proteases that are activated via proteolytic cleavage during apoptosis. Examples of assays that detect activated capases include PhiPhiLux® (Oncolmmunin, Inc., Gaithersburg, Md.) and Caspase-Glo® 3/7 Assay Systems (Promega Corp., Madison, Wis.). Additional assays that can detect apoptosis and changes in the percentage or number of cells undergoing apoptosis in comparative samples include TUNEL/DNA fragmentation assays. These assays detect the 180 to 200 base pair DNA fragments generated by nucleases during the execution phase of apoptosis. Exemplary TUNEL/DNA fragmentation assays include the In Situ Cell Death Detection Kit (Roche *Applied Science*, Indianapolis, Ind.) and the DeadEnd™ Colorimetric and Fluorometric TUNEL Systems (Promega Corp., Madison, Wis.).

Some apoptosis assays detect and quantify proteins associated with an apoptotic and/or a non-apoptotic state. For example, the MultiTox-Fluor Multiplex Cytotoxicity Assay (Promega Corp., Madison, Wis.) uses a single substrate, fluorimetric system to detect and quantify proteases specific to live and dead cells, thus providing a ratio of living cells to cells that have undergone apoptosis in a cell or tissue sample.

Additional assays available for detecting and quantifying apoptosis include assays that detect cell permeability (e.g., APOPercentage™ APOPTOSIS Assay, Biocolor, UK) and assays for Annexin V (e.g., Annexin V-Biotin Apoptosis Detection Kit, BioVision Inc., Mountain View, Calif.).

IV. Treatment of Oncological Disorders

The present invention provides methods of treating or preventing an oncological disorder in a human, comprising administering CoQ10 to the human in an amount sufficient to treat or prevent the oncological disorder, thereby treating or preventing the oncological disorder.

The present invention also provides CoQ10 compositions and methods of preparing the same. Preferably, the compositions comprise at least about 1% to about 25% CoQ10 w/w. CoQ10 can be obtained from Asahi Kasei N&P (Hokkaido, Japan) as UBIDECARENONE (USP). CoQ10 can also be obtained from Kaneka Q10 as Kaneka Q10 (USP UBIDECARENONE) in powdered form (Pasadena, Tex., USA). CoQ10 used in the methods exemplified herein have the following characteristics: residual solvents meet USP 467 requirement; water content is less than 0.0%, less than 0.05% or less than 0.2%; residue on ingnition is 0.0%, less than 0.05%, or less than 0.2% less than; heavy metal content is less than 0.002%, or less than 0.001%; purity of between 98-100% or 99.9%, or 99.5%. Methods of preparing the compositions are provided in the examples section below.

As used herein, "oncological disorder" refers to all types of cancer or neoplasm or malignant tumors found in humans, including, but not limited to: leukemias, lymphomas, melanomas, carcinomas and sarcomas. As used herein, the terms or language "oncological disorder", "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

The term "sarcoma" generally refers to a tumor which is made up of a substance like the embryonic connective tissue and is generally composed of closely packed cells embedded in a fibrillar or homogeneous substance. Examples of sarcomas which can be treated with an environmental influencer of the invention include, but are not limited to, a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with an environmental influencer of the invention include, but are not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with an environmental influencer of the invention include, but are not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

In general, CoQ10 may be used to prophylactically or therapeutically treat any neoplasm. In one embodiment, CoQ10 is used to treat solid tumors. In various embodiments of the invention, CoQ10 is used for treatment, of various types of skin cancer (e.g., Squamous cell Carcinoma or Basal Cell Carcinoma), pancreatic cancer, breast cancer, prostate cancer, liver cancer, or bone cancer. In one embodiment, CoQ10 is used for treatment of a skin oncological disorder including, but not limited to, squamous cell carcinomas (including SCCIS (in situ) and more aggressive squamous cell carcinomas), basal cell carcinomas (including superficial, nodular and infiltrating basal cell carcinomas), melanomas, and actinic keratosis. However, treatment using CoQ10 is not limited to the foregoing types of cancers. Examples of cancers amenable to treatment with CoQ10 include, but are not limited to, cancer of the brain, head and neck, prostate, breast, testicular, pancreas, liver, colon, bladder, kidney, lung, non-small cell lung, melanoma, mesothelioma, uterus, cervix, ovary, sarcoma, bone, stomach and Medulloblastoma.

Additional cancers which can be treated with CoQ10 include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. In one embodiment, the oncological disorder or cancer which can be treated with CoQ10 is not melanoma.

The definition of a cancer cell, as used herein, is intended to include a cancer cell that produces energy by anaerobic glycolysis (e.g., glycolysis followed by lactic acid fermantion in the cytosol), aerobic glycolysis (e.g., glycolysis followed by oxidation of pyruvate in the mitochondria), or a combination of anaerobic glycolysis and aerobic glycolysis. In one embodiment, a cancer cell produces energy predominantly by anaerobic glycolysis (e.g., at least 50%, 60%, 70%, 80%, 90%, 95% or more of the cell's energy is produced by anaerobic glycolysis). In one embodiment, a cancer cell produces energy predominantly by aerobic glycolysis (e.g., at least 50%, 60%, 70%, 80%, 90%, 95% or more of the cell's energy is produced by anaerobic glycolysis). The definition of cancer cells, as used herein, is also intended to include a cancer cell population or mixture of cancer cells comprising cells that produce energy by anaerobic glycolysis and cells that produce energy by aerobic glycolysis. In one embodiment, a cancer cell population comprises predominantly cells that produce energy by anaerobic glycolysis (e.g., at least 50%, 60%, 70%, 80%, 90%, 95% or more of the cells in the population produce energy by anaerobic glycolysis). In one embodiment, a cancer cell population comprises predominantly cells that produce energy by aerobic glycolysis (e.g., at least 50%, 60%, 70%, 80%, 90%, 95% or more of the cells in the population).

As used herein, the phrase "anaerobic use of glucose" or "anaerobic glycolysis" refers to cellular production of energy by glycolysis followed by lactic acid fermentation in the cytosol. For example, many cancer cells produce energy by anaerobic glycolysis.

As used herein, the phrase "aerobic glycolysis" or "mitochondrial oxidative phosphorylation" refers to cellular production of energy by glycolysis followed by oxidation of pyruvate in mitochondria.

As used herein, the phrase "capable of blocking anaerobic use of glucose and augmenting mitochondrial oxidative phosphorylation" refers to the ability of an environmental influencer (e.g., an epitmetabolic shifter) to induce a shift or change in the metabolic state of a cell from anaerobic glycolysis to aerobic glycolysis or mitochondrial oxidative phosphorylation.

In some embodiments of the invention, the oncological disorder being treated is not a disorder typically treated via topical administration with the expectation of systemic delivery of an active agent at therapeutically effective levels. As used herein, the phrase "not a disorder typically treated via topical administration" refers to oncological disorders that are not typically or routinely treated with a therapeutic agent via topical administration but rather are typically treated with a therapeutic agent via, for example, intravenous administration. Oncological disorders not typically treated via topical administration include, but are not limited to, breast cancer, prostate cancer, liver cancer, pancreatic cancer, and bone cancer.

The present invention also provides a method for treating or preventing an aggressive oncological disorder in a human, comprising administering CoQ10 to the human at a selected lower dose than the dosage regimen used or selected for less aggressive or non-aggressive oncological disorders, thereby treating or preventing the aggressive oncological disorder. In a related aspect, the invention provides a method for treating or preventing a non-aggressive oncological disorder in a human, comprising administering an environmental influencer to the human at a selected higher dose over the dosage regimen used or selected for aggressive oncological disorders, thereby treating or preventing the non-aggressive oncological disorder.

As used herein, the term "aggressive oncological disorder" refers to an oncological disorder involving a fast-growing tumor. An aggressive oncological disorder typically does not respond or responds poorly to therapeutic treatment. Examples of an aggressive oncological disorder include, but are not limited to, pancreatic carcinoma, hepatocellular carcinoma, Ewing's sarcoma, metastatic breast cancer, metastatic melanoma, brain cancer (astrocytoma, glioblastoma), neuroendocrine cancer, colon cancer, lung cancer, osteosarcoma, androgen-independent prostate cancer, ovarian cancer and non-Hodgkin's Lymphoma.

As used herein, the term "non-aggressive oncological disorder" refers to an oncological disorder involving a slow-growing tumor. A non-aggressive oncological disorder typically responds favorably or moderately to therapeutic treatment. Examples of a non-aggressive oncological disorder include, but are not limited to, non-metastatic breast cancer, androgen-dependent prostate cancer, small cell lung cancer and acute lymphocytic leukemia. In one embodiment, non-aggressive oncological disorders include any oncological disorder that is not an aggressive oncological disorder.

In one embodiment, CoQ10 reduces tumor size, inhibits tumor growth and/or prolongs the survival time of a tumor-bearing subject. Accordingly, this invention also relates to a method of treating tumors in a human or other animal by administering to such human or animal an effective, non-toxic amount of CoQ10. One skilled in the art would be able, by routine experimentation, to determine what an effective, non-toxic amount of CoQ10 would be for the purpose of treating malignancies. For example, a therapeutically active amount of CoQ10 may vary according to factors such as the disease stage (e.g., stage I versus stage IV), age, sex, medical complications (e.g., immunosuppressed conditions or diseases) and weight of the subject, and the ability of the CoQ10 to elicit a desired response in the subject. The dosage regimen may be adjusted to provide the optimum therapeutic response. For example, several divided doses may be administered daily, or the dose may be proportionally reduced as indicated by the exigencies of the therapeutic situation.

V. Therapeutic Targets for Oncological Disorders

The present invention provides methods for identifying therapeutic targets for oncological disorders. The invention further provides therapeutic targets identified by such methods. The identification of a therapeutic target involves, generally, the exogenous application of an Env-influencer or candidate Env-influencer to a cell or panel of cell lines, and the subsequent evaluation of changes induced to a treated cell as compared to a control, untreated cell. Induced cellular changes which are monitored include, but are not limited to, changes to the morphology, physiology or composition, e.g., RNA, protein, lipid or metabolite levels, of the cell. Induced cellular changes as a result of treatment by a candidate Env-influencer can be monitored by using any of the assays described herein. For example, changes in gene expression at the mRNA level can be evaluated by real-time PCR arrays, while changes in gene expression at the protein level can be monitored by using antibody microarrays and 2-D gel electrophoresis. Genes identified as being modulated by the candidate Env-influencer (e.g., at the mRNA and/or protein level) are then evaluated from a Systems Biology perspective using pathway analysis (Ingenuity IPA software) and by a review of the known literature. Genes identified as potential therapeutic targets are next submitted to confirmatory assays such as Western blot analysis, siRNA knock-down, or recombinant protein production and characterization methods. Screening assays can then be used to identify modulators of the targets. Modulators of the therapeutic targets are useful as novel therapeutic agents for oncological disorders. Modulators of therapeutic targets can be routinely identified using screening assays described in detail herein, or by using routine methodologies known to the skilled artisan.

Genes identified herein as being modulated (e.g., upmodulated or downmodulated, at either the mRNA or protein level) by the MIM/Epi-shifter, CoQ10, are drug targets of the invention. Drug targets of the invention include, but are not limited to, the genes subsequently listed in Tables 1-28 (e.g., 2-4 & 6-28) herein. Based on the results of experiments described by Applicants herein, the key proteins modulated by Q10 are associated with or can be classified into different pathways or groups of molecules, including transcription factors, apoptotic response, pentose phosphate pathway, biosynthetic pathway, oxidative stress (pro-oxidant), membrane alterations, and oxidative phosphorylation metabolism. The key proteins modulated by CoQ10, based on the results provided herein, are summarized as follows. A key protein modulated by CoQ10 and which is a transcription factor is HNF4alpha. Key proteins that are modulated by CoQ10 and associated with the apoptotic response include Bcl-xl, Bcl-xl, Bcl-xS, BNIP-2, Bcl-2, Birc6, Bcl-2-L11 (Bim), XIAP, BRAF, Bax, c-Jun, Bmf, PUMA, and cMyc. A key protein that is modulated by CoQ10 and associated with the pentose phosphate pathway is transaldolase 1. Key proteins that are modulated by CoQ10 and associated with a biosynthetic pathway include COQ1, COQ3, COQ6, prenyltransferase and 4-hydroxybenzoate. Key proteins that are modulated by CoQ10 and associated with oxidative stress (pro-oxidant) include Neutrophil cytosolic factor 2, nitric oxide synthase 2A and superoxide dismutase 2 (mitochondrial). Key proteins that are modulated by CoQ10 and associated with oxidative phosphorylation metabolism include Cytochrome c, complex I, complex II, complex III and complex IV. Further key proteins that are directly or indirectly modulated by CoQ10 include Foxo 3a, DJ-1, IDH-1, Cpt1C and Cam Kinase II.

Accordingly, in one embodiment of the invention, a drug target may include HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II. In a preferred embodiment, a drug target may include HNF4A, Transaldolase, NM23 and BSCv. In one embodiment, the drug target is TNF4A. In one embodiment, the drug target is transaldolase. In one embodiment, the drug target is NM23. In one embodiment, the drug target is BSCv. Screening assays useful for identifying modulators of identified drug targets are described below.

VI. Screening Assays

The invention also provides methods (also referred to herein as "screening assays") for identifying modulators, i.e., candidate or test compounds or agents (e.g., proteins, peptides, peptidomimetics, peptoids, small molecules or other drugs), which modulate the expression and/or activity of an identified therapeutic target of the invention. Such assays typically comprise a reaction between a therapeutic target of the invention and one or more assay components. The other components may be either the test compound itself, or a combination of test compounds and a natural binding partner of a marker of the invention. Compounds identified via assays such as those described herein may be useful, for example, for treating or preventing a oncological disorder.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med.* Chem. 37:2678; Cho et al. (1993) *Science* 261:1303; Carrell et al. (1994) *Angew. Chem.* Int. Ed. Engl. 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria and/or spores, (Ladner, U.S. Pat. No. 5,223,409), plasmids (Cull et al, 1992, Proc Natl Acad Sci USA 89:1865-1869) or on phage (Scott and Smith, 1990, Science 249:386-390; Devlin, 1990, Science 249:404-406; Cwirla et al, 1990, Proc. Natl. Acad. Sci. 87:6378-6382; Felici, 1991, J. Mol. Biol. 222:301-310; Ladner, supra.).

The screening methods of the invention comprise contacting a cell with a test compound and determining the ability of the test compound to modulate the expression and/or activity of a therapeutic target of the invention in the cell. The expression and/or activity of a therapeutic target of the invention can be determined as described herein. The expression and/or activity of a therapeutic target of the invention can also be determined by using routine methods known to the skilled artisan. In one embodiment, a compound is selected based on its ability to increase expression and/or activity of a therapeutic target of the invention. In one embodiment, a compound is selected based on its ability increase expression and/or activity of a therapeutic target selected from the protein listed in Tables 1-28 (e.g., 2-4 & 6-28), wherein the therapeutic target is upmodulated by CoQ10 (e.g., exhibits a positive-fold change). In one embodiment, a compound is selected based on its ability to decrease expression and/or activity of a therapeutic target of the invention. In one embodiment, a compound is selected based on its ability to decrease expression and/or activity of a therapeutic target selected from the proteins listed in Tables 1-28 (e.g., 2-4 & 6-28), wherein the therapeutic targetis is downmodulated by CoQ10 (e.g., exhibits a negative-fold change).

In another embodiment, the invention provides assays for screening candidate or test compounds which are substrates of a therapeutic target of the invention or biologically active portions thereof. In yet another embodiment, the invention provides assays for screening candidate or test compounds which bind to a therapeutic target of the invention or biologically active portions thereof. Determining the ability of the test compound to directly bind to a therapeutic target can be accomplished, for example, by coupling the compound with a radioisotope or enzymatic label such that binding of the compound to the drug target can be determined by detecting the labeled marker compound in a complex. For example, compounds (e.g., marker substrates) can be labeled with $^{131}$I, $^{125}$I, $^{35}$S, $^{14}$C, or $^{3}$H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment as described above.

VII. Pharmaceutical Compositions and Pharmaceutical Administration

The present invention provides compositions comprising CoQ10. CoQ10 can be incorporated into pharmaceutical compositions suitable for administration to a subject. Typically, the pharmaceutical composition comprises CoQ10 and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the environmental influencer.

The compositions of this invention may be in a variety of forms. These include, for example, liquid, semi-solid and solid dosage forms, such as liquid solutions (e.g., injectable and infusible solutions), dispersions or suspensions, tablets, pills, powders, creams, lotions, liniments, ointments or pastes, drops for administration to the eye, ear or nose, liposomes and suppositories. The preferred form depends on the intended mode of administration and therapeutic application.

CoQ10 can be administered by a variety of methods known in the art. For many therapeutic applications, the preferred route/mode of administration is topical, subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. In one embodiment, the mode of administration is parenteral (e.g., intravenous, subcutaneous, intraperitoneal, intramuscular). In one embodiment, the environmental influencer is administered by intravenous infusion or injection. In another embodiment, the environmental influencer is administered by intramuscular or subcutaneous injection. In a preferred embodiment, the environmental influencer is administered topically.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., environmental influencer) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxy-benzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives in addition, detergents may be used to facilitate permeation. Transmucosal administration may be through nasal sprays or using suppositories. For topical administration, the compound(s) of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the compound(s) of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous. For injection, the compound(s) of the invention can be formulated in liquid solutions, preferably in physiologically compatible buffers such as Hank's solution or Ringer's solution. In addition, the compound(s) may be formulated in solid form and redissolved or suspended immediately prior to use. Lyophilized forms are also included.

In a preferred embodiment of the invention, the compositions comprising CoQ10 are administered topically. It is preferable to present the active ingredient, i.e. CoQ10, as a pharmaceutical formulation. The active ingredient may comprise, for topical administration, from about 0.001% to about 20% w/w, by weight of the formulation in the final product, although it may comprise as much as 30% w/w, preferably from about 1% to about 20% w/w of the formulation. The topical formulations of the present invention, comprise an active ingredient together with one or more acceptable carrier(s) therefor and optionally any other therapeutic ingredients(s). The carrier(s) should be "acceptable" in the sense of being compatible with the other ingredients of the formulation and not deleterious to the recipient thereof.

In treating a patient exhibiting a disorder of interest, a therapeutically effective amount of an agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oneogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment of a oncological disorder with topical formulations of CoQ10, in other aspects of the invention CoQ10 might be delivered by other methods. For example, CoQ10 might be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. Compositions of the invention can also be administered in vitro to a cell (for example, to induce apoptosis in a cancer cell in an in vitro culture) by simply adding the composition to the fluid in which the cell is contained.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions. and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methyl-cellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, i.e. CoQ10 is facilitated. Without violating this constraint, the pH may be selected to improve CoQ10 compound stability and to adjust consistency when required.

In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of CoQ10. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myjr 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, .alpha.-pinene, .beta.-carene, .alpha.-terpineol, carvol, carvone, menthone, limonene oxide, .alpha.-pinene oxide, *eucalyptus* oil, and the like. Also suitable as skin penetration enhancers are organic acids and esters such as salicyclic acid, methyl salicylate, citric acid, succinic acid, and the like.

In one embodiment, the present invention provides CoQ10 compositions and methods of preparing the same. Preferably, the compositions comprise at least about 1% to about 25% CoQ10 w/w. CoQ10 can be obtained from Asahi Kasei N&P (Hokkaido, Japan) as UBIDECARENONE (USP). CoQ10 can also be obtained from Kaneka Q10 as Kaneka Q10 (USP UBIDECARENONE) in powdered form (Pasadena, Tex., USA). CoQ10 used in the methods exemplified herein have the following characteristics: residual solvents meet USP 467 requirement; water content is less than 0.0%, less than 0.05% or less than 0.2%; residue on ingnition is 0.0%, less than 0.05%, or less than 0.2% less than; heavy metal content is less than 0.002%, or less than 0.001%; purity of between 98-100% or 99.9%, or 99.5%. Methods of preparing the compositions are provided in the examples section below.

In certain embodiments of the invention, methods are provided for treating or preventing an oncological disorder in a human by topically administering Coenzyme Q10 to the human such that treatment or prevention occurs, wherein the human is administered a topical dose of Coenzyme Q10 in a topical vehicle where Coenzyme Q10 is applied to the target tissue in the range of about 0.01 to about 0.5 milligrams of coenzyme Q10 per square centimeter of skin. In one embodiment, Coenzyme Q10 is applied to the target tissue in the range of about 0.09 to about 0.15 mg CoQ10 per square centimeter of skin. In various embodiments, Coenzyme Q10 is applied to the target tissue in the range of about 0.001 to about 5.0, about 0.005 to about 1.0, about 0.005 to about 0.5, about 0.01 to about 0.5, about 0.025 to about 0.5, about 0.05 to about 0.4, about 0.05 to about 0.30, about 0.10 to about 0.25, or about 0.10 to 0.20 mg CoQ10 per square centimeter of skin. In other embodiments, Coenzyme Q10 is applied to the target tissue at a dose of about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49 or 0.5 mg CoQ10 per square centimeter of skin. In one embodiment, Coenzyme Q10 is applied to the target tissue at a dose of about 0.12 mg CoQ10 per square centimeter of skin It should be understood that ranges having any one of these values as the upper or lower limits are also intended to be part of this invention, e.g., about 0.03 to about 0.12, about 0.05 to about 0.15, about 0.1 to about 0.20, or about 0.32 to about 0.49 mg CoQ10 per square centimeter of skin.

In another embodiment of the invention, the Coenzyme Q10 is administered in the form of a CoQ10 cream at a dosage of between 0.5 and 10 milligrams of the CoQ10 cream per square centimeter of skin, wherein the CoQ10 cream comprises between 1 and 5% of Coenzyme Q10. In one embodiment, the CoQ10 cream comprises about 3% of Coenzyme Q10. In other embodiments, the CoQ10 cream comprises about 1%, 1.5%, 2%, 2.5%, 3%, 3.5%, 4%, 4.5% or 5% of Coenzyme Q10. In various embodiments, the CoQ10 cream is administered at a dosage of about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10 milligrams of CoQ10 cream per square centimeter of skin. It should be understood that ranges having any one of these values as the upper or lower limits are also intended to be part of this invention, e.g., between about 0.5 and about 5.0, about 1.5 and 2.5, or about 2.5 and 5.5 mg CoQ10 cream per square centimeter of skin.

In another embodiment, the Coenzyme Q10 is administered in the form of a CoQ10 cream at a dosage of between 3 and 5 milligrams of the CoQ10 cream per square centimeter of skin, wherein the CoQ10 cream comprises between 1 and 5% of Coenzyme Q10. In one embodiment, the CoQ10 cream comprises about 3% of Coenzyme Q10. In other embodiments, the CoQ10 cream comprises about 1%, 1.5%, 2%, 2.5%, 3%, 3.5%, 4%, 4.5% or 5% of Coenzyme Q10. In various embodiments, the CoQ10 cream is administered at a dosage of about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 milligrams of CoQ10 cream per square centimeter of skin. It should be understood that ranges having any one of these values as the upper or lower limits are also intended to be part of this invention, e.g., between about 3.0 and about 4.0, about 3.3 and 5.3, or about 4.5 and 4.9 mg CoQ10 cream per square centimeter of skin.

Certain aspects of the invention provide methods for treating or preventing an oncological disorder in a human by topically administering Coenzyme Q10 to the human such that treatment or prevention occurs, wherein the Coenzyme Q10 is topically applied one or more times per 24 hours for six weeks or more.

Certain aspects of the invention provide methods for the preparation of a Coenzyme Q10 cream 3% which includes the steps of preparing a Phase A, B, C, D and E and combining all the phases such that an oil-in-water emulsion of 3% CoQ10 cream is formed.

In certain embodiments, the MIMS and Epi-shifters disclosed herein exclude those that are conventionally used as a dietary supplement. In certain embodiments, these MIMS and/or Epi-shifter that are disclosed herein are of pharmaceutical grade. In certain embodiments, the MIMS and/or Epi-shifter of pharmaceutical grade has a purity between about 95% and about 100% and include all values between 95% and 100%. In certain embodiments, the purity of the MIMS and/or Epi-shifter is 95%, 96%, 97%, 98%, 99%, 99.1%, 99.2%, 99.3%, 99.4%, 99.5%, 99.6%, 99.7%, 99.8%, 99.9%, 99.9 or 100%. In certain embodiments, the MIMS and/or Epi-shifter is free of end toxins. In other embodiments, the MIMS and/or Epi-shifter is free of foreign protein materials. In certain embodiments, the MIMS and/or Epi-shifter is CoQ10.

In some embodiments, the Phase A ingredients include Alkyl $C_{12-15}$ benzoate NF at 4.00% w/w, cetyl alcohol NF at 2.00% w/w, glyceryl stearate/PEG-100 at 4.5% w/w and stearyl alcohol NF at 1.50% w/w while the Phase B ingredients include diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion 2% at 40.00% w/w and the Phase C ingredients include lactic acid USP at 0.50% w/w, sodium lactate solution USP at 2.00% w/w, trolamine NF at 1.30% w/w, and purified water USP at 2.50% w/w. Furthermore in these embodiments the Phase D ingredients include titanium dioxide USP at 1.00% w/w while the Phase E ingredients include CoQ10 21% concentrate at 15% w/w.

In certain other embodiments, the Phase A ingredients include capric/caprylic triglyceride at 4.00% w/w, cetyl alcohol NF at 2.00% w/w, glyceril stearate/PEG-100 at 4.5% and stearyl alcohol NF at 1.5% w/w while the Phase B ingredients include diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion 2% at 40.00% w/w and the Phase C ingredients include lactic acid USP at 0.50% w/w, sodium lactate solution USP at 2.00% w/w, trolamine NF at 1.30% w/w, and purified water USP at 2.50% w/w. Furthermore in these embodiments the Phase D ingredients include titanium dioxide USP at 1.00% w/w while the Phase E ingredients include CoQ10 21% concentrate at 15% w/w.

In certain embodiments of the invention, methods are provided for the preparation of a Coenzyme Q10 cream 3% which include the steps of (1) adding the Phase A ingredients to a suitable container and heating to 70-80 degrees C. in a water bath; (2) adding the Phase B ingredients, excluding the Carbomer Dispersion, to a suitable container and mixing to form a mixed Phase B; (3) placing the Phase E ingredients into a suitable container and melting them at 50-60 degrees C. using a water bath to form a melted Phase E; (4) adding the Carbomer Dispersion to a Mix Tank and heating to 70-80 degrees C. while mixing; (5) adding the mixed Phase B to the Mix Tank while maintaining the temperature at 70-80 degrees C.; (6) adding the Phase C ingredients to the Mix Tank while maintaining the temperature at 70-80 degrees C.; (7) adding the Phase D ingredients to the Mix Tank and then continue mixing and homogenizing the contents of the Mix Tank; then (8) stopping the homogenization and cooling the contents of the Mix Tank to 50-60 degrees C.; then (9) discontinuing the mixing and adding the melted Phase E to the Mix Tank to form a dispersion; (10) mixing is then resumed until the dispersion is smooth and uniform; then (11) cooling the contents of the Mix Tank to 45-50 degrees C.

In some other embodiments of the invention, a pharmaceutical composition comprising CoQ10 cream 3% is provided. The cream includes a phase A having $C_{12-15}$ alkyl benzoate at 4.00% w/w of the composition, cetyl alcohol at 2.00% w/w of the composition, stearyl alcohol at 1.5% w/w, glyceryl stearate and PEG-100 at 4.5% w/w; a phase B having glycerin at 2.00% w/w, propylene glycol at 1.5% w/w, ethoxydiglycol at 5.0% w/w, phenoxyethanol at 0.475% w/w, a carbomer dispersion at 40.00% w/w, purified water at 16.725% w/w; a phase C having triethanolamine at 1.300% w/w, lactic acid at 0.500% w/w, sodium lactate solution at 2.000% w/w, water at 2.5% w/w; a phase D having titanium dioxide at 1.000% w/w; and a phase E having CoQ10 21% concentrate at 15.000% w/w. In some embodiments the Carbomer Dispersion includes water, phenoxyethanol, propylene glycol and Carbomer 940.

In some other embodiments of the invention, a pharmaceutical composition comprising CoQ10 cream 3% is provided. The cream includes a phase A having Capric/Caprylic triglyceride at 4.00% w/w of the composition, cetyl alcohol at 2.00% w/w of the composition, stearyl alcohol at 1.5% w/w, glyceryl stearate and PEG-100 at 4.5% w/w; a phase B having glycerin at 2.00% w/w, propylene glycol at 1.5% w/w, ethoxydiglycol at 5.0% w/w, phenoxyethanol at 0.475% w/w, a carbomer dispersion at 40.00% w/w, purified water at 16.725% w/w; a phase C having triethanolamine at 1.300% w/w, lactic acid at 0.500% w/w, sodium lactate solution at 2.000% w/w, water at 2.5% w/w; a phase D having titanium dioxide at 1.000% w/w; and a phase E having CoQ10 21% concentrate at 15.000% w/w. In some embodiments the Carbomer Dispersion includes water, phenoxyethanol, propylene glycol and Carbomer 940.

In some other embodiments of the invention, a pharmaceutical composition comprising CoQ10 cream 1.5% is provided. The cream includes a phase A having $C_{12-15}$ alkyl benzoate at 5.000% w/w, cetyl alcohol at 2.000% w/w, stearyl alcohol at 1.5% w/w, glyceryl stearate and PEG-100 stearate at 4.500% w/w; a phase B having glycerin at 2.000% w/w, propylene at 1.750% w/w, ethoxydiglycol at 5.000% w/w, phenoxyethanol at 0.463% w/w, a carbomer dispersion at 50% w/w, and purified water at 11.377% w/w; a phase C having triethanolamine at 1.3% w/w, lactic acid at 0.400% w/w, sodium lactate solution at 2.000% w/w, and water at 4.210% w/w; a phase D having titanium dioxide at 1.000% w/w; and a phase E having CoQ10 21% concentrate at 7.500% w/w.

In some other embodiments of the invention, a pharmaceutical composition comprising CoQ10 cream 1.5% is provided. The cream includes a phase A having Capric/Caprylic triglyceride at 5.000% w/w, cetyl alcohol at 2.000% w/w, stearyl alcohol at 1.5% w/w, glyceryl stearate and PEG-100 stearate at 4.500% w/w; a phase B having glycerin at 2.000% w/w, propylene at 1.750% w/w, ethoxydiglycol at 5.000% w/w, phenoxyethanol at 0.463% w/w, a carbomer dispersion at 50% w/w, and purified water at 11.377% w/w; a phase C having triethanolamine at 1.3% w/w, lactic acid at 0.400% w/w, sodium lactate solution at 2.000% w/w, and water at 4.210% w/w; a phase D having titanium dioxide at 1.000% w/w; and a phase E having CoQ10 21% concentrate at 7.500% w/w. In some embodiments the Carbomer Dispersion includes water, phenoxyethanol and propylene glycol.

1. Combination Therapies

In certain embodiments, CoQ10 and/or pharmaceutical compositions thereof can be used in combination therapy with at least one other therapeutic agent. CoQ10 and/or pharmaceutical composition thereof and the other therapeutic agent can act additively or, more preferably, synergistically. In one embodiment, CoQ10 and/or a pharmaceutical composition thereof is administered concurrently with the administration of another therapeutic agent. In another embodiment, a compound and/or pharmaceutical composition thereof is administered prior or subsequent to administration of another therapeutic agent.

In one embodiment, the therapeutic methods of the invention comprise additional agents. For example, in one embodiment, an additional agent for use in the therapeutic methods of the invention of the invention is a chemotherapeutic agent.

Chemotherapeutic agents generally belong to various classes including, for example: 1. Topoisomerase II inhibitors (cytotoxic antibiotics), such as the antracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide; 2. Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin; 3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan; 4. Antimetabolites (nucleoside inhibitors), for example, folates, e.g., folic acid, fiuropyrimidines, purine or pyrimidine analogues such as 5-fluorouracil, capecitabine, gemcitabine, methotrexate and edatrexate; 5. Topoisomerase I inhibitors, such as topotecan, irinotecan, and 9-nitrocamptothecin, and camptothecin derivatives; and 6. Platinum compounds/complexes, such as cisplatin, oxaliplatin, and carboplatin; Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-I1, 1O-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10, 11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol) and bleomycin, and combinations thereof which are readily apparent to one of skill in the art based on the appropriate standard of care for a particular tumor or cancer.

In another embodiment, an additional agent for use in the combination therapies of the invention is a biologic agent.

Biological agents (also called biologies) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example: 1. Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leuteinizing hormones; and 2. Enzymes, proteins, peptides, polyclonal and/or monoclonal antibodies, such as interleukins, interferons, colony stimulating factor, etc.

In one embodiment, the biologic is an interferon. Interferons (IFN) are a type biologic agent that naturally occurs in the body. Interferons are also produced in the laboratory and given to cancer patients in biological therapy. They have been shown to improve the way a cancer patient's immune system acts against cancer cells.

Interferons may work directly on cancer cells to slow their growth, or they may cause cancer cells to change into cells with more normal behavior. Some interferons may also stimulate natural killer cells (NK) cells, T cells, and macrophages which are types of white blood cells in the bloodstream that help to fight cancer cells.

In one embodiment, the biologic is an interleukin. Interleukins (IL) stimulate the growth and activity of many immune cells. They are proteins (cytokines and chemokines) that occur naturally in the body, but can also be made in the laboratory.

Some interleukins stimulate the growth and activity of immune cells, such as lymphocytes, which work to destroy cancer cells.

In another embodiment, the biologic is a colony-stimulating factor.

Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Parts of the immune system cannot function without blood cells, thus colony-stimulating factors encourage the bone marrow stem cells to produce white blood cells, platelets, and red blood cells.

With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells.

When cancer-destroying agents are introduced into the body, they seek out the antibodies and kill the cancer cells. Monoclonal antibody agents do not destroy healthy cells. Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti idiotype antibody formation.

Examples of antibodies which may be used in the combination treatment of the invention include anti-CD20 antibodies, such as, but not limited to, cetuximab, Tositumomab, rituximab, and Ibritumomab. Anti-HER2 antibodies may also be used in combination with an environmental influencer for the treatment of cancer. In one embodiment, the anti-HER2 antibody is Trastuzumab (Herceptin). Other examples of antibodies which may be used in combination with an environmental influencer for the treatment of cancer include anti-CD52 antibodies (e.g., Alemtuzumab), anti-CD-22 antibodies (e.g., Epratuzumab), and anti-CD33 antibodies (e.g., Gemtuzumab ozogamicin). Anti-VEGF antibodies may also be used in combination with an environmental influencer for the treatment of cancer. In one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary cancer treatment). Cytokine therapy reaches all parts of the body to kill cancer cells and prevent tumors from growing.

In another embodiment, the biologic is a fusion protein. For example, recombinant human Apo2L/TRAIL (Genentech) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is an antisense nucleic acid molecule.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a biologic agent is an siRNA molecule, e.g., of a molecule that enhances angiogenesis, e.g., bFGF, VEGF and EGFR. In one embodiment, a biologic agent that inhibits angiogenesis mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. Mol Therapy. 7:9-10; McManus M T and Sharp P A. 2002. Nat Rev Genet. 3.737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more chemistries for use in antisense RNA can be employed in molecules that mediate RNAi.

The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J J. (1995) Br. Med. Bull. 51.217-225; Wagner, R. W. (1994) Nature 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences of a molecule that enhances angiogenesis, antisense nucleic acids of the invention can be designed according to the rules of Watson and Crick base pairing. The antisense nucleic acid molecule can be complementary to the entire coding region of the mRNA, but more preferably is an oligonucleotide which is antisense to only a portion of the coding or noncoding region of the mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyl uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an a-anomeric nucleic acid molecule. An a-anomeric nucleic acid molecule forms specific double-stranded hybrids with complementary RNA in which, contrary to the usual a-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330).

In another embodiment, an antisense nucleic acid of the invention is a compound that mediates RNAi. RNA interfering agents include, but are not limited to, nucleic acid molecules including RNA molecules which are homologous to the target gene or genomic sequence, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

Nucleic acid molecules encoding molecules that, e.g., inhibit angiogenesis, may be introduced into the subject in a form suitable for expression of the encoded protein in the cells of the subject may also be used in the methods of the invention. Exemplary molecules that inhibit angiogenesis include, but are not limited to, TSP-I, TSP-2, IFN-g, IFN-a, angiostatin, endostatin, tumastatin, canstatin, VEGI, PEDF, vasohibin, and the 16 kDa fragment of prolactin 2-Methoxyestradiol (see, Kerbel (2004) J. Clin Invest 114: 884, for review).

For example, a full length or partial cDNA sequence is cloned into a recombinant expression vector and the vector is transfected into a cell using standard molecular biology techniques. The cDNA can be obtained, for example, by amplification using the polymerase chain reaction (PCR) or by screening an appropriate cDNA library. The nucleotide sequences of the cDNA can be used for the design of PCR primers that allow for amplification of a cDNA by standard PCR methods or for the design of a hybridization probe that can be used to screen a cDNA library using standard hybridization methods. Following isolation or amplification of the cDNA, the DNA fragment is introduced into a suitable expression vector.

Exemplary biologic agents for use in the methods of the invention include, but are not limited to, gefitinib (Iressa), anastrazole, diethylstilbesterol, estradiol, premarin, raloxifene, progesterone, norethynodrel, esthisterone, dimesthisterone, megestrol acetate, medroxyprogesterone acetate, hydroxyprogesterone caproate, norethisterone, methyltestosterone, testosterone, dexamthasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-1BB, anti-4-1BBL, anti-CD40, anti-CD 154, anti-OX40, anti-OX40L, anti-CD28, anti-CD80, anti-CD86, anti-CD70, anti-CD27, anti-HVEM, anti-LIGHT, anti-GITR, anti-GITRL, anti-CTLA-4, soluble OX40L, soluble 4-IBBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble forms of agents may be made as, for example fusion proteins, by operatively linking the agent with, for example, Ig-Fc region.

It should be noted that more than one additional agent, e.g., 1, 2, 3, 4, 5, may be administered in combination with CoQ10. For example, in one embodiment two chemotherapeutic agents may be administered in combination with CoQ10. In another embodiment, a chemotherapeutic agent, a biologic agent, and CoQ10 may be administered.

Various forms of the biologic agents may be used. These include, without limitation, such forms as proform molecules, uncharged molecules, molecular complexes, salts, ethers, esters, amides, and the like, which are biologically activated when implanted, injected or otherwise inserted into the tumor.

This invention is further illustrated by the following examples which should not be construed as limiting. The contents of all references and published patents and patent applications cited throughout the application are hereby incorporated by reference.

EXEMPLIFICATION OF THE INVENTION

Example 1

Identification of CoQ10 as a MIM

In order to evaluate CoQ10 as a potential MIM, CoQ10 in oxidized form was exogenously added to a panel of cell lines, including both cancer cell lines and normal control cell lines, and the changes induced to the cellular microenvironment profile for each cell line in the panel were assessed. Changes to cell morphology/physiology, and to cell composition, including both mRNA and protein levels, were evaluated and compared for the diseased cells as compared to normal cells. The results of these experiments identified CoQ10 and, in particular, the oxidized form of CoQ10, as a MIM.

In a first set of experiments, changes to cell morphology/physiology were evaluated by examining the sensitivity and apoptotic response of cells to CoQ10. A panel of skin cell lines including a control cell lines (primary culture of keratinocytes and melanocytes) and several skin cancers cell lines (SK-MEL-28, a non-metastatic skin melanoma; SK-MEL-2, a metastatic skin melanoma; or SCC, a squamous cell carcinoma; PaCa2, a pancreatic cancer cell line; or HEP-G2, a liver cancer cell line) were treated with various levels of Coenzyme Q10. The results of these experiments demonstrated that the cancer cell lines exhibited an altered dose dependent response as compared to the control cell lines, with an induction of apoptosis and cell death in the cancer cells only. Exemplary experiments are described in detail in Example 3 below.

Assays were next employed to assess changes in the composition of the cell following treatment with CoQ10. Changes in gene expression at the mRNA level were analyzed using Real-Time PCR array methodology. Exemplary experiments are described in detail in Examples 6 and 9-13 below. In complementary experiments, changes in gene expression at the protein level were analyzed by using antibody microarray methodology, 2-dimensional gel electrophoresis followed by protein identification using mass spectrometry characterization, and by western blot analysis. Exemplary experiments are described in detail below in Examples 4, 7 and 8, respectively. The results from these assays demonstrated that significant changes in gene expression, both at the mRNA and protein levels, were induced in the cell lines examined due to the addition of the oxidized form of CoQ10. Genes modulated by CoQ10 treatment were found to be clustered into several cellular pathways, including apoptosis, cancer biology and cell growth, glycolysis and metabolism, molecular transport, and cellular signaling.

Experiments were carried out to confirm the entry of CoQ10 into cells and to determine the level and form of CoQ10 present in the cells. In particular, the level of Coenzyme Q10, as well as the form of CoQ10 (i.e., oxidized or reduced), present in the mitochondria was determined by analyzing mitochondrial enriched preparations from cells treated with CoQ10. The level of Coenzyme Q10 present in the mitochondria was confirmed to increase in a time and dose dependent manner with the addition of exogenous Q10. In a surprising and unexpected result, CoQ10 was determined to be present in the mitochondria primarily in oxidized form. In addition, changes in levels of proteins from mitochondria enriched samples were analyzed by using 2-D gel electrophoresis and protein identification by mass spectrometry characterization. The results from these experiments demonstrated that the levels of the oxidized form of CoQ10 in the mitochondria over the time course examined correlated with a wide variety of cellular changes, as evidenced by the modulation of mRNA and protein levels for specific proteins related to metabolic and apoptotic pathways. Exemplary experiments are described in detail in Example 5 below.

The results described by Applicants herein identified the endogenous molecule CoQ10 and, in particular, the oxidized form of CoQ10, as a MIM. For example, the results identified CoQ10 as a MIM, since CoQ10 was observed to induce changes in gene expression at both the mRNA and protein level. The results identified CoQ10 as having multidimensional character, since CoQ10 induced differential changes in cell morphology/physiology and cell composition (e.g., differential changes in gene expression at both the mRNA and protein level), in a disease state (e.g., cancer) as compared to a normal (e.g., non-cancerous) state. Moreover, the results identified CoQ10 as having multidimensional character in that CoQ10 was capable of entering a cell, and thus exhibited both therapeutic and carrier effects.

Example 2

Methods for Identifying Disease Relevant Processes and Biomarkers for Oncological Disorders From the cell based assays in which cell lines were treated with a molecule of interest, the differences in treated vs non-treated cells is evaluated by mRNA arrays, protein antibody arrays, and 2D gel electrophoresis. The proteins identified from comparative sample analysis to be modulated by the MIM or Epi-shifter, are evaluated from a Systems Biology perspective with pathway analysis (Ingenuity IPA software) and a review of the known literature. Proteins identified as potential therapeutic or biomarker targets are submitted to confirmatory assays such as Western blot analysis, siRNA knock-down, or recombinant protein production and characterization methods.

Materials and Methods for Examples 3-8

Coenzyme Q10 Stock

A 500 µM Coenzyme Q10 (5% isopropanol in cell growth media) was prepared as follows. A 10 mL 500 µM Coenzyme Q10 stock was made fresh every time.

Molecular Weight: 863.34

(0.0005 mol/L)(0.010 L)(863.34 g/mol)=0.004317 g

To make 10 mL of 500 µM stock, 4.32 mg Coenzyme Q10 was weighted out in a 15 mL falcon tube, and 500 L isopropanol was added. The solution was warmed in a 50-60° C. water bath while swirling to dissolve completely. To this solution, 9.5 mL of media (the same media in which the cells are grown) was added.

Cell Culture

Cells were obtained from the American Type Culture Collection or Gibco. Cells were grown in DMEM/F-12 media supplemented with 5% fetal bovine serum, 0.25 ug/mL Amphotericin, 100 ug/mL Streptomycin, and 100 U mL-1 penicillin. Cells were maintained in an atmosphere of 95% air and 5% CO2 at 37 degrees C.

Coenzyme Q10 Treatment and Total Protein Isolation

Cells were grown to 85% confluency prior to exposure with Q10. Supplemented media was conditioned with Q10 to 50 and 100 micro molar concentrations. Flasks were treated with control, 50 µM Q10, and 100 µM Q10 in triplicate. Protein was isolated from the treated and control flask after 4, 8, 12, and 24 hours. For isolation of proteins, cells were washed three times with 5 mL of ice cold PBS at a pH of 7.4. The cells were then scraped in 3 mL of PBS, pelleted by centrifuge, and re-suspended in a lysis buffer at pH 7.4 (80 mM TRIS-HCl, 1% SDS, with protease and phosphotase inhibitors). Protein concentrations were quantified using the BCA method.

Cell Lines

The cell lines listed below were propagated and a cell bank established for each. Large scale production of cells for various assays were performed and the material harvested for analysis. In general, when a cell specific media was not required for maintenance of cell lines, the media used for cell growth was DMEMF-12 with 5% serum. Cells were typically grown to 75-80% confluence (clear spacing) prior to splitting and use in cell assays and standard practice methods followed. The following cell lines were established for experiments:

SK-MEL-28 (non-metastatic skin melanoma)
SK-MEL-2 (metastatic skin melanoma)
HEKa (kerantinocytes, skin control)
HEMa (melanocyte, skin control)
nFIB (neonatal fibroblasts)
HEP-G2 (liver cancer) [SBH cell line]
SkBr-3 (breast cancer, Her2 overexpressed)
MCF-7 (breast cancer, p53 mutation)
PC-3 (prostate cancer) [SBH cell line]
SkBr-3 (human breast adenocarcinoma)
NCI-ES-0808
SCC (squamous cell carcinoma)
PaCa-2
NIH-3T3
Cell Culture:

Cells were obtained for the American Type Culture Collection or Gibco. Cells were grown in DMEM/F-12 media supplemented with 5% fetal bovine serum, 0.25 ug/mL Amphotericin, 100 ug/mL Streptomycin, and 100 U mL-1 penicillin. Cells were maintained in an atmosphere of 95% air and 5% CO2 at 37 degrees C.

Skin malignant melanoma SK-MEL28 cells were grown and maintained in DMEM/F12 with Glutamax (Invitrogen, Carlsbad Calif.) supplemented with 5% FBS, amphotericin and penicillin/streptomycin. Cells were grown at 37° C. with 5% CO2. Details of additional cell line and growth conditions are outlined in the table below.

TABLE 1

Cell lines analyzed for sensitivity to Q10.

| Cell Line | Description | Growth Conditions |
|---|---|---|
| PaCa2 | Pancreatic Carcinoma | DMEM/F12 with Glutamax + 10% FBS, 2.5% Horse Serum, amphotericin, penicillin/streptomycin. |
| HepG2 | Hepatocellular Carcinoma | MEM with Earles Salts supplemented with 10% FBS, amphotericin, penicillin/streptomycin, sodium pyruvate and non-essential amino acids. |
| PC3 | Prostate Adenocarcinoma | DMEM/F12 with Glutamax, supplemented with 5% FBS, amphotericin and penicillin/streptomycin. |
| SKBr3 | Breast Cancer | DMEM/F12 with Glutamax supplemented with 5% FBS and amphotericin, penicillin/streptomycin. |
| MCF-7 | Breast Cancer | DMEM/F12 with Glutamax supplemented with 5% FBS and amphotericin, penicillin/streptomycin. |

Q10 Treatment of SKMEL28 Cells:

SK-MEL28 cells were treated with 100 μM Q10 or the control vehicle. The formulation of the Q10 was as follows. In a 15 mL capped tube, 4.32 mg of Q10 (supplied by Cytotech) was transferred and then dissolved by the addition of 500 μL of isopropanol. The resulting solution was warmed in a 65° C. water bath and vortexed at high speed. The Q10/isopropanol solution was made to a volume of 10 mL with the addition of equilibrated cell culture media. The stock solution was then vortexed to ensure maximum solubility of Q10. The stock solution was diluted (2 mL of stock with 8 mL of media) to obtain a final concentration of 100 μM Q10. For the control vehicle, 9.5 mL of media was added to 500 μL of isopropanol. The control stock was further diluted (2 mL of stock) with 8 mL of media. Cells were harvested 6, 16, 24, 48 or 72 hours after the start of the treatment.

Q10 Treatment of SCC Cells:

SCC cells were treated with 100 μM Q10 (prepared as described above) either for 6 hours or 24 hours. The control cells were untreated cells. Cells were harvested and pelleted at the different times after treatment and the pellets were flash frozen and stored at −80° C. until the RNA was isolated at XTAL as described below.

RNA Isolation:

Cells were lysed for RNA isolation at different treatment times using the RNeasy Mini kit (Qiagen, Inc., Valencia Calif.) kit following the manufacturer's instructions. RNA was quantified by measuring Optical Density at 260 nm.

First Strand Synthesis:

First strand cDNA was synthesized from 1 μg of total RNA using the RT2 First Strand Synthesis kit (SABiosciences., Frederick Md.) as per manufacturer's recommendations.

Real-time PCR:

Products from the first strand synthesis were diluted with water, mixed with the SYBR green master mix (SABiosciences., Frederick Md.) and loaded onto PCR arrays.

Real time PCR was run on the PCR Arrays (Apoptosis Arrays, Diabetes Arrays, Oxidative stress and Antioxidant defense Arrays and Heat Shock Protein Arrays.) (SABiosciences, Frederick Md.) on a Biorad CFX96.

Determining Cell Line Sensitivity to Coenzyme Q10 by Nexin Assay for Apoptosis:

The percentage of cells in early and late apoptosis was quantified following 24 hours of Coenzyme Q10 treatment. Early and late apoptosis was used as a marker to understand the differences in sensitivity of various cancer cell lines to Coenzyme Q10. The different cell lines tested were PaCa2, HepG2, PC-3, SKBr3, MCF-7 and SK-MEL28. Cells were allowed to adhere overnight in 96-well plates. These cells were treated with either control vehicle, 50 μM Q10 or 100 μM Coenzyme Q10. After 24 hours, the presence of apoptotic cells was estimated on a PCA96 flow cytometer (Guava Technologies, Hayward, Calif.). In addition, some cells were treated with 4 μM Staurosporine for 2 hours as a positive control for apoptosis. Cells were first washed with PBS and detached with 50 μL of Accumax (Innovative Cell Technologies, San Diego, Calif.) at room temperature. The dissociation was stopped by addition of culture medium containing 1% Pluronic F-68 (Sigma-Aldrich, St. Louis, Mo.). Then 100 μL of Nexin reagent (Guava Technologies, Hayward, Calif.) was added to each of the wells. After 20 minutes of incubation in the dark, the assay was performed in low binding plates to minimize reattachment of cells to the substrate. The Nexin Reagent contains two dyes. Annexin-V-PE which detects phosphotidyl serine on the outside of a cell; a characteristic of early apoptotic cells. The second dye, 7-AAD permeates only late apoptotic cells while being excluded from live (healthy) and early apoptotic cells. The percentage of four populations of cells; live, early apoptotic, late apoptotic and debris was determined using the Cytosoft 2.5.7 software (Guava Technologies, Hayward, Calif.).

Immunoblotting

Approximately 50 μg of protein were assayed per sample by immunoblotting. All treatments were run in triplicate with controls. Proteins were separated on 12% TRIS-HCl gels, transferred via electrophoresis to nitro-cellulose membranes and blocked using a 5% milk and TBST solution prior to incubation with primary antibodies. The primary antibodies were incubated overnight at 4 degrees C. in a 5% BSA and TBST solution. Secondary antibodies were incubated for one hour at 4 degrees. All antibodies were purchased from Cell Signaling Technology. Antibodies were used at a ratio of 1:1000, with the exception of βActin at a ratio of 1:5000. Blots were developed and results were quantified using the NIH Java based densitometer analysis software Image J. All blots were also probed for and normalized to their respective βActin expression.

Two-Dimensional Electrophoresis

Before isoelectric focusing (IEF), samples were solubilized in 40 mM Tris, 7 M urea, 2 M thiourea, and 1% C7 zwitterionic detergent, reduced with tributylphosphine, and alkylated with 10 mM acrylamide for 90 min at room temperature. After the sample was run through a 10-kDa cutoff Amicon Ultra device with at least 3 volumes of the resuspension buffer, consisting of 7 M urea, 2 M thiourea, and 2% CHAPS to reduce the conductivity of the sample. One hundred micrograms of protein were subjected to IEF on 11-cm pH 3 to 10, pH 4 to 7 or pH 6 to 11 immobilized pH gradient strips (GE, Amersham, USA) to 100,000 volts hour. After IEF, immobilized pH gradient strips were equilibrated in 6 M urea, 2% SDS, 50 mM Tris-acetate buffer, pH 7.0, and 0.01% bromphenol blue and subjected to SDS-polyacrylamide gel electrophoresis on 8 to 16% Tris-HCl Precast Gel, 1 mm (Bio-Rad, USA). The gels were run in duplicate. They were either fixed, stained in SYPRO Ruby, 80 mL/gel (Invitrogen, USA) and imaged on Fuji FLA-5100 laser scanner or transferred onto PVDF membrane.

Additional information was obtained for a control sample to test the utility of protein identification through the use of methods that utilize dPC (Protein Forest Inc.) selective pI fractionation, followed by trypsin digestion of the dPC plug with mass spec identification and semi-quantization (Nanomate or LC/LTQ/MS). The dPC analysis performed with a control sample demonstrated its utility in identifying a large subset of proteins. The materials produced during the studies were archived so that they may be utilized as a resource should the future need arise 2D Gel Image Analysis:

Analysis of all gel images was performed using Progenesis Discovery and Pro (Nonlinear Dynamics Inc., Newcastle upon Tyne, UK). After spot detection, matching, background subtraction, normalization, and filtering, data for SYPRO Ruby gel images was exported. Pairwise comparisons between groups were performed using the Student's t test in Progenesis Discovery to identify spots whose expression was significantly altered ($p > 0.05$).

Antibody Array:

An antibody microarray (Panorama XP725 Antibody Array, Sigma) was utilized to screen over 700 protein antibodies to assess changes at the protein concentration level in Q10 treated cells (SK-MEL-28, SCC). The expression of a protein in a cell extract is detected when it is bound by a corresponding antibody spotted on the slide. Prior to binding, the proteins are directly labeled with a fluorescent dye which is used for fluorescent visualization and quantitative analysis. The array is used for comparing protein expression profiles of two samples (test versus reference samples), each labeled with a different CyDye (Cy3 or Cy5) and the two samples are applied simultaneously at equal protein concentrations on the array. Fluorescent signal intensity for each sample is then recorded individually at the wavelength corresponding to the dye label of the sample and compared.

High doses of Coenzyme Q10 regulates expression of genes involved in the apoptotic, diabetic and oxidative stress pathways in cultured SKMEL-28 cells.

Experimental details: SKMEL-28 cells (ATCC Catalog # HTB-72) are non metastatic, skin melanoma cells that were cultured in DMEM-F12 containing Glutamax (Invitrogen Cat#10565-042) supplemented with 5% FBS, Penicillin, Streptomycin and Amphotericin, were treated with the vehicle or 100 uM Coenzyme Q10 for varying amounts of time. Any changes in gene expression consequent to Coenzyme Q10 treatment were quantified using Real time PCR Arrays (Apoptosis Cat #PAHS-12, Diabetes Cat #PAHS-023 and Oxidative Stress Cat #PAHS-065). (SABiosciences, Frederick, Md.).

A stock concentration of 500 uM Coenzyme Q10 was prepared by dissolving 4.32 mg in 500 ul of isopropanol which was further diluted to 10 ml by addition of media. Alternate vortexing and heating to 65° C. dissolved the Coenzyme Q10. 2 ml of the stock solution was diluted to 10 ml with media to get a 100 uM Q10 containing media that was used to treat cells. A vehicle was prepared in parallel with a similar protocol except that the Coenzyme Q10 was not added.

SKMEL-28 cells were plated at a density of $1 \times 10^5$ cells/well in a 6-well plate. After 24 hours, when cells had attached and were at 50% confluence, either the vehicle or 100 uM Q10 was added. Cells were harvested by at 6, 16, 24, 48 or 72 hours after Q10 treatment while the vehicle treated cells were harvested after 24 hours. Cells were lysed for RNA isolation at different treatment times using the RNeasy Mini kit (Qiagen, Inc., Valencia Calif. Cat #74104) kit following the manufacturer's instructions using a spin column and on-column DNase treatment. RNA was quantified by measuring absorbance at 260 nm.

Real time PCR was preceded by first strand cDNA synthesis using 0.4-1 ug of total RNA as the template using the RT2 First Strand Synthesis kit (SABiosciences., Frederick Md. Cat# C-03) with a genomic DNA elimination step as per manufacturer's recommendations. Products from the first strand synthesis were diluted with water, mixed with the SYBR green master mix (SABiosciences., Frederick Md. Cat#PA-010-12) and loaded onto PCR arrays that contain primer assays for 84 different genes linked within a common pathway, 5 housekeeping genes used for normalization, reverse transcription and PCR controls. Real time PCR was run on a Biorad Cfx96. The amplification was initiated with a hot start to activate the enzyme, followed by 40 cycles each of (95° C.-15 second denaturation step and 60° C.-1 minute annealing and extension step) followed by a melting curve program. Ct values, the output from the PCR thermocycler for all treatment groups were organized on an excel spreadsheet and loaded onto the comparative analysis software available at http://www.sabiosciences.com/pcr/arrayanalysis.php.

Purification of Mitochondria Enriched Samples:

Experimental details: SKMEL-28, NCI-ES0808 and NIH-3T3 cells that were treated with 100 μM Q10 for 24 or 48 hours along with cells that were harvested at t=0 were harvested by washing and scraping from T160 flasks. Cells were centrifuged, pelleted, flash frozen and stored at −80° C. until the mitochondria were isolated. Cell pellets were thawed, resuspended and ruptured in Dounce homogenizer. The homogenate was centrifuged and mitochondria were isolated using reagents and the protocol recommended by the Mitochondria Isolation kit for Cultured cells (MitoSciences, Eugene Oreg., Cat # MS852). The mitochondrial fraction was aliquoted and stored at −80° C.

Coenzyme Q10 and Ubiquinol-10 Quantification Method:

A method for the simultaneous determination of Coenzyme Q10 (Q10) and the reduced form ubiquinol-10 (Q10H2) was implemented based upon a recently published method (Ruiz-Jimenez, 2007, J. Chromatogr. A, 1175, 242-248) through the use of LC-MS/MS with electrospray ionization (ESI) in the positive ion mode. The highly selective identification and sensitive quantitation of both Q10 and Q10H2 is possible, along with the identification of other selected lipids. An aliquot of the mitochondrial enriched samples from SK-MEL-28 treated with 100 μM Q10 was subjected to a conventional pre-treatment based on protein precipitation (100 μl of packed cells sonicated in 300 μl of 1-propanol), liquid-liquid extraction (add 100 μl of water to supernatant and extract X3 with 200 μl of n-hexane), evaporation of combined hexane extracts to dryness and reconstitution in 50 μl of 95:5 methanol/hexane (v/v). Analysis was by LC-MS/MS on a Waters Quattro II triple quadrupole mass spectrometer with a Prism RP 1×100 mm, 5 μm particle size column (Keystone Scientific). Isocratic elution with 4 mM ammonium formate in 20% isopropyl alcohol 80% methanol at a flow rate of 50 μl/min. Ten μl of each sample was injected. MRM analysis was performed using m/z 882.7>197.00 (Q10H2) and m/z 880.80>197.00 (Q10) transitions with cone voltage of 40 and collision energy of 30.

Example 3

Sensitivity of Cell Lines to CoQ10

A number of cell lines were tested for their sensitivity to Q10 after 24 hours of application by using a reagent (Nexin reagent) that contains a combination of two dyes, 7AAD and Annexin-V-PE. The 7AAD dye will enter into cells with permeabilized cell membranes; primarily those cells that are in late apoptosis. Annexin-V-PE is a dye that binds to Phosphotidyl serine, which is exposed on the outer surface of the plasma membrane in early apoptotic cells. The Nexin reagent thus can be used to differentiate between different populations of apoptotic cells in a flow cytometer.

PaCa2 cells showed an increase in both early and late apoptotic cells (between 5-10% of gated cells) with 50 μM Q10 and 100 μM Q10 after 24 hours of Q10 application. PC-3 cells also showed an increase in both early and late apoptotic population with 50 μM and 100 μM Q10, although the increase was less when compared to PaCa2 cells. MCF-7 and SK-MEL28 cells showed an increase only in early apoptotic population with 50 μM and 100 μM Q10. HepG2 cells were also sensitive to 50 μM Q10 treatment, where there was an increase of about 20% of the gated populated in the late apoptotic and early apoptotic stages. SKBr3 was the only cell line tested that did not show any significant increases of early and late apoptosis with either 50 μM or 100 μM Q10 treatment. The results are depicted in FIGS. 1-6.

Figure 7:
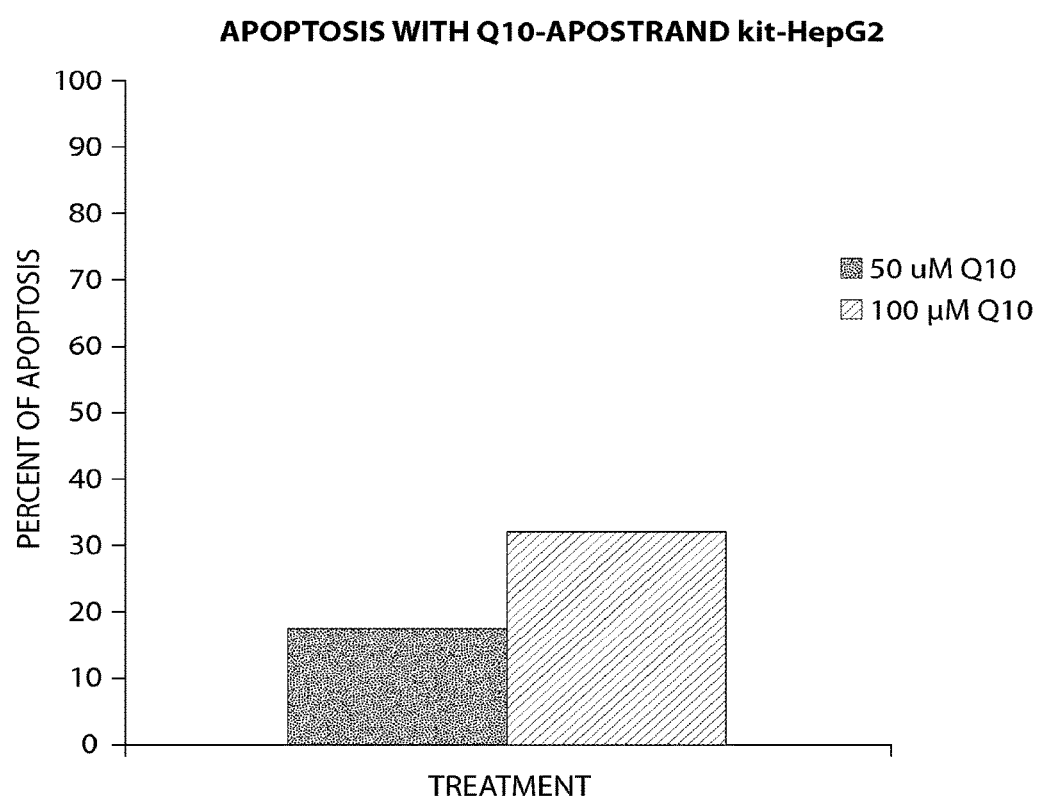
FIG. 7: Measurement of apoptotic cells upon 24 hour treatment with Q10, as measured by Apostrand ELISA method.

To provide additional confirmation that Q10 treatment causes an apoptotic response in HepG2 liver cancer cells, a second apoptosis assay was evaluated using the ApoStrand™ ELISA based method that measures single-stranded DNA. The ApoStrand™ ELISA is based on the sensitivity of DNA in apoptotic cells to formamide denaturation and the detection of the denatured DNA with a monoclonal antibody to single-stranded DNA (ssDNA). Treatment of the liver cancer cell line HepG2 with 50 and 100 μM Q10 resulted in detectable apoptosis, with a dose-response of 17% and 32%, respectively (FIG. 7). These results are consistent with the observation of Q10 inducing apoptosis in other cancer cell lines from other tissues (e.g., SCC, SKMEL-28, MCF-7, and PC-3).

Example 4

Proteomic Analysis of Cells Treated with Q10

Cell pellets of samples treated with Q10 were analyzed using proteomic methods. The cell pellets were lysed and treated for use in 2-D gel and Western blot analysis. Three cell types (SKMEL-28, SCC, and nFib) were treated with Q10 and submitted to proteomic characterization by 2-D gel electrophoresis.

Proteomic Analysis of SKMEL-28 Cells Treated with Q10

The first experimental set processed and evaluated by Western blot and 2-D gel electrophoresis was the skin cancer cell line SKMEL-28. This experimental set involved SK-MEL-28 cells treated at 3, 6, 12, and 24 hours with 0, 50 or 100 μM Q10.

Figure 8:
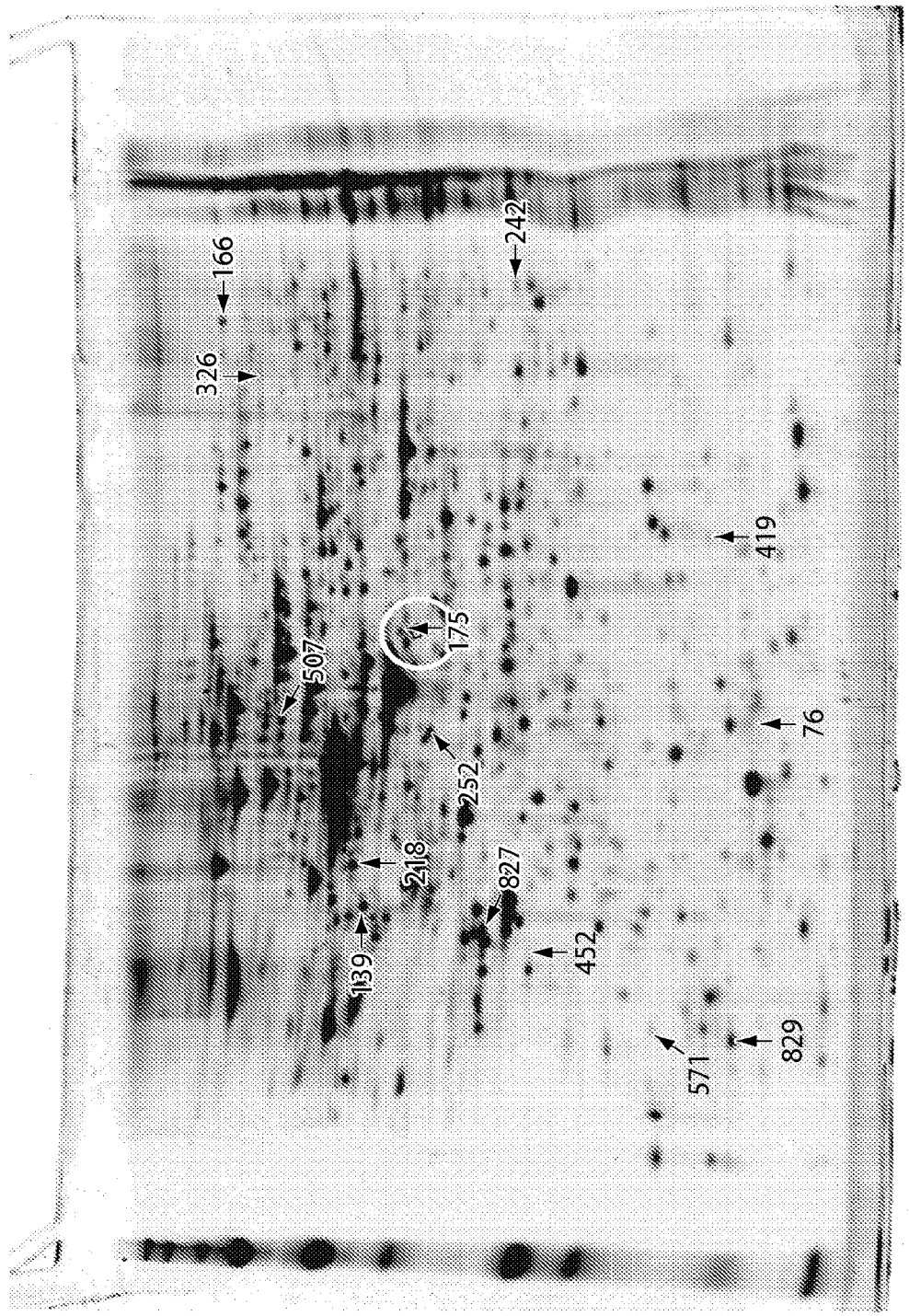
FIG. 8: Example gel analysis of 2-D gel electrophoresis. Spots excised for identification are marked.

The set of Q10 treated SK-MEL-28 samples were subjected to 2-D gel electrophoreses (FIG. 8) and were analyzed to identify protein-level changes relative to the control samples. A comparative analysis of 943 spots across all twenty-four gels was performed, comparing the control sample against all of the treated samples. The analysis included the identification of spot changes over the time course due to increase, decrease, or post-translational modification.

The analysis found thirty-two statistically significant differential spot changes. From this, twenty non-redundant spots were excised and submitted for protein identification by trypsin digestion and mass spectrometry characterization. The characterized peptides were searched against protein databases with Mascot and MSRAT software analysis to identify the protein (Table 2).

TABLE 2

Proteins identified to have a differential response to Q10 treatment in SKMEL-28 cell.

| Time (hr) | Q10 Conc. (uM) | 2D Spot # | Expression | Difference | Protein | Name | Type |
| --- | --- | --- | --- | --- | --- | --- | --- |
| 3 | 50 | 528 | down | 1.234 | cathepsin D | CTSD | peptidase |
| 3 | 50 | 702 | down | 1.575 | chaperonin containing TCP1, subunit 3 | CCT3 | other |
| 3 | 50 | 74 | down | 1.383 | eukaryotic translation initiation factor 3 | EIF3G | translation regulator |
| 3 | 50 | 829 | down | 1.074 | Ribosomal protein P2 | RPLP2 | other |
| 3 | 50 | 368 | down | 1.121 | transaldolase 1 | TALDO1 | enzyme |

TABLE 2-continued

Proteins identified to have a differential response to Q10 treatment in SKMEL-28 cell.

| Time (hr) | Q10 Conc. (uM) | 2D Spot # | Expression | Difference | Protein | Name | Type |
|---|---|---|---|---|---|---|---|
| 6 | 50 | 452 | up | −1.464 | eukaryotic translation initiation factor 6 | EIF6 | translation regulator |
| 6 | 50 | 175 | up | −1.32 | Stomatin; HSPC322 | STOM | other |
| 6 | 50 | 827 | up | −1.457 | Tyrosine 3/Tryptophan 5-monooxygenase activation protein | YWHAZ | enzyme |
| 6 | 50 | 139 | up | −1.628 | Vimentin | VIM | other |
| 6 | 50 | 218 | up | −1.416 | Vimentin | VIM | other |
| 6 | 50 | 218 | up | −1.212 | Vimentin | VIM | other |
| 6 | 50 | 139 | up | −1.036 | Vimentin | VIM | other |
| 6 | 50 | 507 | down | 1.379 | Lamin B1 | LMNB1 | other |
| 6 | 50 | 571 | down | 1.832 | mitochandrial import receptor Tom22 | TOMM22 | transporter |
| 12 | 50 | 166 | up | −1.171 | ALG-2 interacting protein 1 | PDCD6IP | other |
| 12 | 50 | 550 | up | −1.747 | peptidylprolyl isomerase A | PPIA | enzyme |
| 12 | 50 | 613 | down | 1.802 | galectin-1 | LGALS1 | other |
| 12 | 50 | 242 | down | 1.373 | Phosphoglycerate mutase; Posphomannomutase 2 | PGAM2 | phosphatase |
| 24 | 50 | 326 | down | 1.385 | glycyl-tRNA synthase | GARS | enzyme |
| 24 | 50 | 419 | down | 1.451 | Mago-nashi homolog | MAGOH | other |
| 3 | 100 | 528 | down | −1.036 | cathepsin D | CTSD | peptidase |
| 3 | 100 | 702 | down | 1.151 | chaperonin containing TCP1, subunit 3 | CCT3 | other |
| 3 | 100 | 74 | down | 1.122 | eukaryotic translation initiation factor 3 | EIF3G | translation regulator |
| 3 | 100 | 829 | down | 1.145 | Ribosomal protein P2 | RPLP2 | other |
| 3 | 100 | 368 | down | 1.209 | transaldolase 1 | TALDO1 | enzyme |
| 6 | 100 | 139 | up | −1.829 | Vimentin | VIM | other |
| 6 | 100 | 218 | up | −1.761 | Vimentin | VIM | other |
| 6 | 100 | 452 | down | 1.134 | eukaryotic translation initiation factor 6 | EIF6 | translation regulator |
| 6 | 100 | 252 | down | 1.4 | Sec 13 protein, Keratin II | ? | |
| 6 | 100 | 827 | down | 1.12 | Tyrosine 3/Tryptophan 5-monooxygenase activation protein | YWHAZ | enzyme |
| 12 | 100 | 76 | up | −1.679 | galectin-1; keratin II | LGALS1 | other |

A key finding in this experiment was the decrease of Transaldolase 1, which supports the premise that Q10 acts by altering the metabolic state within the cancer cell. Transaldolase 1 is an enzyme in the pentose phosphate pathway (also known as the hexose monophosphate shunt). Transaldolase (EC:2.2.1.2) catalyses the reversible transfer of a three-carbon ketol unit from sedoheptulose 7-phosphate to glyceraldehyde 3-phosphate to form erythrose 4-phosphate and fructose 6-phosphate. This enzyme, together with transketolase, provides a link between the glycolytic and pentose-phosphate pathways. This is relevant to nucleotide and NADPH synthesis, to facilitate production of reducing equivalents for biosynthetic reactions and maintenance of a reducing environment.

A recent publication (Basta, P., et.al. August 2008, Cancer Detect Prevention, 32, 200-208) provided evidence of genetic polymorphism in Transaldolase and was linked to squamous cell carcinoma of the head and neck. Another recent publication (Qian, Y., et.al. May 2008, Biochem J, 415, 123-134) identified transaldolase deficiency as a modulator of mitochondrial homoeostasis, Ca2+ fluxing and apoptosis.

Figure 9:
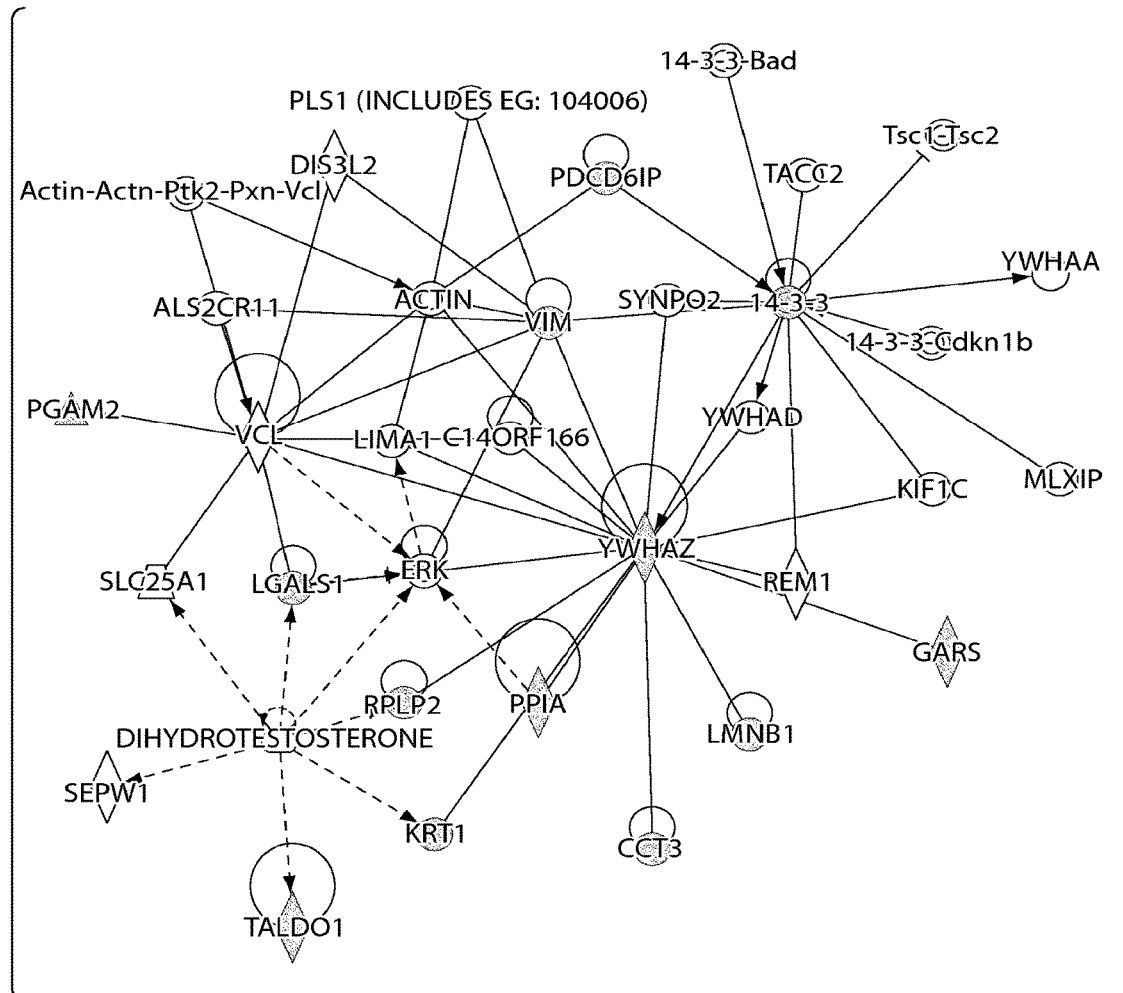
FIG. 9: Network of interaction between proteins identified by 2-D gel electrophoresis as being modulated by Q10 in SK-MEL-28 cells.

From these initial results, the other proteins identified by 2-D gel electrophoresis as being modulated by Q10 in SK-MEL-28 were analyzed for known relationships (FIG. 9). A functional evaluation of these proteins revealed that there was a group involved in 14-3-3-mediated signaling (PDCP6IP, YWHAZ, and VIM), along with individual proteins linked to a variety of processes [cell cycle; pentose phosphate pathway (TALDO1); ceramide signaling (CTSD); aminoacyl-tRNA biosynthesis (GARS), and mitochondrial protein import (TOM22)].

Proteomic Analysis of SCC Cells Treated with Q10

Another skin cancer cell line, Squamous Cell Carcinoma (SCC), was also prepared and analyzed by 2-D gel electrophoreses as a follow-up experiment the previous SK-MEL-28 analysis The SCC cells were treated with 100 μM Q10 for 6 hour or 24 hours before harvesting. A control of untreated cells was also harvested. The cell pellets were lysed and the samples were subjected to 2-D electrophoresis (in duplicate). Analysis of over six hundred protein spots in the comparative study was performed, comparing the control sample against the six hour and twenty-four hour treatments.

The top twenty-five statistically significant differential spot changes were evaluated from the comparative analysis of the 2-D electrophoresis gels. From this, twelve spots were excised and submitted for identification by trypsin digestion and mass spectrometry characterization (results summarized in Table 3 below).

TABLE 3

Proteins identified to have a differential response to 100 µM Q10 treatment in SCC cells at 6 and 24 hours.

| Spot # | Protein | Name | Cellular localization | Function | Response (fold change) |
|---|---|---|---|---|---|
| 331 | Transaldolase 1 | TALDO1 | Cytoplasm | Enzyme | Decrease (1.5) at 6 and 14 hr |
| 23 | Human BSCv (chromosome 20 reading frame 3) | C20ORF3 | Plasma membrane | strictosidine synthase | Decrease (2.1) at 6 and 24 hr |
| 54 | NM23 protein | NME1 | Nucleus, (mitochondria?) | Kinase | Increase (−1.2) at 6 hr, decrease at 24 hr |
| 116 | two Human ESTs from MCF7 breast cancer cell line (HSP 70) | | | HSP70 | Decrease (2.6) at 6 hr, further decrease at 24 hr |
| 176 | Heat shock 27 kDa protein 1 | HSPB1 | Cytoplasm | Response to environmental stresses | Increase (−1.9) at 6 and 24 hr |
| 135 | Keratin I | KRT1 | Cytoplasm | intermediate filaments | Decrease (2.3) at 6 and 24 hr |
| 50 | Keratin 14 | KRT14 | Cytoplasm | intermediate filaments | Increase (−1.6) at 6 and 24 hr |
| 68 | Keratin 13 | KRT13 | Cytoplasm | intermediate filaments | Increase (−1.5) at 6 and 24 hr |
| 49 | Proteasome Beta 7 | PSMB7 | Cytoplasm | Proteasome subunit | Decrease (1.6) at 24 hr only |
| 93 | Proteasome activator subunit 3 | PSME3 | Cytoplasm | peptidase | Decrease (1.3) at 24 hr only |
| 66 | Rho GDP dissociation inhibitor (GDI) alpha | ARHGDIA | Cytoplasm | Inhibitor | Decrease (1.5) at 6 hr only |
| 1 | Unknown? | | | | Decrease (9.5) |

Transaldolase 1: As previously observed in the SKMEL-28 cells treated with Q10, the enzyme Transaldolase 1 was modulated with a decrease in levels. This provides an independent confirmation of the previously observation of a linkage between Q10 and alterations in transaldolase (and thus the metabolic state of the cell).

Figure 10:
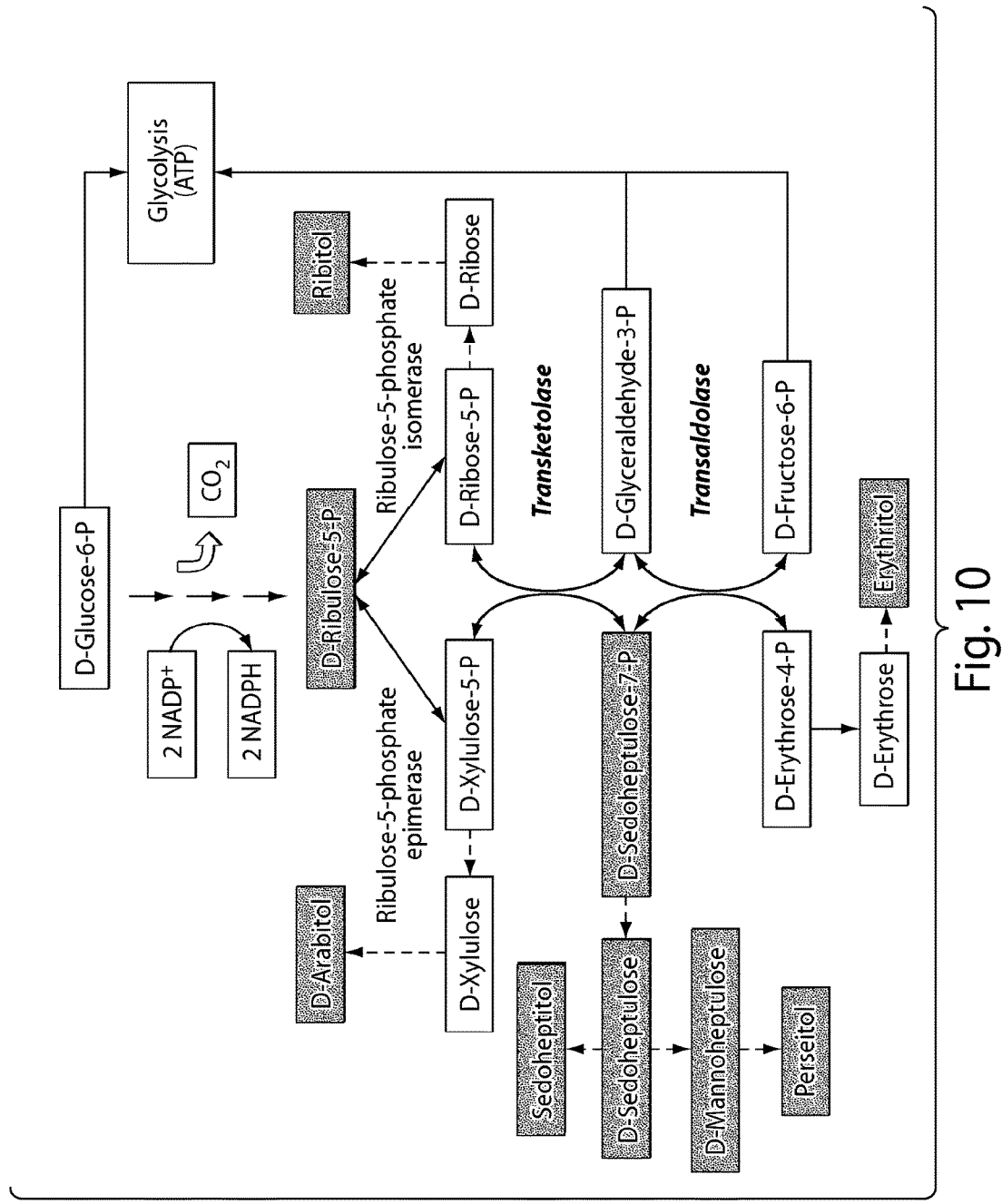
FIG. 10: The pentose phosphate pathway adapted from Verhoeven et al. (*Am. J. Hum. Genet.* 2001 68(5):1086-1092).

Transaldolase is an enzyme in the non-oxidative phase of the pentose phosphate pathway (FIG. 10). The pentose phosphate pathway is critical in the metabolic state of cells for the generation of nicotinamide adenine dinucleotide phosphate (reduced NADH), for reductive biosynthesis, and in the formation of ribose which is an essential component of ATP, DNA, and RNA. Transaldolase also links the pentose phosphate pathway to glycolysis. Glycolysis is the metabolic pathway by which cancer cells obtain the energy needed for cell survival, as the mitochondrial process of oxidative phosphorylation is not utilized. Q10 is an essential coenzyme factor required for oxidatative phosphorylation and mitochondrial ATP production.

BSCv: Spot 23 was a novel human protein from Chromosome 20 named BSCv. BSCv protein is also known as Adipocyte plasma membrane-associated protein (Gene names: APMAP or C20orf3) and is predicted to be a single-pass type II membrane protein with sequence similarity to the strictosidine synthase family of proteins. Q10 treatment caused a reduction in the levels of this protein. This protein is not well characterized, nor has its homology with strictosidine synthases been confirmed. Interestingly, this protein has been associated with a role in adipocyte differentiation (Albrektsen et al., 2001). Recent proteomic studies of human omental adipose tissue identified BSCv as one of nine proteins with differential expression for polcystic ovary syndrome (PCOS) from morbidly obese women (Corton, 2008 Hum. Reprod. 23: 651-661). As a cell surface protein that responds to Q10, an antibody against BSCv would be useful as a biomarker. Based on the current results and the literature available, BSCv may a have a potential role in cancer and diabetes.

NM23A: Non-metastatic cells 1, protein (NM23A, also known as NME1) is thought to be a metastasis suppressor. This gene (NME1) was identified because of its reduced mRNA transcript levels in highly metastatic cells. The protein has activity as a nucleoside diphosphate kinase (NDK) and exists as a hexamer composed of 'A' (encoded by this gene) and 'B' (encoded by NME2) isoforms. Mutations in this gene have been identified in aggressive neuroblastomas. NDK activities maintain an equilibrium between the concentrations of different nucleoside triphosphates such as, for example, when GTP produced in the citric acid (Krebs) cycle is converted to ATP. The NDK complex is associated with p53 through interaction with STRAP. It is noteworthy that STRAP is linked to HNF4A. Thus, NM23A is a potential protein involved in pathways important for cell control and disease treatment.

Rho GDP dissociation inhibitor (GDI) alpha: GDI Regulates the GDP/GTP exchange reaction of the Rho proteins by inhibiting the dissociation of GDP from them, and the subsequent binding of GTP to them. The protein is upregulated in cancer cells.

Example 5

Mitochondrial Enrichment Analysis

Several lines of evidence suggested that a closer evaluation of the role of mitochondrial proteins and cancer biology and Q10 response was warranted. First, there is the essential role of Q10 in the mitochondrial oxidative phosphorylation process for energy production in normal cells. However, the metabolic shift that occurs in cancer cells is to energy production through the alternative pathway of glycolysis, which does not require Q10. Second, the apoptotic response of cells requires mitochondrial proteins to occur. Q10 has been established as stimulating apoptosis in cancer cells (Bcl-2 family proteins, cytochrome c). Finally, new mitochondrial proteins were identified as being modulated by Q10 treatment, as exemplified by the modulation in protein levels of the mitochondrial import receptor protein TOM22 (see experiments described herein).

Production of Mitochondrial Enriched Samples

The skin cancer SKMEL-28 cells were treated with 100 µM Q10 or a mock vehicle for 6, 19, or 48 hours. The cells were harvested by washing and scraping the cells from T-160 flasks (4 for each time point). The cells were collected by centrifugation and the pellets flash frozen and stored at −80° C. The cell pellets were resuspended and ruptured using a 2 mL Dounce homogenizer. The reagents and method were obtained from a Mitochondria Isolation Kit for Cultured Cells (MitoSciences, Cat#MS852). The resultant mitochondria samples were divided into 75 µL aliquots (4-5 aliquots per sample) and stored at −80° C.

Proteomic Analysis of Mitochondria Enriched Samples Isolated from SK-MEL-28 Cells Treated with Q10

Figure 11:
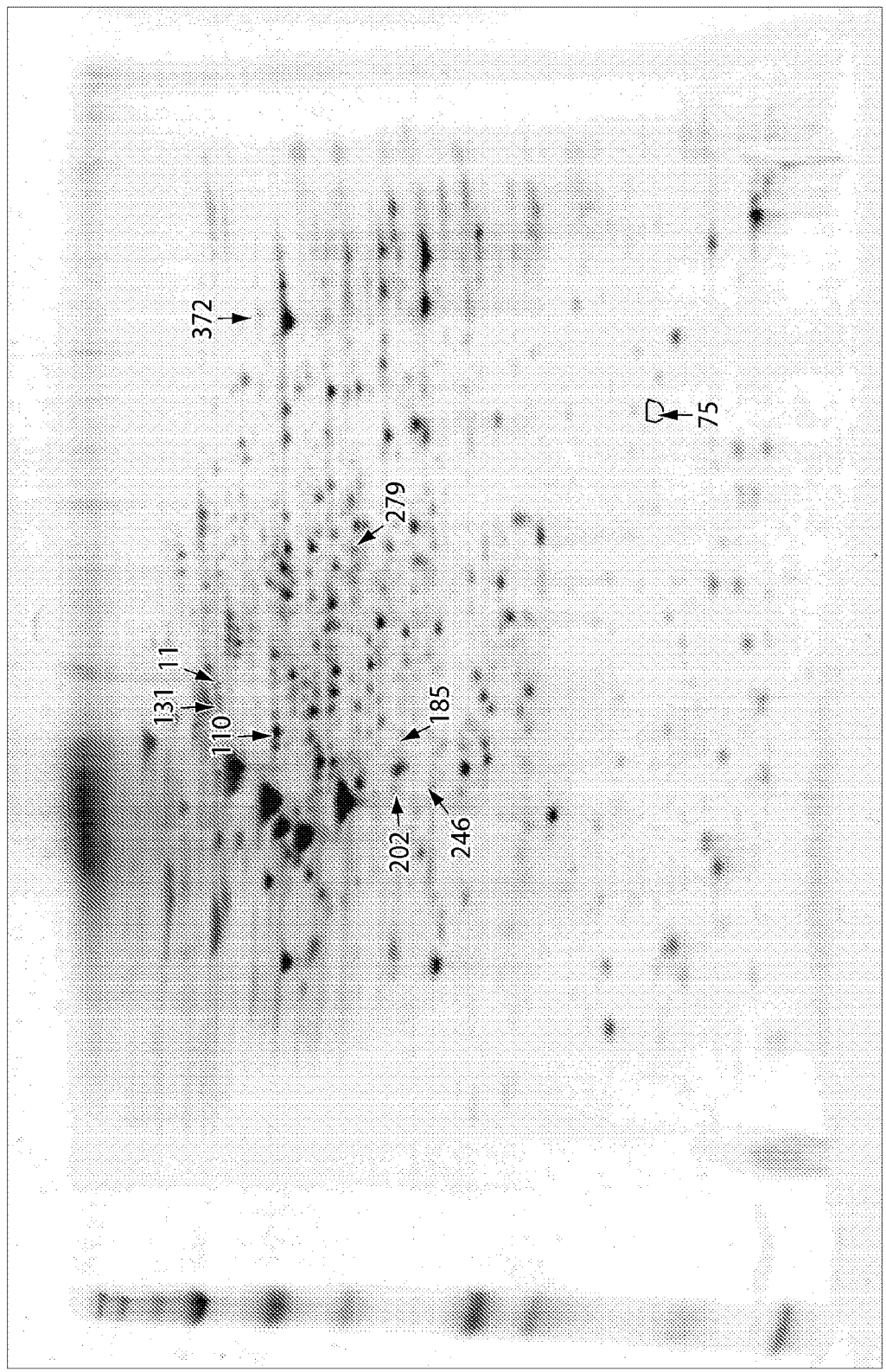
FIG. 11: 2-D gel of the mitochondrial enriched material of SK-MEL-28 cells. Spots excised and identified by mass spectrometry characterization are marked.

2-D gel electrophoresis was performed on proteins solubilized from two aliquots of the SK-MEL-28 mitochondria enriched samples treated with 100 µM Q10 for 6, 19, and 48 hours (along with the corresponding mock vehicle controls). The samples were subjected to 2-D electrophoresis (in duplicate). Analysis of 525 protein spots in the comparative study was performed, comparing the control samples against the other time point samples (FIG. 11).

The nine statistically significant differential spot changes were selected from the comparative analysis of the 2-D electrophoresis gels. From these, 9 spots were excised and submitted for identification by trypsin digestion and mass spectrometry characterization

TABLE 4

Proteins identified to have a differential response to Q10 treatment in SKMEL-28 mitochondria.

| Spot # | Protein | Name | Function | Response (fold change) |
|---|---|---|---|---|
| 11 | Unknown protein | ? | ? | Up (1.3) at 6 hr, drop to low levels after this |
| 131 | Unknown, same as spot #11, modified | ? | ? | Down (1.3) at 6 hr, drops more for 19 and 48 hr |
| 279 | acyl-CoA thioesterase 7 isoform hBACHb | ACOT7 | Cleaves fatty acyl-CoA's into free fatty acids and CoA | Down (1.3) at 6 hr, back to normal at 48 hr |
| 372 | Pyruvate kinase | PKM2 | catalyzes the production of phosphoenolpyruvate from pyruvate and ATP | Up (1.5) at 6 hr, back to normal at 48 hr |
| 110 | ER60 protein | PDIA3 | Protein disulfide isomerase | Up at 19 and 48 hr |
| 185 | Keratin 10 | KRT10 | intermediate filament | Up only at 19 hr |
| 202 | Beta-Actin | | Structural protein | Up only at 19 hr |
| 246 | Malectin | MLEC | carbohydrate-binding protein of the endoplasmic reticulum and a candidate player in the early steps of protein N-glycosylation | Up only at 19 hr |
| 75 | Coiled-coil domain containing 58 | CCDC58 | Conserved hypothetical protein - nuclear pore forming | Up at 48 hr |

Acyl-CoA thioesterase 7: Acyl-CoA thioesterase 7 (ACOT7) is a member of the enzyme family that catalyzes the hydrolysis of fatty acyl-CoA to free fatty acid and CoA. This enzyme thus has a role in the regulation of lipid metabolism and cellular signaling. ACOT7 has a preference for long-chain acyl-CoA substrates with fatty acid chains of 8-16 carbon atoms (C8-C16). The exact cellular function is ACOT7 is not fully understood. The transcription of this gene is activated by sterol regulatory element-binding protein 2, thus suggesting a function in cholesterol metabolism.

The results in this Example indicate that ACOT7 is potentially involved in the metabolism of Q10, either directly or indirectly. Thus, targeting ACOT7 could facilitate modulation of intercellular levels of Q10 and thus impact cellular Q10 effects.

Pyruvate kinase: Pyruvate kinase is an enzyme involved in the last step of glycolysis. It catalyzes the transfer of a phosphate group from phosphoenolpyruvate (PEP) to ADP, yielding one molecule of pyruvate and one molecule of ATP.

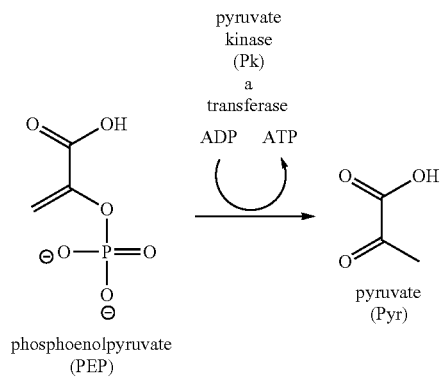

The protein is presumably that of PKM2, the type 2 isoform, as this was identified from the mitochondria enriched SK-MEL-28 sample. This isoform is well known to be involved in tumor cell formation and regulation.

Quantification of Q10 Levels in Mitochondria

A method for the simultaneous determination of Coenzyme Q10, (Q10) and the reduced form ubiquinol-10 (Q10H2) was implemented based upon a recently published method(Ruiz-Jimenez, 2007, J. Chroma A, 1175, 242-248) through the use of LC-MS-MS with electrospray ionization (ESI) in the positive mode. The highly selective identification and sensitive quantitation of both Q10 and Q10H2 is possible, along with the identification of other selected lipids. An aliquot of the mitochondrial enriched samples from SK-MEL-28 treated with 100 µM Q10 were subject to a conventional pre-treatment based on protein precipitation, liquid-liquid extraction, evaporation to dryness and reconstitution with 95:5 methanol/hexane (v/v).

Figure 12:
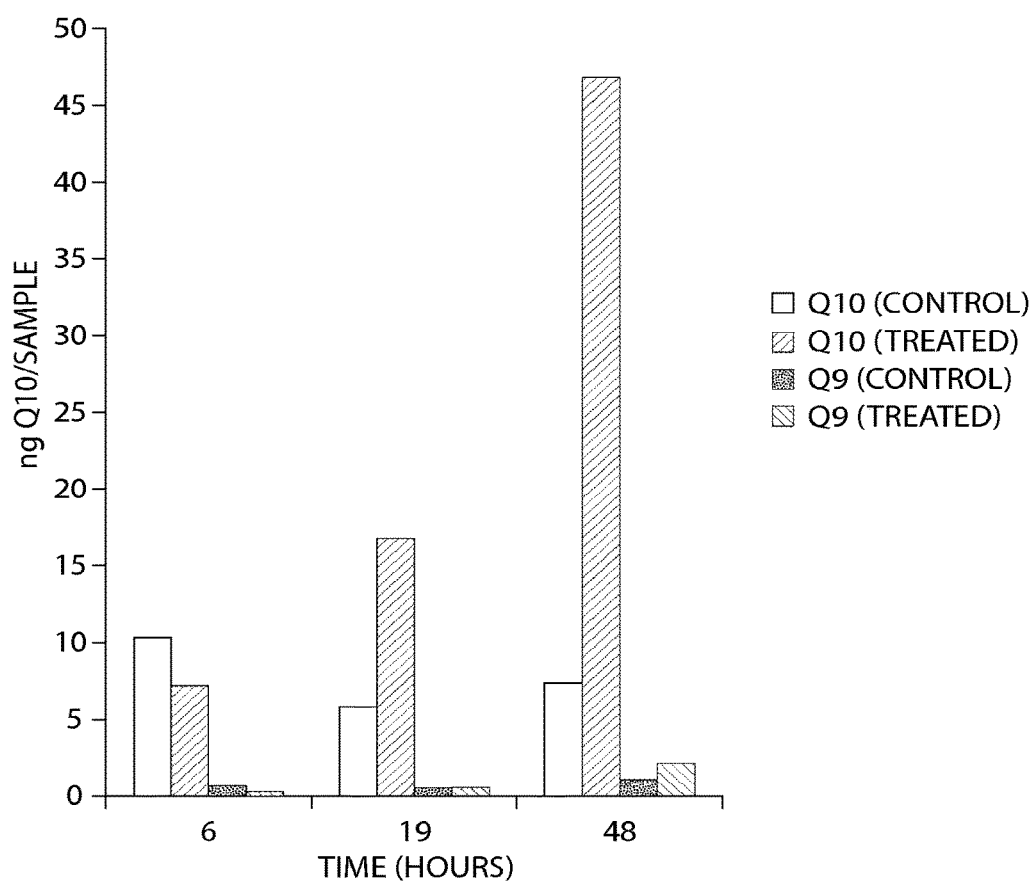
FIG. 12: Comparative plot of the relative amounts of Q10 present in SK-MEL-28 mitochondria following the exogenous addition of 100 μM Q10 into the culture medium.

In this analysis, Q10, Q10H2, and Q9 were quantitated (Table 5). The levels of the related molecule Q9 were low, and near the level of detection. The level of the untreated samples were relatively consistent, with the 6 hour Q10 treated sample having this same level. To control for sample variance in total material, the levels of cholesterol was also measured to confirm that the differences were not due to sample size errors. When the Q10 levels were corrected against total protein values obtained by protein extraction other aliquots of the same mitochondrial preps, the relative ratios were comparative. Thus, a significant increase in Q10 levels was obtained at 19 hours (~3-fold) with an even larger increase by the 48 hour time point (~6-fold) (FIG. 12).

TABLE 5

HPLC-MS Quantification results for the levels of Q10 present in mitochondrial enriched samples from SK-MEL-28 cells treated with 100 µM Q10 in the media.

| | | | Peak Area | | ng/Sample | | | µg/sample |
|---|---|---|---|---|---|---|---|---|
| File | Sample | Injection | Q9 | Q10 | Q9 | Q10 | Q10H$_2$ | Cholesterol |
| 081204-05 | 100 ng Std | | 245,342 | 352792 | | | | |
| 081204-06 | 6 hr mock#1 | 10% | 2560 | 32649 | 1.04 | 9.25 | | |
| 081204-07 | Solvent Blank#1 | 5 ul | 3781 | 3174 | 1.54 | 0.9 | | |
| 081204-08 | Solvent Blank#2 | 5 ul | 2396 | 4399 | 0.98 | 1.25 | | |
| 081204-09 | 6 hr mock#2 | 20% | 1572 | 36328 | 0.64 | 10.3 | | |
| 081204-10 | Solvent Blank#3 | 10 ul | 1722 | 2504 | 0.7 | 0.71 | | |
| 081204-11 | 48 hr Q10 treated | 20% | 4879 | 164496 | 1.99 | 46.63 | 0.28 | 13.86 |
| 081204-12 | 48 hr mock | 20% | 2412 | 25552 | 0.98 | 7.24 | 0.09 | 13.04 |
| 081204-13 | 6 hr Q10 treated | 20% | 692 | 25427 | 0.28 | 7.21 | | |
| 081204-14 | 19 hr Q10 treated | 20% | 1161 | 59164 | 0.47 | 16.77 | | |
| 081204-15 | 19 hr mock | 20% | 901 | 19999 | 0.37 | 5.67 | | |

A surprising result from this study was the finding that the Q10 was supplied to the cells as the oxidized form. For the 48 hour samples, the reduced form Q10H2 was also measured and found to be present in significantly lower amounts (0.28 ng/sample of CoQ10H2 as compared to 46.63 ng/sample of CoQ10). There was a general increase (3-fold) in the levels of Q10H2 in the Q10 treated 48 hour sample, although the levels were near the presumed detection limit of the assay. Interestingly, the oxidized form (Q10) can act as a pro-oxidant in biological systems. According to the literature, when human plasma was evaluated for Q10 and Q10H2, the majority (90%) of the molecule was found in the reduced form of Q10H2 (Ruiz-Jimenez, 2007, J. Chroma A, 1175, 242-248) which can act as an anti-oxidant.

Thus, these results confirm and quantitate that the levels of Q10 increase in the mitochondria upon the exogenous addition of Q10 to the media. A surprising and unexpected discovery was that Q10 was maintained in the supplied oxidized form (pro-oxidant) and not converted to the reduced (anti-oxidant) form of Q10H2 in any significant amounts.

Example 6

Real-Time PCR Arrays

Experiment 1

Apoptosis Array

As discussed above in Example 3, exposure of cancer cells to Q10 induces a portion of these cells to die due to apoptotic processes. To identify proteins that were involved in the Q10 response, real-time polymerase chain reaction (RT-PCR) methods were employed to identify changes in the level of mRNA for genes/proteins involved in targeted pathway arrays for apoptosis.

Using PCR arrays as a screening tool, a spectrum of molecular targets that would potentially offer an insight to the mode of biological action of Q10 within the cells were thus evaluated. Changes in mRNA levels were evaluated using real-time PCR quantification to assess mRNA levels in pre-selected subsets containing 80 pathway specific targets.

For the interpretation of mRNA results, the genes that were altered in their mRNA transcription by a two-fold level were identified and evaluated. The level of gene transcription to produce mRNA only provides a rough estimate of potential changes in the level of the expressed protein. The skilled artisan will appreciate that each mRNA may have different rates at which it is degraded or its translation inefficiently, thus resulting in differing amounts of protein.

SkBr-3 Cells Treated with 50 um Q10 for 24 Hours

The assay method of RT-PCR was utilized to provide a measure of mRNA level changes to a total of 84 apoptotic pathway related proteins. The experiments with the real-time PCR apoptosis analysis on SkBr3 with Q10 (24 hr) identified the following mRNA's being affected: Bcl2, Bcl2L1, Bcl2L11, Birc6, Bax, Xiap, Hprt1, Apaf1, Abl1, Braf. These results again provided supporting evidence for the apoptotic response of cancer cells to Q10 treatment.

TABLE 6A

| Symbol | Up-Down Regulation | Unigene | Refseq | Description | Gname |
|---|---|---|---|---|---|
| BCL2L1 | 13.1957 | Hs.516966 | NM_138578 | BCL2-like 1 | BCL-XL/S |
| BNIP2 | 6.3291 | Hs.646490 | NM_004330 | BCL2/adenovirus E1B 19 kDa interacting protein 2 | BNIP-2/NIP2 |
| BCL2 | 5.4717 | Hs.150749 | NM_000633 | B-cell CLL/lymphoma 2 | Bcl-2 |
| BIRC6 | 4.7966 | Hs.150107 | NM_016252 | Baculoviral IAP repeat-containing 6 (apollon) | APOLLON/BRUCE |
| BCL2L11 | 4.6012 | Hs.469658 | NM_006538 | BCL2-like 11 (apoptosis facilitator) | BAM/BIM |
| XIAP | 4.3832 | Hs.356076 | NM_001167 | X-linked inhibitor of apoptosis | API3/BIRC4 |
| BRAF | 4.3832 | Hs.550061 | NM_004333 | V-raf murine sarcoma viral oncogene homolog B1 | B-raf1/BRAF1 |
| BAX | 3.896 | Hs.631546 | NM_004324 | BCL2-associated X protein | Bax zeta |
| APAF1 | 2.6244 | Hs.708112 | NM_001160 | Apoptotic peptidase activating factor 1 | CED4/DKFZp781B1145 |
| HPRT1 | −160.6748 | Hs.412707 | NM_000194 | Hypoxanthine phosphoribosyltransferase 1 (Lesch-Nyhan syndrome) | HGPRT/HPRT |

Results that are consistent from three independent experiments from SK-MEL-28 cells are summarized below in Table 6B. Many genes are regulated in SCC cells as well with 100 μM Q10 treatment. The genes in the Apoptosis array that appear to be regulated in SCC cells are described in Table 7. We find that many genes are regulated at 6 hours, both in SK-MEL-28 cells and in SCC cells. By 24 hours, the regulation is decreased. Genes that appear to be regulated in both SK-MEL-28 cells and in SCC cells are described in Table 8.

TABLE 6B

Genes in SK-MEL-28 cells regulated by 100 μM Q10 treatment when analyzed by the Apoptosis Array.

| Symbol | Description | Regulation | Location | Possible Functions |
| --- | --- | --- | --- | --- |
| ABL1 | C-abl oncogene 1, receptor tyrosine kinase | Down Regulated at 72 hours | Nucleus | Tyrosine Kinase |
| BAG1 | BCL2-associated athanogene | Up Regulated at 48 hours | Cytoplasm | Anti-apoptotic, glucocorticoid receptor pathway |
| BCL2 | B-cell CLL/lymphoma 2 | Down Regulated at 48 hours | Cytoplasm | Cell death |
| BCL2A1 | BCL2-related protein A1 | Down Regulated at 48 hours | Cytoplasm | Regulates Caspases, phosphorylates TP73 |
| BCL2L1 | BCL2-like 1 | Down Regulated at 72 hours | Cytoplasm | Caspase Inhibitor |
| BCL2L10 | BCL2-like 10 (apoptosis facilitator) | Down Regulated at 48 hours | Cytoplasm | Caspase Activator |
| BCL2L11 | BCL2-like 11 (apoptosis facilitator) | Down Regulated at 48 hours | Cytoplasm | Pro-Apoptotic, Caspase3 Activator |
| BIRC3 | Baculoviral IAP repeat-containing 3 | Down Regulated at 6 hours | Cytoplasm | Anti-apoptotic |
| BIRC8 | Baculoviral IAP repeat-containing 8 | Down Regulated at 48 hours | Cytoplasm | Activates Caspase |
| CARD8 | Caspase recruitment domain family, member 8 | Down Regulated at 48 hours | Nucleus | Caspase Activator |
| CASP14 | Caspase 14, apoptosis-related cysteine peptidase | Down Regulated at 48 hours | Cytoplasm | Apoptosis related cysteine peptidase |
| CASP5 | Caspase 5, apoptosis-related cysteine peptidase | Down Regulated at 48 hours | Cytoplasm | Apoptosis related cysteine peptidase |
| CD40LG | CD40 ligand (TNF superfamily, member 5, hyper-IgM syndrome) | Down Regulated at 48 hours | Extracellular Space | CD40 receptor binding |
| CIDEA | Cell death-inducing DFFA-like effector a | Up Regulated at 48 hours | Cytoplasm | Pro-Apoptotic |
| FADD | Fas (TNFRSF6)-associated via death domain | Down Regulated at 6 hours | Cytoplasm | Pro-Apoptotic |
| FAS | Fas (TNF receptor superfamily, member 6) | Up Regulated at 48 hours | Plasma Membrane | Pro-Apoptotic |
| FASLG | Fas ligand (TNF superfamily, member 6) | Down Regulated at 48 hours | Extracellular Space | Pro-Apoptotic |
| GADD45A | Growth arrest and DNA-damage-inducible, alpha | Up Regulated at 48 hours | Nucleus | Growth Arrest |
| HRK | Harakiri, BCL2 interacting protein (contains only BH3 domain) | Down Regulated at 48 hours | Cytoplasm | Pro-Apoptotic |
| PYCARD | PYD and CARD domain containing | Down Regulated at 6 hours | Cytoplasm | Apoptotic Protease Activator |
| TNF | Tumor necrosis factor (TNF superfamily, member 2) | Up Regulated at 48 hours then down regulated | Extracellular Space | TNF receptor binding |
| TNFRSF10A | Tumor necrosis factor receptor superfamily, member 10a | Up Regulated at 48 hours then down regulated | Plasma Membrane | Caspase Activator |
| TNFRSF10B | Tumor necrosis factor receptor superfamily, member 10b | Down Regulated at 72 hours | Plasma Membrane | p53 signaling, caspase activation. |

TABLE 6B-continued

Genes in SK-MEL-28 cells regulated by 100 μM Q10 treatment when analyzed by the Apoptosis Array.

| Symbol | Description | Regulation | Location | Possible Functions |
|---|---|---|---|---|
| TNFRSF1A | Tumor necrosis factor receptor superfamily, member 1A | Down Regulated at 72 hours | Plasma Membrane | Pro-apoptotic |
| TNFRSF21 | Tumor necrosis factor receptor superfamily, member 21 | Down Regulated at 48 hours | Plasma Membrane | Activates Caspase |
| CD27 | CD27 molecule | Down Regulated at 48 hours | Plasma Membrane | Caspase Inhibitor |
| TNFRSF9 | Tumor necrosis factor receptor superfamily, member 9 | Down Regulated at 48 hours | Plasma Membrane | Pro-apoptotic |
| TNFSF10 | Tumor necrosis factor (ligand) superfamily, member 10 | Upregulated at 48 hours | Extracellular Space | Pro-apoptotic |
| TP73 | Tumor protein p73 | Down Regulated at 48 hours | Nucleus | Transcription factor |
| TRAF3 | TNF receptor-associated factor 3 | Down Regulated at 48 hours | Cytoplasm | Zinc-finger domain |
| TRAF4 | TNF receptor-associated factor 4 | Down Regulated at 48 hours | Cytoplasm | Zinc-finger domain |

TABLE 7

Genes in SCC cells that are regulated by 100 μM Q10 treatment when analyzed by the Apoptosis Array.

| Symbol | Description | Regulation. |
|---|---|---|
| AKT1 | V-akt murine thymoma viral oncogene homolog 1 | Down regulated at 6 hours and then up regulated at 24 hours. |
| BAG4 | BCL2-associated athanogene 4 | Up regulated at 24 hours. |
| BAX | BCL2-associated X protein | Up regulated at 24 hours. |
| BCL2 | B-cell CLL/lymphoma 2 | Up regulated at 24 hours. |
| BCL2L1 | BCL2-like 1 | Down regulated at 6 hours and then up regulated at 24 hours. |
| BIRC3 | Baculoviral IAP repeat-containing 3 | Down regulated at 6 hours. |
| BNIP3 | BCL2/adenovirus E1B 19 kDa interacting protein 3 | Down regulated at 24 hours. |
| CARD6 | Caspase recruitment domain family, member 6 | Down regulated at 6 hours. |
| CASP6 | Caspase 6, apoptosis-related cysteine peptidase | Up regulated at 24 hours. |
| CASP7 | Caspase 7, apoptosis-related cysteine peptidase | Up regulated at 24 hours. |
| CD40 | CD40 molecule, TNF receptor superfamily member 5 | Down regulated at 6 hours. |
| FADD | Fas (TNFRSF6)-associated via death domain | Up regulated at 24 hours. |
| GADD45A | Growth arrest and DNA-damage-inducible, alpha | Up regulated at 24 hours. |
| HRK | Harakiri, BCL2 interacting protein (contains only BH3 domain) | Up regulated at 24 hours. |
| TNFRSF21 | Tumor necrosis factor receptor superfamily, member 21 | Down regulated at 6 hours. |
| TNFRSF25 | Tumor necrosis factor receptor superfamily, member 25 | Down regulated at 6 hours and then up regulated at 24 hours. |
| CD27 | CD27 molecule | Down regulated at 6 hours. |
| TNFRSF9 | Tumor necrosis factor receptor superfamily, member 9 | Down regulated at 6 hours. |
| TNFSF10 | Tumor necrosis factor (ligand) superfamily, member 10 | Up regulated at 24 hours. |
| CD70 | CD70 molecule | Down regulated at 6 hours. |
| TP53 | Tumor protein p53 | Up regulated at 24 hours. |
| TP73 | Tumor protein p73 | Down regulated at 6 hours and then up regulated at 24 hours. |
| TRAF2 | TNF receptor-associated factor 2 | Up regulated at 24 hours. |

TABLE 8

Genes from the apoptosis array regulated with 100 μM Q10
treatment in both SK-MEL-28 and SCC cells.

| Symbol | Description |
|---|---|
| BCL2 | B-cell CLL/lymphoma 2 |
| BCL2L1 | BCL2-like 1 (Bcl-xl) |
| BIRC3 | Baculoviral IAP repeat-containing 3 |
| FADD | Fas (TNFRSF6)-associated via death domain |
| GADD45A | Growth arrest and DNA-damage-inducible, alpha |
| TNFRSF21 | Tumor necrosis factor receptor superfamily, member 21 |
| CD27 | CD27 molecule |
| TNFRSF9 | Tumor necrosis factor receptor superfamily, member 9 |
| TNFSF10 | Tumor necrosis factor (ligand) superfamily, member 10 |
| TP73 | Tumor protein p73 |
| TRAF2 | TNF receptor-associated factor 2 |

Interestingly, the altered mRNA levels showed a significant up-regulation in a series of apoptitic proteins, with Bcl-xl one of the highest. This was also observed in the protein array experiments on SK-MEL-28 cells.

Bcl-xl is a transmembrane molecule in the mitochondria (Bcl-xl stands for "Basal cell lymphoma-extra large"). It is involved in the signal transduction pathway of the FAS-L and is one of several anti-apoptotic proteins which are members of the Bcl-2 family of proteins. It has been implicated in the survival of cancer cells. However, it is known that alternative splicing of human Bcl-x mRNA may result in at least two distinct Bcl-x mRNA species, Bcl-xL and Bcl-xS. The predominant protein product (233 amino acids) is the larger Bcl-x mRNA, Bcl-xL, which inhibits cell death upon growth factor withdrawal (Boise et al., 1993. Cell 74, 597-608). Bcl-xS, on the other hand, inhibits the ability of Bcl-2 to inhibit cell death and renders cells more susceptible to apoptotic cell death. The employed assays utilized do not distinguish which isoform of Bcl-x is being upregulated. The Bcl-x isoform being upregulated by CoQ10 in these studies may be determined by routine methods known in the art, e.g., by using RT-PCR methods to evaluate the ratio of the two mRNA splicing isoforms (Bcl-xL vs Bcl-sL).

From the survey of apoptotic related proteins it was observed multiple pro- and anti-apoptotic factors were in the BCL-2 family or that interact with these factors have modulated expression levels (BCL2L11, BNIP2, BAG1, HRK, BAK1, BCL2, BCL2L1). These proteins govern mitochondrial outer membrane permeabilization.

An early marker for apoptotic response is observed with the upregulation of Caspase-9 (16 hour) which is consistent with previous observations of apoptosis with caspase 3/7 proteins. Induction of stress signaling pathways causes release of cytochrome c from mitochondria and activation of apaf-1 (apoptosome), which in turn cleaves the pro-enzyme of caspase-9 into the active form. Once initiated caspase-9 goes on to cleave procaspase-3 & procaspase-7 to trigger additional apoptotic pathways.

There is also a consistent linkage to the tumor necrosis factor receptor family of proteins being modulated.

Figure 13A:
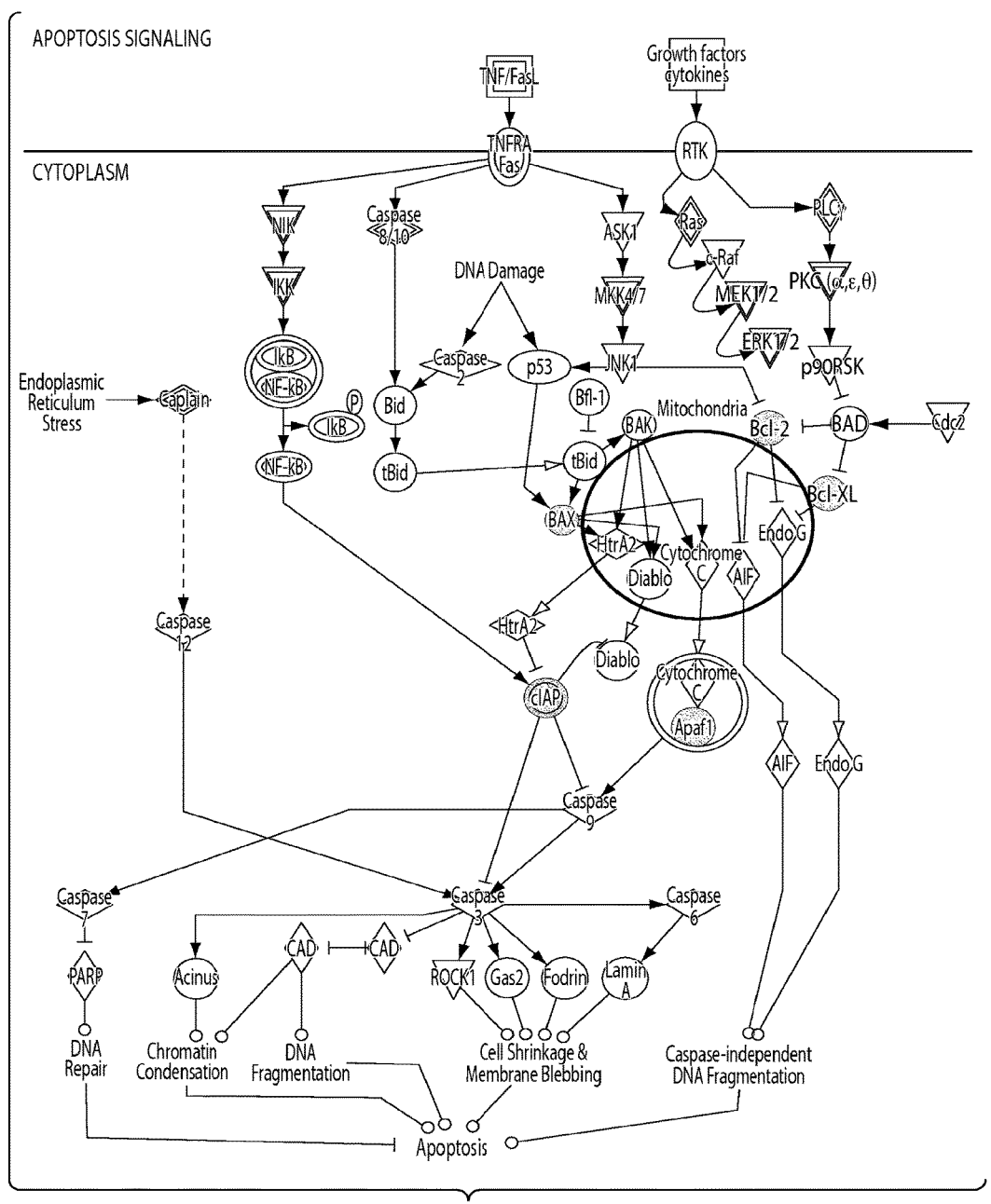
FIG. 13A: Apoptosis pathway mapping known processes.
Figure 13B:
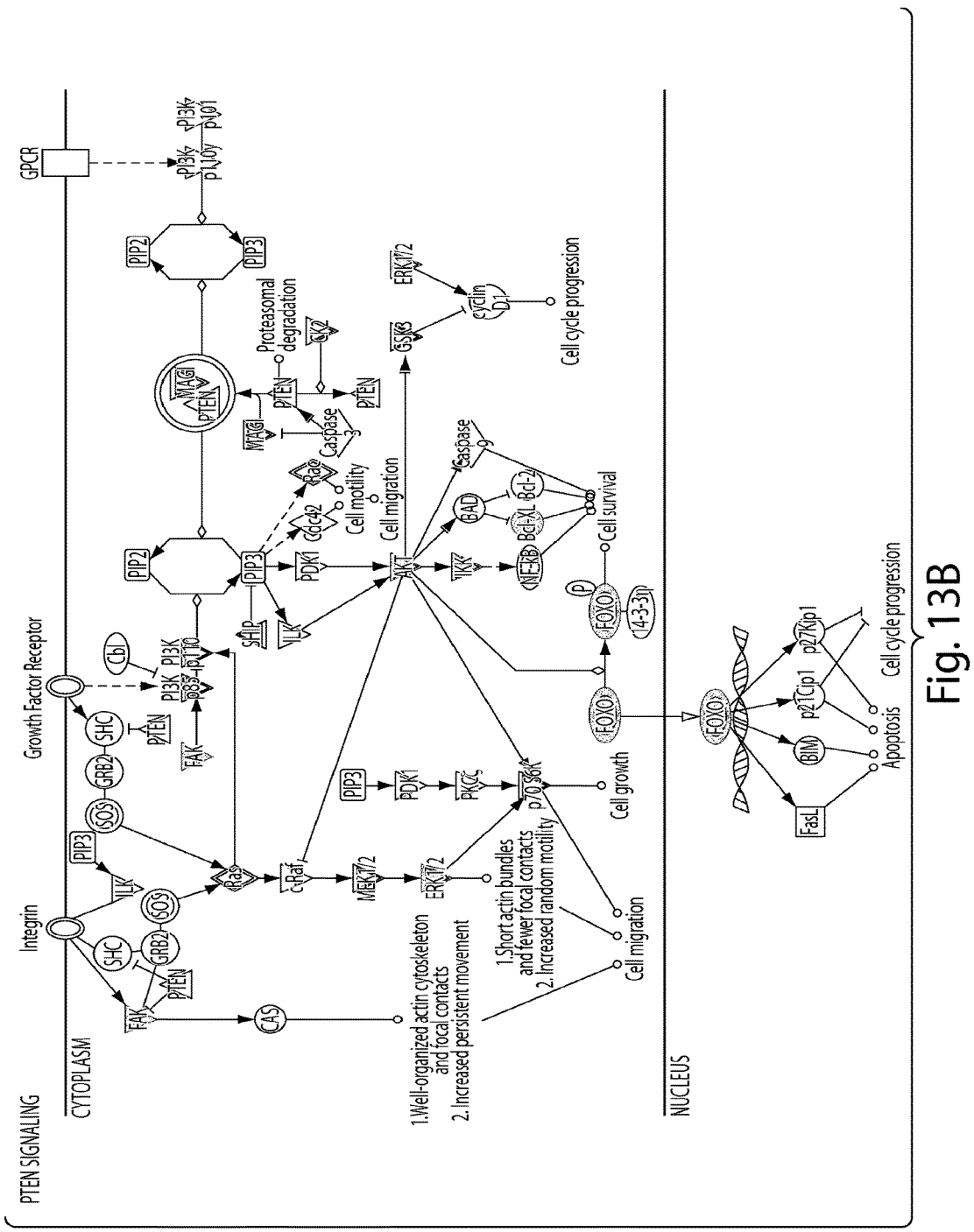
FIG. 13B: Apoptosis pathway mapping known processes.

A strong down regulation of tumor protein p73 is also noted. Analyses of many tumors typically found in humans including breast and ovarian cancer show a high expression of p73 when compared to normal tissues in corresponding areas. Recent finding are suggesting that deregulated over expression of transcription factors within the body involved in cell cycle regulation and synthesis of DNA in mammalian cells (i.e.: E2F-1), induces the expression of p73. The suggestion is that p73 may be an oncoprotein, but may involve different mechanism that the related p53 protein. A schematic showing mapping of the apoptosis pathway is provided in FIG. 13.

SKMEL-28 Cells

From the survey of apoptotic related proteins it was observed multiple pro- and anti-apoptotic factors were in the BCL-2 family or that interact with these factors have modulated expression levels (BCL2L11, BNIP2, BAG1, HRK, BAK1, BCL2, BCL2L1). These proteins govern mitochondrial outer membrane permeabilization. An early marker for apoptotic response is observed with the upregulation of Caspase-9 (16 hour) which is consistent with previous observations of apoptosis with caspase 3/7 proteins. Induction of stress signaling pathways causes release of cytochrome c from mitochondria and activation of apaf-1 (apoptosome), which in turn cleaves the pro-enzyme of caspase-9 into the active form. Once initiated caspase-9 goes on to cleave procaspase-3 & procaspase-7 to trigger additional apoptotic pathways.

TABLE 9

Changes in mRNA levels for SKMEL-28 cells treated with 100 μM A10,
evaluated by RT-PCR arrays focused around apoptotic pathways.

| Refseq | Description | Symbol | 6 hr Q10 | 16 hr Q10 | 24 hr Q10 | 72 hr Q10 |
|---|---|---|---|---|---|---|
| NM_006538 | BCL2-like 11 (apoptosis facilitator) | BCL2L11 | 2.13 | 2.41 | 1.92 | 2.51 |
| NM_000875 | Insulin-like growth factor 1 receptor | IGF1R | 1.77 | 1.09 | 1.33 | 1.25 |
| NM_004048 | Beta-2-microglobulin | B2M | 1.74 | 1.76 | 1.58 | 3.11 |
| NM_003921 | B-cell CLL/lymphoma 10 | BCL10 | 1.55 | 1.87 | 1.48 | −3.11 |
| NM_004330 | BCL2/adenovirus E1B 19 kDa interacting protein 2 | BNIP2 | 1.46 | 1.51 | 1.57 | −1.61 |
| NM_005157 | C-abl oncogene 1, receptor tyrosine kinase | ABL1 | 1.42 | 2.77 | −1.22 | −2.03 |
| NM_004323 | BCL2-associated athanogene | BAG1 | 1.41 | 1.44 | −1.61 | −2.45 |
| NM_001229 | Caspase 9, apoptosis-related cysteine peptidase | CASP9 | 1.32 | 3.96 | 1.83 | 1.14 |

TABLE 9-continued

Changes in mRNA levels for SKMEL-28 cells treated with 100 μM A10, evaluated by RT-PCR arrays focused around apoptotic pathways.

| Refseq | Description | Symbol | 6 hr Q10 | 16 hr Q10 | 24 hr Q10 | 72 hr Q10 |
|---|---|---|---|---|---|---|
| NM_003806 | Harakiri, BCL2 interacting protein (contains only BH3 domain) | HRK | 1.18 | 4.52 | 2.73 | −1.14 |
| NM_001924 | Growth arrest and DNA-damage-inducible, alpha | GADD45A | 1.07 | 3.34 | 1.13 | −2.36 |
| NM_001188 | BCL2-antagonist/killer 1 | BAK1 | 1.06 | 2.73 | −1.00 | −4.54 |
| NM_004295 | TNF receptor-associated factor 4 | TRAF4 | −1.91 | 2.63 | −1.58 | −740.66 |
| NM_003842 | Tumor necrosis factor receptor superfamily, member 10b | TNFRSF10B | −2.07 | 1.53 | −1.81 | −710.49 |
| NM_000633 | B-cell CLL/lymphoma 2 | BCL2 | −2.98 | −1.63 | −2.82 | −11.36 |
| NM_001242 | CD27 molecule | CD27 | −3.40 | −2.38 | −1.35 | −12.72 |
| NM_014430 | Cell death-inducing DFFA-like effector b | CIDEB | −3.48 | 1.56 | −3.69 | −2.59 |
| NM_001065 | Tumor necrosis factor receptor superfamily, member 1A | TNFRSF1A | −4.53 | 2.28 | −3.30 | 1.22 |
| NM_005427 | Tumor protein p73 | TP73 | −4.66 | −9.80 | −8.71 | −26.96 |
| NM_003844 | Tumor necrosis factor receptor superfamily, member 10a | TNFRSF10A | −4.84 | −5.26 | −4.33 | −11.84 |
| NM_138578 | BCL2-like 1 | BCL2L1 | −4.94 | −1.80 | −6.17 | −7.04 |
| NM_001165 | Baculoviral IAP repeat-containing 3 | BIRC3 | −13.68 | −1.98 | −2.42 | −3.42 |

There is a consistent linkage to the tumor necrosis factor receptor family of proteins being modulated.

A strong down regulation of tumor protein p73 is also noted. Analyses of many tumors typically found in humans including breast and ovarian cancer show a high expression of p73 when compared to normal tissues in corresponding areas. Recent finding are suggesting that deregulated over expression of transcription factors within the body involved in cell cycle regulation and synthesis of DNA in mammalian cells (i.e.: E2F-1), induces the expression of p73. The suggestion is that p73 may be an oncoprotein, but may involve different mechanism that the related p53 protein.

Experiment 2

Real-time PCR Arrays Using Oxidative Stress and Antioxidant Defense Array

To identify proteins that were involved in the Q10 response, real-time polymerase chain reaction (RT-PCR) methods were employed to identify changes in the level of mRNA's for genes/proteins involved in targeted pathway arrays for oxidative stress and antioxidant defense.

Table 10 below lists the genes that are regulated in SK-MEL28 cells with 100 μM Q10 treatment. Results are given only for those genes that are regulated in two independent experiments. Although there is a significant amount of gene regulation seen at 6 hours, most significant changes in RNA levels are seen at 48 hours.

TABLE 10

Genes in SK-MEL-28 cells that are regulated by 100 μM Q10 treatement as seen in the Oxidative Stress and Antioxidant Defense Arrays.

| Symbol | Description | Regulation | Location | Possible Functions. |
|---|---|---|---|---|
| ALB | Albumin | Down Regulation at 48 hours | Extracellular space | Carrier protein, anti-apoptotic |
| AOX1 | Aldehyde oxidase 1 | Up regulation from 16 hours | Cytoplasm | Produces free radicals, drug metabolic process. |
| APOE | Apolipoprotein E | Down Regulation at 48 hours | Extracellular space | Lipid metabolism |
| ATOX1 | ATX1 antioxidant protein 1 homolog (yeast) | Down Regulation at 48 hours | Cytoplasm | Copper metabolism |
| BNIP3 | BCL2/adenovirus E1B 19 kDa interacting protein 3 | Down Regulation at 48 hours | Cytoplasm | Anti-apoptotic |
| CSDE1 | Cold shock domain containing E1, RNA-binding | Down Regulation at 48 hours | Cytoplasm | Transcriptional regulation. |

TABLE 10-continued

Genes in SK-MEL-28 cells that are regulated by 100 μM Q10 treatement as seen in the Oxidative Stress and Antioxidant Defense Arrays.

| Symbol | Description | Regulation | Location | Possible Functions. |
|---|---|---|---|---|
| CYBA | Cytochrome b-245, alpha polypeptide | Down Regulation at 48 hours | Cytoplasm | Apoptotic, |
| CYGB | Cytoglobin | Down Regulation at 48 hours | Cytoplasm | Peroxidase, Transporter. |
| DHCR24 | 24-dehydrocholesterol reductase | Down Regulation at 6 hours | Cytoplasm | Electron carrier, binds to TP53, involved in apoptosis. |
| DUOX1 | Dual oxidase 1 | Up Regulation at 48 hours | Plasma Membrane | Calcium ion binding, electron carrier. |
| DUOX2 | Dual oxidase 2 | Down Regulation at 48 hours | Unknown | Calcium ion binding. |
| EPHX2 | Epoxide hydrolase 2, cytoplasmic | Down Regulation at 48 hours | Cytoplasm | Arachidonic acide metabolism. |
| EPX | Eosinophil peroxidase | Down Regulation at 48 hours | Cytoplasm | Phenyl alanine metabolism, apoptosis. |
| GPX2 | Glutathione peroxidase 2 (gastrointestinal) | Down Regulation at 48 hours | Cytoplasm | Electron carrier, binds to TP53, involved in apoptosis. |
| GPX3 | Glutathione peroxidase 3 (plasma) | Up Regulation at 48 hours | Extracellular space | Arachidonic acid metabolims, up regulated in carcinomas. |
| GPX5 | Glutathione peroxidase 5 (epididymal androgen-related protein) | Up Regulation at 48 hours | Extracellular space | Arachidonic acid metabolism. |
| GPX6 | Glutathione peroxidase 6 (olfactory) | Down Regulation at 48 hours | Extracellular space | Arachidonic acid metabolism. |
| GSR | Glutathione reductase | Down Regulation at 48 hours | Cytoplasm | Glutamate and glutathione metabolism, apoptosis. |
| GTF2I | General transcription factor II, i | Down Regulation at 6 hours | Nucleus | Transcriptional activator, transcription of fos. |
| KRT1 | Keratin 1 (epidermolytic hyperkeratosis) | Up Regulation at 48 hours | Cytoplasm | Sugar Binding. |
| LPO | Lactoperoxidase | Down Regulation at 48 hours | Extracellular space | Phenyl alanine metabolism. |
| MBL2 | Mannose-binding lectin (protein C) 2, soluble (opsonic defect) | Down Regulation at 48 hours | Extracellular space | Complement signaling, pattern recognition in receptors. |
| MGST3 | Microsomal glutathione S-transferase 3 | Upregulation at 16 hours | Cytoplasm | Xenobiotic metabolism. |
| MPO | Myeloperoxidase | Down Regulation at 48 hours | Cytoplasm | Anti-apoptotic, phenyl alanine metabolism. |
| MPV17 | MpV17 mitochondrial inner membrane protein | Down Regulation at 6 hours | Cytoplasm | Maintenance of mitochondrial DNA. |
| MT3 | Metallothionein 3 | Down Regulation at 48 hours | Cytoplasm | Copper ion binding. |
| NCF1 | Neutrophil cytosolic factor 1, (chronic granulomatous disease, autosomal 1) | Down Regulation from 6 hours | Cyoplasm | Produces free radicals. |
| NCF2 | Neutrophil cytosolic factor 2 (65 kDa, chronic granulomatous disease, autosomal 2) | Up Regulation at 48 hours | Cytoplasm | Electron carrier. |
| NME5 | Non-metastatic cells 5, protein expressed in (nucleoside-diphosphate kinase) | Down Regulation at 48 hours | Unknown | Kinase, Purine and pyrimidine metabolism. |
| NOS2A | Nitric oxide synthase 2A (inducible, hepatocytes) | Down Regulation at 48 hours | Cytoplasm | Glucocorticoid receptor signaling, apoptosis. |
| OXR1 | Oxidation resistance 1 | Down Regulation at 48 hours | Cytoplasm | Responds to oxidative stress. |
| PDLIM1 | PDZ and LIM domain 1 (elfin) | Up Regulation at 48 hours | Cytoplasm | Transcriptional activator. |
| PIP3-E | Phosphoinositide-binding protein PIP3-E | Down Regulation at 48 hours | Cytoplasm | Peroxidase. |
| PRDX2 | Peroxiredoxin 2 | Down Regulation at 6 hours | Cytoplasm | Role in phenyl alanine metabolism. Role in cell death. |
| PRDX4 | Peroxiredoxin 4 | Down Regulation from 24 hours | Cytoplasm | Thioredoxin peroxidase. |
| PREX1 | Phosphatidylinositol 3,4,5-trisphosphate-dependent RAC exchanger 1 | Down Regulation at 48 hours | Cytoplasm | Forms oxygen free radicals. |

TABLE 10-continued

Genes in SK-MEL-28 cells that are regulated by 100 μM Q10 treatement as seen in the Oxidative Stress and Antioxidant Defense Arrays.

| Symbol | Description | Regulation | Location | Possible Functions. |
|---|---|---|---|---|
| PRG3 | Proteoglycan 3 | Down Regulation at 48 hours | Extracellular space | Role in cell death. |
| PTGS1 | Prostaglandin-endoperoxide synthase 1 (prostaglandin G/H synthase and cyclooxygenase) | Down Regulation at 48 hours | Cytoplasm | arachidonic acid metabolism, prostaglandin synthesis. |
| PTGS2 | Prostaglandin-endoperoxide synthase 2 (prostaglandin G/H synthase and cyclooxygenase) | Up Regulation at 48 hours | Cytoplasm | arachidonic acid metabolism, prostaglandin synthesis. |
| PXDN | Peroxidasin homolog (Drosophila) | Up Regulation at 48 hours | Unknown | binds to TRAF4, calcium ion binding, iron ion binding. |
| PXDNL | Peroxidasin homolog (Drosophila)-like | Down Regulation at 48 hours | Unknown | peroxidase, calcium ion binding, iron ion binding. |
| RNF7 | Ring finger protein 7 | Up Regulation at 16 hours | Nucleus | apoptotic, copper ion binding, ubiquitin pathway. |
| SGK2 | Serum/glucocorticoid regulated kinase 2 | Down Regulation at 48 hours | Cytoplasm | Kinase, potassium channel regulator. |
| SIRT2 | Sirtuin (silent mating type information regulation 2 homolog) 2 (S. cerevisiae) | Up regulation at 16 hours | Nucleus | Transcription factor. |
| SOD1 | Superoxide dismutase 1, soluble (amyotrophic lateral sclerosis 1 (adult)) | Up Regulation at 16 hours | Cytoplasm | Apoptotic, Caspase Activator. |
| SOD2 | Superoxide dismutase 2, mitochondrial | Up regulation at 16 hours | Cytoplasm | Apoptotic, Regulated by TNF. |
| SOD3 | Superoxide dismutase 3, extracellular | Down Regulation at 48 hours | Extracellular space | Pro-apoptotic |
| SRXN1 | Sulfiredoxin 1 homolog (S. cerevisiae) | Down Regulation at 48 hours | Cytoplasm | DNA binding, oxidoreductase |
| TPO | Thyroid peroxidase | Down Regulation at 48 hours | Plasma Membrane | iodination of thyroglobulin, tyrosine metabolism, phenylalanine metabolism. |
| TTN | Titin | Down Regulation at 48 hours | Cytoplasm | Actin cytoskeleton signaling, integrin signaling |
| TXNDC2 | Thioredoxin domain-containing 2 (spermatozoa) | Down Regulation at 48 hours | Cytoplasm | Pyrimidine metabolism |

The Neutrophil cytosolic factor 2 (NCF2, 65 kDa, chronic granulomatous disease, autosomal 2) was one of the initial top induced mRNA's (observed at 6 hours). Subsequently at the 16 hour time point and onward, Neutrophil cytosolic factor 1 (NCF1) (chronic granulomatous disease, autosomal 1) was induced at very high levels after an initial lag phase.

Neutrophil cytosolic factor 2 is the cytosolic subunit of the multi-protein complex known as NADPH oxidase commonly found in neutrophils. This oxidase produces a burst of superoxide which is delivered to the lumen of the neutrophil phagosome.

The NADPH oxidase (nicotinamide adenine dinucleotide phosphate-oxidase) is a membrane-bound enzyme complex. It can be found in the plasma membrane as well as in the membrane of phagosome. It is made up of six subunits. These subunits are: a Rho guanosine triphosphatase (GTPase), usually Rac1 or Rac2 (Rac stands for Rho-related C3 botulinum toxin substrate)

Five "phox" units. (Phox stands for phagocytic oxidase.)
    P91-PHOX (contains heme)
        p22phox
        p40phox
        p47phox (NCF1)
        p67phox (NCF2)

It is noted that another NADPH oxidase levels do not change. The enzyme is NOX5, which is a novel NADPH oxidase that generates superoxide and functions as a H+ channel in a Ca(2+)-dependent manner In addition Phosphatidylinositol 3,4,5-trisphosphate-dependent RAC exchanger 1(PREX1) was also upregulated. This protein acts as a guanine nucleotide exchange factor for the RHO family of small GTP-binding proteins (RACs). It has been shown to bind to and activate RAC1 by exchanging bound GDP for free GTP. The encoded protein, which is found mainly in the cytoplasm, is activated by phosphatidylinositol-3,4,5-trisphosphate and the beta-gamma subunits of heterotrimeric G proteins.

The second major early induced protein was Nitric oxide synthase 2A (inducible, hepatocytes) (NOS2A). Nitric oxide is a reactive free radical which acts as a biologic mediator in several processes, including neurotransmission and antimicrobial and antitumoral activities. This gene encodes a nitric oxide synthase which is expressed in liver and is inducible by a combination of lipopolysaccharide and certain cytokines.

Superoxide dismutase 2, mitochondrial (SOD2) is a member of the iron/manganese superoxide dismutase family. It encodes a mitochondrial protein that forms a homotetramer and binds one manganese ion per subunit. This protein binds to the superoxide byproducts of oxidative phosphorylation and converts them to hydrogen peroxide and diatomic oxygen. Mutations in this gene have been associated with idiopathic cardiomyopathy (IDC), premature aging, sporadic motor neuron disease, and cancer.

An example of a down regulated protein is Forkhead box M1 (FOXM1), which is known to play a key role in cell cycle progression where endogenous FOXM1 expression peaks at S and G2/M phases. Recent studies have shown that FOXM1, regulates expression of a large array of G2/M-specific genes, such as Plk1, cyclin B2, Nek2 and CENPF, and plays an important role in maintenance of chromosomal segregation and genomic stability. The FOXM1 gene is now known as a human proto-oncogene. Abnormal upregulation of FOXM1 is involved in the oncogenesis of basal cell carcinoma (BCC). FOXM1 upregulation was subsequently found in the majority of solid human cancers including liver, breast, lung, prostate, cervix of uterus, colon, pancreas, and brain. Further studies with BCC and Q10 should evaluate FOXM1 levels.

SKMEL-28 Cells

Further experiments were carried out using SKMEL-28 cells. The level of mRNA present in SKMEL-28 cells treated with 100 µM Q10 were compared to the levels in untreated cells at various time points using real-time PCR methods (RT-PCR). The PCR array (SABiosciences) is a set of optimized real-time PCR primer assays on 96-well plates for pathway or disease focused genes as well as appropriate RNA quality controls. The PCR array performs gene expression analysis with real-time PCR sensitivity and the multi-gene profiling capability of a microarray.

TABLE 11

Listing and classification of mRNA levels evaluated in the Oxidative Stress and Antioxidant Defense PCR Array. After six hours of treatment with 100 µM Q10 on SKMEL-28 cells, the largest changes to the mRNA levels are indicated by highlighting the protein code (increased - bold; decreased - underlined; or no change - italics).

Antioxidants:

Glutathione Peroxidases (GPx): GPX1, *GPX2*, GPX3, GPX4, *GPX5*, *GPX6*, *GPX7*, GSTZ1.
Peroxiredoxins (TPx): PRDX1, PRDX2, PRDX3, PRDX4, PRDX5, PRDX6.
Other Peroxidases: CAT, CSDE1, CYGB, *DUOX1*, *DUOX2*, EPX, GPR156, *LPO*, *MPO*, *PIP3-E*, *PTGS1*, PTGS2, PXDN, PXDNL, TPO, TTN.
Other Antioxidants: *ALB*, APOE, GSR, MT3, SELS, SOD1, *SOD3*, SRXN1, TXNDC2, TXNRD1, *TXNRD2l*
Genes Involved in Reactive Oxygen Species (ROS) Metabolism:

Superoxide Dismutases (SOD): SOD1, SOD2, *SOD3*.
Other Genes Involved in Superoxide Metabolism: ALOX12, CCS, CYBA, DUOX1, DUOX2, GTF2I, MTC, NCF1, NCF2, NOS2A, *NOX5*, PREX1, PRG3.
Other Genes Involved in ROS Metabolism: AOX1, BNIP3, *EPHX2*, MPV17, SFTPD.
Oxidative Stress Responsive Genes: ANGPTL7, APOE, ATOX1, CAT, CCL5, CSDE1, CYGB, DGKK, DHCR24, DUOX1, DUOX2, DUSP1, EPX, FOXM1, GLRX2, GPR156, GPX1, *GPX2*, GPX3, GPX4, *GPX5*, *GPX6*, *GPX7*, GSS, KR1, *LPO*, MBL2, *MPO*, MSRA, MTL5, NME5, NUDT1, OXR1, OXSR1, PDLIM1, *PIP3-E*, PNKP, PRDX2, PRDX5, PRDSX, PRNP, RNF7, *SCARA3*, SELS, *SEPP1*, SGK2, SIRT2, SOD1, SOD2, SRXN1, STK25, *TPO*, TTN, *TXNRD2*.

TABLE 12

Time course evaluation of 100 µM treatment of SKMEL-28. The mRNA level changes were monitored by RT-PCR methods and oxidative stress and antioxidant defense proteins array was evaluated.

| Refseq | Symbol | Description | 6 hr Q10 | 16 hr Q10 | 24 hr Q10 | 48 hr Q10 | 72 hr Q10 |
|---|---|---|---|---|---|---|---|
| NM_000265 | NCF1 | Neutrophil cytosolic factor 1, (chronic granulomatous disease, autosomal 1) | 0 | high | 3.3829 | 15.7838 | 31.5369 |
| NM_012423 | RPL13A | Ribosomal protein L13a | −0.9025 | 3.1857 | 2.5492 | 4.9253 | 7.82 |
| NM_020820 | PREX1 | Phosphatidylinositol 3,4,5-trisphosphate-dependent RAC exchanger 1 | −3.2971 | 2.867 | 0.3222 | 6.3719 | 7.476 |
| NM_012237 | SIRT2 | Sirtuin (silent mating type information regulation 2 homolog) 2 (S. cerevisiae) | −0.9025 | 4.0829 | 4.4766 | 5.7166 | 6.6257 |
| NM_005125 | CCS | Copper chaperone for superoxide dismutase | −0.6206 | 3.0077 | 3.452 | 2.9801 | 6.1539 |
| NM_181652 | PRDX5 | Peroxiredoxin 5 | −2.995 | 3.0454 | 3.5381 | 4.7955 | 6.0169 |
| NM_016276 | SGK2 | Serum/glucocorticoid regulated kinase 2 | 0 | 0 | 0 | 0.5995 | 5.937 |
| NIM_003551 | NME5 | Non-metastatic cells 5, protein expressed in (nucleoside-diphosphate kinase) | −0.6652 | 3.1138 | 3.3694 | 3.1549 | 5.782 |

TABLE 12-continued

Time course evaluation of 100 μM treatment of SKMEL-28. The mRNA level changes were monitored by RT-PCR methods and oxidative stress and antioxidant defense proteins array was evaluated.

| Refseq | Symbol | Description | 6 hr Q10 | 16 hr Q10 | 24 hr Q10 | 48 hr Q10 | 72 hr Q10 |
|---|---|---|---|---|---|---|---|
| NM_004417 | DUSP1 | Dual specificity phosphatase 1 | −0.6998 | 0.5902 | 2.7713 | 3.321 | 5.5375 |
| NM_001752 | CAT | Catalase | −0.8589 | 2.8424 | 0.1046 | 3.8557 | 5.3988 |
| NM_000041 | APOE | Apolipoprotein E | −0.8212 | 3.2069 | −0.9543 | 3.7694 | 5.3315 |
| NM_000101 | CYBA | Cytochrome b-245, alpha polypeptide | −0.3945 | 4.3475 | 3.9208 | 6.2452 | 5.0762 |
| NM_000433 | NCF2 | Neutrophil cytosolic factor 2 (65 kDa, chronic granulomatous disease, autosomal 2) | 1.2266 | 3.0077 | 0.0954 | 5.476 | 0 |
| NM_000963 | PTGS2 | Prostaglandin-endoperoxide synthase 2 (prostaglandin G/H synthase and cyclooxygenase) | −0.6912 | 2.7046 | 2.6552 | 4.0553 | −3.3022 |
| NM_183079 | PRNP | Prion protein (p27-30) (Creutzfeldt-Jakob disease, Gerstmann-Strausler-Scheinker syndrome, fatal familial insomnia) | −0.2144 | 3.5236 | 2.9086 | 5.0837 | −3.9396 |
| NM_004052 | BNIP3 | BCL2/adenovirus E1B 19 kDa interacting protein 3 | −2.9376 | 3.3288 | 4.312 | −18.2069 | −4.8424 |
| NM_000242 | MBL2 | Mannose-binding lectin (protein C) 2, soluble (opsonic defect) | −0.3622 | −1.9072 | −3.0142 | −1.1854 | −6.4544 |
| NM_021953 | FOXM1 | Forkhead box M1 | −0.8135 | 0.068 | −0.9216 | 3.3655 | −10.0953 |

The Neutrophil cytosolic factor 2 (NCF2, 65 kDa, chronic granulomatous disease, autosomal 2) was one of the initial top induced mRNA's (observed at 6 hours). Subsequently at the 16 hour time point and onward, Neutrophil cytosolic factor 1 (NCF1) (chronic granulomatous disease, autosomal 1) was induced at very high levels after an initial lag phase.

Neutrophil cytosolic factor 2 is the cytosolic subunit of the multi-protein complex known as NADPH oxidase commonly found in neutrophils. This oxidase produces a burst of superoxide which is delivered to the lumen of the neutrophil phagosome. The NADPH oxidase (nicotinamide adenine dinucleotide phosphate-oxidase) is a membrane-bound enzyme complex. It can be found in the plasma membrane as well as in the membrane of phagosome. It is made up of six subunits. These subunits are: a Rho guanosine triphosphatase (GTPase), usually Rac1 or Rac2 (Rac stands for Rho-related C3 botulinum toxin substrate)

Five "phox" (phagocytic oxidase) units.
   P91-PHOX (contains heme)
   p22phox
   p40phox
   p47phox (NCF1)
   p67phox (NCF2)

It is noted that another NADPH oxidase levels do not change. The enzyme is NOX5, which is a novel NADPH oxidase that generates superoxide and functions as a H+ channel in a Ca(2+)-dependent manner In addition Phosphatidylinositol 3,4,5-trisphosphate-dependent RAC exchanger 1(PREX1) was also upregulated. This protein acts as a guanine nucleotide exchange factor for the RHO family of small GTP-binding proteins (RACs). It has been shown to bind to and activate RAC1 by exchanging bound GDP for free GTP. The encoded protein, which is found mainly in the cytoplasm, is activated by phosphatidylinositol-3,4,5-trisphosphate and the beta-gamma subunits of heterotrimeric G proteins.

The second major early induced protein was Nitric oxide synthase 2A (inducible, hepatocytes) (NOS2A). Nitric oxide is a reactive free radical which acts as a biologic mediator in several processes, including neurotransmission and antimicrobial and antitumoral activities. This gene encodes a nitric oxide synthase which is expressed in liver and is inducible by a combination of lipopolysaccharide and certain cytokines.

An example of a down regulated protein is FOXM1, which is known to play a key role in cell cycle progression where endogenous FOXM1 expression peaks at S and G2/M phases. Recent studies have shown that FOXM1, regulates expression of a large array of G2/M-specific genes, such as Plk1, cyclin B2, Nek2 and CENPF, and plays an important role in maintenance of chromosomal segregation and genomic stability. The FOXM1 gene is now known as a human proto-oncogene. Abnormal upregulation of FOXM1 is involved in the oncogenesis of basal cell carcinoma (BCC). FOXM1 upregulation was subsequently found in the majority of solid human cancers including liver, breast, lung, prostate, cervix, uterus, colon, pancreas, and brain.

Experiment 3

Real-Time PCR Arrays Using Heat Shock Array

Heat Shock Arrays were run for SCC cells and the data of regulated genes is summarized below in Table 13.

TABLE 13

Genes from the Heat Shock Protein array regulated with 100 µM Q10 treatment in SCC cells.

| Symbol | Description | Regulation. | Location. | Possible functions. |
|---|---|---|---|---|
| CCT6B | Chaperonin containing TCP1, subunit 6B (zeta 2) | Down regulated at 24 hours | Cytoplasm | Protein folding and protein complex assembly. |
| DNAJA1 | DnaJ (Hsp40) homolog, subfamily A, member 1 | Up regulated at 6 hours. | Nucleus | Responds to DNA damage and changes in protein folding. |
| DNAJB13 | DnaJ (Hsp40) related, subfamily B, member 13 | Down regulated at 6 hours. | Unknown | Protein folding and apoptosis. |
| DNAJB5 | DnaJ (Hsp40) homolog, subfamily B, member 5 | Down regulated at 6 hours. | Unknown | Binds to HSP, involved in protein folding and in protein complex assembly. |
| DNAJC12 | DnaJ (Hsp40) homolog, subfamily C, member 12 | Down regulated at 6 hours. | Unknown | Binds to HSP, involved in protein folding and in protein complex assembly. |
| DNAJC4 | DnaJ (Hsp40) homolog, subfamily C, member 4 | Down regulated at 6 hours. | Cytoplasm | Binds to HSP, involved in protein folding and in protein complex assembly. |
| DNAJC5B | DnaJ (Hsp40) homolog, subfamily C, member 5 beta | Down regulated at 6 hours. | Unknown | Involved in protein folding responds to changes in protein folding. |
| HSPA8 | Heat shock 70 kDa protein 8 | Up regulated at 6 hours. | Cytoplasm | Regulates TNF, binds BAG1, STUB1, TP53, involved in apoptosis. |
| HSPH1 | Heat shock 105 kDa/110 kDa protein 1 | Up regulated at 6 hours. | Cytoplasm | Binds to HSPA8, important for protein folding, responds to protein unfolding and stress. |

Experiment 4

Real-Time PCR Arrays Using Diabetes Array

The experiments described in this example were performed to test the overall hypothesis that Q10 would have an impact on multiple genes and alter the metabolic state of a cell. The mRNA from SKMEL-28 cells treated with 100 µM Q10 was evaluated by RT-PCR against a panel of target proteins involved in diabetes and related pathways. Results from this experiment demonstrate that several proteins involved in glycolyic pathways and insulin processing are altered in their mRNA expression levels (summarized in Table 14).

TABLE 14

Major mRNA level changes to SKMEL-28 cellstreated with 100 µM Q10 for 16 hours.

| Refseq | Description | Symbol | Fold Change after 16 hours (100 µM Q10) |
|---|---|---|---|
| NM_000162 | Glucokinase (hexokinase 4) | GCK | 8.5386 |
| NM_178849 | Hepatocyte nuclear factor 4, alpha | HNF4A | 8.421 |
| NM_005249 | Forkhead box G1 | FOXG1 | 4.6396 |
| NM_000599 | Insulin-like growth factor binding protein 5 | IGFBP5 | 2.2721 |
| NM_001101 | Actin, beta | ACTB | −2.0936 |
| NM_002863 | Phosphorylase, glycogen; liver (Hers disease, glycogen storage disease type VI) | PYGL | −2.65 |
| NM_001065 | Tumor necrosis factor receptor superfamily, member 1A | TNFRSF1A | −2.8011 |
| NM_021158 | Tribbles homolog 3 (*Drosophila*) | TRIB3 | −2.8011 |
| NM_003749 | Insulin receptor substrate 2 | IRS2 | −2.9404 |
| NM_004578 | RAB4A, member RAS oncogene family | RAB4A | −3.1296 |
| NM_004176 | Sterol regulatory element binding transcription factor 1 | SREBF1 | −3.5455 |
| NM_004969 | Insulin-degrading enzyme | IDE | −4.4878 |
| NM_005026 | Phosphoinositide-3-kinase, catalytic, delta polypeptide | PIK3CD | −6.8971 |
| NM_000208 | Insulin receptor | INSR | −8.6099 |
| NM_003376 | Vascular endothelial growth factor A | VEGFA | −15.5194 |
| NM_001315 | Mitogen-activated protein kinase 14 | MAPK14 | −74.3366 |

The results of this initial experiment show that the mRNA levels for a variety of insulin related proteins were modulated in both directions. The results indicate that Q10 would have an impact on diabetic disease treatment and/or evaluation.

Further experiments were next conducted to confirm the results above obtained from SK-MEL-28 cells treated with Q10. Many of the genes in SK-MEL-28 cells are regulated as early as 6 hours after Q10 treatment. However, the initial regulation becomes less evident by 16 and 24 hours. Around 48 hours, we find that many of the genes in the Diabetes array are again strongly regulated. Results that are consistent from two or more or independent experiments are summarized below in Table 15. SCC cells also appeared to exhibit regulation in some genes, both at 6 and 24 hours after Q10 treatment. These results from SCC cells are summarized in Table 16 while genes that are regulated both in SK-MEL-28 cells and in SCC cells are summarized in Table 17.

TABLE 15

Genes in SK-MEL-28 cells regulated by 100 μM Q10 treatment when analyzed by the Diabetes Array.

| Symbol | Description | Regulation. | Location | Possible Function |
|---|---|---|---|---|
| ADRB3 | Adrenergic, beta-3-, receptor | Down Regulated at 48 hours | Plasma membrane | cAMP signaling, G-protein signaling |
| CEACAM1 | Carcinoembryonic antigen-related cell adhesion molecule 1 (biliary glycoprotein) | Down Regulated at 48 hours | Extracellular space | Anti-apoptotic, positive regulation of angiogenesis. |
| CEBPA | CCAAT/enhancer binding protein (C/EBP), alpha | Up regulated at 48 hours | Nucleus | Glucocorticoid receptor signaling, VDR/RXR activation. |
| CTLA4 | Cytotoxic T-lymphocyte-associated protein 4 | Down Regulated at 48 hours | Plasma Membrane | T cell receptor signaling, activates CASP8. |
| DUSP4 | Dual specificity phosphatase 4 | Down Regulated at 48 hours | Nucleus | Phosphatase |
| ENPP1 | Ectonucleotide pyrophosphatase/phosphodiesterase 1 | Down Regulated at 48 hours | Plasma membrane | Negative regulator of the insulin receptor pathway |
| FOXC2 | Forkhead box C2 (MFH-1, mesenchyme forkhead 1) | Down Regulated at 48 hours | Nucleus | Anti-apoptotic, transcription factor |
| G6PD | Glucose-6-phosphate dehydrogenase | Up regulated at 48 hours, then down regulated | Cytoplasm | Pentose Phosphate Pathway, Glutathione metabolism. |
| HMOX1 | Heme oxygenase (decycling) 1 | Down Regulated at 48 hours | Cytoplasm | Heme oxygenase decycling |
| ICAM1 | Intercellular adhesion molecule 1 (CD54), human rhinovirus receptor | Down Regulated at 48 hours | Plasma membrane | Regulated by atorvastatin, processes some caspases. |
| IL4R | Interleukin 4 receptor | Down Regulated at 48 hours | Plasma membrane | Up regulation by TP73, binds to IRS1 and IRS2 |
| IRS1 | Insulin receptor substrate 1 | Up regulated at 48 hours then down regulated | Plasma membrane | Binds Insulin receptor |
| IRS2 | Insulin receptor substrate 2 | Down Regulated at 48 hours | Plasma membrane | IGF-1 signaling |
| NSF | N-ethylmaleimide-sensitive factor | Down Regulated at 48 hours | Cytoplasm | GABA signaling |
| PIK3CD | Phosphoinositide-3-kinase, catalytic, delta polypeptide | Down Regulated at 48 hours | Cytoplasm | Kinase |
| PPARG | Peroxisome proliferator-activated receptor gamma | Down Regulated at 48 hours | Nucleus | Transcriptional factor |
| PRKCB1 | Protein kinase C, beta 1 | Down Regulated at 48 hours | Cytoplasm | PKC family |
| SELL | Selectin L (lymphocyte adhesion molecule 1) | Down Regulated at 48 hours | Plasma membrane | Activates RAS, MAPK |
| SREBF1 | Sterol regulatory element binding transcription factor 1 | Up regulated at 48 hours then down regulated | Nucleus | Transcriptional factor |
| STXBP1 | Syntaxin binding protein 1 | Down Regulated at 48 hours | Cytoplasm | Present in myelin enriched fraction. |
| TGFB1 | Transforming growth factor, beta 1 | Up regulated at 48 hours then down regulated | Extracellular space | Pro-apoptotic |
| NKX2-1 | NK2 homeobox 1 | Down Regulated at 48 hours | Nucleus | Transcriptional activator |

TABLE 15-continued

Genes in SK-MEL-28 cells regulated by 100 μM Q10 treatment when analyzed by the Diabetes Array.

| Symbol | Description | Regulation. | Location | Possible Function |
|---|---|---|---|---|
| TNF | Tumor necrosis factor (TNF superfamily, member 2) | Up regulated at 48 hours | Extracellular space | Pro-apoptotic |
| TNFRSF1A | Tumor necrosis factor receptor superfamily, member 1A | Down Regulated at 72 hours | Plasma membrane | Pro-apoptotic |
| VEGFA | Vascular endothelial growth factor A | Up regulated at 58 hours then down regulated | Cytoplasm | Kinase |

TABLE 16

Genes in SCC cells regulated by 100 μM Q10 treatment when analyzed by the Diabetes Array.

| Symbol | Description | Regulation. |
|---|---|---|
| G6PD | Glucose-6-phosphate dehydrogenase | Down regulated at 6 hours. |
| ICAM1 | Intercellular adhesion molecule 1 (CD54), human rhinovirus receptor | Down regulated at 6 hours. |
| INPPL1 | Inositol polyphosphate phosphatase-like 1 | Down regulated at 6 hours. |
| NOS3 | Nitric oxide synthase 3 (endothelial cell) | Down regulated at 6 hours. |
| PIK3CD | Phosphoinositide-3-kinase, catalytic, delta polypeptide | Down regulated at 6 hours. |
| PPARA | Peroxisome proliferative activated receptor, alpha | Down regulated at 6 hours. |
| PYGL | Phosphorylase, glycogen; liver (Hers disease, glycogen storage disease type VI) | Down regulated at 6 hours. |
| SREBF1 | Sterol regulatory element binding transcription factor 1 | Down regulated at 6 hours. |
| STXBP2 | Syntaxin binding protein 2 | Down regulated at 6 hours. |
| TNF | Tumor necrosis factor (TNF superfamily, member 2) | Down regulated at 6 hours. |
| TNFRSF1A | Tumor necrosis factor receptor superfamily, member 1A | Down regulated at 6 and 24 hours. |
| VEGFA | Vascular endothelial growth factor A | Down regulated at 6 hours. |

TABLE 17

Genes from the diabetes array regulated with 100 μM Q10 treatment for both SK-MEL-28 and SCC cells.

| Symbol | Description. |
|---|---|
| G6PD | Glucose-6-phosphate dehydrogenase |
| ICAM1 | Intercellular adhesion molecule 1 (CD54), human rhinovirus receptor |
| PIK3CD | Phosphoinositide-3-kinase, catalytic, delta polypeptide |
| SREBF1 | Sterol regulatory element binding transcription factor 1 |
| TNF | Tumor necrosis factor (TNF superfamily, member 2) |
| TNFRSF1A | Tumor necrosis factor receptor superfamily, member 1A |
| VEGFA | Vascular endothelial growth factor A |

The mRNA levels for a variety of insulin related proteins were modulated in both directions. Q10 has an impact on regulation of cellular metabolism, and thus influences metabolic disregulation diseases such as diabetes. Two proteins that were significantly modulated are further discussed below.

Mitogen-activated protein kinase 14 (MAPK14): Mitogen-activated protein kinase 14 (MAPK14) is a member of the MAP kinase family. MAP kinases act as an integration point for multiple biochemical signals, and are involved in a wide variety of cellular processes such as proliferation, differentiation, transcription regulation and development. Results from this experiment show that the MAPK14 was significantly down-regulated.

Hepatocyte nuclear factor 4, alpha (HNF4A): HNF4 (Hepatocyte Nuclear Factor 4) is a nuclear receptor protein mostly expressed in the liver, gut, kidney, and pancreatic beta cells that is critical for liver development. In humans, there are two isoforms of NHF4, alpha and gamma encoded by two separate genes HNF4A and HNF4G respectively. (See, e.g., Chartier F L, Bossu J P, Laudet V, Fruchart J C, Laine B (1994). "Cloning and sequencing of cDNAs encoding the human hepatocyte nuclear factor 4 indicate the presence of two isoforms in human liver". Gene 147 (2): 269-72.)

HNF4 was originally classified as an orphan receptor. However HNF4 was found later to be constitutively active by virtue of being continuously bound to a variety of fatty acids. (See, e.g., Sladek F (2002). "Desperately seeking . . . something". Mol Cell 10 (2): 219-221 and Jump D B, Botolin D, Wang Y, Xu J, Christian B, Demeure O (2005). "Fatty acid regulation of hepatic gene transcription". J Nutr 135 (11)). The ligand binding domain of HNF4, as with other nuclear receptors, adopts a canonical alpha helical sandwich fold (see, e.g., Wisely G B, Miller A B, Davis R G, Thornquest A D Jr, Johnson R, Spitzer T, Sefler A, Shearer B, Moore J T, Miller A B, Willson T M, Williams SP (2002). "Hepatocyte nuclear factor 4 is a transcription factor that constitutively binds fatty acids". *Structure* 10 (9): 1225-34 and Dhe-Paganon S, Duda K, Iwamoto M, Chi Y I, Shoelson S E (2002). "Crystal structure of the HNF4 alpha ligand binding domain in complex with endogenous fatty acid ligand". *J Biol Chem* 277 (41): 37973-6) and interacts with co-activator proteins. (See, e.g., Duda K, Chi Y I, Shoelson S E (2004). "Structural basis for HNF-4alpha activation by ligand and coactivator binding". *J Biol Chem* 279 (22): 23311-6).

Mutations in the HNF4-α gene have been linked to maturity onset diabetes of the young (MODY). (See, e.g., Fajans S S, Bell G I, Polonsky K S (2001). "Molecular mechanisms and clinical pathophysiology of maturity-onset diabetes of the young". *N Engl J Med* 345 (13): 971-80.)

Hepatocyte nuclear factor 4 (HNF4) is a tissue-specific transcription factor known to regulate a large number of genes in hepatocytes and pancreatic cells. Although HNF4 is highly expressed in some sections of the kidney, little is known about its role in this organ and about HNF4-regulated genes in the kidney cells. The abundance and activity of HNF4 are frequently reduced in renal cell carcinoma (RCC) indicating some tumor suppressing function of HNF4 in renal cells. Interestingly, many of the genes regulated by HNF4 have been shown to be deregulated in RCC microarray studies. These genes (ACY1, WT1, SELENBP1, COBL, EFHD1, AGXT2L1, ALDH5A1, THEM2, ABCB1, FLJ14146, CSPG2, TRIM9 and HEY1) are good candidates for genes whose activity is changed upon the decrease of HNF4 in RCC.

Figure 28:
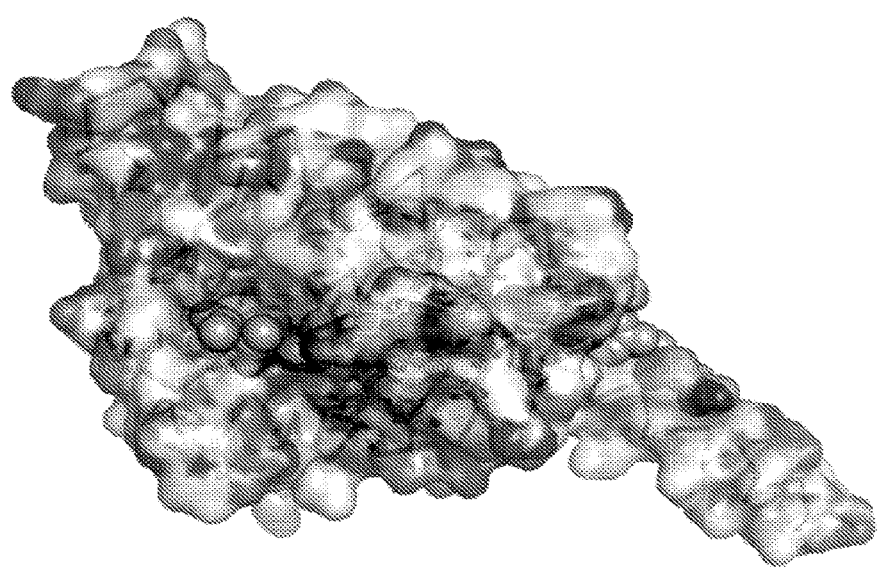
FIG. 28: Theoretical model of Q10 (spheres) inserted into the lipid binding channel of HNF4alpha (1M7W.pdb) in the Helix 10 open conformation.
Figure 29:
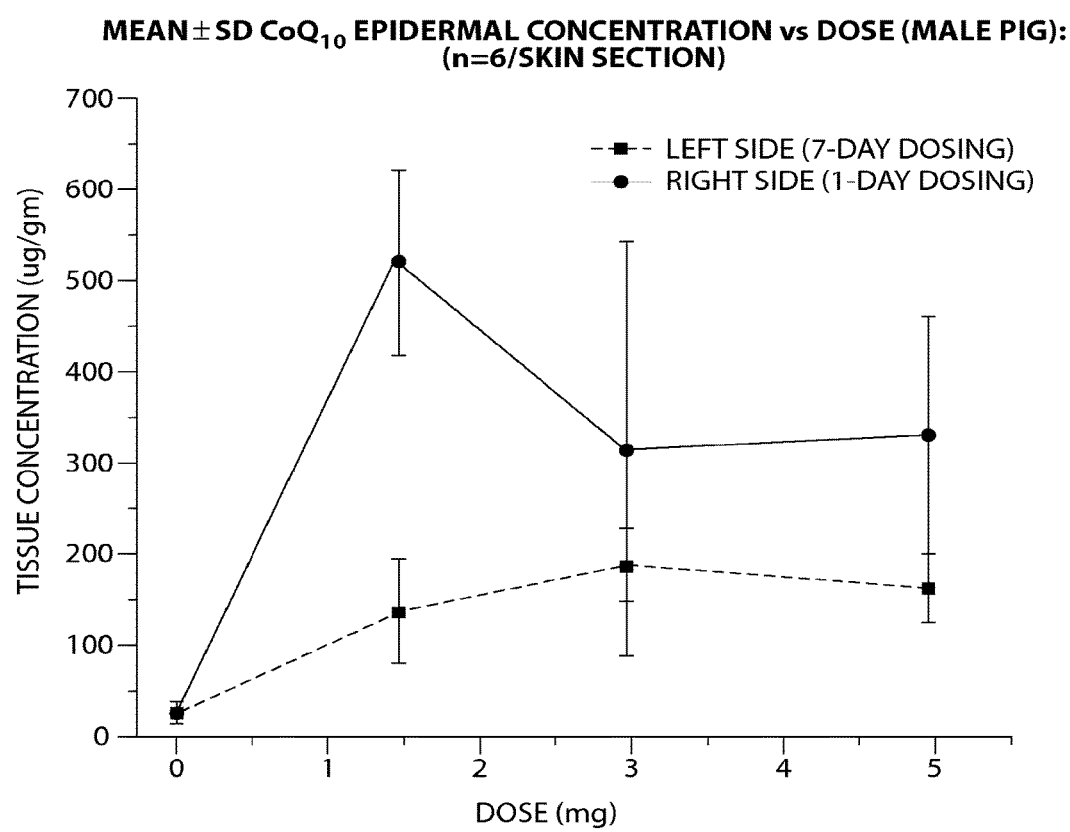
FIG. 29: Graph depicting the epidermal CoQ10 concentration in a male pig after treatment with a composition of the present disclosure having a permeation enhancer.
Figure 30:
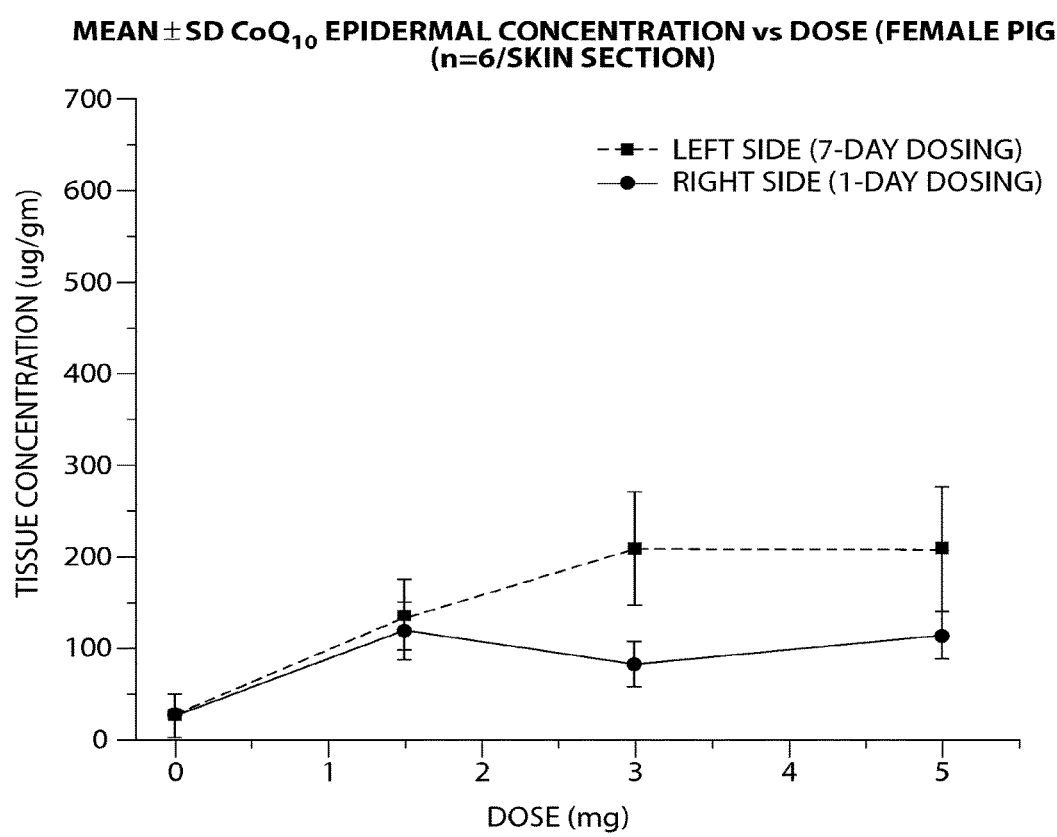
FIG. 30: Graph depicting the epidermal CoQ10 concentration in a female pig after treatment with a control composition.
Figure 31:
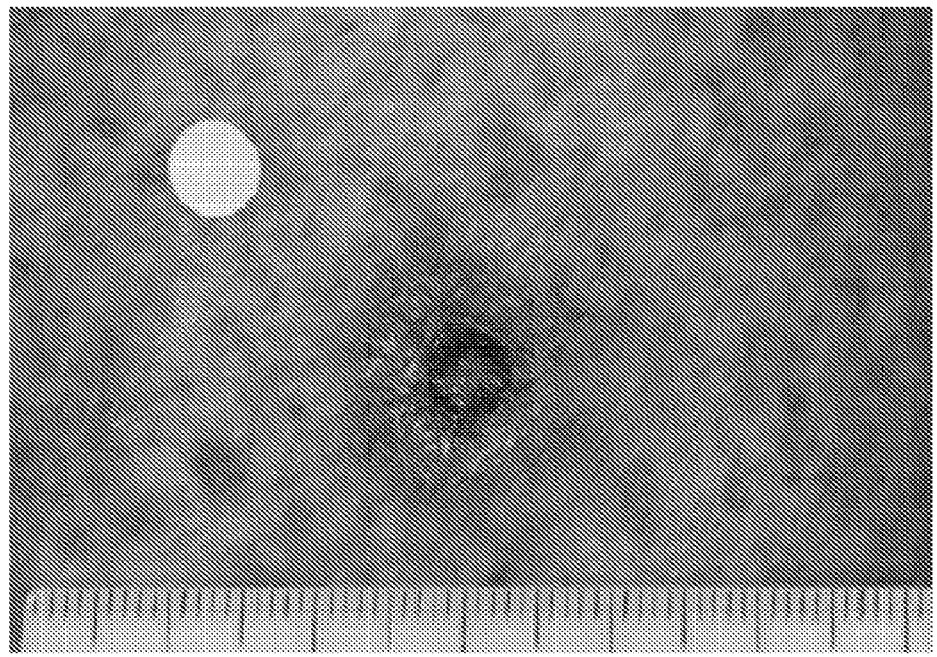
FIG. 31: Photographic depiction of a pre-treated target legion 1.
Figure 32:
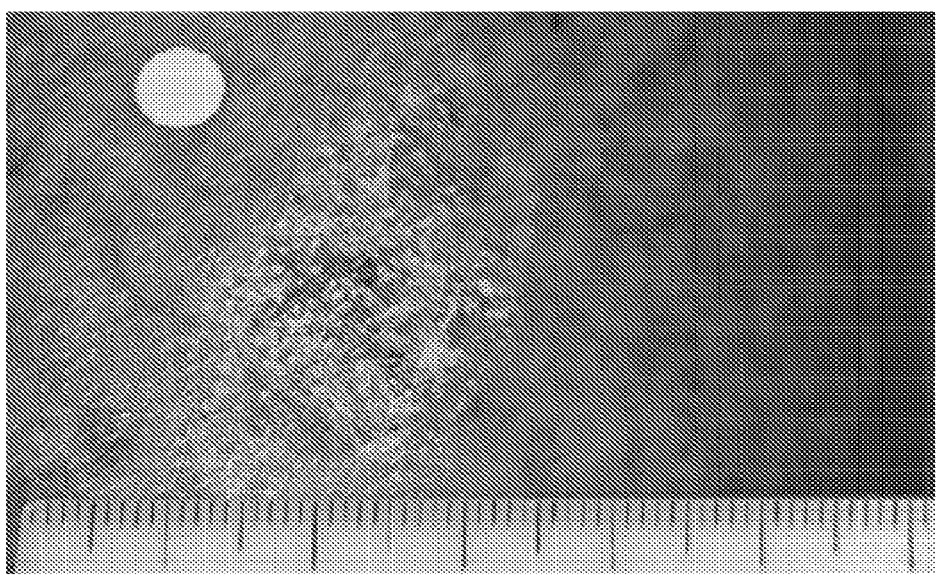
FIG. 32: Photographic depiction of a post-treated target legion 1.
Figure 33:
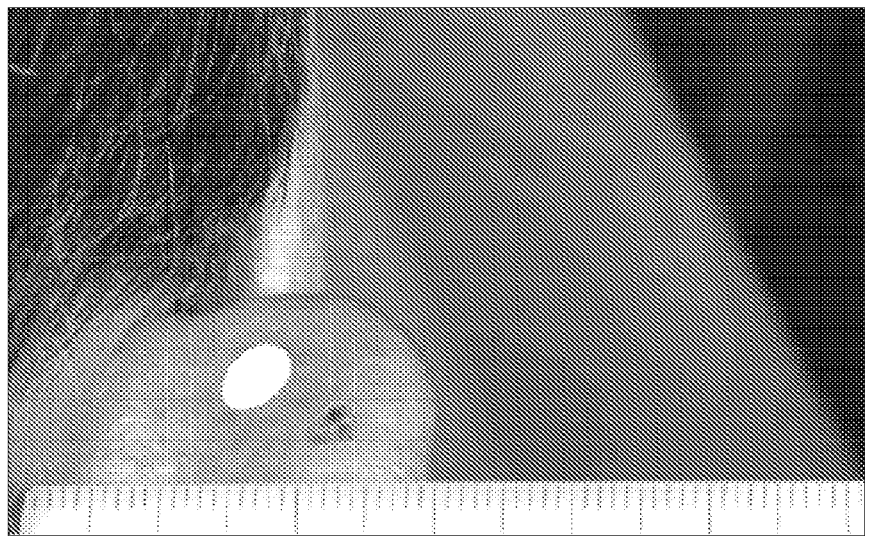
FIG. 33: Photographic depiction of a pre-treated target legion 2.
Figure 34:
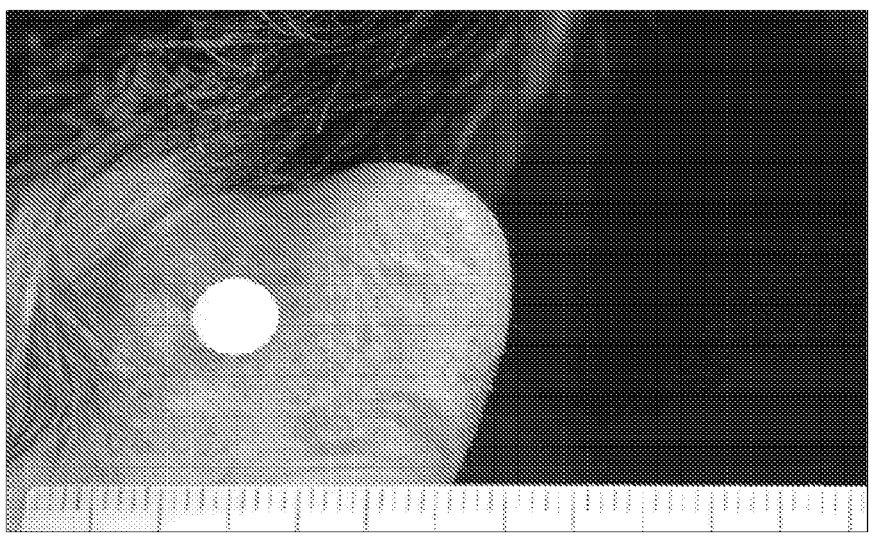
FIG. 34: Photographic depiction of a post-treated target legion 2.
Figure 35:
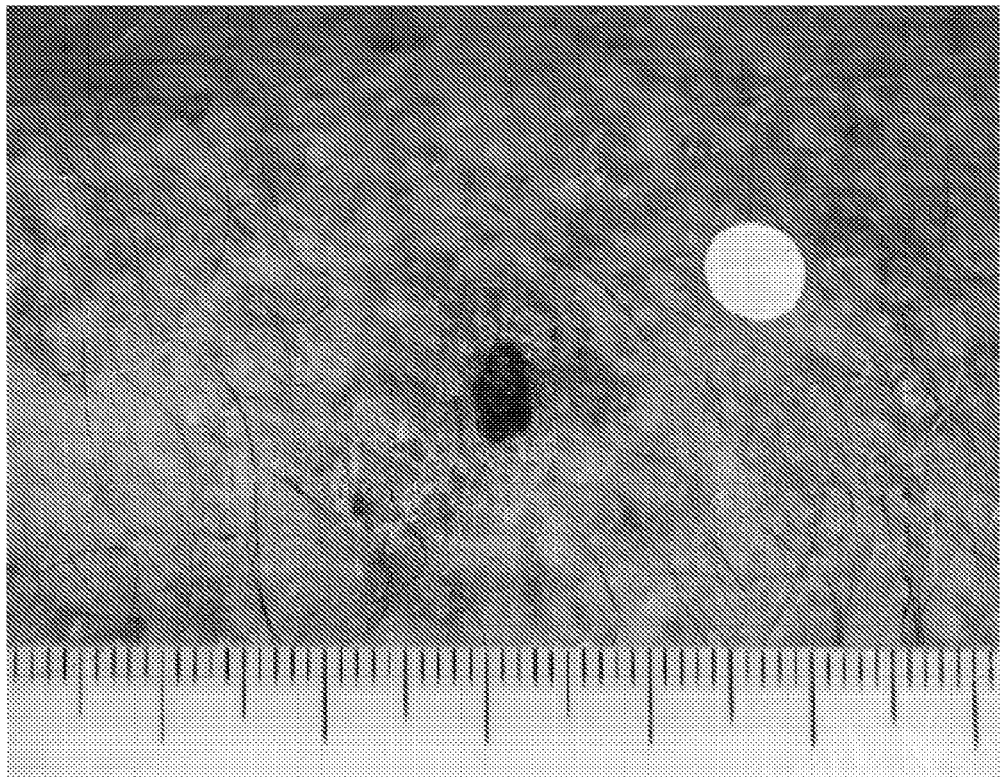
FIG. 35: Photographic depiction of a pre-treated target legion 3.
Figure 36:
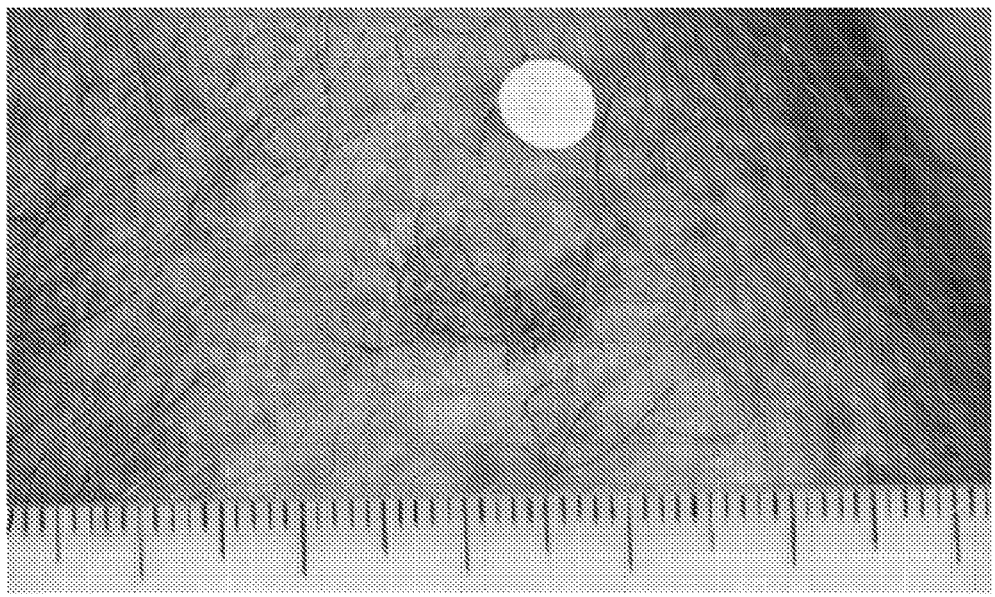
FIG. 36: Photographic depiction of a post-treated target legion 3.

In the structure of the ligand binding domain of HNF4alpha (1M7W.pdb; Dhe-Paganon (2002) JBC, 277, 37973); a small lipid was observed and which co-purified from *E. coli* production. The crystal contains two conformations of the protein, where the elongated helix 10 and short helix 12 have alternate conformations. Upon examination of the lipid binding region, it was interesting to observe that there are two exits regions. One exit region holds the small lipids head group, and it is noted that several pocket regions are co-localized with this exit port. A hypothesis would be that Q10 binds specifically to this transcription factor. When Q10 in modeled into this lipid binding tunnel, the Q10 ring would fit into the surface pocket (FIG. 28). A known loss-of-function mutation (E276Q) would have the potential to order the residues lining this surface pocket, and thus have a negative impact on the putative Q10 binding.

In addition, with this Q10 binding model, the hydrophobic tail would extend out of the internal cavity and would then interact with the elongated helix 10. Thus, this interaction could potential alter the conformation of the helix 10/12 group. This may then alter the activation/inactivation equilibrium of the transcription factor activity.

Example 7

Antibody MicroArray Analysis

The evaluation of protein concentration due to the presence of Q10 was evaluated through the utilization of antibody microarray methods. The microarray contained antibodies for over 700 proteins, sampling a broad range of protein types and potential pathway markers.

An initial experiment to assess changes at the protein concentration level in cells treated with Q10 was conducted with an antibody microarray (Panorama XP725 Antibody Array, Sigma) and SK-MEL-28 cells treated for 6 or 24 hour.

The cells were harvested and extracted to obtain a soluble protein supernatant. Two portions of protein (~1 mg total) from each sample (at 1 mg/mL) were each label with fluorescent dye (Cy3 and Cy5, respectively). The excess dye was removed from the protein and the material utilized for the microarray incubations. To compare two time point samples, equal amounts of protein were mixed, with each sample being of the different label type (e.g., 3 hour extract labeled with Cy3 was mixed with the 24 hour extract labeled with Cy5). After incubation with the microarray chip (according to manufactures recommended protocols), the chips were washed and dried. The microarrays were scanned with a fluorescent laser scanner to measure the relative fluorescence intensity of the Cy3 and Cy5 dyes.

TABLE 18

Proteins with increased levels in SK-MEL-28 cells after 24 hour treatment with 50 µM Q10

| Name | Ratio |
| --- | --- |
| Cdk1 | 0.1 |
| DcR1 | 0.1 |
| Protein Kinase Cb2 | 0.1 |
| Tumor Necrosis Factor Soluble Receptor II | 0.1 |
| BAD | 0.1 |
| Caspase13 | 0.2 |
| FBI1 PAKEMON | 0.2 |
| Zyxin | 0.2 |
| Cdc25A | 0.3 |
| PIASx | 0.3 |
| Nerve Growth Factor b | 0.3 |
| Protein Tyrosine Phosphatase PEST | 0.3 |
| hBRM hSNF2a | 0.4 |
| GRP94 | 0.4 |
| Calmodulin | 0.4 |
| Serine Threonine Protein Phosphatase 2C a b | 0.4 |
| ARC | 0.4 |
| NeurabinII | 0.4 |
| Nitric Oxide Synthase bNOS | 0.4 |
| Serine Threonine Protein Phosphatase 1b | 0.4 |
| Heat Shock Protein 110 | 0.4 |
| Serine Threonine Protein Phosphatase 1g1 | 0.4 |
| COX II | 0.5 |
| HSP70 | 0.5 |
| BLK | 0.5 |
| Cytokeratin 8 12 | 0.5 |
| BUBR1 | 0.5 |
| FOXC2 | 0.5 |
| Serine Threonine Protein Phosphatase 2 A Bg | 0.5 |
| MSH6 | 0.5 |
| DR6 | 0.5 |
| Rad17 | 0.5 |
| BAF57 | 0.5 |
| Transforming Growth Factorb pan | 0.5 |
| BTK | 0.5 |
| SerineThreonine Protein Phosphatase 2 A/B pan2 | 0.5 |
| CNPase | 0.5 |
| SynCAM | 0.5 |
| Proliferating Cell Nuclear Antigen | 0.5 |

TABLE 19

Proteins with increased levels in SK-MEL-28 cells after 24 hour treatment with 50 μM Q10

| Name | Ratio |
|---|---|
| BclxL | 4.2 |
| BID | 3.7 |
| Bmf | 3.7 |
| PUMA bbc3 | 3.0 |
| Zip Kinase | 2.8 |
| Bmf | 2.8 |
| DcR2 | 2.7 |
| E2F1 | 2.7 |
| FAK pTyr577 | 2.5 |
| FKHRL1 FOXO3a | 2.5 |
| MTBP | 2.5 |
| Connexin 32 | 2.5 |
| Annexin VII | 2.4 |
| p63 | 2.4 |
| SUMO1 | 2.4 |
| IAfadin | 2.3 |
| MDMX | 2.3 |
| Pyk2 | 2.3 |
| RIP Receptor Interacting Protein | 2.3 |
| RICK | 2.3 |
| IKKa | 2.3 |
| Bclx | 2.3 |
| Afadin | 2.2 |
| Proliferating Cell Protein Ki67 | 2.2 |
| Histone H3 pSer28 | 2.2 |
| CASK LIN2 | 2.2 |
| Centrin | 2.2 |
| TOM22 | 2.1 |
| Nitric Oxide Synthase Endothelial eNOS | 2.1 |
| Protein Kinase Ba | 2.1 |
| Laminin | 2.1 |
| Myosin Ib Nuclear | 2.1 |
| Caspase 7 | 2.1 |
| MAP Kinase 2 ERK2 | 2.1 |
| KIF17 | 2.1 |
| Claspin | 2.1 |
| GRP75 | 2.1 |
| Caspase 6 | 2.1 |
| ILP2 | 2.1 |
| aActinin | 2.1 |
| Vitronectin | 2.1 |
| DRAK1 | 2.1 |
| PTEN | 2.1 |
| Grb2 | 2.1 |
| HDAC4 | 2.0 |
| HDAC7 | 2.0 |
| Nitric Oxide Synthase bNOS | 2.0 |
| HDAC2 | 2.0 |
| p38 MAPK | 2.0 |
| Reelin | 2.0 |
| Protein Kinase Cd | 2.0 |
| cerbB3 | 2.0 |
| hSNF5 INI1 | 2.0 |
| Protein Kinase Ca | 2.0 |
| Glutamate receptor NMDAR 2a | 2.0 |
| Leptin | 2.0 |
| Dimethyl Histone H3 diMeLys4 | 2.0 |
| BID | 2.0 |
| MeCP2 | 2.0 |
| Nerve growth factor receptor p75 | 2.0 |
| Myosin Light Chain Kinase | 2.0 |
| cRaf pSer621 | 2.0 |
| GRP78 BiP | 2.0 |
| cMyc | 2.0 |
| Raf1 | 2.0 |
| MTA2 MTA1L | 2.0 |
| Sir2 | 2.0 |
| ATF2 pThr69 71 | 2.0 |
| Protein Kinase C | 2.0 |
| Protein Kinase Cb2 | 2.0 |

In order to confirm the previously observed apoptosis proteins, and to expand the evaluation into a larger number of pro-apoptosis and anti-apoptosis proteins, two assay methods were chosen which were capable of screening the broad family of proteins potentially involved.

First, an antibody micro array (Panorama XP725 Antibody Array, Sigma) was utilized to screen over 700 protein antibodies to assess changes at the protein concentration level in SK-MEL-28 cells treated for 24 hours with 50 μM Q10.

From the Antibody array experiments, on SKMEL-28 with Q10 (24 hr), the following are some of the identified proteins with altered levels: Bcl-xl, Bmf, BTK, BLK, cJun (pSer63), Connexin 32, PUMA bbc3, BID, Par4, cCbl. The key conclusion from this initial study was that the expected pro-apoptosis proteins are altered.

Antibody Microarray for SK-MEL-28

An antibody micro array (Panorama XP725 Antibody Array, Sigma) was utilized to screen over 700 protein antibodies to assess changes at the protein concentration level in SK-MEL-28 cells treated for 24 hours with 50 μM Q10.

TABLE 20

Changes in protein levels in SKMEL-28 treated with 50 μM Q10

| Name | Antibody Number (Sigma) | SKMEL28 Q10/ SKMEL28 control | SKMEL28/ HEKa control | HEKa Q10/ HEKa control |
|---|---|---|---|---|
| BclxL | B9429 | 2.46 | 1.04 | 1.83 |
| PUMA bbc3 | P4743 | 2.31 | 1.14 | 2.14 |
| Bmf | B1559 | 2.23 | 1.12 | 2.11 |
| Bmf | B1684 | 2.09 | 1.13 | 1.74 |
| cJun pSer63 | J2128 | 1.99 | 1.14 | 1.85 |
| BLK | B8928 | 1.94 | 1.05 | 1.51 |

From the Antibody array experiments, on SKMEL-28 with Q10 (24 hr), the following are some of the identified proteins with altered levels: Bcl-xl, Bmf, BTK, BLK, cJun (pSer63), Connexin 32, PUMA bbc3, BID, Par4, cCbl. These data confirm that the levels of pro-apoptosis proteins are altered upon incubation with elevated levels of exogenously added Q10.

Bcl-xl ("Basal cell lymphoma-extra large") is a transmembrane molecule in the mitochondria. It is involved in the signal transduction pathway of the FAS-L and is one of several anti-apoptotic proteins which are members of the Bcl-2 family of proteins. It has been implicated in the survival of cancer cells. However, it is known that alternative splicing of human Bcl-x mRNA may result in at least two distinct Bcl-x mRNA species, Bcl-xL and Bcl-xS. The predominant protein product (233 amino acids) is the larger Bcl-x mRNA, Bcl-xL, which inhibits cell death upon growth factor withdrawal (Boise et al., 1993. Cell 74, 597-608). Bcl-xS, on the other hand, inhibits the ability of Bcl-2 to 15 inhibit cell death and renders cells more susceptible to apoptotic cell death.

TABLE 21

Proteins with increased levels in SCC cells after 24 hour treatment with 100 μM Q10.

| Name | Ratio |
|---|---|
| PUMA bbc3 | 3.81 |
| HDAC7 | 3.21 |
| BID | 3.12 |
| MTBP | 3.00 |
| p38 MAP Kinase NonActivated | 2.93 |

TABLE 21-continued

Proteins with increased levels in SCC cells after 24 hour treatment with 100 μM Q10.

| Name | Ratio |
| --- | --- |
| PKR | 2.87 |
| TRAIL | 2.86 |
| DR5 | 2.86 |
| Cdk3 | 2.82 |
| NCadherin | 2.71 |
| Reelin | 2.68 |
| p35 Cdk5 Regulator | 2.63 |
| HDAC10 | 2.60 |
| RAP1 | 2.59 |
| PSF | 2.56 |
| cMyc | 2.55 |
| methyl Histone H3 MeLys9 | 2.54 |
| HDAC1 | 2.51 |
| F1A | 2.48 |
| ROCK1 | 2.45 |
| Bim | 2.45 |
| FXR2 | 2.44 |
| DEDAF | 2.44 |
| DcR1 | 2.40 |
| APRIL | 2.40 |
| PRMT1 | 2.36 |
| Pyk2 pTyr580 | 2.34 |
| Vitronectin | 2.33 |
| Synaptopodin | 2.32 |
| Caspase13 | 2.30 |
| Syntaxin 8 | 2.29 |
| DR6 | 2.29 |
| BLK | 2.28 |
| ROCK2 | 2.28 |
| Sir2 | 2.25 |
| DcR3 | 2.24 |
| RbAp48 RbAp46 | 2.21 |
| OGlcNAc Transferase | 2.21 |
| GRP78 BiP | 2.20 |
| Sin3A | 2.20 |
| p63 | 2.20 |
| Presenilin1 | 2.19 |
| PML | 2.18 |
| PAK1pThr212 | 2.17 |
| HDAC8 | 2.16 |
| HDAC6 | 2.15 |
| Nitric Oxide Synthase Inducible iNOS | 2.15 |
| Neurofibromin | 2.15 |
| Syntaxin 6 | 2.13 |
| Parkin | 2.12 |
| Rad17 | 2.11 |
| Nitric Oxide Synthase bNOS | 2.10 |
| TIS7 | 2.09 |
| OP18 Stathmin (stathmin 1/oncoprotein 18) | 2.08 |
| phospho-b-Catenin pSer45 | 2.07 |
| NeurabinII | 2.07 |
| e Tubulin | 2.07 |
| PKB pThr308 | 2.07 |
| Ornithine Decarboxylase | 2.07 |
| P53 BP1 | 2.06 |
| Pyk2 | 2.05 |
| HDAC5 | 2.05 |
| Connexin 43 | 2.05 |
| a1Syntrophin | 2.04 |
| MRP1 | 2.04 |
| cerbB4 | 2.03 |
| S Nitrosocysteine | 2.03 |
| SGK | 2.02 |
| Rab5 | 2.01 |
| Ubiquitin Cterminal Hydrolase L1 | 2.01 |
| Myosin Ib Nuclear | 2.00 |
| Par4 Prostate Apoptosis Response 4 | 2.00 |

TABLE 22

Proteins with reduced levels in SCC cells after 24 hour treatment with 100 μM Q10.

| Name | Ratio |
| --- | --- |
| AP1 | 0.68 |
| Centrin | 0.55 |
| CUGBP1 | 0.67 |
| Cystatin A | 0.69 |
| Cytokeratin CK5 | 0.60 |
| Fibronectin | 0.63 |
| gParvin | 0.70 |
| Growth Factor Independence1 | 0.63 |
| Nerve Growth Factor b | 0.60 |
| ProCaspase 8 | 0.72 |
| Rab7 | 0.62 |
| Rab9 | 0.73 |
| Serine Threonine Protein Phosphatase 1g1 | 0.71 |
| Serine Threonine Protein Phosphatase 2 A Bg | 0.73 |
| SKM1 | 0.70 |
| SLIPR MAGI3 | 0.67 |
| Spectrin a and b | 0.70 |
| Spred2 | 0.66 |
| TRF1 | 0.74 |

Example 8

Western Blot Analysis

The first experiment processed and evaluated by Western blot and 2-D gel electrophoresis was carried out on the skin cancer cell line SKMEL-28. This experimental set involved SK-MEL-28 cells treated at 3, 6, 12, and 24 hours with 50 or 100 μM Q10.

Figure 14:
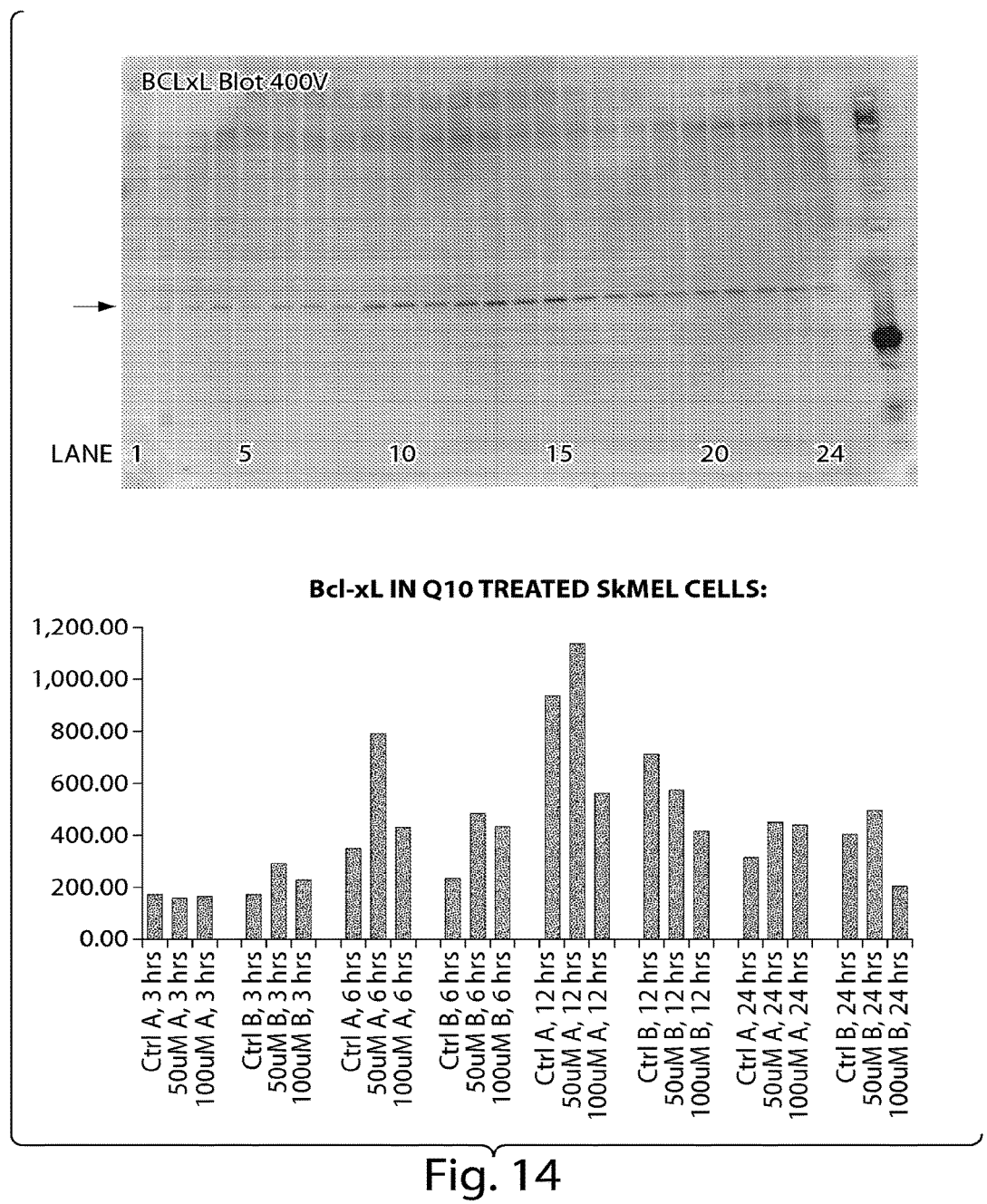
FIG. 14: Western blot analysis of Bcl-xl.
Figure 15:
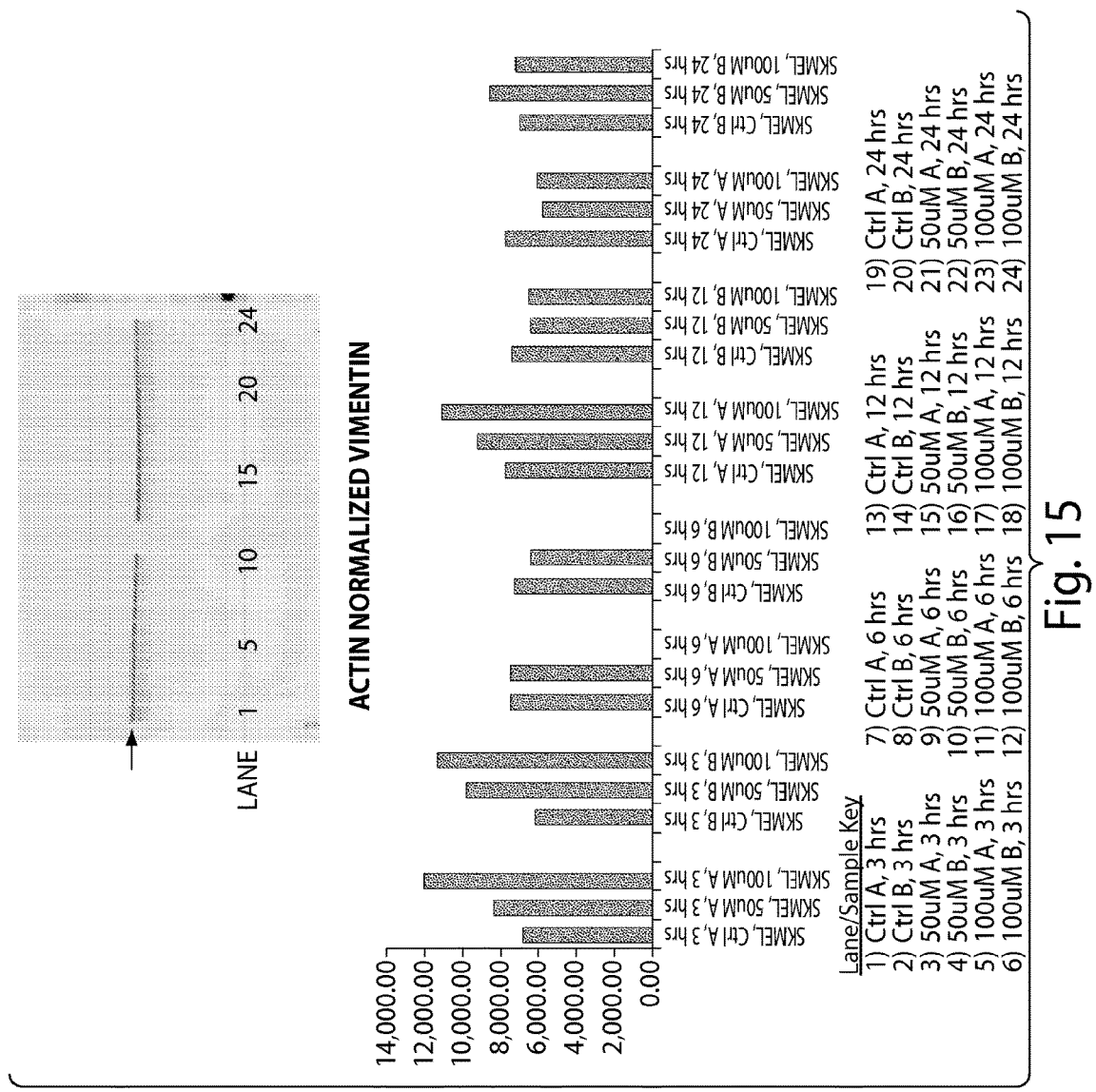
FIG. 15: Western blot analysis of SK-MEL-28 sample set proved with a Vimentin antibody.
Figure 16:
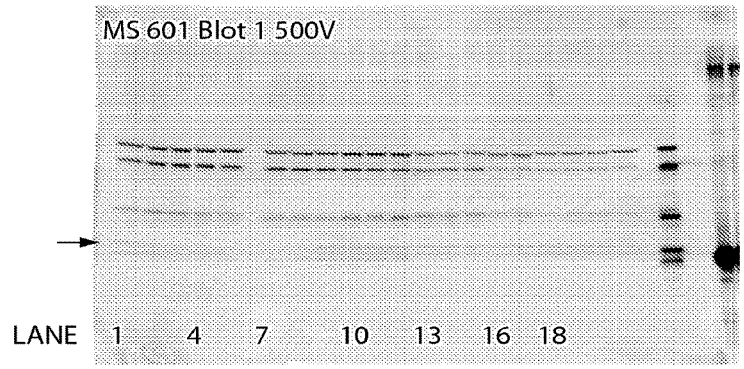
FIG. 16: Western blot analysis of cell lysis from a number of cell lines, evaluated with five antibodies targeting oxidative phosphorylation complexes (MitoSciences #MS601).
Figure 17:
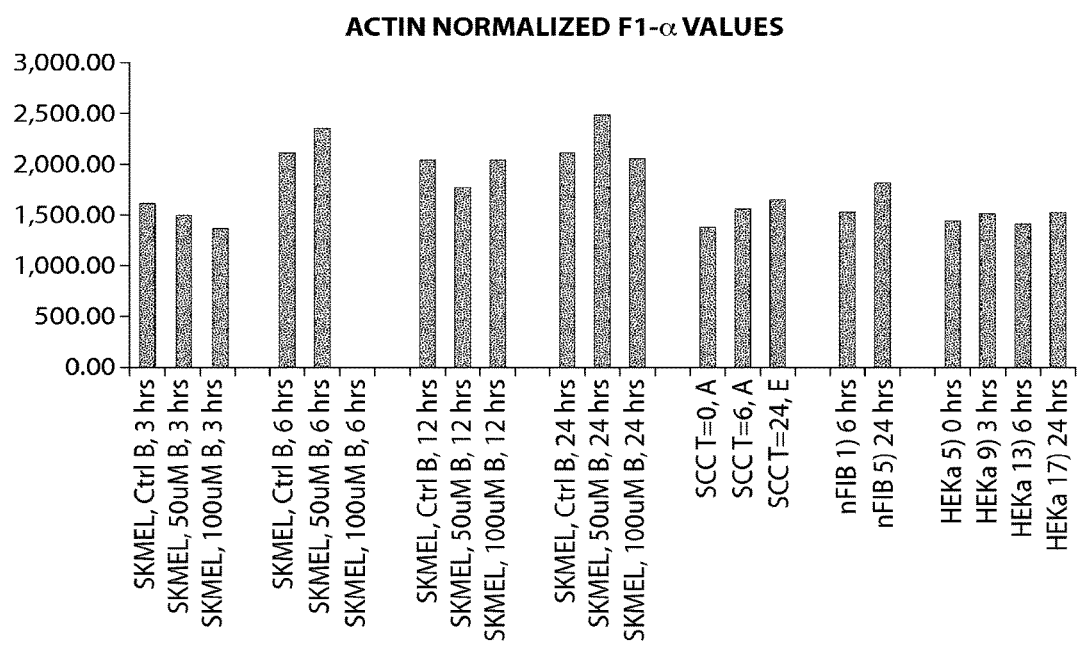
FIG. 17: Western blot comparison of F1-alpha levels.
Figure 18:
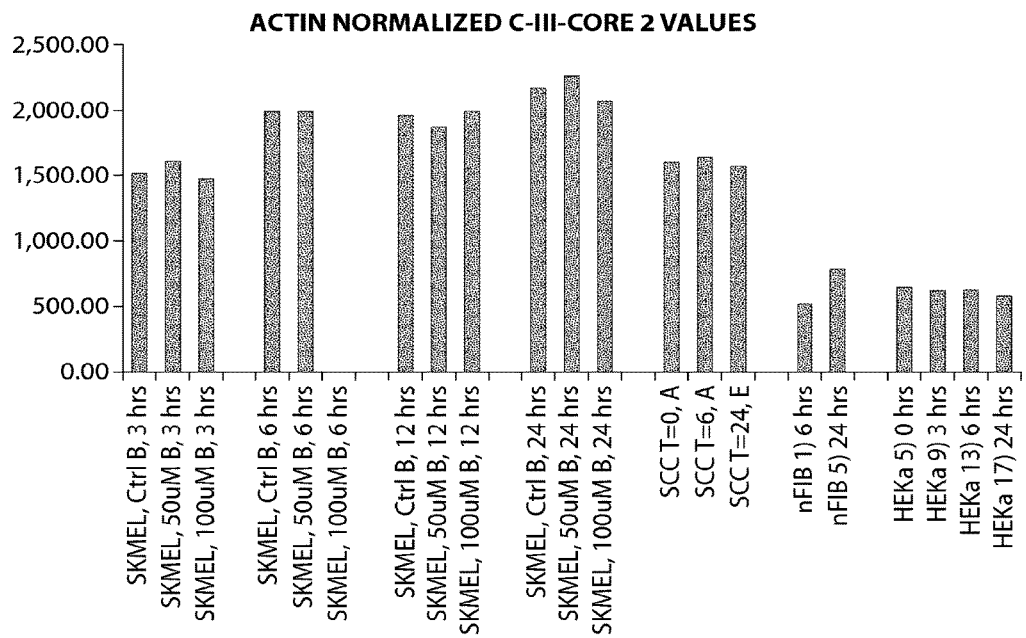
FIG. 18: Western blot comparison of Q10 response with C-III-Core 2.
Figure 19:
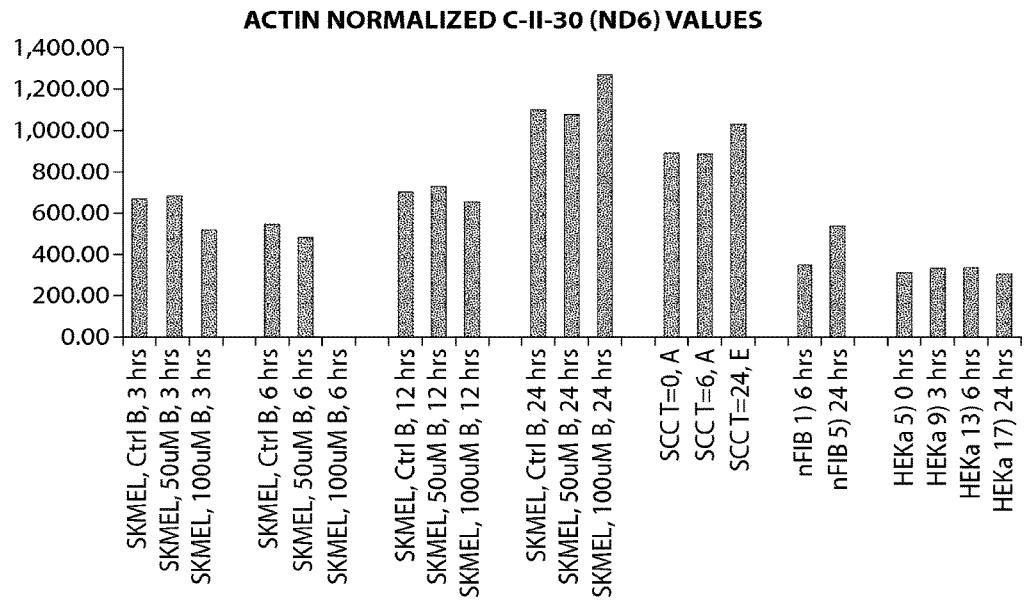
FIG. 19: Western blot comparison of Q10 response with C-II-30.
Figure 20:
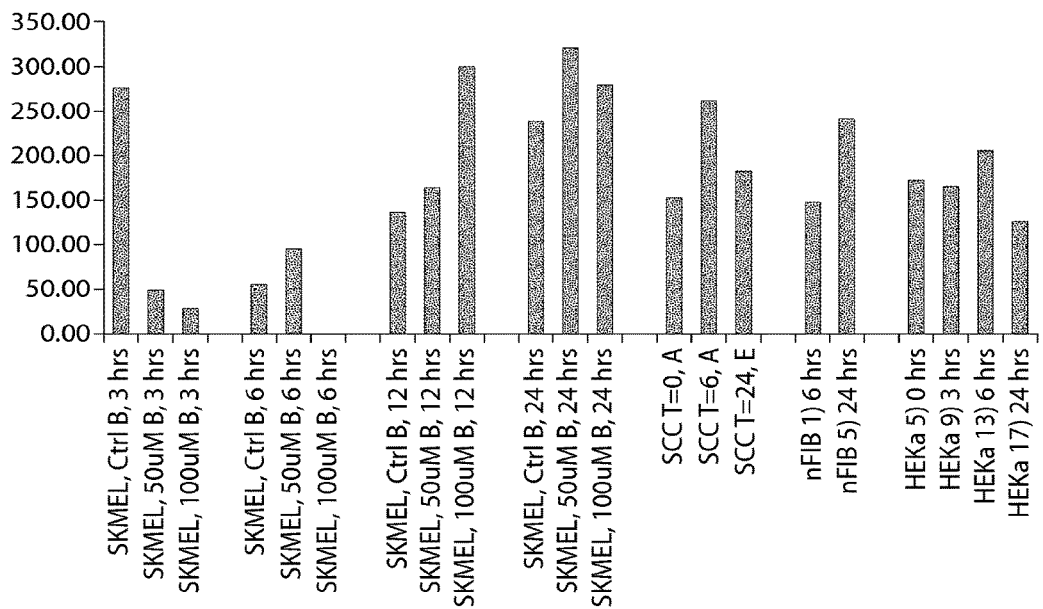
FIG. 20: Western blot comparison of Q10 response with C-IV-COX II.
Figure 21:
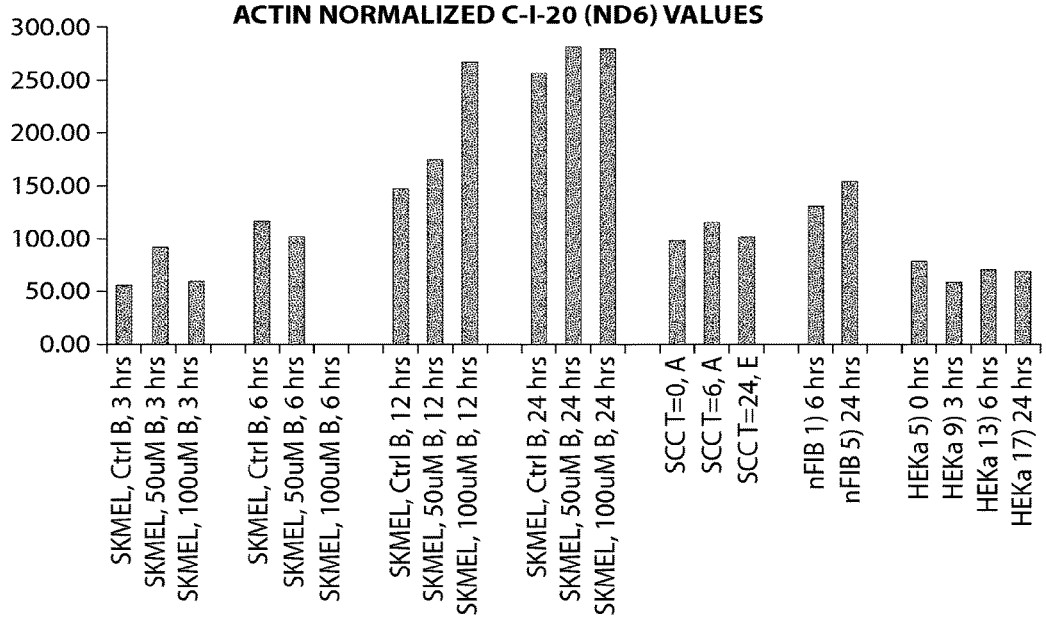
FIG. 21: Western blot comparison of Q10 response with C-I-20 (ND6).
Figure 22:
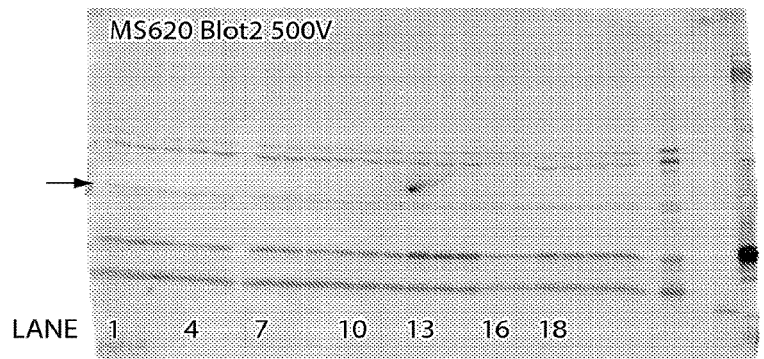
FIG. 22: Western blot analysis of a variety of cell types against five mitochondrial protein.
Figure 23:
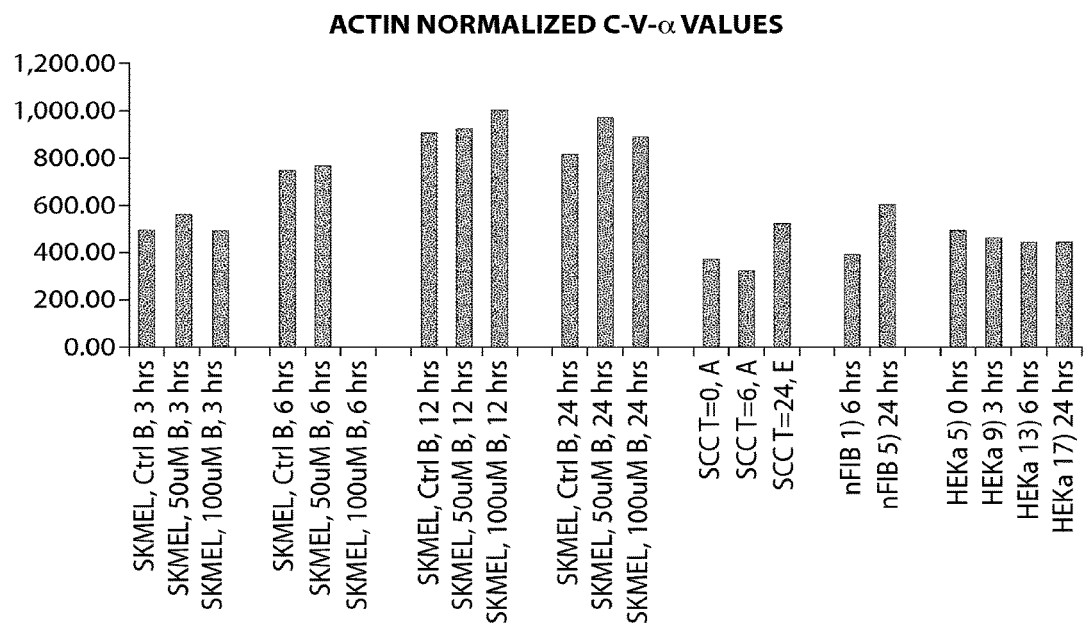
FIG. 23: Western blot comparison of Q10 response with Complex V protein C-V-α.
Figure 24:
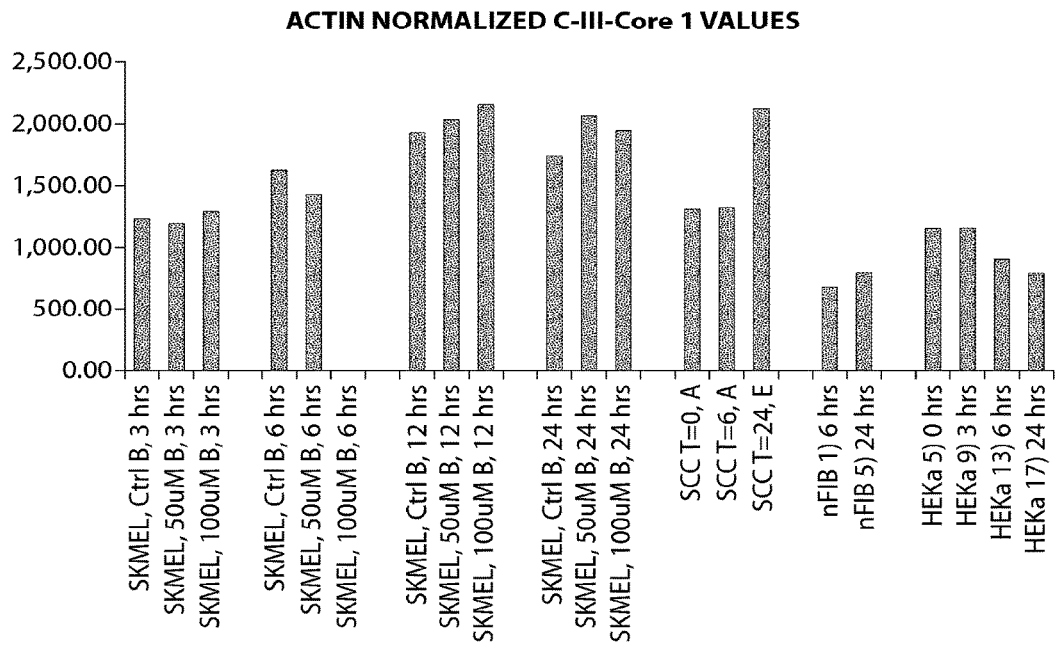
FIG. 24: Western blot comparison of Q10 response with C-III-Core 1.
Figure 25:
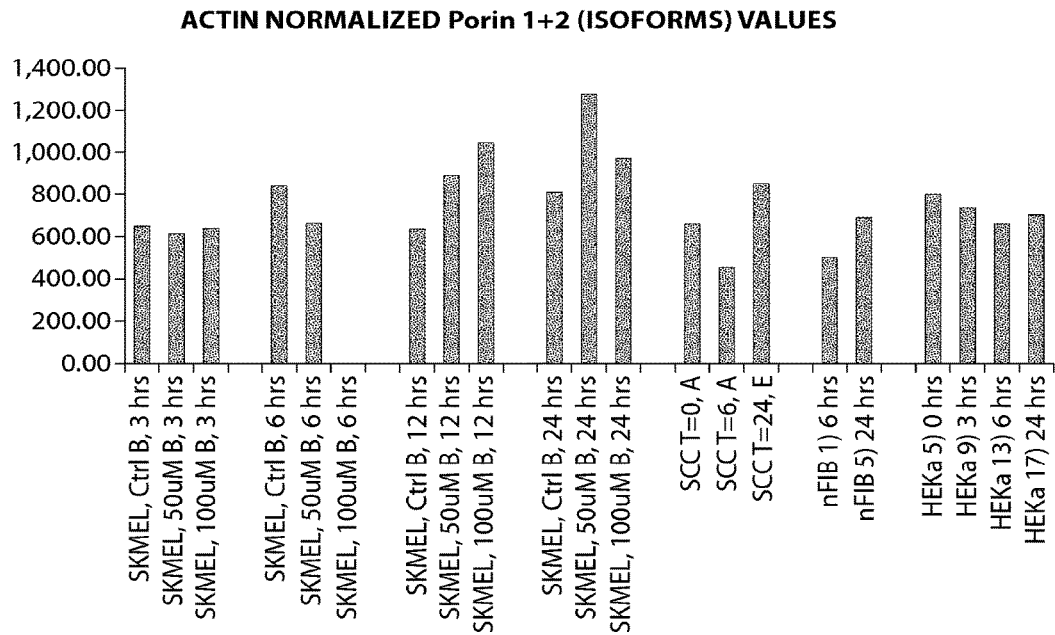
FIG. 25: Western blot comparison of Q10 response with Porin (VDAC1).
Figure 26:
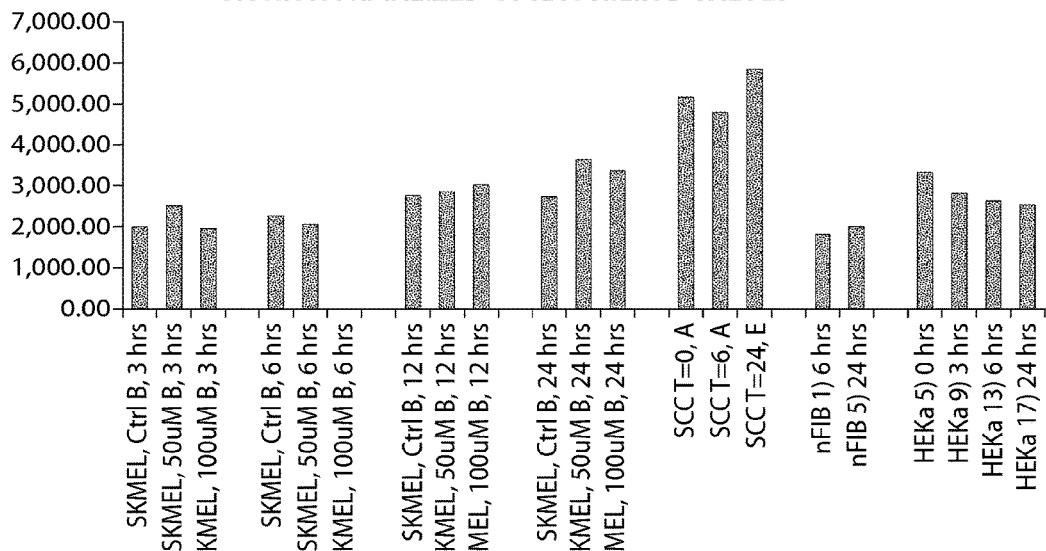
FIG. 26: Western blot comparison of Q10 response with Cyclophilin D.
Figure 27:
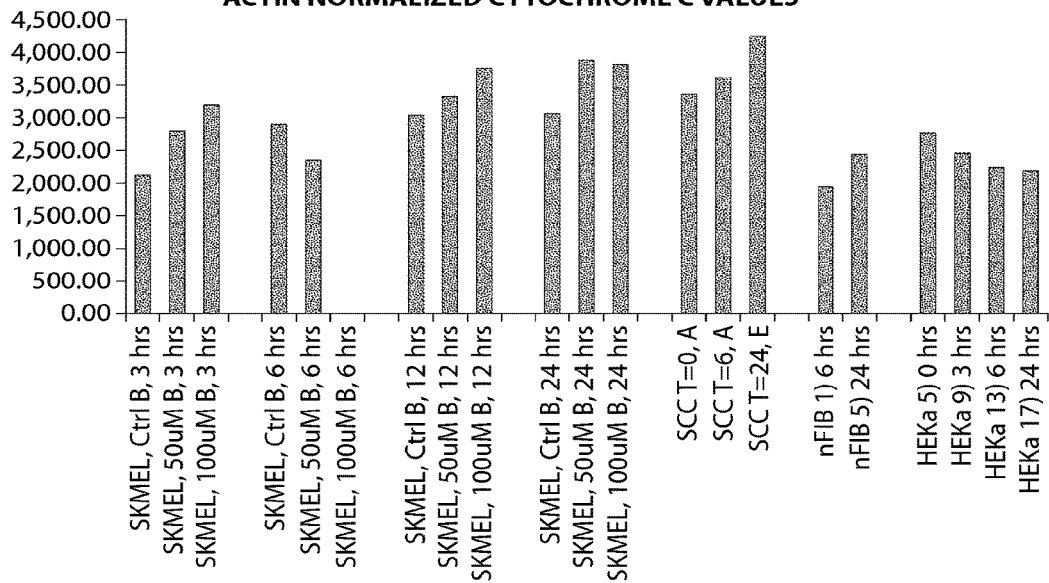
FIG. 27: Western blot comparison of Q10 response with Cytochrome C.

A variety of cell types were evaluated by Western blot analysis against an antibody for Bcl-xL (FIG. 14), an antibody for Vimentin (FIG. 15), a series of antibodies for mitochondrial oxidative phosphorylation function (FIGS. 16-21) and against a series of antibodies related to mitochondrial membrane integrity (FIGS. 22-27). The results from these experiments demonstrated that several of the examined proteins were upregulated or downregulated as a result of cell treatment with Q10.

Example 9

Diabetes Related Genes Identified as being Modulated at the mRNA Level by Treatment of Pancreatic Cancer Cells (PaCa2) with 100 um Q10

Diabetes arrays were run for samples treated with 100 uM Q10 at various times after treatment. Experiments were carried out essentially as described above. The various genes found to be modulated upon Q10 treatment are summarized in Table 23 below. The results showed that the following genes are modulated by Q10 treatment: ABCC8, ACLY, ADRB3, CCL5, CEACAM1, CEBRA, FOXG1, FOXP3, G6PD, GLP1R, GPD1, HNF4A, ICAM1, IGFBP5, INPPL1, IRS2, MAPK14, ME1, NFKB1, PARP1, PIK3C2B, PIK3CD, PPARGC1B, PRKAG2, PTPN1, PYGL, SLC2A4, SNAP25, HNF1B, TNRFSF1A, TRIB3, VAPA, VEGFA, IL4R and IL6.

TABLE 23

Genes from the diabetes array whose expression is regulated with 100 μM Q10 and their possible functions in a cell.

| Gene Name | Gene Function. |
|---|---|
| ADRB | cAMP signaling, G-protein signaling |
| CCL5 | Natural ligands for CCR5 and is regulated by TNF. |
| CEACAM1 | Anti-apoptotic, positive regulation of angiogenesis. |
| GLPR1 | Increases Insulin and decreases glucagon secretion from the pancreas. |
| GPD1 | Carbohydrate metabolism, NADH oxidation. |
| ICAM1 | Regulated by atorvastatin, processes some caspases. |
| MAPK14 | DNA damage checkpoint, angiogenesis, glucose metabolic process. |
| PARP1 | DNA repair, regulates TP53, NOS2A, NFKB, telomere maintenance. |
| PIK3C2B | Phosphoinositide mediated signaling, regulates AKT and AKT1. |
| PIK3CD | Kinase |
| PYGL | carbohydrate metabolism, regulates glycogen and glycogen synthase. |
| SLC2A4 | regulates glucose and is regulated by INS and insulin. |
| SNAP25 | regulation of insulin secretion, nerotransmitter uptake. |
| CEBPA | Glucocorticoid receptor signaling, VDR/RXR activation. |
| FOXP3 | Regulates IL4, IL2. |
| G6PD | Pentose Phosphate Pathway, Glutathione metabolism. |
| IGFBP5 | Regulation of cell growth, regulated by IGF1 |
| INPPL1 | Regulates Akt and glycogen. |
| IRS2 | IGF-1 signaling |
| ME1 | Regulates malic acid and is regulated by T3. |
| NFKB1 | Regulates IL6 and TNF. |
| PPARGC1B | Regulated by MAPK14 |
| PRKAG2 | Fatty acid, cholesterol biosynthesis. |
| PTPN1 | dephosphorylates JAK2 and EGFreceptor kinase. |
| VEGFA | Kinase, angiogenesis. |
| IL4R | Up regulation by TP73, binds to IRS1 and IRS2 |
| HNF1B | HNF4A |
| TNFRSF1A | Pro-apoptotic |
| TRIB3 | Regulates AKT1 and negative regulator of NFkB. |
| VAPA | Regulates NFkB, vesicle trafficking. |

Up-regulated (bold) and down-regulated (not bold).

Example 10

Angiogenesis Related Genes Identified as being Modulated at the mRNA Level by Treatment of Pancreatic Cancer Cells (PaCa2) with 100 μM Q10

Angiogenesis arrays were run for samples treated with 100 uM Q10 at various times after treatment. Experiments were carried out essentially as described above. The various genes found to be modulated upon Q10 treatment are summarized in Table 24 below. The results showed that the following genes are modulated by Q10 treatment: AKT1, ANGPTL4, ANGPEP, CCL2, CDH4, CXCL1, EDG1, EFNA3, EFNB2, EGF, FGF1, ID3, IL1B, IL8, KDR, NRP1, PECAM1, PROK2, SERPINF1, SPHK1, STAB1, TGFB1, VEGFA and VEGFB.

TABLE 24

A list of genes from the angiogenesis array whose expression is regulated with 100 μM Q10 and their possible functions in a cell.

| Gene | Gene Function. |
|---|---|
| ANGPTL4 | antiangiogenesis, negative regulator of apoptosis, lipid metabolism. |
| CDH5 | blood vessel maturation, cell-adhesion, negative regulator of cell proliferation. |
| FGF1 | Cell adhesion, cell proliferation. |
| AKT1 | carbohydrate metabolic process, glycogen biosynthetic process, glucose metabolic process, insulin receptor signaling pathway, activation of pro-apoptotic gene products, apoptotic mitochondrial changes |
| ANPEP | proteolysis, multicellular organismal development, cell differentiation |
| CCL2 | chemotaxis, anti-apoptosis, JAK-STAT cascade, organ morphogenesis, viral genome replication |
| CXCL1 | chemotaxis, inflammatory response, immune response, negative regulation of cell proliferation, actin cytoskeleton organization and biogenesis. |
| EDG1 | positive regulation of cell proliferation, transmission of nerve impulse, regulation of cell adhesion, neuron differentiation, positive regulation of cell migration, positive regulation of Ras |
| EFNB2 | cell-cell signaling, regulated by VEGFA. |
| EGF | activation of MAPKK activity, positive regulation of mitosis, DNA replication |
| IL1B | response to glucocorticoid stimulus, apoptosis, signal transduction, cell-cell signaling, negative regulation of cell proliferation |
| IL8 | cell cycle arrest |
| KDR | VEGF pathway, regulated by AKT. |
| NRP1 | cell adhesion, signal transduction, cell-cell signaling, cell proliferation, regulated by VEGFA |
| PECAM1 | cell adhesion, regulated by TNF. |
| PROK2 | activation of MAPK, anti-apoptosis, cell proliferation, regulates AKT, |
| SPHK1 | anti-apoptosis, cell proliferation, regulates mitosis, cell migration. |
| STAB1 | inflammatory response, cell adhesion, receptor-mediated endocytosis, cell-cell signaling, negative regulation of angiogenesis, defense response to bacterium |
| VEGFA | anti-apoptosis, regulates TNF, regulated by HIF1. |

Up-regulated (bold) and down-regulated (not bold).

Example 11

Apoptosis Related Genes Identified as being Modulated at the mRNA Level by Treatment of Pancreatic Cancer Cells (PaCa2) with 100 μM Q10

Apoptosis arrays were run for samples treated with 100 uM Q10 at various times after treatment. Experiments were carried out essentially as described above. The various genes found to be modulated upon Q10 treatment are summarized in Table 25 below. The results showed that the following genes are modulated by Q10 treatment: ABL1, AKT1, Bcl2L1, BclAF1, CASP1, CASP2, CASP6, CIDEA, FADD, LTA, TNF, TNFSF10A and TNFSF10.

TABLE 25

A list of genes from the apoptosis array whose expression is regulated with 100 μM Q10 and their possible functions in a cell.

| Gene | Gene Function. |
|---|---|
| CASP1 | Pro-Apoptotic, Regulates IL1B, regulated by TNF. |
| CASP6 | Pro-Apoptotic, regulates PARP, MCL1, APP |
| TNF | cell proliferation, differentiation, apoptosis, lipid metabolism, and coagulation |
| TNFSF10 | Pro-Apoptotic, regulates caspases. |
| ABL1 | Regulates Bcl2L1, TP53, Pro-apoptotic, actin cytoskeleon organization and biogenesis. |
| AKT1 | Prop-apoptotic, apoptotic mitochondrial changes, carbohydrate transport, response to heat, glucose metabolism, IGF signaling pathway. |
| BclAF1 | Pro-Apoptotic. |
| Bcl2L1 | Anti-Apoptotic, release of cytochrome c from mitochondria, regulates Caspases, binds to BAD, BAX, BCl2L11 |

TABLE 25-continued

A list of genes from the apoptosis array whose expression is regulated with 100 μM Q10 and their possible functions in a cell.

| Gene | Gene Function. |
|---|---|
| CASP2 | Anti-Apoptotic. |
| CIDEA | Pro-Apoptotic |
| FADD | Pro-Apoptotic |
| LTA | Pro-Apoptotic |
| TNFSF10A | Caspase Activator |

Up-regulated (bold) and down-regulated (not bold).

Example 12

PCR Diabetes Arrays on Liver Cancer (HepG2) Cells

HepG2 (liver cancer) cells were treated with either the vehicle for 24 hours or 100 μM Q10 for different times. The treatment was initiated on 1×105 cells per well, following the procedure utilized in the PaCa2 cells (above, Examples 9-11). However, the total amount of RNA that was extracted from these samples was lower than expected. Reverse transcription is normally done using 1 μg total RNA (determined by measurement at 260 nm). The maximum volume that can be used per reverse transcription is 8 μl. Since the RNA concentration was low, the RT-PCR array analysis using the vehicle, and Q10 treated samples from 16 hours and 48 hours was performed using 0.44 pg of RNA. The arrays provided an initial analysis of trends and patterns in HepG2 gene regulation with 100 pM Q10 treatment, as summarized in Table 26 below. The results showed that each of the genes PPARGCIA, PRKAA1 and SNAP25 were downregulated at 16 hours follow ing treatment (by approximately 20 fold, 6 fold and 5 fold, respectively). At 48 hours following treatment, PPARGCIA and PRKAA1 had normalized or were slightly upregulated, while SNAP25 was downregulated by approximately 2 fold.

TABLE 26

List of genes regulated in the Diabetes Arrays when HepG2 cells were treated with 100 μM Q10.

| Gene | Gene name | Gene Function. |
|---|---|---|
| PPARGC1A | peroxisome proliferator-activated receptor gamma, coactivator 1 alpha | Involved in cell death, proliferation, cellular respiration and transmembrane potential. |
| PRKAA1 | protein kinase, AMP-activated, alpha 1 catalytic subunit | Regulates TP53 and is involved in apoptosis, regulates glycolysis, regulates metabolic enzyme activities. |
| SNAP25 | synaptosomal-associated protein, 25 kDa | Plays in transport, fusion, exocytosis and release of molecules. |

Example 13

PCR Angiogenesis Array on Liver Cancer (HEPG2) Cells

HepG2 (liver cancer) cells were treated with either the vehicle for 24 hours or 100 μM Q10 for different times. The treatment was initiated on 1×105 cells per well, following the procedure utilized in the PaCa2 cells (above Examples 9-11). However, the total amount of RNA that was extracted from these samples was lower than expected. Reverse transcription is normally done using 1 μg of total RNA (determined by measurement at 260 nm). The maximum volume that can be used per reverse transcription is 8 μl. Since the RNA concentration was low, the RT-PCR array analysis using the vehicle, and Q10 treated samples from 16 hours and 48 hours was performed using 0.44 μg of RNA. The arrays provided an initial analysis of trends and patterns in HepG2 gene regulation with 100 μM Q10 treatment, as summarized in Table 27 below. The various genes found to be modulated upon Q10 treatment are summarized in Table 27 below. The results showed that each of the genes ANGPTL3, ANGPTL4, CXCL1, CXCL3, CXCL5, ENG, MMP2 and TIMP3 were upregulated at 16 hours following treatment (by approximately 5.5, 3, 3, 3.2, 3, 3, 1 and 6.5 fold, 6 fold and 5 fold, respectively, over that of control). ID3 was downregulated at 16 hours following Q10 treatment, by approximately 5 fold over control. At 48 hours following treatment, ANGPTL3, CXCL1, CXCL3, ENG and TIMP3 were still upregulated (by approximately 3.5, 1.5, 3.175, 2 and 3 fold, respectively, over control), while ANGPTL4, CXCL5, ID3 and MMP2 were downregulated by approximately 1, 1, 2 and 18 fold, respectively, over control.

TABLE 27

List of genes regulated in the Angiogenesis Arrays when HepG2 cells were treated with 100 μM Q10.

| Gene | Gene Name. | Gene Function. |
|---|---|---|
| ANGPTL3 | angiopoietin-like 3 | Predominantly expressed in live, role in cell migration and adhesion, regulates fatty acid and glycerol metabolism. |
| ANGPTL4 | angiopoietin-like 4 | Regulated by PPARG, apoptosis inhibitor for vascular endothelial cells, role lipid and glucose metabolism and insulin sensitivity |
| CXCL1 | chemokine (C-X-C motif) ligand 1 (melanoma growth stimulating activity, alpha) | Role in cell proliferation and migration |
| CXCL3 | chemokine (C-X-C motif) ligand 3 | Chemokine activation, hepatic stellar cell activation, migration, proliferation. |
| CXCL5 | chemokine (C-X-C motif) ligand 5 | Produced along with IL8 when stimulated with IL1 or TNFA. Role in chemotaxis, migration, proliferation. |

TABLE 27-continued

List of genes regulated in the Angiogenesis Arrays when HepG2 cells were treated with 100 μM Q10.

| Gene | Gene Name. | Gene Function. |
| --- | --- | --- |
| ENG | endoglin | Binds to TGFBR and is involved in migration, proliferation, attachment and invasion. |
| ID3 | inhibitor of DNA binding 3, dominant negative helix-loop-helix protein | Regulates MMP2, Regulated by TGFB1, Vitamin D3, Retinoic acid, VEGFA, involved in apoptosis, proliferation, differentiation, migration. |
| MMP2 | matrix metallopeptidase 2 (gelatinase A, 72 kDa gelatinase, 72 kDa type IV collagenase) | Hepatic stellate cell activation, HIF☐ signaling, binds to TIMP3, involved in tumorigenesis, apoptosis, proliferation, invasiveness, migration and chemotaxis. |
| TIMP3 | TIMP metallopeptidase inhibitor 3 | Regulates MMP2, ICAM1. Regulated by TGFB, EGF, TNF, FGF and TP53. Involved in apoptosis, cell-cell adhesion and malignancy. |

Proteins known to be involved in the process of angiogenesis were components in the RT-PCR array. Angiogenesis is a critical process by which cancer cells become malignant. Some of these proteins are also implicated in diabetes.

ANGPTL3 and ANGPTL4: The literature related to ANGPTL3 connects this protein to the regulation of lipid metabolism. In particular, the literature (Li, C. *Curr Opin Lipidol.* 2006 Apr.; 17(2):152-6) teaches that both angiopoietins and angiopoietin-like proteins share similar domain structures. ANGPTL3 and 4 are the only two members of this superfamily that inhibit lipoprotein lipase activity. However, ANGPTL3 and 4 are differentially regulated at multiple levels, suggesting non-redundant functions in vivo. ANGPTL3 and 4 are proteolytically processed into two halves and are differentially regulated by nuclear receptors. Transgenic overexpression of ANGPTL4 as well as knock-out of ANGPTL3 or 4 demonstrate that these two proteins play essential roles in lipoprotein metabolism: liver-derived ANGPTL3 inhibits lipoprotein lipase activity primarily in the fed state, while ANGPTL4 plays important roles in both fed and fasted states. In addition, ANGPTL4 regulates the tissue-specific delivery of lipoprotein-derived fatty acids. ANGPTL4 is thus an endocrine or autocrine/paracarine inhibitor of lipoprotein lipase depending on its sites of expression.

Lipoprotein lipase is an enzyme that hydrolyzes lipids in lipoproteins, such as those found in chylomicrons and very low-density lipoproteins (VLDL), into three free fatty acids and one glycerol molecule. Lipoprotein lipase activity in a given tissue is the rate limiting step for the uptake of triglyceride-derived fatty acids. Imbalances in the partitioning of fatty acids have major metabolic consequences. High-fat diets have been shown to cause tissue-specific overexpression of LPL, which has been implicated in tissue-specific insulin resistance and consequent development of type 2 diabetes mellitus.

The results in this Example indicate that Q10 is modulating proteins involved in lipid metabolism and thus warrants further investigation of ANGPTL3/ANGPTL4 and their related pathways. For example, ANGPTL3/ANGPTL4 have been implicated to play a role in the following pathways: Akt, cholesterol, fatty acid, HDL-cholesterol, HNF1A, ITGA5, ITGA5, ITGAV, ITG83, L-trilodothynonine, LIPG, LPL, Mapk, Nrth, NR1H3, PPARD, PTK2, RXRA, triacylglerol and 9-cis-retinoic acid.

Example 14

PCR Apoptosis Array on Liver Cancer (HEPG2) Cells

Apoptosis arrays were run for samples treated with 100 uM Q10 for 16 and 48 hours as described above. However, the array for 48 hours was run choosing FAM as the fluorophore instead of SYBR. Both FAM and SYBR fluoresce at the same wavelength.

The various genes found to be modulated upon Q10 treatment are summarized in Table 28 below. The results showed that CASP9 was upregulated at 16 hours following Q10 treatment, by approximately 61 fold over control, while BAG1 and TNFRSF1A were downregulated at 16 hours following treatment by approximately 6 and 4 fold, respectively, over that of control. At 48 hours following treatment, CASP9, BAG1 and TNFRSF1A were upregulated by approximately 55, 1 and 1 fold, respectively, over control.

TABLE 28

List of genes regulated in the Apoptosis Arrays when HepG2 cells were treated with 100 μM Q10.

| Gene | Gene Name | Gene Function. |
| --- | --- | --- |
| BAG1 | BCL2-associated athanogene | Involved with Apoptosis |
| CASP9 | caspase 9, apoptosis-related cysteine peptidase | Apoptosis through release of cytochrome c. |
| TNFRSF1A | tumor necrosis factor receptor superfamily, member 1A | anti-apoptosis, binds many cell death factors, regulates ICAM1 |

Example 15

Assessing Ability of MIM or Epi-Shifter to Treat Oncological Disorder

The ability of a selected MIM or Epi-shifter, e.g., CoQ10, to treat an oncological disorder, e.g., melanoma, is evaluated in a murine model. Melanoma tumors are induced in mice by SK-MEL28 injection into the subcutaneous layer. The animal study consists of both a control and treatment group each containing four mice. The mice are inoculated with two tumors. A topical formulation of the MIM or Epi-shifter is applied to the tumors in the treatment group daily for a period of 30 days, after which, the tumors are excised and the mass is determined. A MIM or Epi-shifter is identified as effective in treating the tumor when the difference in the overall mean mass of the treatment group is significant compared to the control.

Example 16

Identification of a MIM Associated with an Oncological Disorder

In order to evaluate a candidate molecule (e.g., environmental influencer) as a potential MIM, the selected candidate MIM is exogenously added to a panel of cell lines, including both diseased (cancer) cell lines and normal control cell lines, and the changes induced to the cellular microenvironment profile for each cell line in the panel are assessed. Changes to cell morphology, physiology, and/or to cell composition, including for example, mRNA and protein levels, are evaluated and compared for the diseased cells as compared to normal cells.

Changes to cell morphology/physiology are evaluated by examining the sensitivity and apoptotic response of cells to the candidate MIM. These experiments are carried out as described in detail in Example 3. Briefly, a panel of cell lines consisting of at least one control cell line and at least one cancer cell line are treated with various concentrations of the candidate MIM. The sensitivity of the cell lines to the potential MIM are evaluated by monitoring cell survival at various times, and over the range of applied concentrations. The apoptoic response of the cell lines to the potential MIM are evaluated by using, for example, Nexin reagent in combination with flow cytometry methodologies. Nexin reagent contains a combination of two dyes, 7AAD and Annexin-V-PE, and allows quantification of the population of cells in early and late apoptosis. An additional apoptosis assay that measures single-stranded DNA may be used, using for example Apostrand™ ELISA methodologies. The sensitivity and apoptotic response of the disease and control cell lines are evaluated and compared. A molecule that displays differential cytotoxicity and/or that differentially induces the apoptotic response in the diseased cells as compared to the normal cells is identified as a MIM.

Changes in the composition of cells following treatment with the candidate MIM are evaluated. Changes in gene expression at the mRNA level are analyzed using Real-Time PCR array methodology. These experiments are carried out as described in detail in Examples 6 and 9-13. Briefly, the candidate MIM is exogenously added to one or more cell lines including, for example a diseased cell and a normal control cell line, and mRNA is extracted from the cells at various times following treatment. The level of mRNAs for genes involved in specific pathways are evaluated by using targeted pathway arrays, including, for example, arrays specific for apoptosis, oxidative stress and antioxidate defense, angiogenesis, heat shock or diabetes. The genes that are altered in their mRNA transcription by a two-fold level or greater are identified and evaluated. A molecule that induces changes in mRNA levels in cells and/or that induces differential changes in the level of one or more mRNAs in the diseased cells as compared to the normal cells is identified as a MIM.

In complementary experiments, changes in gene expression at the protein level are analyzed by using antibody microarray methodology, 2-dimensional gel electrophoresis followed by protein identification using mass spectrometry characterization, and by western blot analysis. These experiments are carried out as described in detail in Examples 7, 4 and 8, respectively. Briefly, the candidate MIM is exogenously added to one or more cell lines, including, for example a diseased cell and a normal control cell line, and soluble protein is extracted from the cells at various times, e.g., 6 hours or 24 hours, following treatment. Changes induced to protein levels by the candidate MIM are evaluated by using an antibody microarray containing antibodies for over 700 proteins, sampling a broad range of protein types and potential pathway markers. Further complementary proteomic analysis can be carried by employing 2-dimensional (2-D) gel electrophoresis coupled with mass spectrometry methodologies. The candidate MIM is exogenously added to one or more cell lines, including, for example a diseased cell and a normal control cell line, and cell pellets are lysed and subjected to 2-D gel electrophoresis. The gels are analyzed to identify changes in protein levels in treated samples relative to control, untreated samples. The gels are analyzed for the identification of spot changes over the time course of treatment due to increased levels, decreased levels or post-translational modification. Spots exhibiting statistically significant changes are excised and submitted for protein identification by trypsin digestiona dn mass spectrometry characterization. The characterized peptides are searched against protein databases with, for example, Mascot and MSRAT software analysis to identify the proteins. In addition to the foregoing 2-D gel analysis and antibody microarray experiments, potential changes to levels of specific proteins induced by the candidate MIM may be evaluated by Western blot analysis. In all of the proteomic experiments, proteins with increased or decreased levels in the various cell lines are identified and evaluated. A molecule that induces changes in protein levels in cells and/or that induces differential changes in the level of one or more proteins in the diseased cells as compared to the normal cells is identified as a MIM.

Genes found to be modulated by treatment with a candidate MIM from the foregoing experiments are subjected to cellular and biochemical pathway analysis and can thereby be categorized into various cellular pathways, including, for example apoptosis, cancer biology and cell growth, glycolysis and metabolism, molecular transport, and cellular signaling.

Experiments are carried out to confirm the entry of a candidate MIM into cells, to determine if the candidate MIM becomes localized within the cell, and to determine the level and form of the candidate MIM present in the cells. These experiments are carried out, for example, as described in detail in Example 5. For example, to determine the level and the form of the candidate MIM present in the mitochondria, mitochondrial enriched preparations from cells treated with the candidate MIM are prepared and analyzed. The level of the candidate MIM present in the mitochondria can thereby be confirmed to increase in a time and dose dependent manner with the addition of exogenous candidate MIM. In addition, changes in levels of proteins from mitochondria enriched samples are analyzed by using 2-D gel electrophoresis and protein identification by mass spectrometry characterization, as described above for total cell protein samples. Candidate MIMs that are found to enter the cell and to be present at increased levels, e.g., in the mitochondria, are identified as a MIM. The levels of the candidate MIM in the cell, or, for example, specifically in the mitochondria, over the time course examined can be correlated with other observed cellular changes, as evidenced by, for example, the modulation of mRNA and protein levels for specific proteins.

Candidate MIMs observed to induce changes in cell composition, e.g., to induce changes in gene expression at the mRNA or protein level, are identified as a MIM. Candidate MIMs observed to induce differential changes in cell morphology, physiology or cell composition (e.g., differential changes in gene expression at the mRNA or protein level), in a disease state (e.g., cancer) as compared to a normal (e.g., non-cancerous) state are identified as a MIM and, in particular, as having multidimensional character. Candidate MIMs found to be capable of entering a cell are identified as a MIM and, in particular, as having multidimensional character since the candidate MIM thereby exhibits a carrier effect in addition to a therapeutic effect.

Example 17

Identification of CoQ10 as an Epi-shifter Associated with a Oncological Disorder A panel of skin cell lines consisting of a control cell lines (primary culture of keratinocytes and melanocytes) and several skin cancers cell lines (SK-MEL-28, a non-metastatic skin melanoma; SK-MEL-2, a metastatic skin melanoma; or SCC, a squamous cell carcinoma; PaCa2, a pancreatic cancer cell line; or HEP-G2, a liver cancer cell line) were treated with various levels of Coenzyme Q10. The cancer cell lines exhibited an altered dose dependent response when compared to the control cell lines, with an induction of apoptosis and cell death in the cancer cells only. Detailed exemplary experiments are presented in, e.g., Example 3 herein.

Assays were employed to assess changes in the mRNA and protein levels composition of the above-identified cells following treatment with CoQ10. Changes in mRNA expression were analyzed using real-time PCR microarrays specific for each of apoptosis, oxidative stress and antioxidants, angiogenesis and diabetes. Changes in protein expression were analyzed using antibody microarray analysis and western blot analysis. The results from these assays demonstrated that significant changes in gene expression, both at the mRNA and protein levels, were occurring in the cell lines due to the addition of the Coenzyme Q10. Numerous genes known to be associated with or involved in cellular metabolic processes were observed to be modulated as a result of treatment with CoQ10. For example, expression of the nuclear receptor protein HNF4A was found to be upmodulated in cells following Q10 treatment. Expression of transaldolase 1 (TAL) was also modulated in cells treated with Q10. TAL balances the levels of NADPH and reactive oxygen intermediate, thereby regulating the mitochondrial trans-membrande potential, which is a critical checkpoint of ATP synthesis and cell survival. Of particular relevance to oncological disorders, numerous genes known to be associated with, e.g., apoptosis, cancer biology and cell growth, were identified as being regulated by Q10. Detailed exemplary experiments are presented in, e.g., Examples 4, 6, 7, 8 and 9 herein.

Q10 is an essential cofactor for exidative phosphorylation processes in the mitochondria for energy production. The level of Coenzyme Q10, as well as the form of CoQ10, present in the mitochondria was determined by analyzing mitochondrial enriched preparations from cells treated with CoQ10. The level of Coenzyme Q10 present in the mitochondria was confirmed to increase in a time and dose dependent manner with the addition of exogenous Q10. The time course correlated with a wide variety of cellular changes as observed in modulation of mRNA and protein levels for specific proteins related to metabolic and apoptotic pathways. Detailed exemplary experiments are presented in, e.g., Example 5 herein.

The results described herein identified the endogenous molecule CoQ10 as an epi-shifter. In particular, the results identified CoQ10 as inducing a shift in the metabolic state, and partially restoration of mitochondrial function, in cells. These conclusions are based on the following interpretation of the data described herein and the current knowledge in the relevant art.

Q10 is known to be synthesized, actively transported to, enriched in, and utilized in the mitochondrial inner membrane. Q10 is also known to be an essential cofactor for oxidative phosphorylation processes in the mitochondrial for energy production. However, most cancer cells predominantly produce energy by glycolysis followed by lactic acid fermentation in the cytosol, rather than by oxidation of pyruvate in mitochondria like most normal cells. The oxidative phosphorylation involves the electron transport complexes and cytochrome c. Apoptosis involves the disruption of the mitochondria, with permeabilization of the inter mitochondrial membrane by pro-apoptitic factors. By utilizing a different metabolic energy synthesis pathway, cancer cells are able to mitigate the normal apoptosis response to abnormalities in the cell. While not wishing to be bound by theory, Applicants propose that Q10 is functioning by upregulating the oxidative phosphorylation pathway proteins, thus switching the mitochondrial function back to a state that would recognize the oncogenic defects and trigger apoptosis. Thus, Q10 is acting as an Epi-shifter by shifting the metabolic state of a cell.

Example 18

Identification of an Epi-shifter Associated with an Oncological Disorder

A panel of skin cell lines consisting of control cell lines (e.g., primary culture of keratinocytes and melanocytes) and cancer cell lines (e.g., SK-MEL-28, a non-metastatic skin melanoma; SK-MEL-2, a metastatic skin melanoma; or SCC, a squamous cell carcinoma; PaCa2, a pancreatic cancer cell line; or HEP-G2, a liver cancer cell line) are treated with various levels of a candidate Epi-shifter. Changes to cell morphology/physiology are evaluated by examining the sensitivity and apoptotic response of cells to the candidate Epi-shifter. These experiments are carried out as described in detail in Example 3. Briefly, the sensitivity of the cell lines to the candidate Epi-shifter are evaluated by monitoring cell survival at various times, and over a range of applied concentrations. The apoptoic response of the cell lines to the candidate Epi-shifter are evaluated by using, for example, Nexin reagent in combination with flow cytometry methodologies. Nexin reagent contains a combination of two dyes, 7AAD and Annexin-V-PE, and allows quantification of the population of cells in early and late apoptosis. An additional apoptosis assay that measures single-stranded DNA may be used, using for example Apostrand™ ELISA methodologies. The sensitivity and apoptotic response of the disease and control cell lines are evaluated and compared. Candidate Epi-shifters are evaluated based on their ability to inhibit cell growth preferentially or selectively in cancer cells as compared to normal or control cells. Candidate Epi-shifters are further evaluated based on their ability to preferentially or selectively induce apoptosis in cancer cells as compared to normal or control cells.

Assays are employed to assess changes in the mRNA and protein level composition of the above-identified cells following treatment with the candidate Epi-shifter. Changes in mRNA levels are analyzed using real-time PCR microarrays. These experiments are carried out as described in detail in Examples 6 and 9-13. Briefly, mRNA is extracted from the cells at various times following treatment. The level of mRNAs for genes involved in specific pathways are evaluated by using targeted pathway arrays, including, arrays specific for apoptosis, oxidative stress and antioxidate defense, angiogenesis, heat shock or diabetes. The genes that are altered in their mRNA transcription by a two-fold level or greater are identified and evaluated.

Changes in protein expression are analyzed using antibody microarray analysis, 2-D gel electrophoresis analysis coupled with mass spectrometry characterization, and western blot analysis. These experiments are carried out as described in detail in Examples 7, 4 and 8, respectively. Briefly, soluble protein is extracted from the cells at various times, e.g., 6 hours or 24 hours, following treatment with the candidate Epi-shifter. Changes induced to protein levels by the candidate Epi-shifter are evaluated by using an antibody microarray containing antibodies for over 700 proteins, sampling a broad range of protein types and potential pathway markers. Further complementary proteomic analysis can be carried out by employing 2-dimensional (2-D) gel electrophoresis coupled with mass spectrometry methodologies. The candidate Epi-shifter is exogenously added to the cell lines and cell pellets are lysed and subjected to 2-D gel electrophoresis. The gels are analyzed to identify changes in protein levels in treated samples relative to control, untreated samples. The gels are analyzed for the identification of spot changes over the time course of treatment due to increased levels, decreased levels or post-translational modification. Spots exhibiting statistically significant changes are excised and submitted for protein identification by trypsin digestion and mass spectrometry characterization. The characterized peptides are searched against protein databases with, for example, Mascot and MSRAT software analysis to identify the proteins. In addition to the foregoing 2-D gel analysis and antibody microarray experiments, potential changes to levels of specific proteins induced by the candidate MIM may be evaluated by Western blot analysis. In all of the proteomic experiments, proteins with increased or decreased levels in the various cell lines are identified and evaluated.

Candidate Epi-shifters are evaluated based on changes induced to gene expression, at the mRNA and/or protein levels, in the cell lines due to the addition of the candidate Epi-shifter. In particular, candidate Epi-shifters are evaluated based on their ability to modulate genes known to be associated with or involved in cellular metabolic processes. Of particular relevance to oncological disorders, candidate Epi-shifters are evaluated based on their ability to modulate genes known to be associated with, for example, apoptosis, cancer biology and cell growth.

The level of the candidate Epi-shifter, as well as the form of the candidate Epi-shifter, present in the cell or a particular cell location is determined using routine methods known to the skilled artisan. For example, the level of the candidate Epi-shifter in mitochondria over time and over a range of doses is determined by analyzing mitochondrial enriched preparations from cells treated with the candidate Epi-shifter. The levels of the candidate Epi-shifter in the mitochondria over the time course can be compared and correlated with other cellular changes observed, such as modulation of mRNA and protein levels for specific proteins related to metabolic and apoptotic pathways.

Candidate Epi-shifters observed to induce a shift in the metabolic state of a cell based on the results obtained from the foregoing experiments are identified as Epi-shifters. For example, a candidate Epi-shifter that displays cytotoxicity and/or that induces apoptosis in a cell is identified as an Epi-shifter. Preferably, a candidate Epi-shifter that displays differential cytotoxicity and/or that differentially induces the apoptotic response in diseased (cancer) cells as compared to normal cells (e.g., Epi-shifters that differentially modulate expression of proteins involved in apoptosis in cancer cells as compared to normal cells) is identified as an Epi-shifter.

Example 19

Identification of Vitamin D3 as an Epi-shifter

Vitamin D3, or 1α, 25-dihydroxyvitamin D3 (also known as calcitriol), is a vitamine D metabolite that is synthesized from vitamin D by a two-step enzymatic process. Vitamin D3 interacts with its ubiquitous nuclear vitamin D receptor (VDR) to regulate the transcription of a wide spectrum of genes involved in calcium and phosphate homeostasis as well as in cell division and differentiation. Vitamin D3 has been reported to have anticancer effects in numerous model systems, including squamous cell carcinoma, prostate adenocarcinoma, cancers of the ovary, breast and lung (reviewed in Deeb et al. 2007 *Nature Reviews Cancer* 7:684-700).

The anticancer effects of vitamin D3 are reported to involve multiple mechanisms, including growth arrest at the G1 phase of the cell cycle, apoptosis, tumor cell differentiation, disruption of growth factor-mediated cell survival signals, and inhibition of angiogenesis and cell adhesion (reviewed in Deeb et al. 2007 *Nature Reviews Cancer* 7:684-700). For example, with particular respect to apoptosis, Vitamin D3 has been reported to induce apoptosis by regulating key mediators of apoptosis, such as repressing the expression of the anti-apoptotic, pro-survival proteins BCL2 and BCL-XL, or inducing the expression of pro-apoptotic proteins (e.g., BAX, BAK and BAD) (Deeb et al. 2007). In a further example, with particular respect to angiogenesis, Vitamin D3 has been reported to inhibit the proliferation of some tumor-derived endothelial cells and to inhibit the expression of vascular endothelial growth factor (VEGF) that induces angiogenesis in tumors (reviewed in Masuda and Jones, 2006 *Mol. Cancer Ther.* 5(4): 797-8070). In another example, with particular respect to cell cycle arrest, Vitamin D3 has been reported to induce gene transcription of the cyclin-dependent kinase inhibitor p21WAFI/CIPI and to induce the synthesis and/or stabilization of the cyclin-dependent kinase inhibitor p27KIPI protein, both of which are critical for induction of G1 arrest. (Deeb et al. 2007).

Based on the foregoing observations, Vitamin D3 is identified as an Epi-shifter, i.e., owing to its ability to shift the metabolic state of a cell. Vitamin D3 is an Epi-shifter owing to its ability to induce apoptosis in a cell and, in particular, based on its ability to differentially inhibit cell growth and induce the apoptotic response in diseased (cancer) cells as compared to normal cells (e.g., differentially modulate expression of proteins, such as BCL-2, BCL-XL, and BAX, involved in apoptosis in cancer cells as compared to normal cells).

Example 20

Relative Sensitivities of Oncogenic and Normal Cells to Coenzyme Q10

The effects of Coenzyme Q10 treatment on a variety of oncogenic and normal cell lines were examined and compared. The sensitivity of cells to Coenzyme Q10 was assessed by monitoring induction of apoptosis. CoQ10 treatment of cells was carried out as described in detail below in the Materials and Methods. Induction of apoptosis was assessed in the treated cells by monitoring indicators of early apoptosis (e.g., Bcl-2 expression, caspase activation and by using annexin V assays) as described below. From these studies, the minimal CoQ10 dosage, e.g., concentration of CoQ10 and time of treatment, required to induce apoptosis in the panel of cell lines was determined.

In an unexpected and surprising result, the data demonstrated that efficacy of Coenzyme Q10 treatment was greater in cell types that exhibited increased oncogenicity and/or greater metastatic potential, i.e., cell types that were derived from more aggressive cancers or tumors. The results of these studies are summarized below in Table 29. The data demonstrates that CoQ10 is more effective in both a time and concentration dependent manner on cells in a more aggressive cancer state. Moreover, a surprising divergent effect was observed on normal cells as compared to oncogenic cells. Specifically, Coenzyme Q10 was unexpectedly found to exhibit a slightly supportive role in a normal tissue environment, wherein increased proliferation and migration was observed in normal cells, including keratinocytes and dermal fibroblasts.

The effect of Coenzyme Q10 on gene regulatory and protein mechanisms in cancer is different in a normal cell. Key cellular machinery and components, such as membrane fluidity, transport mechanisms, immunomodulation, angiogenesis, cell cycle control, genomic stability, oxidative control, glycolytic flux, metabolic control and integrity of extracellular matrix proteins, are dysregulated and thus the genetic and molecular fingerprint of the cell is altered. The disease environment favors governance of cellular control processes. The data provided herein suggests that CoQ10 exerts a greater level of efficacy (e.g., in cancer cells vs. normal cells, and in cells of a more aggressive cancer state as compared to cells 1 of a less aggressive or non-aggressive cancer state) by normalizing some of the key aforementioned processes in a manner that allows for restored apoptotic potential.

TABLE 29

Minimal CoQ10 concentration and treatment time required for induction of early apoptosis in various cell types.

| Tissue Origin (Cell type) | Indication of Early apoptosis (Bcl-2, annexin V, or caspase activation) | Concentration ($\mu$M) | Time (hr) | Level of aggressiveness: 1 = normal tissue 2 = malignant 3 = metastatic |
|---|---|---|---|---|
| SKIN: | | | | |
| Keratinocytes (Heka, Hekn) | None | N/A | N/A | 1 |
| Fibroblasts (nFib) | None | N/A | N/A | 1 |
| Melanocytes (Hema, LP) | None | N/A | N/A | 1 |
| Melanoma (Skmel 28) | Strong | 20 | 24 | 2 |
| Melanoma (Skmel 2) | Very Strong | 25 | 24 | 3 |
| SCC, Squamous cell carcinoma | Very Strong | 25 | 24 | 3 |
| BREAST: | | | | |
| MCF-7 | Strong | 50 | 48 | 2 |
| SkBr-3 | Very Strong | 50 | 24 | 3 |
| BT-20 | Strong | 100 | 48 | 2 |
| ZR-75 | Slight | 200 | 72 | 2 |
| MDA MB 468 | Strong | 100 | 48 | 2 |
| Mammary fiboblasts: 184A1 and 184B5) (Lawrence Berkeley) | None | N/A | | 1 |
| PROSTATE: | | | | |
| PC3 | Very Strong | 25 | 24 | 3 |
| LIVER: | | | | |
| HepG2 | Very Strong | 50 | 24 | 3 |
| Hep3B | Very Strong | 50 | 24 | 3 |
| BONE: | | | | |
| Osteosarcoma (143b) | Very Strong | 50 | 48 | 2 |
| Ewing's sarcoma (NCI) | Extremely strong | 5 | 1 | 3 |
| PANCREAS: | | | | 3 |
| PaCa2 | Very Strong | 25 | 24 | |
| Heart: | | | | |
| Aortic smooth muscle (HASMC) | None | N/A | N/A | 1 |

Materials and Methods
Cell Preparation and Treatment
Cells Prepared in Dishes or Flasks Cells were cultured in T-75 flasks with relevant medium supplemented with 10% Fetal Bovine Serum (FBS), 1% PSA (penicillin, streptomycin, amphotericin B) (Invitrogen and Cellgro) in a 37° C. incubator with 5% $CO_2$ levels until 70-80% confluence was reached. To harvest cells for treatment, flasks were primed with 1 mL Trypsin, aspirated, trypsinized with an additional 3 mL, and incubated at 37° C. for 3-5 10 minutes. Cells were then neutralized with an equal volume of media and the subsequent solution was centrifuged at 10,000 rpm for 8 minutes. The supernatant was aspirated and the cells were resuspended with 8.5 ml of media. A mixture of 500 ul of the resuspension and 9.5 ml of isopropanol was read twice by a coulter counter and the appropriate number of cells to be seeded into each dish was determined. Control and concentration ranging from 0-200 $\mu$M groups were examined in triplicate. From a 500 $\mu$M CoQ-10 stock solution, serial dilutions were performed to achieve desired experimental concentration in appropriate dishes. Dishes were incubated in a 37° C. incubator with 5% $CO_2$ levels for 0-72 hours depending on cell type and experimental protocol.
Protein Isolation and Quantification
Cells Prepared in Dishes Following cell treatment incubation period was complete, protein isolation was performed. Dishes of all treatment groups were washed twice with 2 ml, and once with 1 ml of ice cold 1x Phosphate Buffered Saline (PBS). The PBS was aspirated from the dishes after the initial 2 washes only. Cells were gently scraped and collected into microcentrifuge tubes using the final volume from the third wash and centrifuged at 10,000 rpm for 10 minutes. After centrifugation, the supernatant was aspirated and the pellet was lysed with 50 uL of lysis buffer (1 uL of protease and phosphotase inhibitor for every 100 uL of lysis buffer). Samples were then frozen overnight at −20° C.

Cells Prepared in Flasks

After the cell treatment incubation period was complete, protein isolation was performed. Flasks of all treatment groups were washed twice with 5 mL, and once with 3 mL of ice cold 1×PBS. The PBS was aspirated from the flasks after the first 2 washes only. Cells were gently scraped and collected into 15 mL centrifuge tubes using the final volume from the third wash and centrifuged for at 10,000 rpm for 10 minutes. After centrifugation, the supernatant was aspirated and the pellet was lysed with an appropriate amount of lysis buffer (1 uL of protease and phosphatase inhibitor for every 100 uL of lysis buffer). Lysis buffer volµme was dependent on pellet size. Samples were transferred in microcentrifuge tubes and frozen overnight at −20° C.

Protein Quantification

Samples were thawed at −4° C. and sonicated to ensure homogenization the day following protein isolation. Protein quantification was performed using the micro BCA protein assay kit (Pierce). To prepare samples for Immuno-blotting, a 1:19 solution of betamercaptoethanol (Sigma) to sample buffer (Bio-Rad) was prepared. Samples were diluted 1:1 with the betamercaptoethanol-sample buffer solution, boiled at 95° C. for 5 minutes, and frozen overnight at −20° C.

Immuno-blotting
Bcl-2, Caspase, 9, Cyotochrome c

The volume of sample to load per well was determined using the raw mean concentration of protein obtained from the BCA protein assay. Approximately 30-60 µg of protein were loaded for each treatment time point. Proteins were run in triplicate on 12% Tris-HCl ready gels (Bio-Rad) or hand cast gels in 1× running buffer at 85 and 100 volts. Proteins were then transferred onto nitrocellulose paper for an hour at 100 volts, and blocked for another hour in a 5% milk solution. Membranes were placed in primary antibody (1 uL Ab:1000 uL TBST) (Cell Signaling) overnight at −4° C. The following day, membranes were washed three times for ten minutes each with Tris-Buffered Saline Tween-20 (TBST), and secondary antibody (anti-rabbit; 1 uL Ab: 1000 uL TBST) was applied for an hour at −4° C. Membranes were washed again three times for ten minutes with TBST and chemoluminescence using Pico or Femto substrate was completed (Pierce). Membranes were then developed at time intervals that produced the best visual results. After developing, membranes were kept in TBST at −4° C. until Actin levels could be measured.

Actin

Membranes were placed in primary Actin antibody (1 uL Ab:5000 uL TBST) (cell signaling) for 1 hour at −4° C., washed three times for ten minutes each with TBST, and secondary antibody (anti-mouse; 1 uL Ab: 1000 uL TBST) was applied for an hour at −4° C. Membranes were washed again three times for ten minutes each with TBST and chemoluminescence using Pico substrate was completed (Pierce). Membranes were then developed at time intervals that produced the best visual results.

Annexin V Assay

Cells were washed twice in PBS10X and resuspended in Binding Buffer (0.1 M HEPES, pH 7.4; 1.4 M NaCl; 25 mM CaCl2). Samples of 100 µl were added to a culture tube with 5 µl of annexin-PE dye or 7-ADD. The cells were mixed and incubated without light at room temperature for 15 minutes. After which, 400 µl of 1× Binding Buffer was added to each sample and they were subjected to analysis by flow cytometry.

Examples 21-25 are herein taken from International Application WO 2008/116135. The contents of which are herein incorporated in its entirety.

Example 21

Method of Preparing a CoQ10 22% Concentrate which Includes Pentylene Glycol

A concentrate was produced with CoQ10 as the lipophilic bioactive agent. About 10 kilograms (kg) of polysorbate 80 was placed in a vacuum kettle and heated to a temperature of from about 50° C. to about 65° C. About 8.8 kg of CoQ10 was added to the polysorbate 80 and vacuum was applied with the temperature maintained at from about 50° C. to about 65° C., and the contents mixed for about 15 minutes. The resulting material may be referred to herein as the CoQ10 phase or the first phase. The CoQ10 was dissolved in the polysorbate 80 with the vacuum kettle sealed, vacuum on, and temperature of the mix of polysorbate/CoQ10 from about 50° C. to about 55° C.

In a separate kettle, about 15.8 kg of water was heated to a temperature of from about 50° C. to about 55° C. and about 0.2 kg of phenoxyethanol and about 2 kg of HYDROLITE 5® Pentylene Glycol, USP were added to the water and mixed until clear and uniform. About 8 kg of PHOSPHOLIPON® 85G was then added until dispersed. The resulting material may be referred to herein as the water phase or the second phase. The water phase achieved a uniform dispersion and hydration of the Phospholipon-type lecithin and was added to the CoQ10/Polysorbate liquid as described below at a temperature from about 50° C. to about 55° C.

A Silverson in-line production scale homogenizer, similar to the Silverson L4RT model used for laboratory scale batches, was utilized to combine the two phases described above, (i.e., the CoQ10 phase and the water phase). Homogenization occurred using the Silverson standard emulsion head screen by mixing at full capacity (from about 7000 rpm to about 10,000 rpm) for a total of about 5 minutes through a closed recirculating loop and under vacuum (from about 18 mm to about 20 mm Hg) at temperatures of from about 50° C. to about 55° C. with sweep agitation until the solubilized CoQ10 was completely encapsulated and uniformly dispersed thereby creating a thick, uniform liposomal dispersion. The resulting CoQ10 concentrate possessed CoQ10 at a concentration of about 22% by weight. The PHOSPHOLIPON® 85G concentration was about 8% by weight of the total composition, that is, of the combination of the two phases described above.

In separate experiments, a one kg laboratory batch of the 22% CoQ10 concentrate described above was produced and samples were taken at 5 minute intervals during homogenization. The particle size of the liposomes at the various sampling times was determined utilizing laser diffraction equipment (Malvern 2000) following the manufacturer's directions. Details of the homogenization process and the particle sizes obtained during homogenization are set forth below in Table 30.

TABLE 30

| Process time (minutes) | Silverson L4RT Head Speed | Avg. particle diameter (nm) | Particle Intensity; % < 300 nm | Approx. peak temp. exposure (° C.) |
|---|---|---|---|---|
| 5 | 7000 | 108 | 84.9 | 55 |
| 10 | 7000 | 162 | 57.8 | 65 |
| 15 | 7000 | 112 | 85.4 | 55 |
| 20 | 7000 | 149 | 67.0 | 62 |
| 30 | 7000 | 120 | 83.0 | 55 |
| 45 | 7000 | 107 | 85.0 | 55 |

As can be seen from Table 30, the CoQ10 concentrate formula and process described above was capable of producing liposomes with an average diameter of 107 nm and a particle distribution that included 85% of all liposomes produced within a size of from about 59 nm to about 279 nm. A short process time (about 5 minutes) produced a liposome dispersion of CoQ10 just as efficiently as a long process time (about 45 minutes). As can also be seen from the above, optimal liposome particles were obtained where the CoQ10 was not exposed to temperatures above about 55° C.

Example 22

Method of Preparing A 2% Carbomer Dispersion

A cross linked acrylic acid polymer dispersion was prepared for use as a viscosity agent in a cream composition. The acrylic acid utilized, CARBOMER 940, was prepared in a 2% dispersion with the following components set forth below in Table 31:

TABLE 31

| Phase | Trade Name | CTFA Name | Percent | Amount (Kg) |
|---|---|---|---|---|
| 1 | phenoxyethanol | phenoxyethanol | 0.500 | 0.0750 |
| 1 | hydrolite-5 | pentylene glycol | 5.000 | 0.7500 |
| 2 | purified water, USP | water | 92.500 | 13.8750 |
| 3 | ACRITAMER 940 | CARBOMER 940 | 2.000 | 0.3000 |
| | Totals | | 100.000 | 15.0000 |

The manufacturing process was conducted as follows. The equipment was first cleaned and sanitized. On a benchtop, the phase 1 ingredients were mixed until clear and uniform. The required amount of water (phase 2) was weighed and added to a phase vessel kettle of the homgenizer described above in Example 1. The water was heated with a hot water/steam jacket to a temperature of from about 60° C. to about 65° C. Phase 1 was then added to the phase 2 water with moderate agitation until clear and uniform. The phase 1 container was rinsed with process water and the temperature was maintained at from about 60° C. to about 65° C. The agitator was then turned on high and CARBOMER 940 powder (phase 3) was added.

The temperature was maintained at from about 60° C. to about 65° C. and mixing continued at medium-high speed of from about 500 rpm to about 800 rpm until all the CARBOMER 940 powder was added. The CARBOMER powder was added slowly to the vortex of the mixture of phases 1 and 2. The powder was hand sifted slowly so that the total amount of CARBOMER was added in no less than about 10 minutes.

Mixing continued at medium-high agitation until all powder was thoroughly dispersed and no "fish-eyes" were present. The manufacturing process was conducted so that all of the unneutralized CARBOMER 940 powder was completely dispersed to create a smooth translucent dispersion of fully hydrated CARBOMER polymer. Agitation of the batch was high enough to create a visible vortex, but not so high to cause splashing of the batch. Adequate mixing of the batch occurred at a high speed of from about 800 rpm to about 1300 rpm over a period of time from about 60 minutes to about 90 minutes. The batch temperature was maintained at from about 60° C. to about 65° C. at the start of mixing and from about 55° C. to about 65° C. during mixing. The elevated temperature assisted in dispersion of the CARBOMER polymer and helped prevent agglomeration.

The batch was cooled to from about 25° C. to about 30° C. with chilled water through a jacket and mixing continued with medium-high agitation. Samples were taken to determine microquality, pH, specific gravity and viscosity.

Example 23

Method of Preparing CoQ10 Creams (1.5%, 3.0% and 5.0%) Using a CoQ10 22% Concentrate A cream emulsion base was formed utilizing several phases for combination with the CoQ10 concentrate possessing liposomes of Example 1. Phases A, B, C and D were combined to form the base cream. Phase E was the CoQ10 22% concentrate of Example 1 (22% w/w CoQ10). Details of the preparation of the cream emulsion base and the subsequent addition of the CoQ10 22% concentrate of Example 1 are set forth below.

For preparation of the cream possessing CoQ10 22% concentrate at 1.5% by weight ("CoQ10 cream 1.5%"), the procedure for combining the various phases was as follows with the ingredients set forth below in Tables 32-37:

TABLE 32

CoQ10 Cream 1.5%

| Phase | Trade Name | CTFA Name | Percent | Amount (g) |
|---|---|---|---|---|
| A | RITAMOLLIENT TN | C12-15 ALKYL BENZOATE | 5.000 | 1.0000 |
| A | RITA CA | CETYL ALCOHOL | 2.500 | 0.5000 |
| A | RITA SA | STEARYL ALCOHOL | 2.000 | 0.4000 |
| A | RITAPRO 165 | GLYCERYL STEARATE AND PEG-100 STEARATE | 4.500 | 0.9000 |

Phase A (the "Oil Phase") included $C_{12-15}$ alkyl benzoates, which are light esters added for emolliency and spreadability. The cetyl alcohol and stearyl alcohol were waxes added to impart body or texture to the cream and the glyceryl stearate and PEG-100 stearate mixture was a primary emulsifier included to form an oil-in-water (o/w) emulsion. On a benchtop, the Phase A ingredients were weighed in a vacuum kettle and heated to from about 70° C. to about 75° C. in water bath.

TABLE 33

| Phase | Trade Name | CTFA Name | Percent | Amount (g) |
|---|---|---|---|---|
| B | RITA GLYCERIN | glycerin | 2.000 | 0.4000 |
| B | HYDROLITE-5 | pentylene glycol | 2.125 | 0.4250 |

TABLE 33-continued

| Phase | Trade Name | CTFA Name | Percent | Amount (g) |
|---|---|---|---|---|
| B | TRANSCUTOL P | ethoxydiglycol | 5.000 | 1.0000 |
| B | phenoxyethanol | phenoxyethanol | 0.463 | 0.0926 |
| B | ACRITAMER 940, 2% dispersion | water, CARBOMER 940 | 50.000 | 10.0000 |
| B | purified water USP | Water | 11.000 | 2.2000 |

Phase B (the "Water Phase"), contained glycerine for skin moisturization and humectancy; propylene glycol for humectancy, to aid in skin penetration and to improve the microbiological preservation profile; ethoxydiglycol to enhance CoQ10 skin penetration of the liposomes; phenoxyethanol for microbiological preservation; purified water as the phase solvent, and CARBOMER 940 dispersion of Example 2 above to control the rheological properties of the cream formulas and to add stability to the primary emulsion.

Phase B ingredients were placed in a separate mixing kettle. The ingredients were mixed with moderate sweep mixing while heating to from about 70° C. to about 75° C. (no vacuum). When the Phase B ingredients reached from about 70° C. to about 75° C., Phase A ingredients were added at from about 70° C. to about 75° C. with moderate sweep mixing. The mixture of Phases A and B was recirculated through a Silverson homogenizer as described above in Example 1 (standard head) and continued to the next part of the process.

TABLE 34

| Phase | Trade Name | CTFA Name | Percent | Amount (g) |
|---|---|---|---|---|
| C | TEALAN 99% | triethanolamine | 1.300 | 0.2600 |
| C | RITALAC LA USP | lactic acid | 0.300 | 0.0600 |
| C | RITALAC NAL | Sodium lactate, water | 2.000 | 0.4000 |
| C | distilled water | Water | 3.312 | 0.6624 |

In Phase C (the "Neutralization and Buffer Phase"), purified water acted as a solvent and a diluent for the other ingredients in this phase. Triethanolamine was the primary neutralizer of the CARBOMER acrylic acid copolymer in the water phase (Phase B); sodium lactate solution (60% w/w in water) and lactic acid were added as a buffer system to adjust and maintain the final pH of the cream from about 5 to about 5.5, which is within the natural pH range of the skin.

On a benchtop, Phase C ingredients were weighed and mixed until uniform and heated to from about 60° C. to about 65° C. The Phase C mixture was then added to the vacuum mixing kettle containing Phases A and B with sweep mixer on medium-high.

Mixing continued while moving to the next part of the process.

TABLE 35

| Phase | Trade Name | CTFA Name | Percent | Amount (g) |
|---|---|---|---|---|
| D | TITANIUM DIOXIDE, #3328 | titanium dioxide | 1.000 | 0.2000 |

Phase D (the "Pigment Phase"). A water-dispersible grade of Titanium Dioxide powder was used in the formula solely for the purpose of lightening the color of the final cream color. The yellow-orange color of the cream, imparted by CoQ10, was substantially reduced and cosmetically improved by the addition of about 1% w/w Titanium Dioxide.

For Phase D of the process, weighed $TiO_2$ was added to the batch (Phases A, B and C) and mixed and recirculated through the Silverson homogenizer (high shear head) for about 10 minutes or until completely uniform and fully extended (color was checked to confirm).

It was important to ensure there was no agglomeration or clumping of the titanium dioxide on the sweep mixing blades; this was confirmed by visual inspection. A Silverson in line homogenizer as described above in Example 1 was used with a high shear screen to insure maximum deagglomeration and grinding of the titanium dioxide. The final dispersion of the titanium dioxide was checked with a Hegman PH-175 fineness of grind gauge.

TABLE 36

| Phase | Trade Name | CTFA Name | Percent | Amount (g) |
|---|---|---|---|---|
| E | CoQ10 CONCENTRATE 22% (From Example 1 above) | WATER, POLYSORBATE 80, UBIQUINONE, LECITHIN, PENTYLENE GLYCOL, PHENOXYETHANOL | 7.500 | 1.5000 |
| | Totals | | 100.000 | 20.000 |

Recirculation was stopped and the batch was cooled to from about 50° C. to about 55° C. with the sweep mixer on medium, at a speed of about 30 rpm. The previously weighed CoQ10 22% concentrate (Phase E) from Example 1 was warmed to from about 45° C. to about 50° C. and added to the batch (Phases A, B, C and D).

All phases were mixed with sweep agitation at about 60 rpm with a vacuum applied until uniform. Temperature was maintained at about 50° C.

The batch was cooled to from about 35° C. to about 45° C. with mixing at about 60 rpm and the application of a vacuum.

The resulting material was placed into holding containers.

For preparation of a cream possessing CoQ10 22% concentrate at 3% ("CoQ10 cream 3%") by weight, the exact same procedure described above for forming the cream possessing CoQ10 22% concentrate at 1.5% ("CoQ10 cream 1.5%") by weight was followed. The materials for each phase, and the amounts utilized, are set forth below in Tables 37-41:

TABLE 37

| CoQ10 Cream 3% | | | | Amount |
|---|---|---|---|---|
| Phase | Trade Name | CTFA Name | Percent | (g) |
| A | RITAMOLLIENT TN | C12-15 alkyl benzoate | 4.000 | 0.8000 |
| A | RITA CA | cetyl alcohol | 2.500 | 0.5000 |
| A | RITA SA | stearyl alcohol | 2.000 | 0.4000 |
| A | RITAPRO 165 | glyceryl stearate and PEG-100 stearate | 4.500 | 0.9000 |

TABLE 38

| Phase | Trade Name | CTFA Name | Percent | Amount (g) |
|---|---|---|---|---|
| B | RITA GLYCERIN | glycerin | 2.000 | 0.4000 |
| B | HYDROLITE-5 | pentylene glycol | 2.250 | 0.4500 |
| B | TRANSCUTOL P | ethoxydiglycol | 5.000 | 1.0000 |
| B | phenoxyethanol | phenoxyethanol | 0.463 | 0.0926 |
| B | ACRITAMER 940, 2% dispersion | water, CARBOMER 940 | 40.000 | 8.0000 |
| B | purified water, USP | water | 15.000 | 3.0000 |

TABLE 39

| Phase | Trade Name | CTFA Name | Percent | Amount (g) |
|---|---|---|---|---|
| C | TEALAN 99% | triethanolamine | 1.300 | 0.2600 |
| C | RITALAC LA | Lactic acid | 0.500 | 0.1000 |
| C | RITALAC NAL | sodium lactate, water | 2.000 | 0.4000 |
| C | purified water, USP | water | 2.487 | 0.4974 |

TABLE 40

| Phase | Trade Name | CTFA Name | Percent | Amount (g) |
|---|---|---|---|---|
| D | TITANIUM DIOXIDE, #3328 | titanium dioxide | 1.000 | 0.2000 |

TABLE 41

| Phase | Trade Name | CTFA Name | Percent | Amount (g) |
|---|---|---|---|---|
| E | CoQ10 CONCENTRATE 22% (From Example 1 above) | water, POLYSORBATE 80, ubiquinone, LECITHIN, pentylene glycol, phenoxyethanol | 15.000 | 3.0000 |
| | Totals | | 100.000 | 20.000 |

A similar cream was prepared by using the CoQ10 22% concentrate from Example 1 in an amount of about 25% by weight to create a cream having CoQ10 22% concentrate at a concentration of about 5% by weight.

A summary of the contents of CoQ10 creams having 1.5% CoQ10 by weight, 3% CoQ10 by weight, and 5% CoQ10 by weight are set forth below in Tables 42, 43 and 44 respectively. Note that in all the formulation examples given above and below for CoQ10 creams, the amount of CoQ10 22% concentrate used would actually yield a final theoretical concentration of CoQ10 22% concentrate of about 5% above the target concentration. So, for "CoQ10 Cream 1.5%", the actual batch amount used was 7.5% by weight of a CoQ10 22% concentrate that yielded 1.58% w/w CoQ10. The "CoQ10 Cream 3%" was made with 15% by weight of the CoQ10 22% concentrate that yielded a theoretical content of 3.15% CoQ10 by weight. The 5% excess drug was added to extend the overall shelf life of the product and maintain the drug content from about 90% to about 110% of the label or expected drug content.

TABLE 42

| CoQ10 CREAM, 1.5% | | | | |
|---|---|---|---|---|
| Phase | Trade Name | INCI Name | Percent | Supplier |
| A | RITAMOLLIENT TN | C12-15 alkyl benzoates | 5.000 | RITA |
| A | RITA CA | cetyl alcohol | 2.000 | RITA |
| A | RITA SA | stearyl alcohol | 1.500 | RITA |
| A | RITAPRO 165 | glyceryl stearate and PEG-100 stearate | 4.500 | RITA |
| B | RITA GLYCERINE | Glycerine | 2.000 | RITA |
| B | HYDROLITE 5 | pentylene glycol | 2.125 | SYMRISE |
| B | TRANSCCUTOL P | Ethoxydiglycol | 5.000 | GATTEFOSSE' |
| B | phenoxyethanol | Phenoxyethanol | 0.463 | RITA |
| B | PURIFIED WATER | deionized water | 11.000 | |
| B | ACRITAMER 940 dispersion, 2% | water, pentylene glycol, CARBOMER 940, phenoxyethanol | 50.000 | |
| C | purified water USP | water | 4.212 | |
| C | triethanolamine | triethanolamine | 1.300 | RITA |
| C | RITALAC NAL | sodium lactate and water | 2.000 | RITA |
| C | RITALAC LA USP | lactic acid | 0.400 | RITA |
| D | TITANIUM DIOXIDE #3328 | titanium dioxide | 1.000 | MPSI |
| E | CoQ10 liposome concentrate, 22% W/W (From Example 1) | water, POLYSORBATE 80, ubiquinone, lecithin, pentylene glycol, phenoxyethanol | 7.500 | |
| | Totals | | 100.000 | |

TABLE 43

CoQ10 Cream 3%

| Phase | Ingredient | % w/w |
|---|---|---|
| A | C12-C15 Alkyl Benzoate | 4.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.250 |
| B | Ethoxydiglycol | 5.000 |
| B | Phenoxyethanol | 0.476 |
| B | Carbomer | 40.000 |
| B | Purified Water | 16.000 |
| C | Sodium Lactate | 2.000 |
| C | Purified Water | 2.474 |
| C | Triethanolamine | 1.300 |
| C | Lactic Acid | 0.500 |
| D | Titanium Dioxide | 1.000 |
| E | CoQ10 Concentrate 22% (From Example 1) | 15.000 |
|   | Total: | 100.000 |
| B | Ethoxydiglycol | 5.000 |
| B | Phenoxyethanol | 0.476 |
| B | Carbomer | 40.000 |
| B | Purified Water | 16.000 |
| C | Sodium Lactate | 2.000 |
| C | Purified Water | 2.474 |
| C | Triethanolamine | 1.300 |
| C | Lactic Acid | 0.500 |
| D | Titanium Dioxide | 1.000 |
| E | CoQ10 Concentrate 22% (From Example 1) | 15.000 |
|   | Total: | 100.000 |

TABLE 44

CoQ10 Cream 5%

| Phase | Ingredient | % w/w |
|---|---|---|
| A | C12-C15 Alkyl Benzoate | 3.000 |
| A | Cetyl Alchool | 2.000 |
| A | Stearyl Alcohol | 1.500 |
| A | Glyceryl Stearate & PEG 100 Stearate | 4.500 |
| B | Glycerin | 2.000 |
| B | Pentylene Glcycol | 2.000 |
| B | Ethoxydiglycol | 5.000 |
| B | Phenoxyethanol | 0.450 |
| B | Carbomer | 35.000 |
| B | Purified Water | 14.000 |
| C | Sodium Lactate | 2.000 |
| C | Purified Water | 0.750 |
| C | Triethanolamine | 1.300 |
| C | Lactic Acid | 0.500 |
| D | Titanium Dioxide | 1.000 |
| E | CoQ10 Concentrate 22% (From Example 1) | 25.000 |
|   | Total: | 100.000 |

Note: 5% manufacturing overage of CoQ10 22% concentrate was added to the CoQ10 cream 1.5%, CoQ10 cream 3.0% and the CoQ10 cream 5% batches (1.5% plus 0.075%, 3% plus 0.15%, and 5% plus 2.5%).

Example 24

Topical Application of a CoQ10 Cream (1.5%, 3.0% or 5.0%)

Creams possessing CoQ10 produced in Example 3 (i.e., CoQ10 cream 1.5%, CoQ10 cream 3%, and CoQ10 cream 5%) above were applied to porcine skin. The topical dose study was conducted on two pigs each, one male and one female. Each animal had 6 test areas; three test areas on each side. For each pig, one side (3 sites) was dosed once per day for 7 days, while the opposite test side (3 test areas) for each pig was dosed only one time on day 1. The creams from Example 3, prepared with ethoxydiglycol, were used on the male animals. The female animals received 3 test formulas that contained the same ingredients as the samples produced in Example 3 above, except they contained 5% 1,3-butylene glycol instead of 5% ethoxydiglycol. Details of these formulations made with 1,3-butylene glycol, which possessed 1.5% CoQ10 22% concentrate by weight, 3% CoQ10 22% concentrate by weight and 5% CoQ10 22% concentrate by weight, are set forth below in Tables 45, 46, and 47 respectively.

TABLE 45

CoQ10 Cream 1.5% Nominal Active Butylene Glycol Base

| Phase | Ingredient | % w/w |
|---|---|---|
| A | C12-C15 Alkyl Benzoate | 5.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.125 |
| B | Butylene Glycol | 5.000 |
| B | Phenoxyethanol | 0.463 |
| B | Carbomer | 50.000 |
| B | Purified Water | 11.001 |
| C | Sodium Lactate | 2.000 |
| C | Purified Water | 4.211 |
| C | Triethanolamine | 1.300 |
| C | Lactic Acid | 0.400 |
| D | Titanium Dioxide | 1.000 |
| E | CoQ10 Concentrate 22% (From Example 1) | 7.500 |
|   | Total: | 100.000 |

TABLE 46

CoQ10 Cream 3% Nominal Active Butylene Glycol Base

| Phase | Ingredient | % w/w |
|---|---|---|
| A | C12-C15 Alkyl Benzoate | 4.000 |
| A | Cetyl Alcohol | 2.000 |
| A | Stearyl Alcohol | 1.500 |
| A | Glyceryl Stearate & PEG 100 Stearate | 4.500 |
| B | Glycerin | 2.000 |
| B | Pentylene Glycol | 2.250 |
| B | Butylene Glycol | 5.000 |
| B | Phenoxyethanol | 0.476 |
| B | Carbomer | 40.000 |
| B | Purified Water | 16.000 |
| C | Sodium Lactate | 2.000 |
| C | Purified Water | 2.474 |
| C | Triethanolamine | 1.300 |
| C | Lactic Acid | 0.500 |
| D | Titanium Dioxide | 1.000 |

TABLE 46-continued

CoQ10 Cream 3% Nominal Active
Butylene Glycol Base

| Phase | Ingredient | % w/w |
|---|---|---|
| E | CoQ10 Concentrate 22% (From Example 1) | 15.000 |
|  | Total: | 100.000 |

TABLE 47

CoQ10 Cream 5% Nominal Active
Butylene Glycol Base

| Phase | Ingredient | % w/w |
|---|---|---|
| A | C12-C15 Alkyl Benzoate | 3.000 |
| A | Cetyl Alcohol | 2.000 |
| A | Stearyl Alcohol | 1.500 |
| A | Glyceryl Stearate & PEG 100 Stearate | 4.500 |
| B | Glycerin | 2.000 |
| B | Pentylene Glycol | 2.000 |
| B | Butylene Glycol | 5.000 |
| B | Phenoxyethanol | 0.450 |
| B | Carbomer | 35.000 |
| B | Purified Water | 14.000 |
| C | Sodium Lactate | 2.000 |
| C | Purified Water | 0.750 |
| C | Triethanolamine | 1.300 |
| C | Lactic Acid | 0.500 |
| D | Titanium Dioxide | 1.000 |
| E | CoQ10 Concentrate 22% (From Example 1) | 25.000 |
|  | Total: | 100.000 |

All animals received the same dose of each formulation, which was 200 mg, to a 121 cm² application area applied once or daily for 7 days.

After application, skin samples were obtained and analyzed as follows. The skin test area was gently washed with a mild soap and water mixture (e.g., 1% Ivory Soap in water or equivalent) to remove any residual topical test formulation. If the area to be excised was larger than the dosed area, the dosed area was demarked with indelible ink to delineate the skin area that was dosed. A full thickness skin section was removed by scalpel with a size approximating 10 cm×10 cm, to the depth and including the adipose layer. Following excision, the skin section was laid flat and wrapped in two layers of plastic wrap (SARAN WRAP™ or equivalent), and frozen to about −70° C. or colder in a timely manner. Each skin section was identified as appropriate (e.g. animal identification, study number, date, etc.). Samples were maintained at about −70° C. or lower until examined.

Each skin section was placed in a watertight plastic bag and thawed in from about 30° C. to about 35° C. water baths. Once thawed, each skin section was gently rinsed with distilled deionized water to remove any residual surface dose and blood. All subcutaneous tissue (e.g. adipose) was removed by scalpel to the level of the papular dermis.

Each skin section was then tape stripped (TRANS-PORE™, from 3M) from about 10 to about 20 times until approximately 10-25% surface glistening was observed. This process removed the stratum corneum and any residual surface dose.

On each full skin sheet, 6 areas were demarcated with ink. The demarcated areas were 1 cm² in area.

Each skin section was placed in a watertight plastic bag and immersed in a .about.65° C. (.+/−.3° C.) water bath to initiate the separation process of the epidermis from the dermis. The test sites were then excised from the skin sheet by punch, and the epidermis removed from the dermis by forceps. The individual skin sections were weighed and the weight recorded. The individual skin sections were minced with a scalpel, placed into pre-labeled tubes, and saved for subsequent analysis.

The skin samples were extracted in isopropanol (IPA) on a shaker for about 47 hours, then stored at about −20° C. until further processed. The samples were then centrifuged at about 13,500 rpm for about 10 minutes and the supernatant was collected into 2 mL amber vials.

Quantification of CoQ10 was performed by High Performance Liquid Chromatography (HPLC-UV). Briefly, HPLC was conducted on a Hewlett-Packard 1100 Series HPLC system with an Agilent 1100 Series LC/MSD. A solvent system including about 65% Ethanol and about 35% Methanol was run through an Aquasil C18 column (about 3 mm.times.about 100 mm, 5. mu.) at a flow rate of about 1 mL/min. Ten microliters of sample were injected. Peak areas were quantified to concentration using an external standard curve prepared from the neat standard. The curve was spiked into IPA due to solubility issues of CoQ10 in water.

Figure 2:
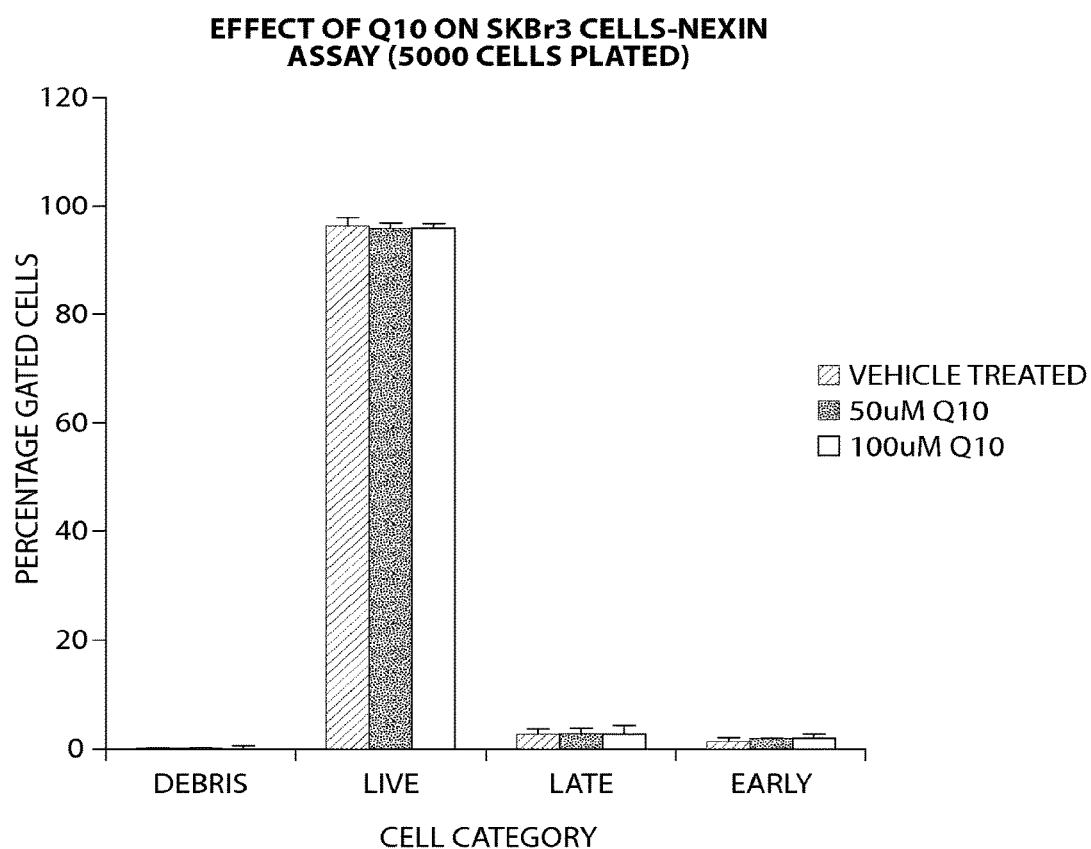
FIG. 2: Sensitivity of SKBR3 to 24 hours of Q10 treatment measured by the amount of early and late apoptotic cells.
Figure 3:
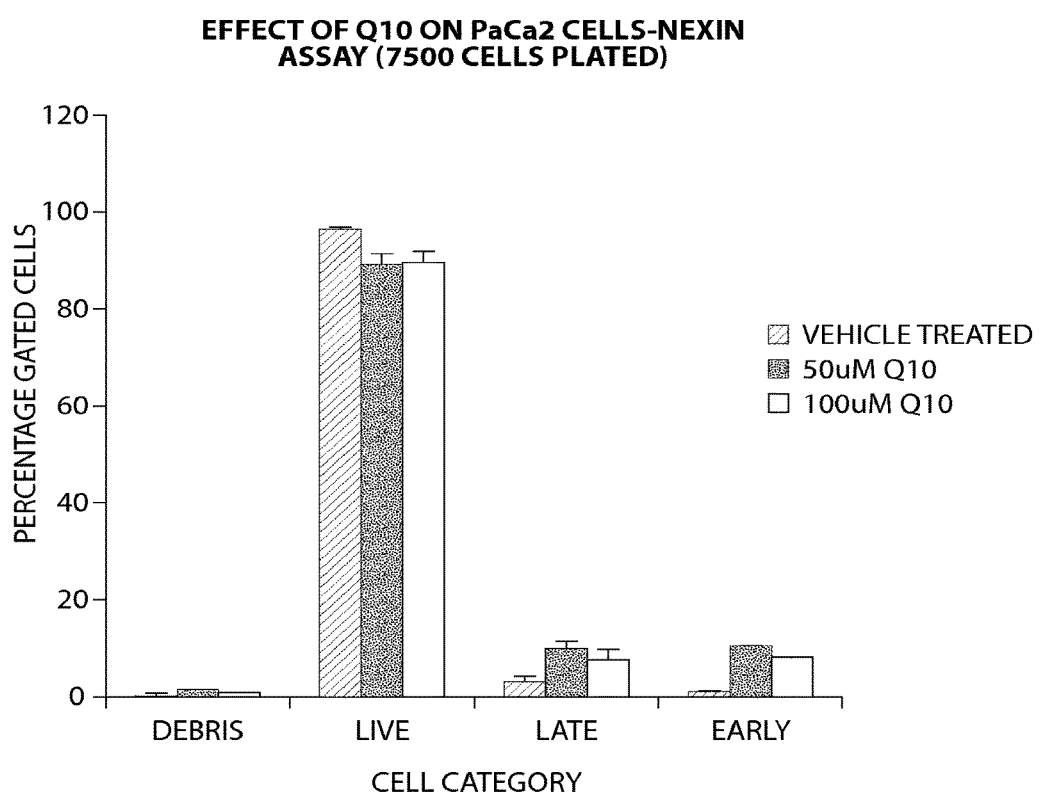
FIG. 3: Sensitivity of PaCa2 to 24 hours of Q10 treatment measured by the amount of early and late apoptotic cells.
Figure 4:
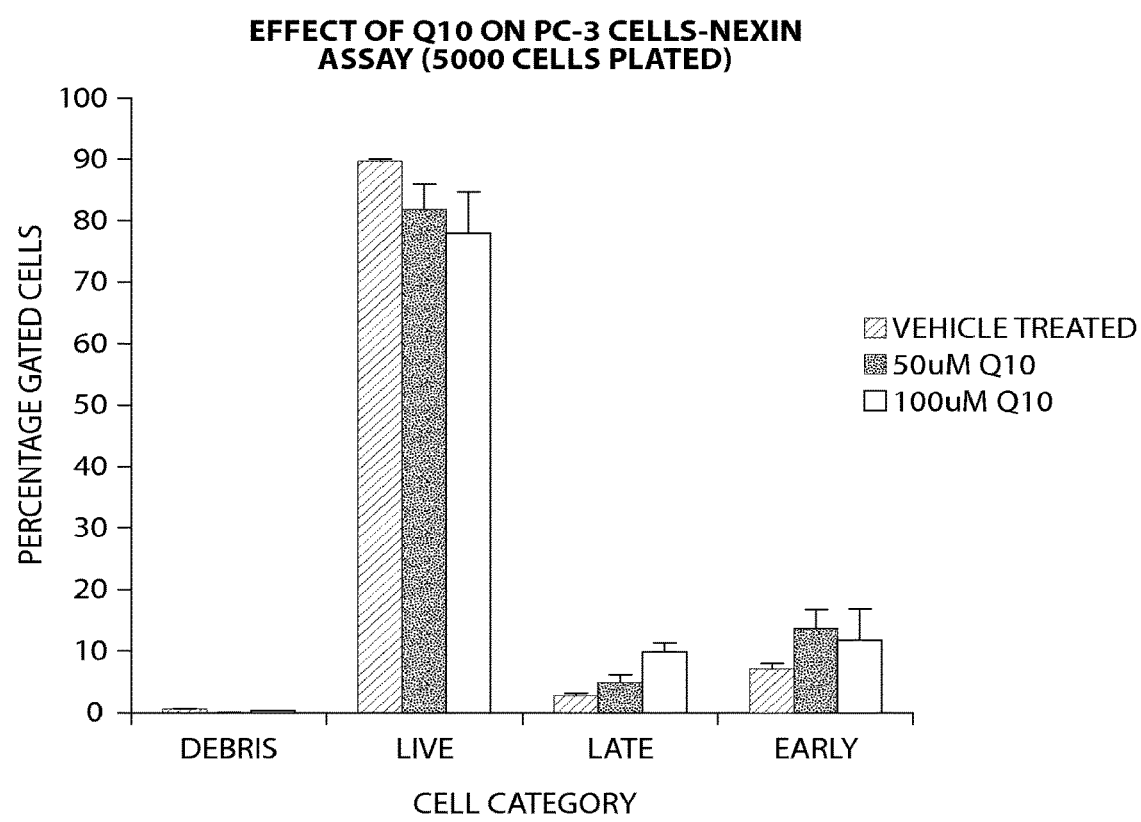
FIG. 4: Sensitivity of PC-3 to 24 hours of Q10 treatment measured by the amount of early and late apoptotic cells.
Figure 5:
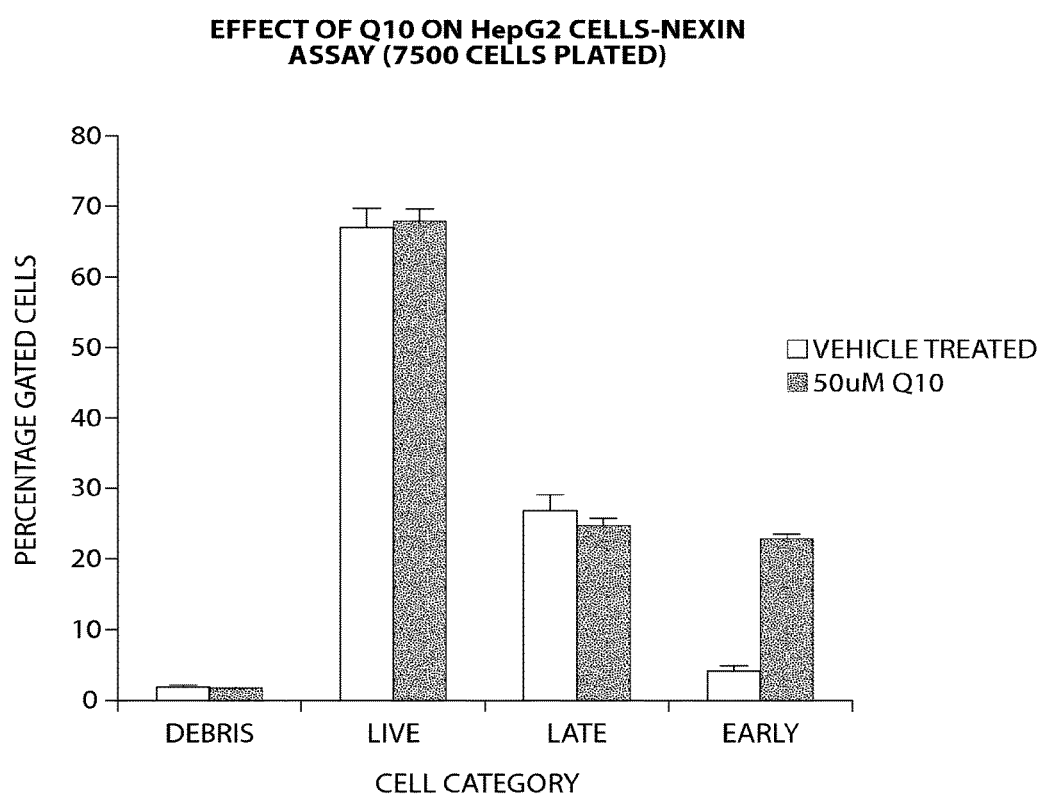
FIG. 5: Sensitivity of HepG2 to 24 hours of Q10 treatment measured by the amount of early and late apoptotic cells.
Figure 6:
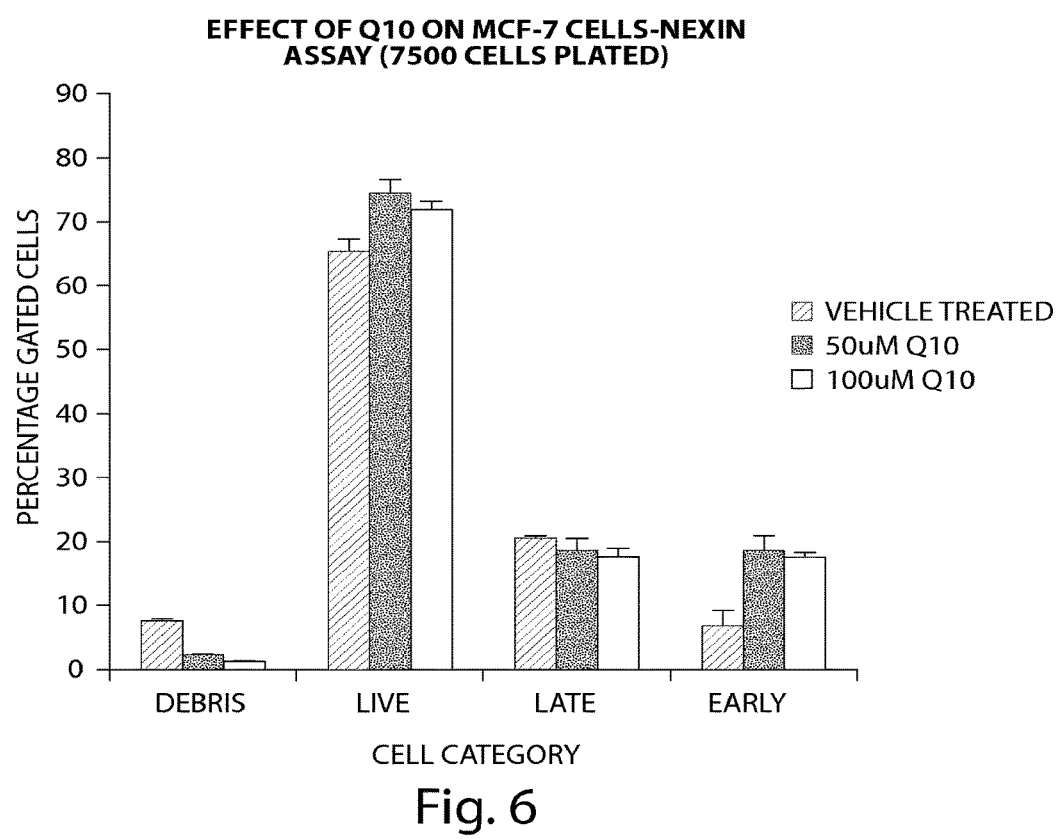
FIG. 6: Sensitivity of MCF-7 to 24 hours of Q10 treatment measured by the amount of early and late apoptotic cells.

The results for the content of CoQ10 in mini-pig skin are summarized in FIGS. 1 and 2, and Tables 48 and 49 below. The 6 replicates per skin section were corrected to tissue weight and averaged to obtain a mean for each dosed site.

TABLE 48

Mean +/− SD Tissue Weight (n = 42)

| Donor # | Epidermis (grams) | Dermis (gm) |
|---|---|---|
| 5061873 (Male) | 0.037 + 0.012 | 0.682 + 0.129 |
| 5061521 (Female) | 0.026 + 0.007 | 0.603 + 0.090 |

TABLE 49

Mean: +/−SD Measured Concentration of CoQ10
in Porcine Sin (n = 6/section)

| Donor # | Sex | Side | Dose (mg) | Epidermis (μg/gm) | Dermis (μg/gm) |
|---|---|---|---|---|---|
| 5061873 | Male | Left | 1.5 | 137.7 ± 58.2 | 0.72 ± 1.12 |
| 5061873 | Male | Left | 3.0 | 188.7 ± 40.3 | <LLQ |
| 5061873 | Male | Left | 5.0 | 163.4 ± 39.1 | 0.16 ± 0.39 |
| 5061873 | Male | Right | 1.5 | 519.3 ± 101.2 | 0.93 ± 0.81 |
| 5061873 | Male | Right | 3.0 | 315.3 ± 227.0 | <LLQ |
| 5061873 | Male | Right | 5.0 | 331.2 ± 128.7 | <LLQ |
| 5061873 | Male | Center | 0 | 24.6 ± 11.5 | <LLQ |
| 5061521 | Female | Left | 1.5 | 135.6 ± 39.2 | <LLQ |
| 5061521 | Female | Left | 3.0 | 211.8 ± 60.5 | <LLQ |
| 5061521 | Female | Left | 5.0 | 211.9 ± 67.8 | <LLQ |
| 5061521 | Female | Right | 1.5 | 118.4 ± 32.6 | <LLQ |
| 5061521 | Female | Right | 3.0 | 84.7 ± 24.6 | <LLQ |
| 5061521 | Female | Right | 5.0 | 118.1 ± 26.6 | <LLQ |
| 5061521 | Female | Center | 0 | 25.7 ± 21.8 | <LLQ |

<LLQ = below lower level of quality validation range (i.e., not detected)

The data indicated that measurable amounts of CoQ10 were observed in all epidermal samples and in selected dermal samples.

All dosed sites for the epidermis were found to contain CoQ10 at levels that were significantly greater than the non-dosed sites ($p<0.001$).

There were no significant differences between the epidermal contents for CoQ10 across the three dosing concentrations in either the male or female pig skin sections ($p>0.02$)

Between the male and female pig, for the sites from the animal's right side (1-day dosing), the epidermal content for the 1.5% CoQ10 and 5% CoQ10 applied doses from the male's skin was significantly greater than that seen in the female's skin (p<0.003), but not for the 3% CoQ10 dose (p=0.0329). Thus, as can be seen from the data, the penetration of the CoQ10 on a single dose basis was significantly greater for the ethoxydiglycol formula vs. the butylene glycol formula (p<0.003 for the 1.5% and 5% doses and p=0.0329 for the 3% dose).

The epidermal levels for both male and female skin sections, for all three dose applications, for the 7-day dosing period (left side), were statistically identical.

Dermal content was only observed in the male skin sections for the 1.5% CoQ10 and 5% CoQ10 dose applications from the 7-day dosing period (left side), and the 1.5% CoQ10 dose application from the 1-day dosing period (right side).

A summary of the data is provided as follows in Table 50:

TABLE 50

| % Concentration | 1.5 | 3 | 5 |
|---|---|---|---|
| µg drug/mg formulation | 15 | 30 | 50 |
| Amount applied (mg): | 200 | 200 | 200 |
| Total drug applied (µg) | 3000 | 6000 | 10000 |
| Area applied (cm2) | 121 | 121 | 121 |
| µg Drug/cm$^2$ | 24.79 | 49.59 | 82.64 |
| Male Left side (×7 d) | | | |
| Epidermis (µg/cm$^2$) | 3.470 | 6.688 | 7.311 |
| % Dose/cm$^2$ | 14.0 | 13.5 | 8.8 |
| Dermis (µg/cm$^2$) | 0.575 | 0 | 0.106 |
| % Dose/cm$^2$ | 2.3 | 0.0 | 0.1 |
| Male Right side (×1 d) | | | |
| Epidermis (µg/cm$^2$) | 18.309 | 8.215 | 10.986 |
| % Dose/cm$^2$ | 73.8 | 16.6 | 13.3 |
| Dermis (µg/cm$^2$) | 0.582 | 0 | 0 |
| % Dose/cm$^2$ | 2.3 | 0.0 | 0.0 |

If one were to extrapolate the data from Table 50 to the total area of skin, the penetration of the CoQ10 would be as set forth below in Table 51.

TABLE 51

| | If expanded out to total area: | | |
|---|---|---|---|
| | 1.5 | 3 | 5 |
| Epidermis (µg/121 cm$^2$) | 419.87 | 809.248 | 884.631 |
| % Dose | 14.0 | 13.5 | 8.8 |
| Epidermis (µg/121 cm$^2$) | 2215.389 | 994.015 | 1329.306 |
| % Dose | 73.8 | 16.6 | 13.3 |

A single application of the CoQ10 cream formulation delivered an average of 12%, 17%, or 70% of the applied dose for the respective 5%, 3%, and 1.5% CoQ10 cream formulations. In general, the penetration of the CoQ10 on a single dose basis was significantly greater for the ethoxydiglycol formula vs. the butylene glycol formula (p<0.003 for the 1.5% and 5% doses and p=0.0329 for the 3% dose). The data indicated that there was a rise in epidermal content with applied concentration to 3% CoQ10 with the 5% CoQ10 dose being essential equal to the 3% CoQ10 dose. This suggests that the skin became saturated with CoQ10 at the 3% CoQ10 dose, or that the vehicle was unable to deliver more CoQ10 above the 3% CoQ10 concentration. It can be seen that the levels achieved in the skin following 7 days of topical application were identical between the 2 animals.

For the ethoxydiglycol formulations, and for the single application data, average penetration of 73.8%, 16.6%, and 13.3% for the respective 1.5%, 3% and 5% ethoxydiglycol containing creams was obtained.

An interesting and unexpected finding was the disproportional amount of CoQ10 found in the epidermis for the 1.5% cream, the lowest dose of CoQ10 tested. Without wishing to be bound by any theory, this enhanced penetration of CoQ10 may be a function of the ratio of CoQ10 to ethoxydiglycol in the cream formulations, or may possibly be related to the ratio of ethoxydiglycol to CoQ10 and the phospholipid liposome. The relatively higher ratio of ethoxydiglycol to CoQ10 used in the cream containing a lower concentration of CoQ10 may be responsible for the higher amounts of CoQ10 found in the epidermis.

The 1.5% cream and 3% cream also successfully completed 9 weeks accelerated testing (storage at about 35° C. and about 50° C.); passed 5 freeze-thaw cycles packaged in both plastic jar and metal tube packaging; and passed USP microbiological challenge testing. Results were confirmed for the same system with multiple development batches and at 1.5%, 3% and 5% by weight concentrations of CoQ10 in the cream prototype formulation base.

Example 25

Method of Forming CoQ10 Creams (1.5%, 3.0% and 5.0%) Using a CoQ10 21% Concentrate Creams were produced as described in Example 3 above, except propylene glycol was utilized instead of pentylene glycol (1,2-pentane diol; Hydrolite-5, Symrise). A concentrate was first produced as described in Example 1 above, with the components listed below in Table 52:

TABLE 52

Batch Formula - CoQ10 Concentrate

| | | Theoretical Quantity | |
|---|---|---|---|
| Phase | Raw Material Name | % w/w | kg |
| A | Polysorbate 80 NF | 25.000 | 5.000 |
| A | Ubidecarenone USP | 21.000 | 4.200 |
| B | Propylene Glycol USP | 10.000 | 2.000 |
| B | Phenoxyethanol NF | 0.500 | 0.100 |
| C | Purified Water USP | 35.500 | 7.100 |
| C | Lecithin NF | 8.000 | 1.600 |
| | Totals | 100.000 | 20.000 |

The resulting CoQ10 concentrate (CoQ10 21% concentrate) possessed CoQ10 at a concentration of about 21% by weight.

A CARBOMER dispersion was prepared as described in Example 2 above for use in forming the cream with the components listed in Table 53:

TABLE 53

Batch Formula -Carbomer Dispersion

| | | Theoretical Quantity | |
|---|---|---|---|
| Phase | Raw Material Name | % w/w | kg |
| A | Phenoxyethanol NF | 0.500 | 0.0900 |
| A | Propylene Glycol USP | 5.000 | 0.9000 |

TABLE 53-continued

Batch Formula -Carbomer Dispersion

| Phase | Raw Material Name | Theoretical Quantity % w/w | kg |
|---|---|---|---|
| B | Purified Water USP | 92.500 | 16.6500 |
| C | Carbomer 940 NF | 2.000 | 0.3600 |
| | Totals | 100.000 | 18.000 |

A cream having 1.5% by weight CoQ10 21% concentrate and another cream having 3% by weight CoQ10 21% concentrate were prepared as described above in Example 3, with the components listed below in Tables 54 and 55:

TABLE 54

Batch Formula - CoQ10 Cream 1.5%

| Phase | Raw Material Name | Theoretical Quantity % w/w | kg |
|---|---|---|---|
| A | AlkylC12-15Benzoate NF | 5.000 | 1.000 |
| A | Cetyl Alcohol NF | 2.000 | 0.400 |
| A | Stearyl Alcohol NF | 1.500 | 0.300 |
| A | Glyceryl Stearate/PEG-100 Stearate | 4.500 | 0.900 |
| B | Glycerin USP | 2.000 | 0.400 |
| B | Propylene Glycol USP | 1.750 | 0.350 |
| B | Diethylene Glycol Monoethyl Ether NF | 5.000 | 1.000 |
| B | Phenoxyethanol NF | 0.463 | 0.093 |
| B | Carbomer Dispersion, 2% | 50.000 | 10.000 |
| B | Purified Water USP | 8.377 | 1.675 |
| B | Purified Water USP (for rinsing) | 3.000 | 0.600 |
| C | Trolamine NF | 1.300 | 0.260 |
| C | Lactic Acid USP | 0.400 | 0.080 |
| C | Sodium Lactate Solution USP, 60% | 2.000 | 0.400 |
| C | Purified Water USP | 4.210 | 0.842 |
| D | Titanium Dioxide USP | 1.000 | 0.200 |
| E | CoQ10 Concentrate, 21% | 7.500 | 1.500 |
| | Totals | 100.000 | 20.00 |

TABLE 55

Batch Formula -CoQ10 Cream 3%

| Phase | Raw Material Name | Theoretical Quantity % w/w | kg |
|---|---|---|---|
| A | AlkylC12-15Benzoate NF | 4.000 | 0.800 |
| A | Cetyl Alchol NF | 2.000 | 0.400 |
| A | Stearyl Alcohol NF | 1.500 | 0.300 |
| A | Glyceryl Stearate/PEG-100 Stearate | 4.500 | 0.900 |
| B | Glycerin USP | 2.000 | 0.400 |
| B | Proylene Glycol USP | 1.500 | 0.300 |
| B | Diethylene Glycol Monoethyl Ether | 5.000 | 1.000 |
| B | Phenoxyethanol NF | 0.475 | 0.095 |
| B | Carbomer Dispersion, 2% | 40.000 | 8.000 |
| B | Purified Water USP | 13.725 | 2.745 |
| B | Purified Water USP (for rinsing) | 3.000 | 0.600 |
| C | Trolamine NF | 1.300 | 0.260 |
| C | Lactic Acid USP | 0.500 | 0.100 |
| C | Sodium Lactate Solution USP, 60% | 2.000 | 0.400 |
| C | Purified Water USP | 2.500 | 0.500 |
| D | Titanium Dioxide USP | 1.000 | 0.200 |
| E | CoQ10 Concetrate, 21% | 15.000 | 3.000 |
| | Totals | 100.000 | 20.000 |

Example 26

Method of Forming a CoQ10 21% Concentrate which Includes Propylene Glycol

A CoQ10 21% concentrate composition was prepared by combining phases A and B as described below. Phase A included Ubidecarenone USP (CoQ10) at 21% w/w and polysorbate 80 NF at 25% w/w. Phase B included propylene glycol USP at 10.00% w/w, phenoxyethanol NF at 0.50% w/w, lecithin NF (PHOSPHOLIPON 85G) at 8.00 10% w/w and purified water USP at 35.50% w/w. All weight percentages are relative to the weight of the entire CoQ10 21% concentrate composition. The percentages and further details are listed in the following table.

TABLE 56

| Phase | Trade Name | INCI Name | Percent |
|---|---|---|---|
| A | RITABATE 80 | POLYSORBATE 80 | 25.000 |
| A | UBIDECARENONE | UBIQUINONE | 21.000 |
| B | PURIFIED WATER | WATER | 35.500 |
| B | PROPYLENE GLYCOL | PROPYLENE GLYCOL | 10.000 |
| B | PHENOXYETHANOL | PHENOXYETHANOL | 0.500 |
| B | PHOSPHOLIPON 85G | LECITHIN | 8.000 |
| | Totals | | 100.000 |

The phenoxyethanol and propylene glycol were placed in a suitable container and mixed until clear. The required amount of water was added to a second container (Mix Tank 1). Mix Tank 1 was heated to between 45 and 55° C. while being mixed. The phenoxyethanol/propylene glycol solution was added to the water and mixed until it was clear and uniform. When the contents of the water phase in Mix Tank 1 were within the range of 45 to 55° C., Phospholipon G was added with low to moderate mixing. While avoiding any foaming, the contents of Mix Tank 1 was mixed until the Phospholipon 85G was uniformly dispersed. The polysorbate 89 was added to a suitable container (Mix Tank 2) and heated to between 50 and 60° C. The Ubidecarenone was then added to Mix Tank 2. While maintaining the temperature at between 50 and 60° C. Mix Tank 2 was mixed until all the Ubidecarenone was dissolved. After all the Ubidecarenone had been dissolved, the water phase was slowly transferred to Mix Tank 2. When all materials have been combined, the contents were homogenized until dispersion is smooth and uniform. While being careful not to overheat, the temperature was maintained at between 50 and 60° C. The homogenization was then stopped and the contents of Mix Tank 2 were transferred to a suitable container for storage.

Example 27

Method of Forming a 0.5 kg Batch of CoQ10 21% Concentrate which Includes Propylene Glycol A 0.5 kg of CoQ10 21% concentrate composition was prepared by combining phases A and B as described below. Phase A included Ubidecarenone USP (CoQ10) at 21% w/w and polysorbate 80 NF at 25% w/w. Phase B included propylene glycol USP at 10.00% w/w, phenoxyethanol NF at 0.50% w/w, lecithin NF (PHOSPHOLIPON 85G) at 8.00% w/w and purified water USP at 35.50% w/w. All weight percentages are relative to the weight of the entire CoQ10 cream 21% concentrate composition. The percentages, amounts and further details are listed above in the following table.

TABLE 57

| Phase | Trade Name | INCI Name | Percent | Amount (Kg) |
|---|---|---|---|---|
| A | RITABATE 80 | POLYSORBATE 80 | 25.000 | 0.1250 |
| A | UBIDECARENONE | UBIQUINONE | 21.000 | 0.1050 |
| B | PURIFIED WATER | WATER | 35.500 | 0.1775 |
| B | PROPYLENE GLYCOL | PROPYLENE GLYCOL | 10.000 | 0.0500 |
| B | PHENOXY-ETHANOL | PHENOXY-ETHANOL | 0.500 | 0.0025 |
| B | PHOSPHOLIPON 85G | LECITHIN | 8.000 | 0.0400 |
| Totals | | | 100.000 | 0.5000 |

All equipment was clean and sanitary. Polysorbate 80 was directly weighed in PK-2 kettle and heat in vacuum kettle PK-2 to 50-55° C. The Ubidecarenone USP was weighed on benchtop and the weight double checked by adding to tared PK-2 vessel (agitators off). The PK-2 was closed and sealed. The closed and sealed PK-2 was mixed with sweep mixers on low while maintaining 50-55° C. temperature and vacuum on for 15 minutes. The Phase was examined to insure all powder has dissolved in polysorbate before moving to the next step. In PK-1, the required amount of water was added and heated to 50-55° C. On benchtop, phenoxyethanol and Hydrolite-5 were weighed and mixed until clear and uniform and water was added with moderate mixing until clear and uniform. When above water mixture reached 50-55° C., lecithin was added with low-moderate mixing, avoid foaming and mixed until dispersed. Water phase was transfer from PK-1 to a 5 gallon container. With both water phase and CoQ10 phase at 50-55° C., the water phase was added to CoQ10 phase with moderate sweep mixing. Once all materials have been transferred to PK-2, the batch was recirculated through Silverson with standard shear head at 7000 rpm for 3-5 minutes with PK-2 vessel closed and vacuum on. Temperature was maintained at 50-55° C. and was not allowed to overheat. Recirculation was stopped and the batch was cooled to 30-35° C. with moderate sweep mixing. The concentrate was pumped into temporary transfer containers.

Example 28

Method of Preparing a 20 kg Batch of CoQ10 21% Concentrate which Includes Propylene Glycol A 20 kg batch of CoQ10 21% concentrate was prepared by combining the ingredients of phases A, B and C. Phase A included polysorbate 80 NF at 25.00% w/w and Ubidecarenone USP at 21.00% w/w. Phase B included propylene glycol USP at 10.00% w/w and phenoxyethanol NF at 0.50% w/w. Phase C included purified water USP at 35.50% w/w and lecithin NF at 8.00% w/w. The percentages, amounts and further details are presented in the following table.

TABLE 58

| Phases | RM Number | Raw Material Name | Theoretical Quantity % w/w | gm |
|---|---|---|---|---|
| A | RM-002 | RM-002: Polysorbate 80 NF | 25.000 | 5,000 |
| A | RM-010 | RM-010: Ubidecarenone USP | 21.000 | 4,200 |
| B | RM-021 | RM-021: Propylene Glycol USP | 10.000 | 2,000 |
| B | RM-013 | RM-013: Phenoxyethanol NF | 0.500 | 100.0 |
| C | RM-011 | RM-011: Purified Water USP | 35.500 | 7,100 |
| C | RM-017 | RM-017: Lecithin NF | 8.000 | 1,600 |
| | | Totals | 100.000 | 20,000 |
| | | For purging PK-2 (Lee Vacuum Tank) | | |
| | RM-019 or RM-020 | Nitrogen 97% NF Nitrogen NF | q.s. | q.s. |

In preparing the 20 kg batch of CoQ10 21% concentrate, the area was cleaned and verified clean. All equipment was cleaned and within expiration/calibration. 100.0 gm phenoxyethanol was weighed and placed into a clean beaker.

To prepare Phase B, two thousand grams (2,000 gm) of propylene glycol was weighed and placed into a clean 2-L SS beaker. Further, 2000 gm of purified water was weighed and placed into a clean container labeled "water for rinsing."

To the 2-L SS beaker containing the pre-weighed 2,000 gm propylene glycol, the pre-weighed 100 gm phenoxyethanol was added. The beaker that contained the phenoxyethanol was rinsed into the 2-L beaker with ⅓ of the water for rinsing. The contents of the 2-L beaker was mixed with a spatula until clear and uniform and was labeled as Phase B.

In the following step, 1,600 gm of lecithin was weighed and 5,100 gm of purified water was weighed. Appropriately labeled charts were placed in the temperature recorders TIC-1 for the PK-1 and TIC-2 for the PK-2. 5,100 gm of purified water was added to the PK-1 and the water was manually heated in the PK-1 to 50-55° C. The agitator was turned on and a slight vortex was maintained. The Phase B solution was then slowly added from the 2-L SS beaker into the PK-1. The SS beaker was then rinsed with the approximately ⅓ of the water for rinsing. The rinsate was slowly added to the PK-1. The temperature was manually maintained at 50-55° C. The lecithin NF was then slowly added and mixed until it was dispersed. The temperature was manually maintained at 50-55° C. and the mixing continued until Phase B was ready for transfer to PK-2.

To prepare Phase A, 5,000 gm of polysorbate 80 was weighed and placed into a clean container while 4,200 gm of Ubidecarenone USP was weighed. To compound the concentrate, the equipment included a Lee Vacuum Tank (PK-2), a Silverson Homogenizer (P-2) and a Waukesha Pump (P-1). First, it was confirmed that the bottom valve of the PK-2 was closed. The pre-weighed 5,000 gm of polysorbate 80 was then added into the PK-2 through the sight glass portal. The sight glass was replaced on the PK-2 after the addition was complete.

The PK-2 agitator was then turned on and the polysorbate 80 was manually heated in the PK-2 to 50-55° C. When the temperature of the polysorbate 80 reached that temperature range, the 4,200 gm of pre-weighed Ubidecarenone USP was added through the access portal on the PK-2. A spatula was use to remove any Ubidecarenone which was caked on the agitator blades during addition. When addition was completed, the sight glass was replaced. The temperature was manually maintained at between 50-55° C. and mixed for 15 minutes. The contents of the PK-2 was inspected through the sight glass portal to evaluate if the Ubidecarenone was dissolved in the polysorbate 80. The PK-1 agitator (A-1) was then turned off.

Through the access portal of the PK-2, the contents of the PK-1 (Phase B) were added to the PK-2. The PK-1 was then rinsed with the remaining "water for rinsing." The PK-2 was manually heated to 50-55° C. The contents of the PK-2 were then recirculated through the P-1 and P-2 with the Silverson high shear screen in P-2 at maximum rpm for 5-10 minutes. The vacuum was turned on and was maintained at maximum to prevent foaming. The temperature was manually maintained at 50-55° C.

Four samples were removed: two 30 gm samples for Micro test and two 400 gm samples for physico/chemical testing. One set of sample was labeled as retain. The product was then transferred into a clean HDPE closed-top container. The batch size was 20,000 gm.

Example 29

Method of Preparing a CoQ10 Cream 1.5%

A CoQ10 cream 1.5% composition was prepared by combining phases A-E as described below. Phase A included alkyl $C_{12-15}$ benzoate NF at 5.000% w/w, cetyl alcohol NF at 2.000% w/w, glyceryl stearate/PEG-100 stearate at 4.5% w/w and stearyl alcohol NF at 1.5% w/w. The percentages and amounts are reflected in the following table.

TABLE 59

| Phase | Trade Name | CTFA Name | Percent |
|---|---|---|---|
| A | RITAMOLLIENT TN | C12-15 ALKYL BENZOATE | 4.000 |
| A | RITA CA | CETYL ALCOHOL | 2.000 |
| A | RITA SA | STEARYL ALCOHOL | 1.500 |
| A | RITAPRO 165 | GLYCERYL STEARATE AND PEG-100 STEARATE | 4.500 |

Phase B included diethylene glycol monoethyl ether NF at 5.000% w/w, glycerin USP at 2.000% w/w, propylene glycol USP at 1.750% w/w, phenoxyethanol NF at 0.463% w/w, purified water USP at 11.377% w/w and carbomer dispersion 2% at 50.00% w/w. The percentages and amounts are reflected in the following table.

TABLE 60

| Phase | Trade Name | CTFA Name | Percent |
|---|---|---|---|
| B | RITA GLYCERIN | GLYCERIN | 2.000 |
| B | PROPYLENE GLYCOL | PROPYLENE GLYCOL | 1.750 |
| B | TRANSCUTOL P | ETHOXYDIGLYCOL | 5.000 |
| B | PHENOXYETHANOL | PHENOXYETHANOL | 0.463 |
| B | ACRITAMER 940, 2% DISPERSION | WATER, PHENOXYETHANOL, PROPYLENE GLYCOL, AND CARBOMER 940 | 50.000 |
| B | PURIFIED WATER USP | WATER | 11.377 |

Phase C included lactic acid USP at 0.400% w/w, sodium lactate solution USP at 2.000% w/w, trolamine NF at 1.300% w/w and purified water USP at 4.210% w/w. The percentages and amounts are reflected in the following table.

TABLE 61

| Phase | Trade Name | CTFA Name | Percent |
|---|---|---|---|
| C | TEAlan 99% | TRIETHANOLAMINE | 1.300 |
| C | RITALAC LA USP | LACTIC ACID | 0.400 |
| C | RITALAC NAL | SODIUM LACTATE, WATER | 2.000 |
| C | DISTILLED WATER | WATER | 4.210 |

Phase D included titanium dioxide USP at 1.000% w/w. While Phase E included CoQ10 21% concentrate, 21% at 7.500% w/w. All weight percentages are relative to the weight of the entire 1.5% CoQ10 cream composition. The percentages, amounts and further details are reflected in the following tables.

TABLE 62

| Phase | Trade Name | CTFA Name | Percent |
|---|---|---|---|
| D | TITANIUM DIOXIDE, #3328 | TITANIUM DIOXIDE | 1.000 |

TABLE 63

| Phase | Trade Name | CTFA Name | Percent |
|---|---|---|---|
| E | CoQ10 21% CONCENTRATE | WATER, POLYSORBATE 80, UBIQUINONE, LECITHIN, PROPYLENE GLYCOL, PHENOXYETHANOL | 7.500 |

In preparing the CoQ10 cream 1.5% composition, Phase A ingredients were added to a suitable container and heated to between 70 and 80° C. in a water bath. Phase B ingredients, excluding the Carbomer Dispersion, were added to a PK-2 Kettle and mixed with moderate sweep mixing while heating to between 70 and 80° C. The Phase C ingredients were added to a suitable container and heated to between 70 and 80° C. in a water bath. The Phase E CoQ10 concentrate was placed in a suitable container and melted between 50 and 60° C. using a water bath, while mixing as necessary to assure uniformity. The Carbomer Dispersion was added to a suitable container (Mix Tank) and heated to between 70 and 80° C. while mixing. While continuing to mix, Phase B ingredients were added to the heated Carbomer Dispersion in the Mix Tank while maintaining the temperature. While continuing to mix, Phase C ingredients were added to the contents of the Mix Tank while maintaining the temperature. The Mix Tank was continually mixed and homogenized. The mixer was then turned off but homogenization continued while adding the Phase D ingredient to the Mix Tank. The mixer was then turned on and the ingredients was mixed and homogenized until completely uniform and fully extended (check color). Homogenization was then stopped and the batch was cooled to between 50 and 60° C. The mixer was then turned off and the melted CoQ10 concentrate was added to the Mix Tank. The mixer was then turned on and the contents mixed/recirculated until dispersion was smooth and uniform. The contents of the Mix Tank was then cooled to between 45 and 50° C. The cooled contents were then transferred to a suitable container for storage until packaging.

Example 30

Method of Preparing a 0.5 kg Batch of CoQ10 Cream 1.5%

A 1.5% CoQ10 cream composition was prepared by combining phases A-E as described below. Phase A included alkyl $C_{12-15}$ benzoate NF at 5.000% w/w, cetyl alcohol NF at 2.000% w/w, glyceryl stearate/PEG-100 stearate at 4.5% w/w and stearyl alcohol NF at 1.5% w/w. The percentages, amounts and further details are reflected in the following table.

TABLE 64

| Phase | Trade Name | CTFA Name | Percent | Amount (kg) |
|---|---|---|---|---|
| A | RITAMOLLIENT TN | C12-15 ALKYL BENZOATE | 4.000 | 0.0250 |
| A | RITA CA | CETYL ALCOHOL | 2.000 | 0.0100 |
| A | RITA SA | STEARYL ALCOHOL | 1.500 | 0.0075 |
| A | RITAPRO 165 | GLYCERYL STEARATE AND PEG-100 STEARATE | 4.500 | 0.0225 |

Phase B included diethylene glycol monoethyl ether NF at 5.000% w/w, glycerin USP at 2.000% w/w, propylene glycol USP at 1.750% w/w, phenoxyethanol NF at 0.463% w/w, purified water USP at 11.377% w/w and carbomer dispersion 2% at 50% w/w. The percentages, amounts and further details are reflected in the following table.

TABLE 65

| Phase | Trade Name | CTFA Name | Percent | Amount (kg) |
|---|---|---|---|---|
| B | RITA GLYCERIN | GLYCERIN | 2.000 | 0.0100 |
| B | PROPYLENE GLYCOL | PROPYLENE GLYCOL | 1.750 | 0.0088 |
| B | TRANSCUTOL P | ETHOXYDIGLYCOL | 5.000 | 0.0250 |
| B | PHENOXY-ETHANOL | PHENOXY-ETHANOL | 0.463 | 0.0023 |
| B | ACRITAMER 940, 2% DISPERSION | WATER, PHENOXY-ETHANOL, PROPYLENE GLYCOL, AND CARBOMER 940 | 50.000 | 0.2500 |
| B | PURIFIED WATER USP | WATER | 11.377 | 0.0569 |

Phase C included lactic acid USP at 0.400% w/w, sodium lactate solution USP at 2.000% w/w, triethanolamine NF at 1.300% w/w and purified water USP at 4.210% w/w. The percentages, amounts and further details are reflected in the following table.

TABLE 66

| Phase | Trade Name | CTFA Name | Percent | Amount (kg) |
|---|---|---|---|---|
| C | TEAlan 99% | TRIETHANOLAMINE | 1.300 | 0.0065 |
| C | RITALAC LA USP | LACTIC ACID | 0.400 | 0.0020 |
| C | RITALAC NAL | SODIUM LACTATE, WATER | 2.000 | 0.0100 |
| C | DISTILLED WATER | WATER | 4.210 | 0.0211 |

Phase D included titanium dioxide USP at 1.000% w/w. While Phase E included CoQ10 concentrate, 21% at 7.500% w/w. All weight percentages are relative to the weight of the entire 1.5% CoQ10 cream composition. The percentages, amounts and further details are reflected in the following table.

TABLE 67

| Phase | Trade Name | CTFA Name | Percent | Amount (kg) |
|---|---|---|---|---|
| D | TITANIUM DIOXIDE, #3328 | TITANIUM DIOXIDE | 1.000 | 0.0050 |
| E | CoQ10 21% CONCENTRATE | WATER, POLYSORBATE 80, UBIQUINONE, LECITHIN, PROPYLENE GLYCOL, PHENOXYETHANOL | 7.500 | 0.0375 |

In preparing the 1.5% CoQ10 cream composition, the Phase A ingredients were weighed and heated to between 70-75° C. in a water bath. Phase B ingredients were added to a PK-2 Kettle and mixed with moderate sweep mixing while heating to between 70-75° C. When Phase B reaches 70-75° C. Phase A was added at 70-75° C. with moderate sweep mixing. Phase A and B were then recirculated through Silverson. The Phase C ingredients were weighed, mixed until uniform and heated to 60-65° C. Phase C ingredients were then added to the PK-2 kettle with sweep mixer on medium-high. While continuing to mix, Phase D was added to the batch in the PK-2 kettle. The batch was continually mixed and recirculated through the Silverson for 10 minutes or until completely uniform and fully extended.

The circulation was discontinued and the batch was cooled to between 50-55° C. with sweep mixer on medium. After warming the Phase E ingredients to between 45 and 50° C., they were added to the batch and the batch was mixed with vacuum at moderate speed until uniform. The temperature was maintained at 50° C. The batch was then cooled to 30-35° C. with low-moderate mixing and vacuum. The batch was then pumped to a holding container.

Example 31

Method of Preparing a 20 kg Batch CoQ10 Cream 1.5%

A 20 kg batch of CoQ10 Cream 1.5% composition was prepared by combining the ingredients of Phases A-E. The weight percentages, amounts and further details of the ingredients for each phase are presented in the following table.

TABLE 68

| Phase | RM Number | Raw Material Name | Theoretical Quantity % w/w | Theoretical Quantity Gm |
|---|---|---|---|---|
| A | RM-026 | RM-026: Capric/Caprylic Triglyceride | 5.000 | 1000.0 |
| A | RM-003 | RM-003: Cetyl Alcohol NF | 2.000 | 400.0 |
| A | RM-005 | RM-005: Stearyl Alcohol NF | 1.500 | 300.0 |
| A | RM-016 | RM-016: Glyceryl Stearate/ PEG-100 Stearate | 4.500 | 900.0 |
| B | RM-001 | RM-001: Glycerin USP | 2.000 | 400.0 |
| B | RM-021 | RM-021: Propylene Glycol USP | 1.750 | 350.0 |

TABLE 68-continued

| Phase | RM Number | Raw Material Name | Theoretical Quantity % w/w | Gm |
|---|---|---|---|---|
| B | RM-007 | RM-007: Diethylene Glycol Monoethyl Ether NF | 5.000 | 1000.0 |
| B | RM-013 | RM-013: Phenoxyethanol NF | 0.465 | 93.0 |
| B | IP-003 | IP-003: Carbomer Dispersion, 2% | 50.000 | 10000.0 |
| B | RM-011 | RM-011: Purified Water USP | 8.375 | 1675.0 |
| B | RM-011 | RM-011: Purified Water USP (for rinsing) | 3.000 | 600.0 |
| C | RM-009 | RM-009: Trolamine NF | 1.300 | 260.0 |
| C | RM-006 | RM-006: Lactic Acid USP | 0.400 | 80.0 |
| C | RM-012 | RM-012: Sodium Lactate Solution USP, 60% | 2.000 | 400.0 |
| C | RM-011 | RM-011: Purified Water USP | 4.210 | 842.0 |
| D | RM-008 | RM-008: Titanium Dioxide USP | 1.000 | 200.0 |
| E | IP-004 | IP-004: CoQ10 Concentrate, 21% | 7.500 | 1500.0 |
| | | Totals | 100.00 | 20000.0 |
| | | For Purging PK-2 (Vacuum Tank) | | |
| | RM-019 or RM-020 | Nitrogen 97% NF or Nitrogen NF | q.s. | q.s. |

The chemicals were weighed with special care taken to avoid spillage onto the weighing pan. First 200 gm of titanium dioxide (Phase D) was weighed. Then 600 gm of purified water was weighed and labeled as "water for rinsing-Phase B".

In preparing Phase A, 1000 gm of Capric/Caprylic Triglyceride, 400 gm of cetyl alcohol NF, 300 gm of stearyl alcohol NF, and 900 gm of glyceryl stearate/PEG-100 were weighed. These pre-weighed Phase A ingredients were then added to a 4-L SS beaker and the container labeled as Phase A. Note that this pre-mix must be used within 24 hours. The Phase A container was then covered and put aside for later use.

In preparing Phase B, 10,000 gm of Carbomer Dispersion 2%, as in example 11A, was weighed. Further, 400 gm of glycerin USP, 350 gm of propylene glycol, 1,000 gm of diethylene glycol monoethyl ether NF and 93 gm phenoxyethanol NF were weighed. 1675 gm of purified water was weighed and the container was labeled as "purified water for Phase B". These pre-weighed Phase B ingredients were added to a 10-L SS beaker and labeled as Phase B. Note that this pre-mix must be used within 24 hours. The contents of the Phase B container were manually mixed with a spatula until clear and uniform. The Phase B container was then covered and put aside for later use.

In preparing Phase C, 260 gm of triethanolamine NF, 400 gm of sodium lactate solution USP, 60%, 842 gm of purified water (labeled as "purified water for Phase C"), and 80 gm of lactic acid USP were weighed. These pre-weighed Phase C ingredients were then added to a 2-L SS beaker in the following order: (1) 260 gm of triethanolamine, (2) 400 gm sodium lactate solution, 60%, (3) 842 gm purified water USP for Phase C and (4) 80 gm lactic acid USP. Note that this pre-mix must be used within 24 hours. The contents of the Phase C container were then manually mixed with a spatula until clear and uniform. The Phase C container was then covered and put aside for later use.

In preparing Phase E, 1500 gm of CoQ10 21% Concentrate was weighed and covered in a Phase E container and put aside for later use.

In preparing the 20 kg batch of CoQ10 Cream 1.5% 2 water baths are required. The Phase A beaker was placed into a water bath set to 70-75° C. and the contents were mixed manually with a spatula until clear and uniform. The Phase C beaker was then placed into a water bath set at 60-65° C. and the contents of the Phase C beaker were mixed manually with a spatula until clear and uniform. Similarly, the Phase E beaker was placed into a water bath and set to 50-55° C. The contents of the Phase E container were mixed manually with a spatula until clear and uniform.

Additional equipment used included a water bath (E-1), a Lee vacuum Tank (PK-2), a Waukesha Pump (P-1) and a square hole high shear screen for Silverson Homogenizer.

First, it was confirmed that the bottom of the valve of PK-2 was closed and that the PK-2 was properly sealed. The sight glass was then removed from the PK-2. The pre-weighed 10,000 gm of Carbomer Dispersion 2.0% was then added to the PK-2 through the sight glass portal. A spatula was used to transfer the Carbomer Dispersion 2.0% from the walls of its container. The TIC-2 (temperature recorder) for the PK-2 was then turned on and was checked to ensure proper operation. The agitator for the PK-2 (A-2) was then turned on and the Carbomer Dispersion 2.0% in the PK-2 was heated with the steam jacket to 70-80° C. The vacuum was turned off. The sight glass was then removed from the PK-2 and Phase B, from the SS beaker, was slowly added into PK-2 through the sight glass portal. The Phase B container was then rinsed with the "water for rinsing Phase B." The rinsate was added into the PK-2 through the sight glass portal. Phase A was then slowly added to the PK-2. A spatula was used to transfer any Phase A from the walls of the SS beaker. Note that the Phase A temperature must be between 70-80° C. when added to the PK-2. The bottom valve from the PK-2 was then opened. The P-1 (Waukesha Pump) and the P-2 (Silverson Homogenizer) were turned on and the contents of the PK-2 (Vacuum Tank) were homogenized. Phase C was slowly added to the PK-2 through the access port. Note that the temperature must be between 70-80° C. when added to the PK-2. It was then ensured that the Homogenization was for greater than 5 minutes then the A-2 (agitator) was turned off. The pre-weighed 200.0 gm titanium dioxide of Phase D was then slowly sifted through a 100 mesh screen into the PK-2. A spatula was used to dislodge any titanium dioxide which sticks to the blades of the PK-2.

The sight glass was then replaced and A-2 was turned on. The contents were continued to be mixed while recirculating through P-1 (Waukesha Pump) and P-2. The contents were homogenized for 10 minutes or until completely uniform and fully extended (check color). P-2 was stopped after 10 minutes. The contents of the PK-2 were cooled to 50-60° C. The sight glass was removed and the melted CoQ10 21% Concentrate (Phase E, as in Example 7A) was slowly added to the PK-2. The sight glass was then replaced.

The contents of the PK-2 were mixed until uniform and recirculated through P-1. The temperature was maintained at 50-60° C. The nitrogen NF flow was started and then the C-2 (vacuum pump) was turned on. Note that it is best to avoid foam up of the product. The batch was then cooled to 45-50° C. and both the vacuum and the nitrogen NF were turned on. When the product had cooled to temperature, the C-2 was turned off and any vacuum with the nitrogen NF was relieved. The nitrogen NF flow remained on. The outlet valve was then purged with product before collecting samples or packaging the product. The product was transferred into pre-weighed, clean, HDPE closed-top containers.

The A-2, P-1 and nitrogen NF flow were turned off and the batch was completed and indicated on the TIC-2 chart.

Two 30 gm (minimum) samples were removed for micro testing and two 400 gm (minimum) samples were removed for physico/chemical testing. One set of samples was labeled as "retain". The filled containers were weighed. The yielded batch size was 20,000 gm.

Example 32

Method of Preparing an 18 kg Batch of Carbomer Dispersion 2%

An 18 kg batch of Carbomer Dispersion 2.0% composition was prepared by combining phases A-C as described below. Phase A included propylene glycol USP at 0.50% w/w and phenoxyethanol NF at 5.00% w/w. Phase B included purified water USP at 92.50% w/w while Phase C included Carbomer 940 NF at 2.00% w/w. All weight percentages are relative to the weight of the entire CoQ10 cream 2.0% composition. The percentages and amounts of the ingredients are listed in the following table.

TABLE 69

| Phase | Trade Name | CTFA Name | Percent | Amount (kg) |
|---|---|---|---|---|
| A | PHENOXY-ETHANOL | PHENOXY-ETHANOL | 5.00 | 0.9 |
| A | PROPYLENE GLYCOL | PROPYLENE GLYCOL | 0.500 | 0.09 |
| B | PURIFIED WATER, USP | PURIFIED WATER | 92.500 | 16.65 |
| C | ACRITAMER 940 | CARBOMER 940 NF | 2.000 | 0.3600 |
| | Totals | | 100.000 | 18.00 |

In a suitable container, the Phase A ingredients were mixed until clear and uniform. To a second container (Mix Tank) the purified water of Phase B was added. A portion of the purified water ("water for rinse") was retained for rinsing the Phase A container. The water in the second container was heated to between 60 and 65° C. The Phase A ingredients were added to the water of Phase B and the "water for rinse" was used to rinse the Phase A container. The contents of the Phase A container were then mixed until clear and uniform. The mixer speed was increased while slowly adding (sprinkle) the Carbomer 940 of Phase C to the Mix Tank. Mixing was continued until all powder had been thoroughly dispersed and no "fish-eyes" were present. The temperature was maintained between 60 to 65° C. The contents were then transferred to a suitable container for storage.

Example 33

Method of Preparing a 3 kg Batch of Carbomer Dispersion 2%

A 3 kg batch of Carbomer Dispersion 2.0% composition was prepared by combining phases A-C as described below. Phase A included propylene glycol USP at 5.00% w/w and phenoxyethanol NF at 0.50% w/w. Phase B included purified water USP at 92.50% w/w while Phase C included Carbomer 940 NF at 2.00% w/w. All weight percentages are relative to the weight of the entire CoQ10 cream 2.0% composition. The percentages, amounts and further details are listed in the following table.

TABLE 70

| Phase | Trade Name | CTFA Name | Percent | Amount (kg) |
|---|---|---|---|---|
| A | PHENOXYETHANOL | PHENOXY-ETHANOL | 0.500 | 0.0150 |
| A | PROPYLENE GLYCOL | PROPYLENE GLYCOL | 5.000 | 0.1500 |
| B | PURIFIED WATER, USP | WATER | 92.500 | 2.7750 |
| C | ACRITAMER 940 | CARBOMER 940 | 2.000 | 0.0600 |
| | Totals | | 100.000 | 3.0000 |

All equipment was cleaned and sanitized. On benchtop, phase A ingredients were mixed until clear and uniform. The required amount of water was weighed and added to Kettle PK-1 (phase vessel). The water in PK-1 was heated with hot water/steam jacket to 60-65° C. Phase A was added to Phase B water with moderate agitation until clear and uniform. Phase A container was rinsed with process water phase while maintaining the temperature at 60-65° C. Mixing was continued at medium-high agitation until all powder had been thoroughly dispersed and no "fish-eyes" were present. The contents were sampled for micro quality, pH, specific gravity and viscosity. The batch was then pumped into a clean & sanitized 5 gallon closed top carboy based on pH, specific gravity and viscosity within specifications.

Example 34

Method of Preparing an 18 kg Batch of Carbomer Dispersion 2%

An 18 kg batch of Carbomer Dispersion 2% was prepared by combining the ingredients of Phases A, B and C. Phase A included phenoxyethanol NF at 0.50% w/w, propylene glycol USP at 5.00% w/w, purified water USP at 92.50% w/w and Carbomer 940 NF at 2.00% w/w.

TABLE 71

| | RM | | Theoretical Quantity | |
|---|---|---|---|---|
| Phase | Number | Raw Material Name | % w/w | GMS |
| A | RM-013 | Phenoxyethanol NF | 0.500 | 90.0 |
| A | RM-021 | Propylene Glycol USP | 5.000 | 900 |
| B | RM-011 | Purified Water USP | 92.500 | 16,650 |
| C | RM-004 | Carbomer 940 NF | 2.000 | 360 |
| | | Totals | 100.000 | 18,000 |

The equipment used in this batch preparation included a Sartorius Balance, a Mettler Balance, a Chart Recorder, a Lee Phase Tank and a 2-L stainless steel (SS) beaker.

Before weighing the ingredients, the production area was cleaned and verified as being clean. All equipment were likewise cleaned and verified as clean and within expiration/calibration. The balance calibration was checked and recorded. The weighing containers were tared to avoid spillage onto the weighing pan. First 1,650 gms of purified water was weighed and placed in a container labeled "water for rinsing." Another 15,000 gms of purified water was also weighed. 360 gms of Carbomer 940 NF was also weighed.

Phase A was prepared by weighing 90 gms of phenoxyethanol into a beaker. 900 gms of propylene glycol USP was then weighed into a 2-L SS beaker. The pre-weighed phenoxyethanol NF was then added to the 2-L SS beaker containing the pre-weighed propylene glycol. Phenoxyethanol residue remaining in the beaker was rinsed with approximately ⅓ of the "water for rinsing." The container was then labeled as Phase A. Note that the pre-mix must be used within 24 hours.

Phase A was mixed with a spatula until clear and uniform. The spatula was removed while rinsing with ⅓ of the "water for rinsing."

Following the preparation of Phase A, the dispersion was compounded using a Lee Phase Tank (PK-1). An appropriate labeled chart was placed in the TIC-1 (temperature recorder). The TIC-1 (Honeywell Temperature Recorder) was turned on and was ensured to be operating properly. Once the bottom valve on the PK-1 was confirmed to be closed, the pre-weighed purified water USP was added to the PK-1. The SS beaker was rinsed into the PK-1 with the remaining "water for rinsing." The agitator was turned on to moderate and the contents of the PK-1 were heated with the hot water/steam jacket to 60-65° C. Acceptable ranges also includes 55-70° C. The agitator was set to the highest speed without causing splashing. The pre-weighed Carbomer 940 NF was evenly sifted through a 50 mesh screen into PK-1 over a period of at least 15 minutes but not more than 20 minutes. The targeted temperature was 60-65° C., however the acceptable range was 55-70° C. The agitator was then turned on to high. Mixing continued for at least 1 hour at high agitation until all powder had been thoroughly dispersed and no "fish-eyes" were present. A spatula was used to disperse any powder that was caught on the edge into the vortex.

Two 30 gm samples of the dispersion was removed for micro testing and two 400 gm sales for physico/chemical testing. One set was labeled as "retain." The product was then transferred to clean HDPE closed-top containers. The resulting batch size was 18,000 gm.

Example 35

Method of Preparing a CoQ10 Cream 3% which Includes CoQ10 21% Concentrate and Alkyl Benzoate A CoQ10 cream 3.0% composition was prepared by combining the following phases. Phase A included alkyl $C_{12-15}$ benzoate NF at 4.00% w/w, cetyl alcohol NF at 2.00% w/w, glyceryl stearate/PEG-100 stearate at 4.50% w/w and stearyl alcohol NF at 1.5% w/w. The percentages, amounts and further details are listed in the following table.

TABLE 72

| Phase | Trade Name | CTFA Name | Percent |
|---|---|---|---|
| A | RITAMOLLIENT TN | C12-15 ALKYL BENZOATE | 4.000 |
| A | RITA CA | CETYL ALCOHOL | 2.000 |
| A | RITA SA | STEARYL ALCOHOL | 1.500 |
| A | RITAPRO 165 | GLYCERYL STEARATE AND PEG-100 STEARATE | 4.500 |

Phase B included diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion, 2% at 40% w/w. The percentages and amounts of the ingredients are listed in the following table.

TABLE 73

| Phase | Trade Name | CTFA Name | Percent |
|---|---|---|---|
| B | RITA GLYCERIN | GLYCERIN | 2.000 |
| B | PROPYLENE GLYCOL | PROPYLENE GLYCOL | 1.500 |
| B | TRANSCUTOL P | ETHOXYDIGLYCOL | 5.000 |
| B | PHENOXYETHANOL | PHENOXYETHANOL | 0.475 |
| B | ACRITAMER 940, 2% DISPERSION | WATER, PHENOXYETHANOL, PROPYLENE GLYCOL, CARBOMER 940 | 40.000 |
| B | PURIFIED WATER, USP | WATER | 16.725 |

Phase C included lactic acid USP at 0.50% w/w, sodium lactate solution USP at 2.00% w/w, Triethanolamine NF at 1.30% w/w and purified water USP at 2.50% w/w. The percentages and amounts of the ingredients are listed in the following table.

TABLE 74

| Phase | Trade Name | CTFA Name | Percent |
|---|---|---|---|
| C | TEALAN 99% | TRIETHANOLAMINE | 1.300 |
| C | RITALAC LA | LACTIC ACID | 0.500 |
| C | RITALAC NAL | SODIUM LACTATE, WATER | 2.000 |
| C | PURIFIED WATER, USP | WATER | 2.500 |

Table 45

Phase D included titanium dioxide USP at 1.00% w/w while Phase E included CoQ10 21% concentrate, at 15.00% w/w. The percentages and amounts of the ingredients are listed in the following table.

TABLE 75

| Phase | Trade Name | CTFA Name | Percent |
|---|---|---|---|
| D | TITANIUM DIOXIDE, #3328 | TITANIUM DIOXIDE | 1.000 |
| E | CoQ10 21% CONCENTRATE | PROPYLENE GLYCOL, POLYSORBATE 80, UBIQUINONE, WATER, PHENOXYETHANOL | 15 |

All weight percentages are relative to the weight of the entire CoQ10 cream 3.0% composition.

The Phase A ingredients were added to a suitable container and heated to between 70 and 80° C. in a water bath. The Phase B ingredients, not including the Carbomer Dispersion, were added to a suitable container and mixed. The Phase C ingredients were also added to a suitable container and then heated to between 70 and 80° C. in a water bath. The CoQ10 concentrate of Phase E was placed in a suitable container and melted between 50 and 60° C. using a water bath. The ingredients were mixed as necessary to assure uniformity. The Carbomer Dispersion was then added to a suitable container (Mix Tank) and heated to between 70 and 80° C. while being mixed. While the ingredients were being mixed, the Phase B ingredients were added to the contents of the Mix Tank while maintaining the temperature. The contents were continually mixed and homogenized. The mixer was then turned off, however, homogenization was sustained. While the homogenization continued, the titanium dioxide of Phase D was added to the Mix Tank. The mixer was then turned on and the contents were mixed and further homogenized until completely uniform and fully extended (check color). Homogenization was then stopped and the batch was cooled to between 50 and 60° C. The mixer was then turned off and the melted CoQ10 concentrated was added to the Mix Tank. The mixer was subsequently turned on and the contents mixed/recirculated until dispersion was smooth and uniform. The contents of the Mix Tank were then cooled to between 45 and 50° C. The contents were then transferred to a suitable container for storage until unpacking.

Example 36

Method of Preparing a 0.5 kg Batch of CoQ10 Cream 3% which Includes CoQ10 21% Concentrate and Alkyl Benzoate A 0.5 kg batch of CoQ10 cream 3.0% composition was prepared by combining the following phases. Phase A included $C_{12-15}$ alkyl benzoate at 4.00% w/w, cetyl alcohol NF at 2.00% w/w, glyceryl stearate/PEG-100 stearate at 4.50% w/w and stearyl alcohol NF at 1.5% w/w. The percentages and amounts are listed in the following table.

TABLE 76

| Phase | Trade Name | CTFA Name | Percent | Amount (kg) |
|---|---|---|---|---|
| A | CAPRYLIC | $C_{12-15}$ alkyl benzoate | 4.000 | 0.0200 |
| A | RITA CA | CETYL ALCOHOL | 2.000 | 0.0100 |
| A | RITA SA | STEARYL ALCOHOL | 1.500 | 0.0075 |
| A | RITAPRO 165 | GLYCERYL STEARATE AND PEG-100 STEARATE | 4.500 | 0.0225 |

Phase B included diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion, 2% at 40% w/w. The percentages and amounts are listed in the corresponding phase table below.

TABLE 77

| Phase | Trade Name | CTFA Name | Percent | Amount (kg) |
|---|---|---|---|---|
| B | RITA GLYCERIN | GLYCERIN | 2.000 | 0.0100 |
| B | PROPYLENE GLYCOL | PROPYLENE GLYCOL | 1.500 | 0.0075 |
| B | TRANSCUTOL P | ETHOXYDIGLYCOL | 5.000 | 0.0250 |
| B | PHENOXY-ETHANOL | PHENOXYETHANOL | 0.475 | 0.0024 |
| B | ACRITAMER 940, 2% DISPERSION | WATER, PHENOXYETHANOL, PROPYLENE GLYCOL, CARBOMER 940 | 40.000 | 0.2000 |
| B | PURIFIED WATER, USP | WATER | 16.725 | 0.0836 |

Phase C included lactic acid USP at 0.50% w/w, sodium lactate solution USP at 2.00% w/w, triethanolamine NF at 1.30% w/w and purified water USP at 2.50% w/w. The percentages, amounts and further details are listed in the following table.

TABLE 78

| Phase | Trade Name | CTFA Name | Percent | Amount (kg) |
|---|---|---|---|---|
| C | TEALAN 99% | TRIETHANOLAMINE | 1.300 | 0.0065 |
| C | RITALAC LA | LACTIC ACID | 0.500 | 0.0025 |
| C | RITALAC NAL | SODIUM LACTATE, WATER | 2.000 | 0.0100 |
| C | PURIFIED WATER, USP | WATER | 2.500 | 0.0125 |

Phase D included titanium dioxide USP at 1.00% w/w while Phase E included CoQ10 21% concentrate at 15.00% w/w. The percentages, amounts and further details are listed in the following table.

TABLE 79

| Phases | Trade Name | CTFA Name | Percent | Amount (kg) |
|---|---|---|---|---|
| D | TITANIUM DIOXIDE, #3328 | TITANIUM DIOXIDE | 1.000 | 0.0050 |
| E | CoQ10 21% CONCENTRATE | PROPYLENE GLYCOL, POLYSORBATE 80, WATER, UBIQUINONE, LECITHIN, PHENOXYETHANOL | 15.000 | 0.0750 |

All weight percentages are relative to the weight of the entire CoQ10 cream 3.0% composition.

The Phase A ingredients were added to a suitable container and heated to between 70 and 80° C. in a water bath. The Phase B ingredients, not including the Carbomer Dispersion, were added to a suitable container and mixed. The Phase C ingredients were also added to a suitable container and then heated to between 70 and 80° C. in a water bath. The CoQ10 21% concentrate of Phase E was placed in a suitable container and melted between 50 and 60° C. using a water bath. The ingredients were mixed as necessary to assure uniformity. The Carbomer Dispersion was then added to a suitable container (Mix Tank) and heated to between 70 and 80° C. while being mixed. While the ingredients were being mixed, the Phase B ingredients were added to the contents of the Mix Tank while maintaining the temperature. The contents were continually mixed and homogenized. The mixer was then turned off, however, homogenization was sustained. While the homogenization continued, the titanium dioxide of Phase D was added to the Mix Tank. The mixer was then turned on and the contents were mixed and further homogenized until completely uniform and fully extended (check color). Homogenization was then stopped and the batch was cooled to between 50 and 60° C. The mixer was then turned off and the melted CoQ10 21% concentrated was added to the Mix Tank. The mixer was subsequently turned on and the contents mixed/recirculated until dispersion was smooth and uniform. The contents of the Mix Tank were then cooled to between 45 and 50° C. The contents were then transferred to a suitable container for storage until unpacking.

Example 37

Method of Preparing a 0.5 kg Batch CoQ10 Cream 3% which Includes CoQ10 21% Concentrate and Caprylic/Capric Triglyceride A 0.5 kg batch of CoQ10 cream 3.0% composition was prepared by combining the following phases. Phase A included Caprylic/Capric Triglyceride at 4.00% w/w, cetyl alcohol NF at 2.00% w/w, glyceryl stearate/PEG-100 stearate at 4.50% w/w and stearyl alcohol NF at 1.5% w/w. The percentages and amounts are listed in the following table.

TABLE 80

| Phase | Trade Name | CTFA Name | Percent | Amount (kg) |
|---|---|---|---|---|
| A | CAPRYLIC | Capric Triglyceride | 4.000 | 0.0200 |
| A | RITA CA | CETYL ALCOHOL | 2.000 | 0.0100 |
| A | RITA SA | STEARYL ALCOHOL | 1.500 | 0.0075 |
| A | RITAPRO 165 | GLYCERYL STEARATE AND PEG-100 STEARATE | 4.500 | 0.0225 |

Phase B included diethylene glycol monoethyl ether NF at 5.00% w/w, glycerin USP at 2.00% w/w, propylene glycol USP at 1.50% w/w, phenoxyethanol NF at 0.475% w/w, purified water USP at 16.725% w/w and Carbomer Dispersion, 2% at 40% w/w. The percentages and amounts are listed in the corresponding phase table below.

TABLE 81

| Phase | Trade Name | CTFA Name | Percent | Amount (kg) |
|---|---|---|---|---|
| B | RITA GLYCERIN | GLYCERIN | 2.000 | 0.0100 |
| B | PROPYLENE GLYCOL | PROPYLENE GLYCOL | 1.500 | 0.0075 |
| B | TRANSCUTOL P | ETHOXYDIGLYCOL | 5.000 | 0.0250 |
| B | PHENOXY-ETHANOL | PHENOXYETHANOL | 0.475 | 0.0024 |
| B | ACRITAMER 940, 2% DISPERSION | WATER, PHENOXYETHANOL, PROPYLENE GLYCOL, CARBOMER 940 | 40.000 | 0.2000 |
| B | PURIFIED WATER, USP | WATER | 16.725 | 0.0836 |

Phase C included lactic acid USP at 0.50% w/w, sodium lactate solution USP at 2.00% w/w, triethanolamine NF at 1.30% w/w and purified water USP at 2.50% w/w. The percentages, amounts and further details are listed in the following table.

TABLE 82

| Phase | Trade Name | CTFA Name | Percent | Amount (kg) |
|---|---|---|---|---|
| C | TEALAN 99% | TRIETHANOLAMINE | 1.300 | 0.0065 |
| C | RITALAC LA | LACTIC ACID | 0.500 | 0.0025 |
| C | RITALAC NAL | SODIUM LACTATE, WATER | 2.000 | 0.0100 |
| C | PURIFIED WATER, USP | WATER | 2.500 | 0.0125 |

Phase D included titanium dioxide USP at 1.00% w/w while Phase E included CoQ10 21% concentrate at 15.00% w/w. The percentages, amounts and further details are listed in the following tables.

TABLE 83

| Phases | Trade Name | CTFA Name | Percent | Amount (kg) |
|---|---|---|---|---|
| D | TITANIUM DIOXIDE, #3328 | TITANIUM DIOXIDE | 1.000 | 0.0050 |
| E | CoQ10 21% CONCENTRATE | PROPYLENE GLYCOL, POLYSORBATE 80, WATER, UBIQUINONE, LECITHIN, PHENOXYETHANOL | 15.000 | 0.0750 |

All weight percentages are relative to the weight of the entire CoQ10 cream 3.0% composition.

The Phase A ingredients were added to a suitable container and heated to between 70 and 80° C. in a water bath. The Phase B ingredients, not including the Carbomer Dispersion, were added to a suitable container and mixed. The Phase C ingredients were also added to a suitable container and then heated to between 70 and 80° C. in a water bath. The CoQ10 21% concentrate of Phase E was placed in a suitable container and melted between 50 and 60° C. using a water bath. The ingredients were mixed as necessary to assure uniformity. The Carbomer Dispersion was then added to a suitable container (Mix Tank) and heated to between 70 and 80° C. while being mixed. While the ingredients were being mixed, the Phase B ingredients were added to the contents of the Mix Tank while maintaining the temperature. The contents were continually mixed and homogenized. The mixer was then turned off, however, homogenization was sustained. While the homogenization continued, the titanium dioxide of Phase D was added to the Mix Tank. The mixer was then turned on and the contents were mixed and further homogenized until completely uniform and fully extended (check color). Homogenization was then stopped and the batch was cooled to between 50 and 60° C. The mixer was then turned off and the melted CoQ10 21% concentrated was added to the Mix Tank. The mixer was subsequently turned on and the contents mixed/recirculated until dispersion was smooth and uniform. The contents of the Mix Tank were then cooled to between 45 and 50° C. The contents were then transferred to a suitable container for storage until unpacking.

Example 38

Method of Preparing a 20 kg Batch CoQ10 Cream 3% which Includes CoQ10 21% Concentrate and Caprylic/Capric Triglyceride A 20 kg batch of CoQ10 Cream 3.0% composition was prepared by combining the ingredients of Phases A-E. The weight percentages, amounts and further details of the ingredients for each phase are presented in the following table.

TABLE 84

| | RM | | Theoretical Quantity | |
|---|---|---|---|---|
| Phase | Number | Raw Material Name | % w/w | Gm |
| A | RM-026 | RM-026: Capric/Caprylic Triglyceride | 4.000 | 800.0 |
| A | RM-003 | RM-003: Cetyl Alcohol NF | 2.000 | 400.0 |
| A | RM-005 | RM-005: Stearyl Alcohol NF | 1.500 | 300.0 |
| A | RM-016 | RM-016: Glyceryl Stearate/PEG-100 Stearate | 4.500 | 900.0 |
| B | RM-001 | RM-001: Glycerin USP | 2.000 | 400.0 |
| B | RM-021 | RM-021: Propylene Glycol USP | 1.500 | 300.0 |

TABLE 84-continued

| Phase | RM Number | Raw Material Name | Theoretical Quantity % w/w | Gm |
|---|---|---|---|---|
| B | RM-007 | RM-007: Diethylene Glycol Monoethyl Ether NF | 5.000 | 1000.0 |
| B | RM-013 | RM-013: Phenoxyethanol NF | 0.475 | 95.0 |
| B | IP-003 | IP-003: Carbomer Dispersion, 2% | 40.000 | 8000.0 |
| B | RM-011 | RM-011: Purified Water USP | 13.725 | 2745.0 |
| B | RM-011 | RM-011: Purified Water USP (for rinsing) | 3.000 | 600.0 |
| C | RM-009 | RM-009: Trolamine NF | 1.300 | 260.0 |
| C | RM-006 | RM-006: Lactic Acid USP | 0.500 | 100.0 |
| C | RM-012 | RM-012: Sodium Lactate Solution USP, 60% | 2.000 | 400.0 |
| C | RM-011 | RM-011: Purified Water USP | 2.500 | 500.0 |
| D | RM-008 | RM-008: Titanium Dioxide USP | 1.000 | 200.0 |
| E | IP-004 | IP-004: CoQ10 Concentrate, 21% | 15.000 | 3000.0 |
| | | Totals | 100.00 | 20000.0 |
| | | For Purging PK-2 (Vacuum Tank) | | |
| | RM-019 or RM-020 | Nitrogen 97% NF or Nitrogen NF | q.s. | q.s. |

In preparing the 20 kg batch of CoQ10 Cream 3%, the following procedures were followed. Before the chemical ingredients were weighed, special care was taken to make sure that the area and all equipment was clean. First the chemical ingredients were weighed and special care was taken to avoid any spillage onto the weighing pan.

First 200 gm of titanium dioxide USP (Phase D) was weighed. Then 600 gm of purified water (labeled "water for rinsing-Phase B") was weighed.

In preparing Phase A, 800 gm of Capric/Caprylic Triglyceride, 400 gm of cetyl alcohol NF, 300 gm of stearyl alcohol NF, 900 gm of glyceryl stearate/PEG-100 stearate were weighed. These pre-weighed Phase A ingredients were added to a 4-L SS beaker and labeled as Phase A. Note that this premix must be used within 24 hours. The Phase A container is then covered and put aside for later use.

In preparing Phase B, 8,000 gm of Carbomer Dispersion 2.0%, 400 gm of glycerin USP, 300 gm of propylene glycol, 1,000 gm diethylene glycol monoethyl Ether NF, 95 gm of phenoxyethanol NF, and 2,745 gm purified water USP (labeled "Purified Water for Phase B") were weighed. These pre-weighed Phase B ingredients were then added to a 10-L SS beaker. Note that this pre-mix must be used within 24 hours. The contents of the Phase B container were manually mixed using a spatula until clear and uniform. The Phase B container was then covered and put aside for later use.

In preparing Phase C, 260 gm of triethanolamine NF, 400 gm of sodium lactate solution USP, 60%, 500 gm of purified water (labeled "Purified Water for Phase C"), and 100 gm of lactic acid USP were weighed. These Phase C ingredients were then added to a 2-L SS beaker in the following order: (1) 260 gm of trolamine, (2) 400 gm of sodium lactate solution, 60%, (3) 500 gm of purified water for Phase C, and (4) 100 gm of lactic acid USP. The container was labeled Phase C. Note that this premix must be used within 24 hours. The contents of the Phase C container were then manually mixed with a spatula until clear and uniform. The Phase C container was then covered and put aside for later use.

In preparing Phase E, 3,000 gm of CoQ10 21% Concentrate was weighed and placed in a container labeled Phase E. The Phase E container was covered and put aside for later use.

For compounding the CoQ10 Cream 3%, 2 water baths were used to heat Phases A, C and E. First, the Phase A beaker was placed into a water bath set to 70-75° C. and the contents were mixed manually with a spatula until clear and uniform. The Phase C beaker was placed into a water bath that was set to 60-65° C. The contents of the Phase C beaker were manually mixed with a spatula until clear and uniform. The Phase E beaker was placed into a water bath and was set to a temperature of 50-55° C. The contents of the Phase E beaker were manually mixed with a spatula until clear and uniform.

For compounding the cream, a water bath (E-1), a Lee Vacuum Tank (PK-2), a Waukesha Pump (P-1) and a square hole high shear screen for Silverson Homogenizer were used.

First, it was confirmed that the bottom valve of PK-2 was closed and that the PK-2 was properly sealed. The sight glass was then removed from the PK-2 and the pre-weighed 10,000 gm Carbomer Dispersion 2.0% was added to the PK-2 tank through the sight glass portal. A spatula was used to transfer any Carbomer Dispersion 2.0% from the walls of its container. The TIC-2 (temperature recorder) for the PK-2 was then turned on and it was ensured that the recorder was properly operational.

The agitator (A-2) for the PK-2 was turned on and the Carbomer Dispersion 2.0% was heated with the steam jacket to 70-80° C. The sight glass was then removed from the PK-2 and Phase B was slowly added, from the SS beaker to the PK-2, through the sight glass portal. The Phase B container was then rinsed with the "water for rinsing-Phase B." This rinsate was then added to the PK-2 through the sight glass portal.

Phase A was then slowly added to the PK-2. A spatula was used to transfer any Phase A remaining on the walls of the SS beaker. Note that the temperature of the Phase A must be between 70-80° C. when added to the PK-2.

The bottom valve of the PK-2 was then opened and the P-1 pump and P-2 (Silverson homogenizer) were turned on. The contents of the PK-2 were homogenized.

Phase C was then slowly added to the PK-2 through the access port. Note that the temperature must be between 70-80° C. when added. It was ensured the homogenization endured for at least 5 minutes, then the A-2 agitator was turned off. The pre-weighed 200 gm titanium dioxide USP was then slowly sifted through a 100 mesh screen to the PK-2. A spatula was used to dislodge any titanium dioxide that had been stuck to the blades of the PK-2.

The sight glass was then replaced and the A-2 agitator turned on. The contents were continued to be mixed while recirculating through P-1 and P-2. Homogenization was allowed to continue for 10 minutes or until completely uniform and fully extended. After 10 minutes P-2 was stopped. The contents of PK-2 were then cooled to 50-60° C. The sight glass was then removed, and the melted CoQ10 21% concentrate of Phase E was slowly added through the access port. The sight glass was then replaced.

The contents of the PK-2 were then mixed with A-2 until uniform. The temperature was maintained at 50-60° C. and the contents were recirculated through the P-1. The nitrogen NF flow was then started and the C-2 vacuum pump turned on. Note that avoidance of foam up of the product is preferred. The batch was then cooled to 45-50° C. When both the vacuum and the nitrogen were turned on. When the product was cooled to temperature, C-2 (vacuum pump) was turned off and any vacuum was relieved with the nitrogen NF. The nitrogen NF flow remained on. The outlet valve was purged with product before collecting samples or packaging the product.

The product was then transferred into pre-weighed, clean, HDPE closed-top containers. The A-2 agitator, P-1 Waukesha pump and the nitrogen NF flow were turned off. The batch was completed and indicated on the TIC-2 chart.

Two 30 gm (minimum) samples were removed for micro testing and two 400 gm (minimum) samples for physico/chemical testing. One set of samples was labeled as "retain". The filled containers were weighed. A batch size of 20 kg was obtained.

Example 39

Method of Treating SCCIS by Topical Application of CoQ10 Cream 3%

A CoQ10 cream 3.0% composition, as described above (e.g., examples 15 and 16), was topically applied to in situ cutaneous squamous cell carcinomas (SCCIS). Thirty five (35) subjects were topically treated with a 3.0% CoQ10 water-in-oil emulsion cream base medication. The medication was shipped and stored at room temperature in light-resistant containers.

The analysis populations were defined as (1) Intent-to-Treat (ITT) Population, (2) Safety Population and (3) Per Protocol (PP) population. The ITT population included all subjects who were dispensed the investigational drug (CoQ10 3%). The Safety population included all subjects who took at least one dose of the investigational product. The PP population included all subjects who had SCCIS confirmed via histological results at baseline, had a Week 6 histological examination and did not miss any interim visits.

The subjects were otherwise healthy male or female adults with at least one histologically confirmed non-facial SCCIS lesion. The SCCIS lesions which were suitable for excision, had a minimum area of 0.5 cm$^2$ and a maximum diameter of 2.0 cm, and were in a location that could be protected from sunlight by clothing during the study. At approximately the same time each morning, the subject washed the lesion site then dispensed a small pea sized (50-100 mg) amount of the topical cream medication onto a piece of wax paper or applicator. The subject then applied the appropriate amount of cream to the lesion and surrounding area using a cotton swab or applicator stick. The treated area was not washed for at least 8 hours following application. At approximately the same time each evening, the procedure was repeated. The lesion and surrounding area was protected from sunlight with clothing.

On the first day of treatment the lesion's diameter was measured and the area was calculated. The lesions were also photographed. At Weeks 1, 2, 3, 4 and 5 the subjects were evaluated and a record was taken of their vital signs: blood pressure, pulse rate, respiratory rate, oral temperature. The following clinical signs/symptoms of cutaneous irritation based on the following tables were also graded as a measure of the safety of the CoQ10 3% treatment: erythema, peeling, dryness, itching, burning/stinging.

TABLE 85

| | Erythema |
|---|---|
| 0 | No observable erythema |
| 1 | Slight pinkness, limited to a small area |
| 2 | Mild redness over much of the treated area |

TABLE 85-continued

| | Erythema |
|---|---|
| 3 | Marked redness over much of the treated area |
| 4 | Severe redness, presence of edema, possible erosion |

TABLE 86

| | Peeling/Scaling |
|---|---|
| 0 | No observable scaling or peeling |
| 1 | Slight flaking or occasional small lifting scales may be present in isolated areas |
| 2 | Moderate flaking/scaling. Cracks easily evident. Edges of scales lifting over large portion of the treated area |
| 3 | Marked scaling, slight fissuring, cracking and lifting scales on most of the treated area |
| 4 | Large peeling sheets of epidermis present |

TABLE 87

| | Dryness |
|---|---|
| 0 | Oily shine over much of the treated area |
| 1 | Normal, no dryness, no appreciable shine |
| 2 | Slightly dry, dull appearance over a small portion of the treated area |
| 3 | Moderately dry, very dull appearance over much of the treated area |
| 4 | Severely dry, cracking over entire treated area |

TABLE 88

| | Itching |
|---|---|
| 0 | No itching |
| 1 | Mild itching on occasion, no impact on daily activities |
| 2 | Mild itching present most of the time, no impact on daily activities or sleep |
| 3 | Moderate itching, occasionally interferes with daily activities or sleep |
| 4 | Intense itching that interferes with daily activities or sleep |

TABLE 89

| | Burning/Stinging |
|---|---|
| 0 | No burning/stinging |
| 1 | Mild burning/stinging on occasion, no impact on daily activities |
| 2 | Mild burning/stinging present most of the time, no impact on daily activities or sleep |
| 3 | Moderate burning/stinging, occasionally interferes with daily activities or sleep |
| 4 | Intense burning/stinging that interferes with daily activities or sleep |

Safety evaluation by Erythema: At Baseline, 32 subjects (91.4%) had some degree of erythema. This sign was considered slight to mild in most subjects (28 subjects, 80%) and 4 subjects (11.4%) had marked (Grade 3) redness. At Week 6, erythema was absent in 4 subjects (11.8%) and slight or mild in 30 subjects (88.2%), while no Grade 3 erythema was observed. The maximum erythema score observed during the study improved compared with Baseline in 7 subjects, did not change in 15 subjects, and worsened in 13 subjects. The final erythema score was improved relative to Baseline in 11 subjects, was unchanged in 22 subjects, and worsened in 2 subjects.

Safety evaluation by Peeling/Scaling: At Baseline, 27 subjects (77.1%) had some degree of peeling or scaling, and 8 subjects (22.9%) had none. At Week 6, visible peeling or scaling was absent for 16 subjects (47.1%), was slight in 17 subjects (50%), and was moderate in only 1 subject (2.9%). The maximum score for peeling/scaling observed during the study improved compared with Baseline in 7 subjects, did not change in 20 subjects, and worsened in 8 subjects. The final peeling/scaling score was improved relative to Baseline in 16 subjects, was unchanged in 14 subjects, and worsened in 5 subjects.

Safety evaluation by Dryness: Eight subjects (22.9%) had slight or moderate dryness at Baseline, while 77.1% had no dryness (Grade 1) or an oily shine (Grade 0) at the treatment area. At Week 6, all but 1 subject had Grade 0 or Grade 1 dryness (97.1%). The maximum dryness score observed during the study improved compared with Baseline in 7 subjects, did not change in 23 subjects, and worsened in 5 subjects. The final dryness score was improved relative to Baseline in 13 subjects, was unchanged in 21 subjects, and worsened in 1 subject.

Safety evaluation by itching: A majority of subjects at Baseline reported no itching (74.3%) or mild, occasional itching (20%), while 2 subjects (5.7%) reported itching of Grade 2 or 3. At Week 6, itching had improved so that 94.1% had no itching, and only 2 subjects (5.9%) had mild, occasional itching. From Week 1 through Week 6, no subject had itching worse than Grade 1 (mild, occasional itching). The maximum itching score observed during the study improved compared with Baseline in 5 subjects, did not change in 24 subjects, and worsened in 6 subjects. The final itching score was improved relative to Baseline in 9 subjects, was unchanged in 24 subjects, and worsened in 2 subjects.

Safety evaluation by burning/stinging: At Baseline, burning or stinging was absent in most subjects (94.3%) and mild in 2 subjects (5.7%). These scores remained virtually unchanged during the study. No subject had a score above Grade 1 (mild), and no more than 2 subjects had a Grade 1 score at any visit from Day 1 (Baseline) through Week 6. The maximum score for burning/stinging observed during the study improved compared with Baseline in 2 subjects, did not change from "no burning/stinging" in 28 subjects, and worsened (from none to mild) in 5 subjects. The final burning/stinging score was improved relative to Baseline in 2 subjects, was unchanged in 31 subjects, and worsened in 2 subjects.

The lesions' diameters were also measured and the areas calculated to evaluate the efficacy of the CoQ10 3% treatment. At the end of the 6 week treatment period there was a discontinuation visit where a record was taken of the vital signs and the clinical signs/symptoms were graded. A physical examination was also performed at the 6 week discontinuation visit. At the discontinuation visit fasting blood samples were also collected within 3 hours of the final cream application to determine CoQ10 plasma concentrations. The lesions were photographed, the diameters were measured and the area was calculated.

Results of the topical treatment of SCCIS with CoQ10 cream 3% showed efficacy as depicted in the before and after photographs of FIGS. 4-9. The primary efficacy endpoint was the percentage of subjects with a complete response defined as a negative histology assessment of the target lesion at Week 6. Secondary efficacy endpoints are reflected in the percentage of subjects with a partial response, defined as at least a 50% decrease in the area (the product of the two principal diameters) of the treated lesion at Week 6. The results showed that 23.5% of the ITT population had a complete response at Week 6 while 18.5% of the PP Population had a complete response at Week 6.

Secondary efficacy results showed that the ITT Population had a 26.5% partial 50% response and 2.9% had a 75% partial response at Week 6. A partial response was observed as early as Week 1 in 2 subjects and Week 2 in 8 subjects. The highest partial response rates occurred at Weeks 4 and 5. Interestingly, of the 8 subjects with a complete response at Week 6, 4 subjects did not have a partial response based on visual inspection, and none had a 75% response. In the PP Population, 22.2% had a 50% partial response while 0% had a 75% partial response. The mean change and mean percentage change in lesion area were −0.3 $cm^2$ and −26.1% respectively, in the ITT Population at Week 6 and −0.3 $cm^2$ and −23.4% respectively in the PP Population.

Overall, CoQ10 3% cream was safe and well tolerated. Complete cure was achieved by approximately 25% of subjects in the ITT Population.

Example 40

Method of Treating BCC By Topical Application of CoQ10 Cream 3%

Basal cell carcinoma (BCC) is the most common form of cutaneous malignancy, and overall the most common form of cancer in the United States. The American Cancer Society estimates that over 800,000 new cases of basal cell carcinoma are diagnosed each year. Superficial basal cell carcinoma (sBCC) rarely metastasizes and is usually curable through surgical excision or topical agents.

A CoQ10 cream 3.0% composition, as described above in examples 15-16, was topically applied to one hundred and sixty (160) otherwise healthy male or female adults with one or more histologically confirmed superficial basal cell carcinoma (sBCC) lesions. One target lesion, with a minimum area of 0.5 $cm^2$ and a maximum diameter of 2.0 cm was designated for treatment. The sBCC lesion was non-facial and was capable of being protected from sunlight during the study.

This study was a randomized, double-blind vehicle-controlled, parallel study. Each subject was randomized to one of four (4) study arms: 1.5% CoQ10 cream qd (once daily) plus vehicle cream qd (once daily), 3.0% CoQ10 cream qd (once daily) plus vehicle cream qd (once daily), 3.0% CoQ10 cream bid (twice daily), or vehicle cream bid (twice daily). Each arm had 40 patients.

TABLE 90

|   | AM | PM |
|---|---|---|
| 1. | 3% CoQ10 | 3% CoQ10 |
| 2. | Vehicle B | 3% CoQ10 |
| 3. | Vehicle A* | 1.5% CoQ10 |
| 4. | Vehicle A | Vehicle A |

At an initial screening visit, the lesion diameters were measured and the area calculated. The area is determined by measuring the two largest perpendicular diameters and multiplying for a result in $cm^2$. The subjects' vital signs were taken and recorded and a physical examination was performed. Fasting blood samples were collected and a complete blood count (CBC) test was performed as well as a clinical chemistry with lipid panel test. Blood samples were collected for determination of baseline CoQ10 plasma concentrations, duplicate samples were collected and packaged. Urinalysis was also performed and for women of childbearing potential a urine pregnancy test was performed. The subjects were then graded for the following clinical signs/ symptoms of cutaneous irritation: erythema, peeling, dryness, itching and burning/stinging.

On the first day of the study (Day 1), the subjects' vital signs were again recorded and the clinical signs/symptoms of cutaneous irritation were graded as in the screening visit. The subject was also interviewed for adverse events, use of concurrent topical products and use of concurrent medications. The target sBCC lesions were then photographed and measured for diameter and area as in the screening visit. The subjects were then given a medication kit containing the CoQ10 medication. The CoQ10 cream was applied by the patient twice daily for six weeks to the sBCC lesion and 1 cm of surrounding skin.

The dosing regimen consisted of washing the lesion site at approximately the same time each morning, dispensing a small pea sized (50-100 mg) amount of topical cream from the AM tub onto a piece of wax paper or applicator. The subject then applied the appropriate amount of cream to the lesion and surrounding area using a Q-tip or applicator stick. The treated area was not washed for at least 8 hours. At approximately the same time each evening, the procedure was repeated using topical cream from the PM tube.

There were interim visits by the subject which occurred at weeks 1, 2, 3, 4, and 5. At each of these visits, the vital signs were recorded as at the initial treatment visit and the clinical signs/symptoms were graded. The lesion diameter was measured and the area was calculated. The subject was then interviewed for adverse events, use of concurrent topical products, and use of concurrent medications. Clinical evaluations were done weekly.

At the end of the treatment period, 6 weeks, the vital signs were recorded as at the initial treatment visit and the clinical signs/symptoms were graded. The lesion diameter was measured and the area was calculated. A physical examination was also performed. Fasting blood samples were also collected after the final cream application. Blood samples were collected no more than 3 hours after the final cream application for determination of CoQ10 plasma concentrations. A complete blood count (CBC) test was performed and a clinical chemistry with lipid panel test was performed.

At four weeks post-treatment (study week 10), the subject returned for final evaluation and excision of the sBCC lesion site. Vital signs were taken and recorded and clinical signs/symptoms, similar to those in the initial screening visit, were graded.

Treatment results showed, after reviewing the pathology of 110 subjects, that at least 20% of the patients who were topically treated with the CoQ10 cream 3% demonstrated diminishment of symptoms as measured by an art recognized endpoint. In particular, 24 out the 110 subjects had no evidence of sBCC based on biopsy of the lesion site at 8 weeks.

Example 41

Pharmacokinetic Results of CoQ10 Topical Treatment

Seventy-two BALB/c mice were randomly divided into nine groups of eight mice each (Groups I-IX). Group I was untreated. On day 0, groups II-VIII were topically treated with 0.1 g of the test article (an oil-in-water cream emulsion containing 3% w/w CoQ10 cream spiked with C-14 radiolabeled API 31510) at a rate of 5 mg/cm². The radioactive API 31510 was added to the 3% cream batch to yield an experimental cream formulation with a specific activity of approximately 50 µCi/g of product or 5 µCi/application dose. The test article was topically applied to the skin of the back of each mouse in Groups II-IX with a glass rod. Immediately following dosing the group II animals were sacrificed and a measured amount of blood, urine, feces and the target organs (liver, pancreas and spleen) were collected and weighed. The blood was processed for serum and each organ was homogenized. Groups III-VIII were sacrificed at 2, 4, 8, 12, 18 and 24 hours following dosing, respectively, and the same samples were collected. Group IX was treated topically with 0.1 g of the test article for seven days (Days 0-6). On day 7, 24 hours following the final application of the test article on Day 6, groups I and IX were sacrificed and the same samples collected as for the previous groups. Each sample was measured for disintegrations per minute (DPM) and the mean DPM/sample type was calculated for each group.

Evaluation was based on the measurement of levels of radioactivity of serum, urine, feces and target organs (liver, pancreas and spleen) at the various time points with the objective of determining relative levels of percutaneous penetration of the test article over 24 hours and determining where the drug accumulates with the method of application.

A summary of the average sample weights in grams for each group is presented in the chart below. Please note that the present application as filed does not contain a Table 91.

TABLE 92

| | Pancreas | Liver | Spleen | Feces | Urine | Blood |
|---|---|---|---|---|---|---|
| Group I | 0.2907 | 1.4468 | 0.0776 | 0.0654 | NA | 0.4318 |
| Group II | 0.1691 | 1.3352 | 0.0935 | 0.0164 | NA | 0.4530 |
| Group III | 0.1300 | 1.0688 | 0.1777 | 0.0324 | 0.0890 | 0.4429 |
| Group IV | 0.1377 | 0.9893 | 0.0846 | 0.0292 | 0.0802 | 0.3770 |
| Group V | 0.1780 | 0.7105 | 0.0760 | 0.0299 | 0.0864 | 0.3222 |
| Group VI | 0.1156 | 0.8994 | 0.0595 | 0.9328 | NA | 0.3273 |
| Group VII | 0.2864 | 1.1312 | 0.3355 | 0.0160 | 0.0671 | 0.2077 |
| Group VIII | 0.1969 | 1.1929 | 0.0905 | 0.0350 | 0.0097 | 0.3093 |
| Group IX | 0.3068 | 1.2912 | 0.0839 | 0.1034 | NA | 0.3439 |
| Mean | 0.2012 | 1.1184 | 0.1199 | 0.041 | 0.0665 | 0.3572 |

Figure 41:
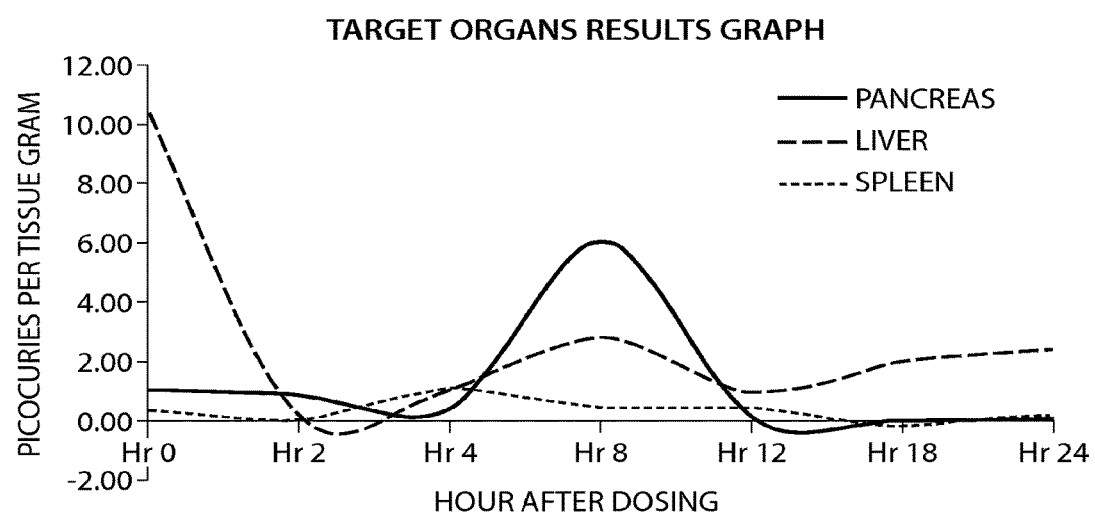
FIG. 41: Graph depicting radioactivity levels in target organs.

Disintegrations per minute (DPM) are presented in Table 63 and were measured on a scintillation counter for each type of tissue sample from each animal. The average DPM for each sample type was calculated. After the results were converted to 1 mL amounts, the averages were then divided by average organ weights to obtain the DPM per tissue gram result. The control (Group I) results were then subtracted from each of the other group results to remove background radiation amounts and obtain the actual number of average DPM per tissue gram for each sample in the group. By dividing by a constant of 2,220,000, the results were converted to microcuries per tissue gram. The final results represent picocuries (microcuries×1000) per tissue gram. The results for the organs were presented in the chart below and in FIG. 41. Please note that the present application does not contain a Table 94.

TABLE 93

Target Organ Results

| | Picocuries per tissue gram | | |
|---|---|---|---|
| | Pancreas | Liver | Spleen |
| Hr 0 - Group II | 1.09 | 10.34 | 0.40 |
| Hr 2 - Group III | 0.87 | 0.14 | 0.09 |
| Hr 4 - Group IV | 0.47 | 1.11 | 1.07 |
| Hr 8 - Group V | 6.05 | 2.80 | 0.45 |

TABLE 93-continued

Target Organ Results

Picocuries per tissue gram

|  | Pancreas | Liver | Spleen |
|---|---|---|---|
| Hr 12 - Group VI | 0.13 | 0.96 | 0.46 |
| Hr 18 - Group VII | 0.03 | 2.02 | −0.15 |
| Hr 24 - Group VIII | 0.07 | 2.40 | 0.30 |

The data reflects that the test article accumulated substantially in the pancreas at approximately eight (8) hours after dosing and also, in lesser amounts, in the liver at eight hours after dosing. The amount of picocuries per tissue gram in the spleen and pancreas decreased to nearly zero by 18 hours after dosing. The Hour 0 liver results were abnormal because of a single animal with an exceptionally high amount of DPM at zero hours after dosing. One possible explanation for this abnormally high result is that the animal managed to ingest the test article directly, either by licking its own skin or licking its paws after rubbing the dose site. That possibility would send the test article to the liver much quicker than percutaneous absorption. After the 8 hour peak, the liver amounts decreased slightly at 12 hours but then increased slightly at 18 hours and remained consistent through 24 hours.

TABLE 95

Target Organ Results (cont.)
Of the amount of test article that accumulated in each of the target organs for all animals in Groups II-VIII, the percentage of picocuries per tissue grams is presented in the chart below.

|  | Pancreas | Liver | Spleen |
|---|---|---|---|
| Hr 0 | 12.51% | 52.30% | 15.21% |
| Hr 2 | 9.99% | 0.71% | 3.42% |
| Hr 4 | 5.40% | 5.61% | 40.68% |
| Hr 8 | 69.46% | 14.16% | 17.49% |
| Hr 12 | 1.49% | 4.86% | 17.49% |
| Hr 18 | 0.34% | 10.22% | −5.70% |
| Hr 24 | 0.80% | 12.14% | 11.41% |

Groups II-VIII were dosed with 4.112 microcuries of test article. The chart below presents the amount of microcuries in each target organ at each time period.

TABLE 96

|  | Pancreas | Liver | Spleen |
|---|---|---|---|
| Group II - 0 hrs | 0.0011 | 0.0103 | 0.0004 |
| Group III - 2 hrs | 0.0009 | 0.0001 | 0.0001 |
| Group IV - 4 hrs | 0.0005 | 0.0011 | 0.0011 |
| Group V - 8 hrs | 0.0060 | 0.0028 | 0.0005 |
| Group VI - 12 hrs | 0.0001 | 0.0010 | 0.0005 |
| Group VII - 18 hrs | 0.0000 | 0.0020 | −0.0002 |
| Group VIII - 24 hrs | 0.0001 | 0.0024 | 0.0003 |

By dividing those numbers by 4.112 (the amount of microcuries in each dose), a percentage results that represents the amount of test article that was in each organ for each time period. The chart below presents those percentages.

TABLE 97

|  | Pancreas | Liver | Spleen |
|---|---|---|---|
| Hr 0 | 0.03% | 0.25% | 0.01% |
| Hr 2 | 0.02% | 0.00% | 0.00% |

TABLE 97-continued

|  | Pancreas | Liver | Spleen |
|---|---|---|---|
| Hr 4 | 0.01% | 0.03% | 0.03% |
| Hr 8 | 0.15% | 0.07% | 0.01% |
| Hr 12 | 0.00% | 0.02% | 0.01% |
| Hr 18 | 0.00% | 0.05% | 0.00% |
| Hr 24 | 0.00% | 0.06% | 0.01% |

The average percentage of test article in microcuries that reached the target organs is 0.03%, 0.07% and 0.01% for the pancreas, liver and spleen, respectively.

Figure 42:
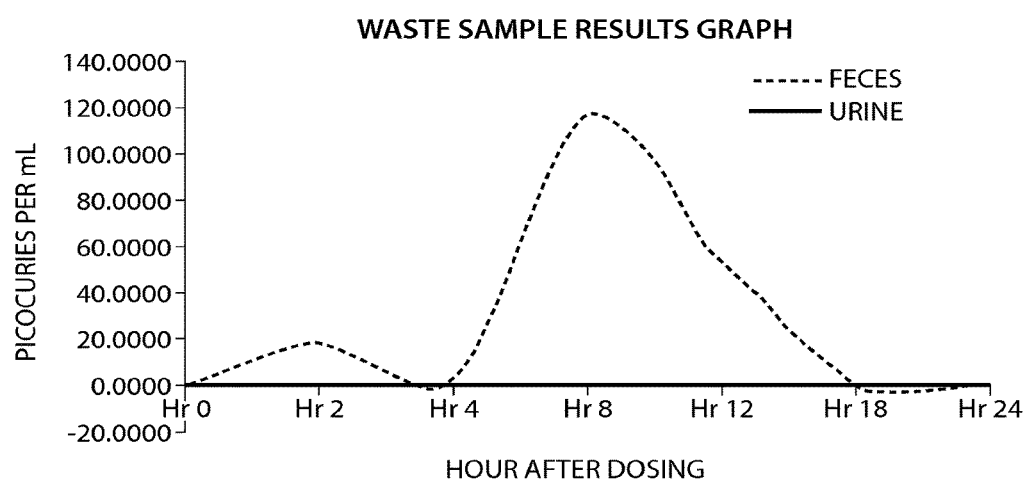
FIG. 42: Graph depicting radioactivity levels in waste samples.

For the body waste samples, final results were presented in picocuries per mL. This amount was obtained by converting the DPM to 1 mL, subtracting the Group I results, and then dividing by the constant 2,220,000 to obtain microcuries per mL. By multiplying that result by 1000, picocuries per mL was obtained. The average picocuries per mL for the feces and the urine are presented in the chart below and in FIG. 42. Please note that the present application does not contain a Table 99.

TABLE 98

|  | 1 mL Feces | 1 mL Urine |
|---|---|---|
| Hr 0 - Group II | −0.0433 | 0.0002 |
| Hr 2 - Group III | 18.2417 | 0.0000 |
| Hr 4 - Group IV | 3.9548 | 0.0305 |
| Hr 8 - Group V | 117.1009 | 0.0081 |
| Hr 12 - Group VI | 52.7089 | −0.0015 |
| Hr 18 - Group VII | 0.7791 | 0.0057 |
| Hr 24 - Group VIII | 0.1303 | 0.0016 |

The data reflects that the test article accumulated substantially in the feces at eight hours after dosing, continued to be present at 12 hours after dosing but was substantially lower by 18 hours after dosing. There was no indication that the test article accumulated in the urine at any point during the study.

Figure 43:
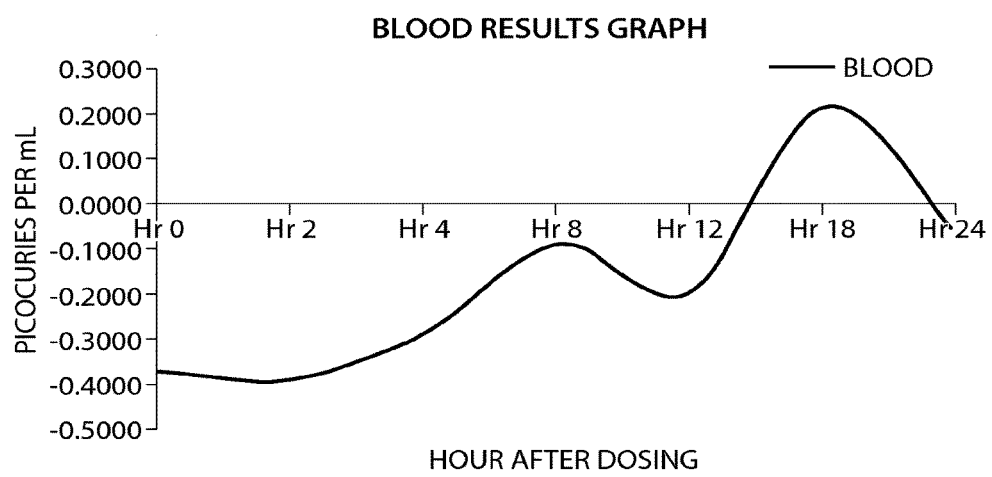
FIG. 43: Graph depicting radioactivity levels in blood samples.

Blood results were calculated in the same way as the waste sample results were calculated. The calculations for the picocuries per mL in the blood resulted in negative numbers because of the high amount of DPM in Group I—Control's blood results. This was a result of two animals having higher than expected DPM readings in the blood. The results for the blood are presented in the chart below and in FIG. 43. Please note that the present application does not contain a Table 101.

TABLE 100

|  | 1 mL Blood |
|---|---|
| Hr 0 - Group II | −0.3706 |
| Hr 2 - Group III | −0.3896 |
| Hr 4 - Group IV | −0.2877 |
| Hr 6 - Group V | −0.0890 |
| Hr 12 - Group VI | −0.1965 |
| Hr 18 - Group VII | 0.2164 |
| Hr 24 - Group VIII | −0.0545 |

The data indicates that the test article did not accumulate in the blood; with the exception that test article may have been present in the blood at 18 hours after dosing. It is an oddity that there was no significant amounts of test article found in the blood, especially since test article was observed in the liver and pancreas. One explanation is percutaneous absorption of the test article through the skin directly to the organs; however, it is unlikely that the test article would not enter the blood after penetrating the skin. Another possibility is that the blood immediately recognized a foreign substance and deposited the test material in the liver. The last dosing for Group II was at 10:23 am and the first sacrificed for Group II was at 10:45 am. Twenty-two minutes may have been enough time for the blood to rid itself of the foreign material.

Group IX data was calculated separately as the animals in Group IX were dosed repeatedly instead of once and were allowed 7 days to absorb the test article. Group IX data is presented in the charts below.

TABLE 102

Picocuries per tissue gram for organ samples

|  | Pancreas | Liver | Spleen |
|---|---|---|---|
| Group IX | 0.12 | 2.07 | 1.19 |

Average picocuries per tissue gram for Groups II-VIII were 1.24, 2.83 and 0.38 for the pancreas, liver and spleen respectively. Group IX results for the organs were lower than average for the pancreas, close to average for the liver and higher than average for the spleen. The data indicates that there were increasing amounts of test article in the spleen by Day 7 and that the amounts of test article in the liver at Day 7 were comparable to the same amounts found in the liver at 18 and 24 hours after dosing.

TABLE 103

Picocuries per mL for waste samples

|  | Feces | Urine |
|---|---|---|
| Group IX | 25.0650 | −0.0011 |

Average picocuries per mL for the feces for Groups II-VIII was 27.55 and for urine was 0.0064. Group IX feces and urine results were not abnormal and showed only minimal signs of test article in the feces.

TABLE 104

Picocuries per mL for blood

|  | Blood |
|---|---|
| Group IX | −0.0538 |

As with other groups, Group IX blood results indicate that the test article was not present in the blood.

The overall results indicate that there were no significant differences within the weights of the target organs, feces, urine or blood amounts between groups. No significant amounts of the test article were detected in the urine. There was no urine collected from Groups I (control), II (Hour 0) or VI (Hour 12). Except for Group VII (18 hours after dosing), the test article was not detected in significant amounts in the blood at any time during the study. The highest amounts of picocuries per tissue gram and picocuries per mL were recorded for Group V (8 hours after dosing) and were found most concentrated in the feces and the pancreas at that time. Also in Group V, increased levels of picocuries per tissue gram were found in the liver. Within the liver, after a slight dip at Hour 12, levels remained consistent at Hour 18 and Hour 24 and comparable levels were found in the liver for Group IX (Day 7 animals). After the peak at 8 hours after dosing, the pancreas amounts dropped to near zero levels, including Group IX results. The spleen amounts rose at Hour 4 and then decreased to near zero levels by Hour 18. However those amounts increased for Group IX, indicating accumulated test article in the spleen on Day 7. There was percutaneous absorption of the test article or a metabolite of the test material because the compound was found in the liver and the pancreas. It is strange that no test material was present in the blood in significant amounts since the expected route of transport would be the blood flow. A possible explanation could be rapid clearance of the test article from the blood by the liver and pancreas. Another possibility is that the test article could have been ingested directly by the animals, either by licking the dose itself or licking paws that had rubbed on the dose site.

Example 42

Western Plot

Over the past five decades enormous volume of information has been generated implicating endogenous/exogenous factors influencing specific processes as the underlying cause of malignant transformations. Clinical and basic literature provides evidence that changes in the DNA structure and function play a significant role in the initiation and progression of cancer, defining cancer as a genetic disease (Wooster, 2010; Haiman, 2010). In the early 1920s, Otto Warburg and other investigators involved in characterizing fundamental changes in etiology of oncogenesis described two major observations (a) the ability of cells to transport and utilize glucose in the generation of ATP for energy production in the presence of oxygen—also known as Warburg Effect and (b) alterations in the mitochondrial structure and function—including changes in the electron transport leading to a decrease in the production of mitochondrial ATP. The past few years has seen a resurgence in the investigating the central role of cellular bioenergetics in the etiology of cancer i.e. viewing cancer as a metabolic disease.

Historically, although mutations in genes has been thought to be responsible for changes in gene expression, there is accumulating literature in support of epigenetic processes playing a critical role in influencing gene expression in supporting carcinogenesis. This is evidenced by the observation that mutation rate for most genes is low and cannot account for the numerous (spectrum of) mutations found in the cancer cells. Epigenetic alteration is regulated by methylation and modification of histone tails, both changes inherently linked to the energy (nutrient) status of the cells since they require the availability of co-factors e.g. acetyl CoA requirement for histone acetylation (ref). The biosynthesis of acetyl CoA depends on glycolysis and Kreb's Cycle, directly linking the intracellular energy status to regulation of gene expression and activity.

In normal cells, mitochondrial oxidative phosphorylation generates sufficient ATP to meet the energy demands for maintaining normal physiological activities and cell survival. A consequence of mitochondrial energy production is the generation of reactive oxygen species (ROS), aberrant production of which leads to damage of mitochondria (refs). It is well established that chronic ROS generation by the mitochondria leads to cumulative accumulation of genetic mutations, a phenomenon that has been implicated in the etiology of carcinogenesis. It has been suggested that cancer cells decrease mitochondrial respiration to minimize ROS generation, and switch to glycolysis to sustain energy production. Thus, a progressive shift of energy generation from oxidative phosphorylation to glycolysis would be essential for a cell to maintain energy production to maintain physiological functions and could be associated with the progression of a normal cell phenotype to that of a cancer cell. The progressive shift in cellular energy (bioenergetic) profile in tandem with accumulated alteration (mutations) in mitochondrial genetic make-up alters the cellular metabolome. Changes in the whole cell metabolomic profile as a consequence of mitochondrial phosphorylation to glycolysis transition corresponds to an abnormal bioenergetic induced metabolomic profile and is the underlying cause supporting carcinogenesis. Targeted intervention using an endogenous molecule to elicit a cellular metabolomic shift towards conditions of a non-cancerous normal mitochondrial oxidative phosphorylation associated cellular bioenergetic state represents a therapeutic endpoint in the treatment of cancer. Coenzyme Q10 as a MIM causing an Epi-Metabolomic Shift The data presented herein demonstrates that treatment of normal and cancer cells with Coenzyme Q10 is associated with changes in the expression of proteins that regulate key biochemical terminals within the glycolysis-mitochondrial oxidative stress continuum. The combination of data describing assessment of protein expression by western blotting and oxygen consumption rates demonstrates that in normal cells, there is no significant alteration in normal glycolytic and mitochondrial respiration rates following exposure to Coenzyme Q10. Thus, the values for expression of the proteins and mitochondrial respiration rates in normal cell lines e.g. HDFa (normal human adult fibroblast), HASMC (normal human aortic smooth muscle cell), nFib (normal fibroblast) and HeKa (normal human keratinocytes) can be considered as representatives of baseline physiological state. Any deviation in expression of proteins and mitochondrial respiration rates in cancer cell lines, e.g. HepG2 (liver cancer), PaCa-2 (pancreatic cancer), MCF7 (breast cancer), SK-MEL (melanoma) and SCC-25 (squamous cell carcinoma), is representative of alteration due to initiation/progression of the disease, in this case cancer. The experimental evidence provides support to the hypothesis that exposure of Coenzyme Q10 to cancer cells is associated with cellular pathophysiological reorganization that is reminiscent of normal cells. Specifically, the data provided herein demonstrates that Coenzyme Q10 exposure in cancer cells is associated with a shift in the glycolytic pathways and mitochondrial oxidative phosphorylation responsible for induction of global reorganization of cellular architecture to that observed in normal cells.

In normal cells, the end-points of glycolytic output are linked to mitochondrial oxidative phosphorylation (OXPHOS), i.e. generation of pyruvate from glucose via the glycolytic pathway for the entry into the Kreb's Cycle (also known as Tricarboxylic acid cycle, TCA, or Citric Acid Cycle) to generate reducing equivalents to support the mitochondrial OXPHOS for ATP production. Thus, in normal cells the expression and functional orientation of gene products involved in glycolysis is primed towards adequate generation of pyruvate and its entry into the Kreb's Cycle. Dysregulated expression and function of key proteins participating in glycolysis and Kreb's Cycle pathways in cancer cells results in enhanced glycolysis with a significant decrease in mitochondrial function. Exposure of cancer cells to Coenzyme Q10, an endogenous molecule that selectively influences the mitochondrial respiratory chain, alters (normalizes) expression of proteins of the glycolyis and Kreb's Cycle pathways to facilitate a bioenergetic shift such that energy production (i.e. ATP generation) is restored to the mitochondria.

EXPERIMENTAL PROCEDURE

Western Blot Experiment 1

The cells that were used for the experiment were HDFa, and MCF-7 cells that were treated or not with Coenzyme Q10 at two different concentrations, 50 µM and 100 µM, and harvested after 24 hours of treatment. The whole cell pellets were resuspended one at a time in 1 mL of C7 buffer and transferred to labeled 15 mL tubes. The samples were then sonicated in the cold room on ice using 6 sonic pulses with the setting at #14. The samples were spun for a short time to 2500 g after sonication and the samples transferred to 2 ml tubes. The pH was verified of each sample (pH should be 9.0) using the foam remaining in the 50 mL sample tubes.

Alkylation and reduction of samples was performed for each sample by adding 10 ul of 1M acrylamide, 25 ul of tributylphoshene and incubation for 90 mins with intermittent mixing. After incubation, 10 ul of 1M DTT was added and the tubes were spun at 20,000 g at 20 deg C. for 10 minutes and transferred the supernatant to labeled Amicon Ultra centrifugal filter units with a 10 k cut off (Millipore catalog # UFC 801024). The samples were spun for 15 minutes at 2500 g in 2 intervals. The conductivity was measured for Chaps alone as well as the samples using a conductivity meter. If the conductivity of samples is high, then 1 ml of chaps was added for buffer exchange and spun again at 2500 g until the volume was down to 250 ul. When the conductivity was 200 or less the samples were spun in 5 min intervals at 2500 g until the volume of the supernatant was between 150-100 ul. The sample supernatants were transferred to eppendorf tubes and Bradford assay was performed using BSA as standard.

The samples were processed as per standard protocols as described above and the amount of protein in each of the samples was determined by Bradford assay. Sample volumes equivalent to 10 ug of protein were prepared as shown below with Lamelli Loading dye (LDS) and MilliQ water were run on a 4-12% Bis-Tris Novex NuPAGE gel (Invitrogen, cat # NP0323Box)

The gels were run for 50 minutes using 1×MOPS buffer using a NOVEX Xcell Surelock system at 200 V. The gels were then transferred for 1 hour using a NOVEX Xcell Surelock wet transfer protocol at 30 V. The blots were stained with Simply Blue Safestain from Invitrogen (LC6065).

IDH1 and ATP Citrate Lyase Levels in HDFa and MCF-7 Samples.

After transfer each of the blots was placed in between 2 Whatman Filter papers and dried for 15-20 minutes. After drying the blots were labeled with the date, the type of samples and either blot 1 or blot 2 using a HB pencil. The molecular weight markers were outlined with the pencil and with single lines for the blue and a doublet for the colored markers. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each). Blot 1 was probed with the primary antibody for IDH1 (Cell Signaling #3997) in TBST with 5% BSA (at 1:1000 dilutions) and blot 2 with the rabbit polyclonal antibody for ATP Citrate Lyase in 5% BSA (Cell Signaling #4332) at 1:1000 dilution by incubation overnight at 4 deg C. with shaking. After the overnight incubation with primary antibodies, the blots were washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 mins and then each blot scanned with 5100 Fuji Laser scanner at 25 uM resolution, 16 bit, green laser, at 400V and at 500 V.

Actin Levels in HDFa and MCF-7 Samples.

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. The blots were then activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the antibody for Actin in 5% BSA (Sigma catalog # A5316, clone AC-74) at 1:5000 dilutions for 1 hour at room temperature with shaking. After 1 hour of incubation with primary antibody for Actin, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Western Blot Experiment 2

The cells used in this experiment were SKMEL28, SCC-25, nFib and Heka that were treated or not with coenzyme Q10 at two different concentrations, 50 μM or 100 μM, and harvested after 3, 6 and/or 24 hours of treatment. The samples were processed and run on a 4-12% Bis-Tris Novex NuPAGE gel as described above. The gels were run, transferred and stained essentially as described above.

Levels of IDH1 for the 4 Cell Lines

After transfer the blot was dried for 15-20 minutes, activated with methanol for 5 seconds, washed with water for 5 minutes, and TBST for 15 minutes. The blot was blocked for 1 hour with 5% blocking reagent in TBS-T at room temperature and then washed 3 times with TBS-T (1×-15'; 2×5' each). This was then probed with the primary antibody for IDH1 (Cell Signaling #3997) in TBST with 5% BSA (at 1:1000 dilutions) by incubation overnight at 4 deg C. with shaking. After the overnight incubation with primary antibody for IDH1, the blot was washed 3 times with TBS-T (1×-15'; 2×5' each) and probed with the secondary antibody (antirabbit; 1:10,000 dilution) for 1 h at room temperature. After 1 h of incubation with secondary antibodies, the blot was washed 3 times with TBS-T (1×-15'; 2×5' each) and then incubated with ECF reagent for 5 mins and then each blot scanned with 5100 Fuji Laser scanner at 25 uM resolution, 16 bit, green laser, at 400V and at 500 V.

ATP Citrate Lyase Levels in 4 Different Cell Lines.

The Isocitrate dehydrogenase blot was stripped by incubating for 30 minutes with methanol, followed by two 10 minute washes with TBS-T, then 30 minutes of incubation with stripping buffer at 50 deg C., and followed by two washes with 100 ml or more of TBS-T for 30' each. The blot was scanned in laser scanner to check for complete stripping. The blot was activated with methanol for 5 seconds, washed with water for 5 minutes, and TBST for 15 minutes. The blot was blocked for 1 hour with 5% blocking reagent in TBS-T at room temperature and then washed 3 times with TBS-T (1×-15'; 2×5' each). This was then probed with the rabbit polyclonal antibody for ATP Citrate Lyase in 5% BSA (Cell Signaling #4332) at 1:1000 dilution overnight at 4 deg C. with shaking. After the overnight incubation with primary antibody for ATP Citrate Lyase, the membrane was washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blot was washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Actin Levels in 4 Different Cell Lines.

The ATP Citrate Lyase blot was stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blot was scanned in laser scanner to check for complete stripping. The blot was activated with methanol for 5 seconds, washed with water for 5 minutes, and TBST for 15 minutes. The blot was blocked for 1 hour with 5% blocking reagent in TBS-T at room temperature and then washed 3 times with TBS-T (1×-15'; 2×5' each) and probed with the antibody for Actin in 5% BSA (Sigma catalog # A5316, clone AC-74) at 1:5000 dilutions for 1 hour at room temperature with shaking. After 1 hour of incubation with primary antibody for Actin, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Western Blot Experiment 3

The cells used in this experiment were HepG2, HASMC, and PACA2 cells that were treated or not with Coenzyme Q10 at two different concentrations (50 μM and 100 μM) and harvested 48 hours of treatment. In this experiment (western blot experiment 3), and in all of the experiments described below in this Example (i.e., western blot experiments 4 through 9), the cells were additionally treated with either 5 mM glucose ("5G") or 22 mM glucose ("22G"). The samples derived from the cells were processed and run on a 4-12% Bis-Tris Novex NuPAGE gel as described above. The gels were run, transferred and stained essentially as described above.

IDH1, ATP Citrate Lyase and Actin Levels in HASMC Vs. PACA2 and HepG2.

The levels of IDH1, ATP citrate lyase and actin levels were determined by probing the blots with primary antibodies for IDH1, ATP citrate lyase and actin, essentially as described above.

Western Blot Experiment 4

The cells used in this experiment were HepG2 cells that were treated or not with Coenzyme Q10 at two different concentrations, 50 or 100 µM, and harvested after 24 or 48 hours of treatment. In this experiment, the cells were additionally treated with either 5 mM glucose ("5G") or 22 mM glucose ("22G"). The samples derived from the cells were processed and run on a 4-12% Bis-Tris Novex NuPAGE gel as described above. The gels were run, transferred and stained essentially as described above.

Lactate Dehydrogenase Levels in HepG2 Cells.

After transfer each blot was dried for 15-20 minutes, activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Lactate Dehydrogenase (abcam ab2101; polyclonal) in 5% BSA (at 1:1000 dilutions) by incubation overnight at 4 deg C. with shaking. After the overnight incubation with primary antibody for Lactate Dehydrogenase, the blots were washed 3 times with TBS-T (1×-15'; 2×5' each) and probed with the secondary antibody (rabbit antigoat; 1:10,000 dilution) for 1 h at room temperature. After 1 h of incubation with secondary antibodies, the blots were washed 3 times with TBS-T (1×-15'; 2×5' each) and then incubated with ECF reagent for 5 mins and then each blot scanned with 5100 Fuji Laser scanner at 25 uM resolution, 16 bit, green laser, at 400V and at 500 V.

Pyruvate Kinase Muscle Form (PKM2) Levels in HepG2 Cells.

The lactate dehydrogenase blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the rabbit polyclonal antibody for Pyruvate Kinase M2 in 5% BSA (NOVUS BIOLOGICALS catalog # H00005315-D01P) at 1:500 dilution overnight at 4 deg C. with shaking. After the overnight incubation with primary antibody for Pyruvate Kinase M2, the membranes were washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Pyruvate Dehydrogenase Beta Levels in HepG2 Cells.

The pyruvate kinase blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. After making sure stripping of the antibody and the ECF reagent has worked, the blots were activated with methanol for 5 seconds, washed with water for 5 minutes, and TBST for 15 minutes. The blots are blocked for 1 hour with 5% blocking reagent in TBS-T at room temperature and then washed 3 times with TBS-T (1×-15'; 2×5' each) and probed with the antibody for Pyruvate Dehydrogenase in 5% BSA (ABNOVA catalog # H00005162-M03) at 1:500 dilutions) overnight at 4 deg C. with shaking. After the overnight incubation with primary antibody for Pyruvate Dehydrogenase, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Actin Levels in HepG2 Cells.

The Pyruvate Dehydrogenase blots were stripped and then reprobed for actin, essentially as described above.

Western Blot Experiment 5

The cells used in this experiment were MIAPACA2 (PACA2) cells that were treated or not with Coenzyme Q10 at two different concentrations, 50 or 100 µM, and harvested after 24 or 48 hours of treatment. In this experiment, the cells were additionally treated with either 5 mM glucose ("5G") or 22 mM glucose ("22G"). The samples derived from the cells were processed and the gels were run, transferred, stained and scanned essentially as described above.

Lactate Dehydrogenase (LDH) and Pyruvate Dehydrogenase (PDH) Levels in PaCa2 cells The levels of LDH and PDH were determined by probing the blots successively with primary antibodies for LDH and PDH, essentially as described above.

Caspase 3 Levels in PaCa2 Cells.

The blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the antibody for Caspase 3 in 5% BSA (Santacruz Biotechnology # sc7272) at 1:200 dilutions) overnight at 4 deg C. with shaking. After the overnight incubation with primary antibody for Caspase 3, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Western Blot Experiment 6

The cells that were used for this Western blot experiment were PC-3, HepG2, MCF-7, HDFa and PACA2 that were treated or not with a Coenzyme Q10 IV formulation and harvested after 24 hours of treatment. In this experiment, the cells were additionally treated with either 5 mM glucose ("5G") or 22 mM glucose ("22G"). The samples derived from the cells were processed and the gels were run, transferred, stained and scanned essentially as described above.

Capase 3 and Actin Levels in Different Cell Types.

The levels of Caspase 3 and actin were determined by probing the blots successively with primary antibodies for Caspase 3 and actin, essentially as described above.

Western Blot Experiment 7

The cells used in this experiment were Human Aortic Smooth Muscle (HASMC) cells that were treated or not with Coenzyme Q10 at two different concentrations, 50 µM or 100 µM, and harvested after 24 or 48 hours of treatment. The HASMC samples were processed and the gels were run, transferred, stained and scanned essentially as described above.

Experimental Protocol for Actin:

The levels of actin were determined by probing the blots with a primary antibody for actin, essentially as described above.

Experimental Protocol for Hif 1Alpha, Caspase3 and PDHB:

The Actin blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Hif 1 alpha, Caspase 3 or PDHB in 5% BSA (at 1:200 by incubation overnight at 4 deg C. with gentle shaking. The primary antibody for Hif 1 alpha (Abcam ab2185; antirabbit) was at 1:500 dilution in 5% BSA. The primary antibody for Caspase 3 (Santacruz sc7272; antirabbit) was at 1:200 dilution in 5% BSA. The primary antibody for Pyruvate Dehydrogenase beta (PDHB) (Novus Biologicals H00005162-M03; antimouse) was at 1:500 dilution in 5% BSA. After incubation with primary antibodies, the membranes were washed 3 times with TBS-T (1×-15'; 2×5' each) and probed with the secondary antibody (PDHB antimouse; Hif 1a and Caspase 3 antirabbit; 1:10,000 dilution) for 1 h at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Experimental Protocol for PKM2, SDHB and SDHC:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for PKM2, SDHB or SDHC in 5% BSA in TBS-T by incubation overnight at 4 deg C. with gentle shaking. The primary antibody for SDHC (ABNOVA H00006391-M02; antimouse) was at 1:500 dilution. The primary antibody for SDHB was from Abcam ab4714-200; antimouse; at 1:1000 dilution. The primary antibody for Pyruvate Kinase M2 (PKM2) was from Novus Biologicals H00005315-D0IP; antirabbit; at 1:500 dilution. After incubation with primary antibodies, the membranes were washed 3 times with TBS-T (1×-15'; 2×5' each) and probed with the secondary antibody (SDHB & C antimouse; and PKM2 antirabbit; 1:10,000 dilution) for 1 h on the orbital tilting shaker at room temperature. After 1 h of incubation, the blots were washed 3 times with TBS-T (1×-15'; 2×5' each) and incubated with ECF reagent for 5 minutes and then each blot scanned with 5100 Fuji Laser scanner at 25 uM resolution, 16 bit, green laser, at 400V and at 500 V.

Experimental Protocol for LDH and Bik:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for LDH or Bik in 5% BSA in TBS-T by incubation overnight at 4 deg C. with gentle shaking. The primary antibody for LDH was from Abcam ab2101; antigoat; at 1:1000 dilution. The primary antibody for Bik was from Cell Signaling #9942; antirabbit; at 1:1000 dilution. After incubation with primary antibodies, the membranes were washed 3 times with TBS-T (1×-15'; 2×5' each) and probed with the secondary antibody (LDH antigoat; Jackson Laboratories) and Bik antirabbit; 1:10,000 dilution) for 1 h on the orbital tilting shaker at room temperature. After 1 h of incubation, the blots were washed 3 times with TBS-T (1×-15'; 2×5' each) and incubated with ECF reagent for 5 minutes and then each blot scanned with 5100 Fuji Laser scanner at 25 uM resolution, 16 bit, green laser, at 400V and at 500 V.

Western Blot Experiment 9

The cells used were HepG2 cells that were treated or not with Coenzyme Q10 at two different concentrations, 50 µM or 100 µM, and harvested after 24 or 48 hours of treatment. In this experiment, the cells were additionally treated with either 5 mM glucose ("5G") or 22 mM glucose ("22G"). The samples derived from the cells were processed and the gels were run, transferred, stained and scanned essentially as described above.

Experimental Protocol for Actin:

The levels of actin were determined by probing the blots with a primary antibody for actin, essentially as described above.

Experimental Protocol for Caspase3 and MMP-6:

The Actin blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Caspase 3 or MMP-6 in 5% BSA by incubation overnight at 4 deg C. with gentle shaking. The primary antibody for Caspase 3 (Abcam ab44976-100; antirabbit) was at 1:500 dilution in 5% BSA. The primary antibody for MMP-6

(Santacruz scMM0029-ZB5; antimouse) was at 1:100 dilution in 5% BSA. After incubation with primary antibodies, the membranes were washed 3 times with TBS-T (1×-15'; 2×5' each) and probed with the secondary antibody (MMP-6 antimouse; Caspase 3 antirabbit; 1:10,000 dilution) for 1 h at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Experimental Protocol for LDH:

The above blots were stripped by incubating for 30 minutes with methanol, followed by two 10 minute washes with TBS-T, then 30 minutes of incubation with stripping buffer at 50 deg C., and followed by two washes with 100 ml or more of TBS-T for 30' each. The blots were activated with methanol for 5 seconds, washed with water for 5 minutes, and TBST for 15 minutes. The blots ere blocked for 1 hour with 5% blocking reagent in TBS-T at room temperature and then washed 3 times with TBS-T (1×-15'; 2×5' each) and probed with the primary antibody for LDH in 5% BSA or 5% milk by incubation overnight at 4 deg C. with gentle shaking. The primary antibody for LDH 080309b1 (Abcam ab2101; antigoat) was at 1:1000 dilution in 5% BSA. The primary antibody for LDH 080309b2 (Abcam ab2101; antigoat) was at 1:1000 dilution in 5% milk. After incubation with primary antibodies, the membranes were washed 3 times with TBS-T (1×-15'; 2×5' each) and probed with the secondary antibody (Jackson Immuno Research antigoat; 1:10,000 dilution; 305-055-045) for 1 h. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Experimental Protocol for Transaldolase and Hif1a:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots are blocked for 1 hour with 5% blocking reagent in TBS-T at room temperature and then washed 3 times with TBS-T (1×-15'; 2×5' each) and probed with the primary antibody for Transaldolase or Hif1a in 5% BSA by incubation overnight at 4 deg C. with gentle shaking. The primary antibody for Transaldolase (Abcam ab67467; antimouse) was at 1:500 dilution. The primary antibody for Hif1a (Abcam ab2185; antirabbit) was at 1:500 dilution. After incubation with primary antibodies, the membranes were washed 3 times with TBS-T (1×-15'; 2×5' each) and probed with the secondary antibody (antimouse or antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400 & 500V.

Experimental Protocol for IGFBP3 and TP53:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots are blocked for 1 hour with 5% blocking reagent in TBS-T at room temperature and then washed 3 times with TBS-T (1×-15'; 2×5' each) and probed with the primary antibody for IGFBP3 or TP53 in 5% BSA by incubation overnight at 4 deg C. with gentle shaking. The primary antibody for IGFBP3 (Abcam ab76001; antirabbit) was at 1:100 dilution. The primary antibody for TP53 (Sigma Aldrich AV02055; antirabbit) was at 1:100 dilution. After incubation with primary antibodies, the membranes were washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400 & 500V.

Experimental Protocol for Transaldolase and PDHB:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Transaldolase or PDHB in 5% BSA by incubation overnight at 4 deg C. with gentle shaking. The primary antibody for Transaldolase (Santacruz sc51440; antigoat) was at 1:200 dilution. The primary antibody for PDHB (Novus Biologicals H00005162-M03; antimouse) was at 1:500 dilution. After incubation with primary antibodies, the membranes were washed 3 times with TBS-T (1×-15'; 2×5' each) and probed with the secondary antibody (antigoat or antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400 & 500V.

Results

Isocitrate Dehydrogenase-1 (IDH-1)

Isocitrate dehydrogenase is one of the enzymes that is part of the TCA cycle that usually occurs within the mitochondrial matrix. However, IDH1 is the cytosolic form of the enzyme that catalyzes the oxidative decarboxylation of isocitrate to α-ketoglutarate and generates carbon dioxide in a two step process. IDH1 is the $NADP^+$ dependent form that is present in the cytosol and peroxisome. IDH1 is inactivated by Ser113 phosphorylation and is expressed in many species including those without a citric acid cycle. IDH1 appears to function normally as a tumor suppressor which upon inactivation contributes to tumorigenesis partly through activation of the HIF-1 pathway (Bayley 2010; Reitman, 2010). Recent studies have implicated an inactivating mutation in IDH1 in the etiology of gliobasotoma (Bleeker, 2009; Bleeker, 2010).

Treatment with Coenzyme Q10 increased expression of IDH1 in cancer cell lines including MCF-7, SKMEL28, HepG2 and PaCa-2 cells. There was a moderate increase in expression in the SCC25 cell lines. In contrast cultures of primary human derived fibroblasts HDFa, nFIB and the human aortic smooth muscle cells HASMC did not demonstrate significant changes in the expression pattern of the IDH1 in response to Coenzyme Q10. α-ketoglutarate (α-KG) is a key intermediate in the TCA cycle, biochemically synthesized from isocitrate and is eventually converted to succinyl coA and is a druggable MIM and EpiShifter. The generation of α-KG serves as a critical juncture in the TCA cycle as it can be used by the cell to replenish intermediates of the cycle, resulting in generation of reducing equivalents to increase oxidative phosphorylation. Thus, Coenzyme Q10 mediated increase in IDH1 expression would result in formation of intermediates that can be used by the mitochondrial TCA cycle to augment oxidative phosphorylation in cancer cells. The results are summarized in the tables below.

TABLE 105

IDH1 in HDFa and MCF-7

| Composition | Average Normalized Intensity |
| --- | --- |
| HDF, Media | 346 |
| HDF24-50-Coenzyme Q10 | 519 |
| HDF24-100-Coenzyme Q10 | 600 |
| MCF, Media | 221 |
| MCF24-50-Coenzyme Q10 | 336 |
| MCF24-100-Coenzyme Q10 | 649 |

TABLE 106

IDH1 in HASMC vs. HepG2 after Treatment

| Amount-Composition | Normalized Intensity |
| --- | --- |
| HAS5g48-media | 20 |
| HAS5g48-50-Coenzyme Q10 | 948 |
| HAS5g48-100-Coenzyme Q10 | 1864 |
| HAS22G48-Media | 1917 |
| HAS22G48-50-Coenzyme Q10 | 1370 |
| HAS22G48-100-Coenzyme Q10 | 1023 |
| Hep5g48-Media | 14892 |
| Hep5g48-50-Coenzyme Q10 | 14106 |
| Hep5g48-100-Coenzyme Q10 | 15774 |
| Hep22G48-Media | 16558 |
| Hep22G48-50-Coenzyme Q10 | 15537 |
| Hep22G48-100-Coenzyme Q10 | 27878 |

TABLE 107

IDH1 in HASMC vs. PACA2 after Treatment

| Amount-Composition | Normalized Intensity |
| --- | --- |
| HAS5g48-media | 562 |
| HAS5g48-50-Coenzyme Q10 | 509 |
| HAS5g48-100-Coenzyme Q10 | 627 |
| HAS22G48-Media | 822 |
| HAS22G48-50-Coenzyme Q10 | 1028 |
| HAS22G48-100-Coenzyme Q10 | 1015 |
| PACA5g48-Media | 1095 |
| PACA5g48-50-Coenzyme Q10 | 1095 |
| PACA5g48-100-Coenzyme Q10 | 860 |
| PACA22G48-Media | 1103 |
| PACA22G48-50-Coenzyme Q10 | 1503 |
| PACA22G48-100-Coenzyme Q10 | 1630 |

ATP Citrate Lyase (ACL)

ATP citrate Lyase (ACL) is a homotetramer (~126 kd) enzyme that catalyzes the formation of acteyl-CoA and oxaloacetate in the cytosol. This reaction is a very important first step for the biosynthesis of fatty acids, cholesterol, and acetylcholine, as well as for glucogenesis (Towle et al., 1997). Nutrients and hormones regulate the expression level and phosphorylation status of this key enzyme. Ser454 phosphorylation of ACL by Akt and PKA has been reported (Berwick., DC M W et al., 2002; Pierce M W et al., 1982).

The data describes the effect of Coenzyme Q10 on ATP citrate Lyase is that in normal and cancer cells. It is consistently observed that in cancer cells there is a dose-dependent decrease in the expression of ACL enzymes. In contrast there appears to be a trend towards increased expression of ACL in normal cells. Cytosolic ACL has been demonstrated to be essential for histone acetylation in cells during growth factor stimulation and during differentiation. The fact that ACL utilizes cytosolic glucose derived citrate to generate Acetyl CoA essential for histone acetylation, a process important in the neoplastic process demonstrates a role of Coenzyme Q10 induced ACL expression in influencing cancer cell function. Acetyl CoA generated from citrate by cytosolic ACL serves as a source for biosynthesis of new lipids and cholesterol during cell division. Thus, Coenzyme Q10 induced changes in ACL expression alters Acetyl CoA availability for synthesis of lipids and cholesterol in normal versus cancer cells. The results are summarized in the tables below.

TABLE 108

ATPCL in HDFa and MCF-7

| Composition | Average Normalized Intensity |
| --- | --- |
| HDF-Media | ~15000 |
| HDF-50-Coenzyme Q10 | ~17500 |
| HDF-100-Coenzyme Q10 | ~25000 |
| MCF-Media | ~7500 |
| MCF-50-Coenzyme Q10 | ~7500 |
| MCF-100-Coenzyme Q10 | ~12500 |

TABLE 109

ATP Citrate Lysase ~kd band in HASMC vs. HepG2

| Amount-Composition | Normalized Intensity |
| --- | --- |
| HAS5g48-media | 24557 |
| HAS5g48-50-Coenzyme Q10 | 23341 |
| HAS5g48-100-Coenzyme Q10 | 25544 |
| HAS22G48-Media | 27014 |
| HAS22G48-50-Coenzyme Q10 | 21439 |
| HAS22G48-100-Coenzyme Q10 | 19491 |
| Hep5g48-Media | 28377 |
| Hep5g48-50-Coenzyme Q10 | 24106 |
| Hep5g48-100-Coenzyme Q10 | 22463 |
| Hep22G48-Media | 24262 |
| Hep22G48-50-Coenzyme Q10 | 31235 |
| Hep22G48-100-Coenzyme Q10 | 50588 |

TABLE 110

ATP Citrate Lysase ~kd band in HASMC vs. PACA2

| Amount-Composition | Normalized Intensity |
| --- | --- |
| HAS5g48-media | 11036 |
| HAS5g48-50-Coenzyme Q10 | 12056 |
| HAS5g48-100-Coenzyme Q10 | 15265 |
| HAS22G48-Media | 18270 |
| HAS22G48-50-Coenzyme Q10 | 15857 |
| HAS22G48-100-Coenzyme Q10 | 13892 |
| PACA5g48-Media | 11727 |
| PACA5g48-50-Coenzyme Q10 | 8027 |
| PACA5g48-100-Coenzyme Q10 | 4942 |

TABLE 110-continued

ATP Citrate Lysase ~kd band in HASMC vs. PACA2

| Amount-Composition | Normalized Intensity |
|---|---|
| PACA22G48-Media | 8541 |
| PACA22G48-50-Coenzyme Q10 | 9537 |
| PACA22G48-100-Coenzyme Q10 | 14901 |

TABLE 111

ATP Citrate Lysase in HepG2 and PACA2 as % of CTRL

| Amount-Composition | Normalized Intensity |
|---|---|
| PACA5g48-Media | 1.00 |
| PACA5g48-50-Coenzyme Q10 | 0.68 |
| PACA5g48-100-Coenzyme Q10 | 0.42 |
| PACA22G48-Media | 1.00 |
| PACA22G48-50-Coenzyme Q10 | 1.12 |
| PACA22G48-100-Coenzyme Q10 | 1.74 |
| Hep5g48-Media | 1.00 |
| Hep5g48-50-Coenzyme Q10 | 0.85 |
| Hep5g48-100-Coenzyme Q10 | 0.79 |
| Hep22G48-Media | 1.00 |
| Hep22G48-50-Coenzyme Q10 | 1.29 |
| Hep22G48-100-Coenzyme Q10 | 2.09 |

Pyruvate Kinase M2 (PKM2)

Pyruvate Kinase is an enzyme involved in the glycolytic pathway. It is responsible for the transfer of phosphate from phosphoenolpyruvate (PEP) to adenosine diphosphate (ADP) to generate ATP and pyruvate. PKM2 is an isoenzyme of the glycolytic pyruvate kinase, expression of which is characterized by the metabolic function of the tissue i.e. M2 isoenzyme is expressed in normal rapidly proliferating cells with high energy needs such as embryonic cells and also expressed in few normal differentiated tissues such as lung and pancreatic islet cells that require high rate of nucleic acid synthesis. PKM2 is highly expressed in tumor cells due to their dependence on glycolytic pathway for meeting cellular energetic requirements. The PKM2 isoform normally thought to be embryonically restricted is re-expressed in cancerous cells. Cells expressing PKM2 favor a stronger aerobic glycolytic phenotype (show a shift in metabolic phenotype) with increased lactate production and decreased oxidative phosphorylation. Thus, decrease in expression of PKM2 in cancer cells would shift or down-regulate energy generation via the glycolytic pathway, a strategy that is useful in the treatment of cancer. Data demonstrates variable expression pattern of PKM2 in normal and cancer cells, with cancer cells demonstrating higher levels of expression compared to normal. Treatment of cells with Coenzyme Q10 altered expression pattern of the PKM2 upper and lower band levels in normal and cancer cells (FIGS. 81-85). In cancer cells tested, there was a dose-dependent decrease in the PKM2 expression, and no major changes in normal cells were observed. The results are summarized in the tables below.

TABLE 112

Pyruvate Kinase Muscle form 2 Upper Band in HepG2

| Amount-Composition | Normalized Volume (24 h) | Normalized Intensity (48 h) |
|---|---|---|
| 5g-Media | 28386 | 413 |
| 5g-50-Coenzyme Q10 | 29269 | 303 |

TABLE 112-continued

Pyruvate Kinase Muscle form 2 Upper Band in HepG2

| Amount-Composition | Normalized Volume (24 h) | Normalized Intensity (48 h) |
|---|---|---|
| 5g-100-Coenzyme Q10 | 18307 | 354 |
| 22G-Media | 25903 | 659 |
| 22G-50-Coenzyme Q10 | 22294 | 562 |
| 22G-100-Coenzyme Q10 | 19560 | 601 |

TABLE 113

Pyruvate Kinase Muscle form 2 Lower Band (58 KD) in HepG2

| Amount-Composition | Normalized Volume (24 h) | Normalized Volume (48 h) |
|---|---|---|
| 5g-Media | 10483 | 310 |
| 5g-50-Coenzyme Q10 | 11197 | 185 |
| 5g-100-Coenzyme Q10 | 7642 | 122 |
| 22G-Media | 9150 | 306 |
| 22G-50-Coenzyme Q10 | 6302 | 344 |
| 22G-100-Coenzyme Q10 | 6904 | 465 |

TABLE 114

Pyruvate Kinase Muscle form 2 Upper Band in HASMC Cells after Treatment

| Amount-Composition | Normalized Intensity |
|---|---|
| 5g48-Media | 608 |
| 5g48-50-Coenzyme Q10 | 811 |
| 5g48-100-Coenzyme Q10 | 611 |
| 22G48-Media | 516 |
| 22G48-50-Coenzyme Q10 | 595 |
| 22G48-100-Coenzyme Q10 | 496 |
| 22G24-Media | 301 |
| 22G24-50-Coenzyme Q10 | 477 |
| 22G24-100-Coenzyme Q10 | 701 |

Lactate Dehydrogenase (LDH)

LDH is an enzyme that catalyzes the interconversion of pyruvate and lactate with the simultaneous interconversion of NADH and $NAD^+$. It has the ability to convert pyruvate to lactate (lactic acid) under low cell oxygen tension for generation of reducing equivalents and ATP generation at the expense of mitochondrial oxidative phosphorylation. Cancer cells typically demonstrate increased expression of LDH to maintain the glycolytic flux to generate ATP and reducing equivalents and reducing mitochondrial OXPHOS. Thus, reducing the expression of the LDH in cancer cells would shift metabolism from generation of lactate to facilitate entry of pyruvate into the TCA cycle. Treatment with Coenzyme Q10 reduced Lactate Dehydrogenase (LDH) expression in cancer with minimal effect on normal cells, supporting a role for Coenzyme Q10 in eliciting a shift in cancer cell bioenergtics for the generation of ATP from glycolytic to mitochondrial OXPHOS sources by minimizing the conversion of cytoplasmic pyruvate to lactic acid. The results are summarized in the tables below.

TABLE 115

Lactate Dehydrogenase in HepG2

| Amount-Composition | Normalized Volume (24 h) | Normalized Volume (48 h) |
| --- | --- | --- |
| 5g-Media | 7981 | 5997 |
| 5g-50-Coenzyme Q10 | 7900 | 5188 |
| 5g-100-Coenzyme Q10 | 6616 | 7319 |
| 22G-Media | 9171 | 7527 |
| 22G-50-Coenzyme Q10 | 7550 | 6173 |
| 22G-100-Coenzyme Q10 | 7124 | 9141 |

TABLE 116

Lactate Dehydrogenase in HepG2 as % Control from 2 Experiments

| Amount-Composition | Average Volume as a % of Control |
| --- | --- |
| 5g24-Media | 1.00 |
| 5g24-50-Coenzyme Q10 | 0.64 |
| 5g24-100-Coenzyme Q10 | 1.06 |
| 5g48-Media | 1.00 |
| 5g48-50-Coenzyme Q10 | 1.12 |
| 5g48-100-Coenzyme Q10 | 1.21 |
| 22G24-Media | 1.00 |
| 22G24-50-Coenzyme Q10 | 1.21 |
| 22G24-100-Coenzyme Q10 | 1.44 |
| 22G48-Media | 1.00 |
| 22G48-50-Coenzyme Q10 | 0.95 |
| 22G48-100-Coenzyme Q10 | 0.67 |

TABLE 117

Lactate Dehydrogenase in PACA2

| Amount-Composition | Normalized Volume (24 h) | Normalized Volume (48 h) |
| --- | --- | --- |
| 5g-Media | 2122 | 2360 |
| 5g-50-Coenzyme Q10 | 5068 | 2978 |
| 5g-100-Coenzyme Q10 | 3675 | 2396 |
| 22G-Media | 4499 | 2332 |
| 22G-50-Coenzyme Q10 | 10218 | 2575 |
| 22G-100-Coenzyme Q10 | 7158 | 3557 |

Pyruvate Dehydrogenase—B (PDH-E1)

Pyruvate Dehydrogenase beta (PDH-E1) is the first enzyme component that is part of the pyruvate dehydrogenase complex (PDC) that converts pyruvate to acetyl CoA. PDH-E1 requires thiamine as cofactor for its activity, performs the first two biochemical reactions in the PDC complex essential for the conversion of pyruvate to acetyl CoA to enter the TCA cycle in the mitochondria. Thus, concomitant decreases in PKM2 and LDH expression along with increase in expression of PDH-E1 in cancer cells would enhance the rate of entry of pyruvate towards augmenting the mitochondrial OXPHOS for generation of ATP. The data shows that for expression of PDH-E1 in normal and cancer cell lines, the baseline expressions of this enzyme is decreased in cancer compared to normal cells. Treatment with Coenzyme Q10 is associated with progressive increase in the expression of the PDH-E1 proteins in cancer cells with minimal changes in the normal cells. The results are summarized in the tables below.

TABLE 118

Pyruvate Dehydrogenase Beta in HepG2

| Amount-Composition | Normalized Volume (24 h) | Normalized Volume (48 h) |
| --- | --- | --- |
| 5g-Media | 517 | 100 |
| 5g-50-Coenzyme Q10 | 921 | 123 |
| 5g-100-Coenzyme Q10 | 433 | 205 |
| 22G-Media | 484 | 181 |
| 22G-50-Coenzyme Q10 | 426 | 232 |
| 22G-100-Coenzyme Q10 | 340 | 456 |

TABLE 119

Pyruvate Dehydrogenase Beta in PACA2

| Amount-Composition | Normalized Volume (24 h) | Normalized Volume (48 h) |
| --- | --- | --- |
| 5g-Media | 323 | 375 |
| 5g-50-Coenzyme Q10 | 492 | 339 |
| 5g-100-Coenzyme Q10 | 467 | 252 |
| 22G-Media | 572 | 276 |
| 22G-50-Coenzyme Q10 | 924 | 279 |
| 22G-100-Coenzyme Q10 | 1201 | 385 |

TABLE 120

Pyruvate Dehydrogenase Beta in HASMC after Treatment

| Amount-Composition | Normalized Volume |
| --- | --- |
| 5g48-Media | 140 |
| 5g48-50-Coenzyme Q10 | 147 |
| 5g48-100-Coenzyme Q10 | 147 |
| 22G48-Media | 174 |
| 22G48-50-Coenzyme Q10 | 149 |
| 22G48-100-Coenzyme Q10 | 123 |
| 22G24-Media | 140 |
| 22G24-50-Coenzyme Q10 | 145 |
| 22G24-100-Coenzyme Q10 | 150 |

Caspase 3

Control of the onset of apoptosis is often exerted at the level of the initiator caspases, caspase-2, -9 and -8/10. In the extrinsic pathway of apoptosis, caspase-8, once active, directly cleaves and activates executioner caspases (such as caspase-3). The active caspase-3 cleaves and activates other caspases (6, 7, and 9) as well as relevant targets in the cells (e.g. PARP and DFF). In these studies, the levels of effectors caspase-3 protein were measured in the cancer cell lines and in normal cell lines in response to Coenzyme Q10. It should be noted although control of apoptosis is through initiator caspases, a number of signaling pathways interrupt instead the transmission of the apoptotic signal through direct inhibition of effectors caspases. For e.g. P38 MAPK phosphorylates caspase-3 and suppresses its activity (Alvarado-Kristensson et al., 2004). Interestingly, activation of protein phosphates (PP2A) in the same study or protein kinase C delta (PKC delta) (Voss et al., 2005) can counteract the effect of p38 MAPK to amplify the caspase-3 activation and bolster the transmission of the apoptotic signal. Therefore, events at the level of caspase-3 activation or after Caspase 3 activation may determine the ultimate fate of the cell in some cases.

Caspase-3 is a cysteine-aspartic acid protease that plays a central role in the execution phase of cell apoptosis. The levels of caspase 3 in the cancer cells were increased with Coenzyme Q10 treatment. In contrast the expression of Caspase-3 in normal cells was moderately decreased in normal cells. The results are summarized in the tables below.

TABLE 121

Caspase 3 in PACA2

| Amount-Composition | Normalized Volume (24 h) | Normalized Volume (48 h) |
|---|---|---|
| 5g-Media | 324 | 300 |
| 5g-50-Coenzyme Q10 | 325 | 701 |
| 5g-100-Coenzyme Q10 | 374 | 291 |
| 22G-Media | 344 | 135 |
| 22G-50-Coenzyme Q10 | 675 | 497 |
| 22G-100-Coenzyme Q10 | 842 | 559 |

TABLE 122

Caspase 3 in HepG2 cells as % Control from 2 Experiments

| Amount-Composition | Normalized Volume as a % of Control |
|---|---|
| 5g24-Media | 1.00 |
| 5g24-50-Coenzyme Q10 | 1.08 |
| 5g24-100-Coenzyme Q10 | 1.76 |
| 5g48-Media | 1.00 |
| 5g48-50-Coenzyme Q10 | 1.44 |
| 5g48-100-Coenzyme Q10 | 0.95 |
| 22G24-Media | 1.00 |
| 22G24-50-Coenzyme Q10 | 1.39 |
| 22G24-100-Coenzyme Q10 | 1.78 |
| 22G48-Media | 1.00 |
| 22G48-50-Coenzyme Q10 | 1.50 |
| 22G48-100-Coenzyme Q10 | 1.45 |

TABLE 123

Caspase 3 in HASMC after Treatment

| Amount-Composition | Normalized Volume |
|---|---|
| 5g48-Media | 658 |
| 5g48-50-Coenzyme Q10 | 766 |
| 5g48-100-Coenzyme Q10 | 669 |
| 22G48-Media | 846 |
| 22G48-50-Coenzyme Q10 | 639 |
| 22G48-100-Coenzyme Q10 | 624 |
| 22G24-Media | 982 |
| 22G24-50-Coenzyme Q10 | 835 |
| 22G24-100-Coenzyme Q10 | 865 |

Succinate Dehydrogenase (SDH)

Succinate dehydrogenase, also known as succinate-coenzyme Q reductase is a complex of the inner mitochondrial membrane that is involved in both TCA and electron transport chain. In the TCA, this complex catalyzes the oxidation of succinate to fumarate with the concomitant reduction of ubiquinone to ubiquinol. (Baysal et al., Science 2000; and Tomlinson et al., Nature Genetics 2002). Germline mutations in SDH B, C and D subunits were found to be initiating events of familial paraganglioma or leiomyoma (Baysal et al., Science 2000).

Western blotting analysis was used to characterize expression of SDH Subunit B in mitochondrial preparations of cancer cells treated with Coenzyme Q10. The results suggest that Coenzyme Q10 treatment is associated with increase SDH protein levels in the mitochondrion of the cells. These results suggest one of the mechanisms of action of Coenzyme Q10 is to shift the metabolism of the cell towards the TCA cycle and the mitochondrion by increasing the levels of mitochondrial enzymes such as SDHB. The results are summarized in the table below.

TABLE 124

Succinate Dehydrogenase B in NCIE0808 Mitopreps

| Composition-Time | Average Normalized Volume |
|---|---|
| Media | 531 |
| 50 uM Coezyme Q10, 3 h | 634 |
| 100 uM Coenzyme Q10, 3 h | 964 |
| 50 uM Coenzyme Q10, 6 h | 1077 |
| 100 uM Coenzyme Q10, 6 h | 934 |

Hypoxia Induced Factor-1

Hypoxia inducible factor (Hif) is a transcription factor composed of alpha and beta subunits. Under normoxia, the protein levels of Hif1 alpha are very low owing to its continuous degradation via a sequence of post translational events. The shift between glycolytic and oxidative phosphorylation is generally considered to be controlled by the relative activities of two enzymes PDH and LDH that determine the catabolic fate of pyruvate. Hif controls this crucial bifurgation point by inducing LDH levels and inhibiting PDH activity by stimulating PDK. Due to this ability to divert pyruvate metabolism from mitochondrion to cytosol, Hif is considered a crucial mediator of the bioenergetic switch in cancer cells.

Treatment with Coenzyme Q10 decreased Hif1 alpha protein levels after in mitochondrial preparations of cancer cells. In whole cell lysates of normal cells, the lower band of Hif1a was observed and showed a decrease as well. The results are summarized in the tables below.

TABLE 125

Hif1 alpha Lower Band in HASMC Cells after Treatment

| Amount-Composition | Normalized Volume |
|---|---|
| 5g48-Media | 22244 |
| 5g48-50-Coenzyme Q10 | 21664 |
| 5g48-100-Coenzyme Q10 | 19540 |
| 22G48-Media | 14752 |
| 22G48-50-Coenzyme Q10 | 17496 |
| 22G48-100-Coenzyme Q10 | 23111 |
| 22G24-Media | 21073 |
| 22G24-50-Coenzyme Q10 | 18486 |
| 22G24-100-Coenzyme Q10 | 17919 |

TABLE 126

Hif1 alpha Upper Band in HepG2 after Treatment

| Amount-Composition | Normalized Volume |
|---|---|
| 5g24-Media | 12186 |
| 5g24-50-Coenzyme Q10 | 8998 |
| 5g24-100-Coenzyme Q10 | 9315 |
| 5g48-Media | 8868 |
| 5g48-50-Coenzyme Q10 | 8601 |
| 5g48-100-Coenzyme Q10 | 10192 |
| 22G24-Media | 11748 |

TABLE 126-continued

Hif1 alpha Upper Band in HepG2 after Treatment

| Amount-Composition | Normalized Volume |
|---|---|
| 22G24-50-Coenzyme Q10 | 14089 |
| 22G24-100-Coenzyme Q10 | 8530 |
| 22G48-Media | 8695 |
| 22G48-50-Coenzyme Q10 | 9416 |
| 22G48-100-Coenzyme Q10 | 5608 |

Example 43

Analysis of Oxygen Consumption Rates (OCR) and Extracellular Acidification (ECAR) in Normal and Cancer cCells Treated with CoQ10

This example demonstrates that exposure of cells to treatment by a representative MIM/epi-shifter of the invention—CoQ10—in the absence and/or presence of stressors (e.g., hyperglycemia, hypoxia, lactic acid), is associated with a shift towards glycolysis/lactate biosynthesis and mitochondrial oxidative phosphorylation (as measured by ECAR and OCR values) representative of values observed in a normal cells under normal physiological conditions.

Applicants have demonstrated in the previous section that treatment with CoQ10 in cancer cells is associated with changes in expression of specific proteins that enhance mitochondrial oxidative phosphorylation, with a concomitant decrease in glycolysis and lactate biosynthesis. This example shows that a direct measure of mitochondrial oxidative phosphorylation can be obtained by measuring the oxygen consumption rates (OCR) in cell lines using the SeaHorse XF analyzer, an instrument that measures dissolved oxygen and extracellular pH levels in an in vitro experimental model. (SeaHorse Biosciences Inc, North Billerica, Mass.).

The pH of the extracellular microenvironment is relatively acidic in tumors compared to the intracellular (cytoplasmic) pH and surrounding normal tissues. This characteristic of tumors serves multiple purposes, including the ability to invade the extracellular matrix (ECM), a hallmark attribute of tumor metastasis that subsequently initiates signaling cascades that further modulate:

tumor angiogenesis
  increased activation of arrest mechanisms that control cell cycle turn-over
  immuno-modulatory mechanisms that facilitate a cellular evasion system against immunosurveilance
  metabolic control elements that increase dependency on glycolytic flux and lactate utilization
  dysregulation of key apopototic gene families such as Bcl-2, IAP, EndoG, AIF that serve to increase oncogenicity While not wishing to be bound by any particular theory, the acidic pH of the external microenvironment in the tumor is a consequence of increase in hydrogen ion concentrations extruded from the tumor cells due to the increased lactate production from an altered glycolytic phenotype.

In this experiment, the OCR and extracellular acidification rate (ECAR) in normal cells lines were obtained in the presence and absence of CoQ10 to determine baseline values. It was observed that in its native nutrient environment, the basal OCR rates in normal cells lines are different, and are usually a function of the physiological roles of the cells in the body.

For example, one set of experiments were conducted using the non-cancerous cell line HDFa, which is a human adult dermal fibroblast cell line. Fibroblasts are cells that primarily synthesize and secrete extracellular matrix (ECM) components and collagen that form the structural framework (stroma) for tissues. In addition, fibroblasts are known to serve as tissue ambassadors of numerous functions such as wound healing and localized immunomodulation. Under normal physiological conditions, energy requirements in normal fibroblasts are met using a combination of glycolysis and oxidative phosphorylation—the glycolysis providing the necessary nutrients for synthesis of ECM.

In contrast to HDFa, the HASMC (human aortic smooth muscle cell) is found in arteries, veins, lymphatic vessels, gastrointestinal tracts, respiratory tract, urinary bladder and other tissues with the ability to undergo regulated excitation-contraction coupling. The ability of smooth muscles such as HASMC cells to undergo contraction requires energy provided by ATP. These tissues transition from low energy modes wherein ATP may be supplied from mitochondria to high energy modes (during exercise/stress) where energy is provided by switching to glycolysis for rapid generation of ATP. Thus, normal smooth muscle cells can use a combination of mitochondrial OXPHOS and glycolysis to meet their energy requirements under normal physiological environment.

Figure 37:
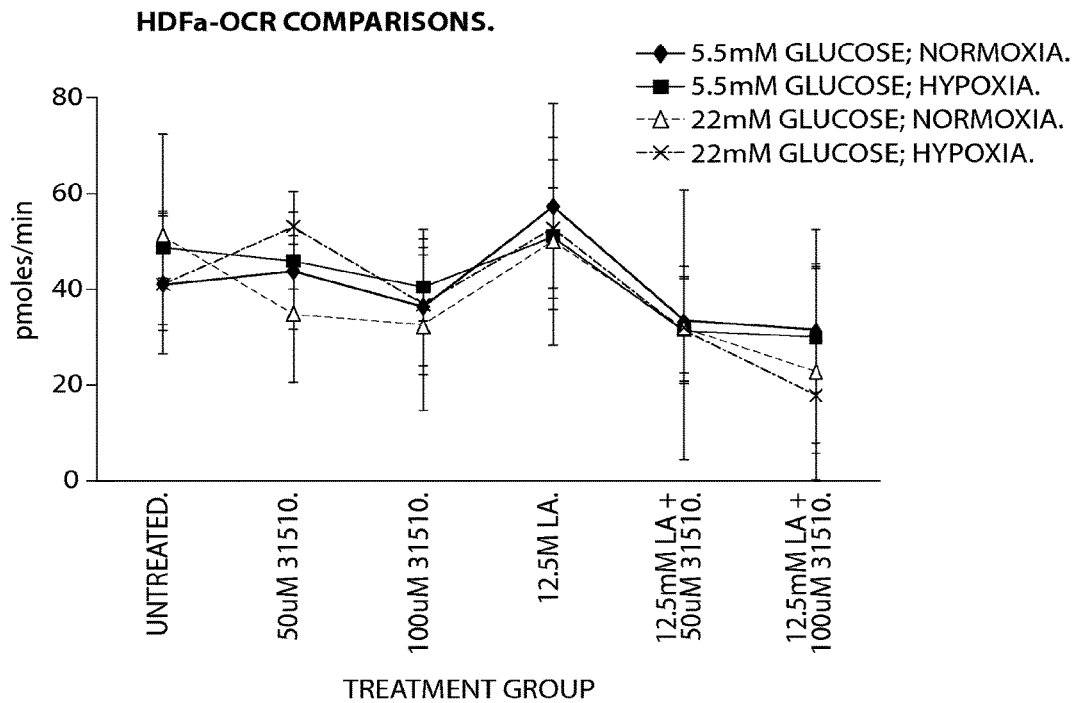
FIG. 37: OCR in HDFa cells in various glucose conditions in normoxic and hypoxic conditions.
Figure 38:
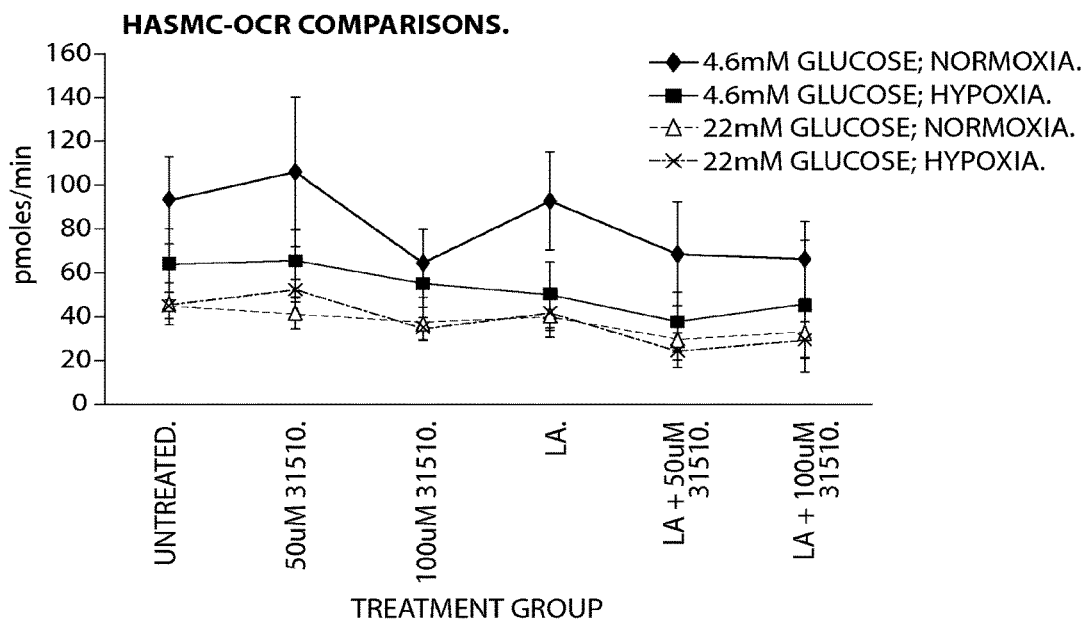
FIG. 38: OCR in HASMC cells in various glucose conditions in normoxic and hypoxic conditions.

The differences in their respective physiological roles (i.e., HDFa and HASMC) were observed in the resting OCR values measured in these cells lines using the SeaHorse XF analyzer. FIGS. 37 and 38 below describes the OCR in HDFa and HASMC cells grown in physiologically normal glucose (about 4.6 mM) and high glucose (hyperglycemic) conditions.

The baseline OCR values for HDFa in the absence of any treatments under normal oxygen availability is approximately 40 pmoles/min (FIG. 37) in the presence of 5.5 mM glucose. This value was slightly elevated when the cells were maintained at 22 mM glucose. In contrast, in HASMC cells, the OCR values at 5.5 mM glucose is approximately 90 pmoles/min, and the OCR value declined to approximately 40 pmoles/min while at 22 mM glucose. Thus, under hyperglycemic conditions, there is a differential response between HDFa and HASMC, further demonstrating inherent differences in their respective physiological make-up and function.

Treatment with CoQ10 in cells is associated with changes in OCR that is representative of conditions observed at normal (5 mM) glucose conditions. The complexity of physiological response is compounded in the presence of low oxygen tension. Thus, CoQ10 exposure is associated with changes in OCR rates in normal cells towards a physiological state that is native to a particular cell.

Table 127 below describes the ECAR values (mpH/min) in HDFa cells in the presence or absence of CoQ10 under normoxic and hypoxic conditions at 5.5 mM and 22 mM glucose. It can be observed that in normal cells, treatment with CoQ10 had minimal influence on ECAR values, even though it influenced OCR in these cells. In high glucose hypoxic conditions, treatment with CoQ10 was associated with lowering of elevated ECAR to a value that was observed in untreated normoxic conditions.

TABLE 127

ECAR values in HDFa cells in the absence and presence of CoQ10 under normoxic and hypoxic conditions at 5.5 mM and 22 mM glucose

| Treatment | Normoxia (5.5 mM) ECAR | SEM | Hypoxia (5.5 mM) ECAR | SEM | Normoxia (22 mM) ECAR | SEM | Hypoxia (22 mM) ECAR | SEM |
|---|---|---|---|---|---|---|---|---|
| Untreated | 5 | 1.32 | 5 | 0.62 | 5 | 0.62 | 9 | 0.81 |
| 50 μM 31510 | 6 | 1.11 | 5 | 0.78 | 5 | 0.78 | 6 | 0.70 |
| 100 μM 31510 | 6 | 0.76 | 5 | 1.19 | 5 | 1.19 | 8 | 1.07 |

In Table 128 the measured baseline ECAR values (mpH/min) in HASMC were higher compared to that of HDFa. Induction of hypoxic conditions caused an increase in ECAR most likely associated with intracellular hypoxia induced acidosis secondary to increased glycolysis.

TABLE 128

ECAR values in HASMC cells in the absence and presence of CoQ10 under normoxic and hypoxic conditions at 5.5 mM and 22 mM glucose

| Treatment | Normoxic (5.5 mM) ECAR | SEM | Hypoxic (5.5 mM) ECAR | SEM | Normoxic (22 mM) ECAR | SEM | Hypoxic (22 mM) ECAR | SEM |
|---|---|---|---|---|---|---|---|---|
| Untreated | 9 | 2.22 | 11 | 2.18 | 22 | 2.08 | 19 | 1.45 |
| 50 μM 31510 | 9 | 2.13 | 11 | 2.54 | 21 | 1.72 | 17 | 1.60 |
| 100 μM 31510 | 9 | 1.72 | 13 | 2.30 | 22 | 1.64 | 17 | 1.47 |

Treatment with CoQ10 was observed to be associated with a downward trend of ECAR rates in hyperglycemic HASMC cells in hypoxic conditions towards a value that would be observed in normoxic normal glucose conditions. These data demonstrate the presence of physiological variables that is inherent to the physiological role of a specific type of cell, alterations observed in abnormal conditions (e.g. hyperglycemia) is shifted towards normal when treated with CoQ10.

Figure 39:
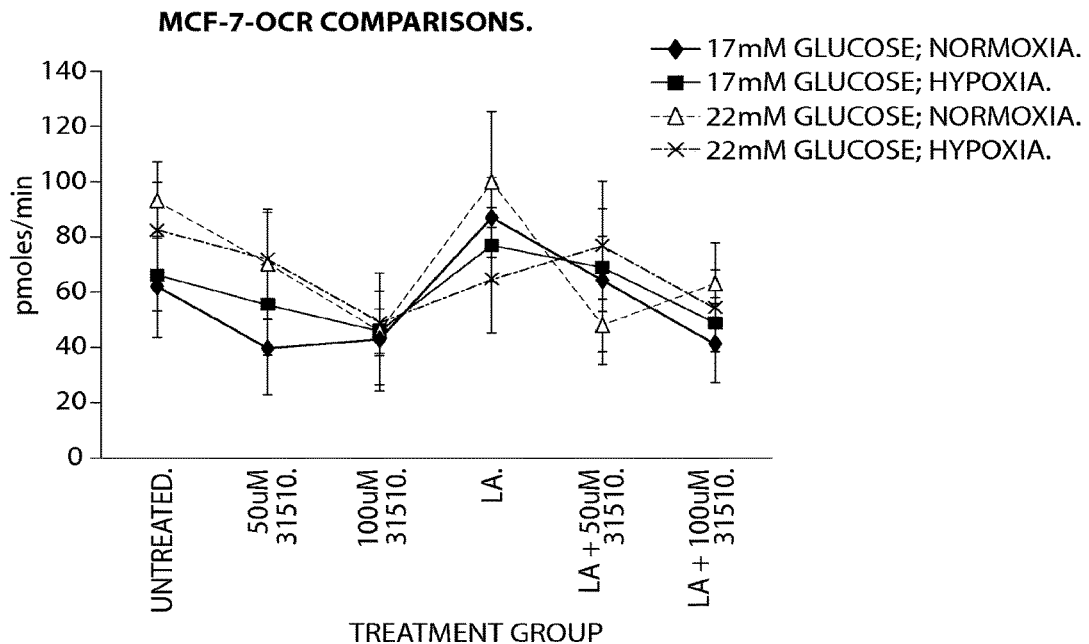
FIG. 39: OCR values in MCF-7 breast cancer cells in the absence and presence of CoQ10 and stressors.
Figure 40:
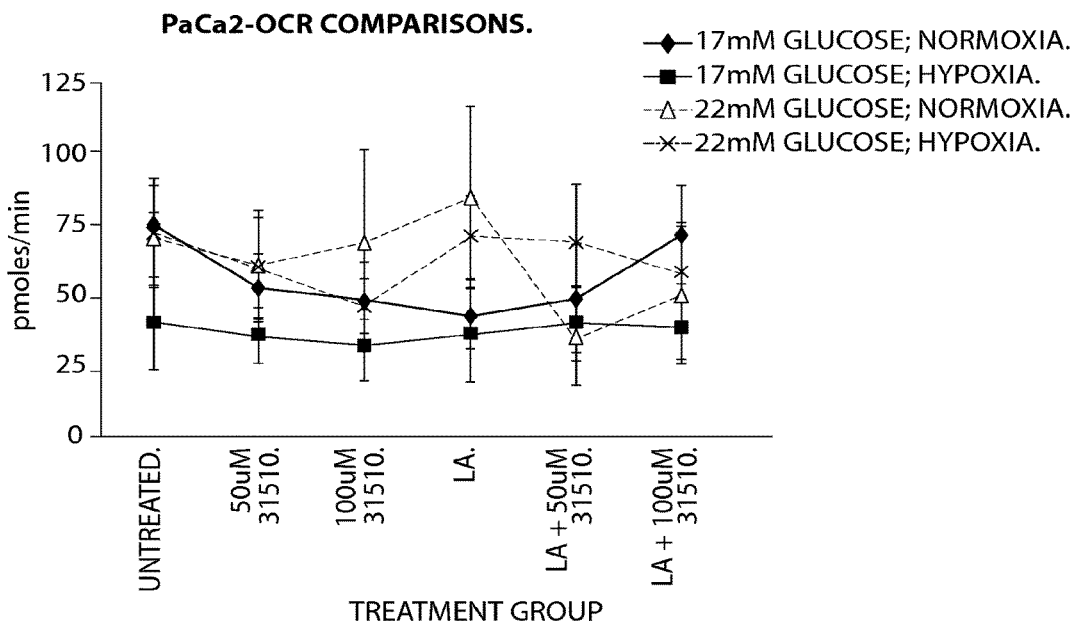
FIG. 40: OCR values in PaCa-2 pancreatic cancer cells in the absence and presence of CoQ10 and stressors.

In contrast, cancer cells (e.g., MCF-7, PaCa-2) are inherently primed to culture at higher levels of glucose compared to normal cells due to their glycolytic phenotype for maintenance in culture. Treatment with CoQ10 caused a consistent reduction in OCR values (FIG. 39 and FIG. 40).

The effects of CoQ10 on OCR values in MCF-7 and PaCa-2 cells was similar to that of the normal HDFa and HASMC cells, wherein the variable response was suggestive of a therapeutic response based on individual metabolic profile of the cancer cell line.

TABLE 129

ECAR values in PaCa-2 cells in the absence and presence of CoQ10 under normoxic and hypoxic conditions at 5.5 mM and 22 mM glucose

| Treatment | Normoxia (17 mM) ECAR | SEM | Hypoxia (17 mM) ECAR | SEM | Normoxia (22 mM) ECAR | SEM | Hypoxia (22 mM) ECAR | SEM |
|---|---|---|---|---|---|---|---|---|
| Untreated | 21 | 5.97 | 16 | 3.41 | 24 | 4.35 | 36 | 5.65 |
| 50 μM 31510 | 13 | 3.08 | 12 | 1.66 | 20 | 5.15 | 25 | 4.58 |
| 100 μM 31510 | 14 | 2.14 | 17 | 2.59 | 19 | 3.38 | 30 | 5.62 |

Table 129 describes the ECAR values in PaCa-2 cells. In contrast to normal cells, cancer cells are phenotypically primed to use high glucose for ATP generation (enhanced glycolysis) resulting in higher ECAR (Table 129, ECAR for untreated normoxia 17 mM) at 21 mpH/min. Treatment with CoQ10 produces a significant decrease in ECAR rates under these conditions, most likely associated with a decrease in the glycolysis generated lactic acid. The associated decrease in OCR in these cells was likely associated with increased efficiency of the mitochondrial OXPHOS.

A similar comparison of OCR and ECAR values (data not shown) were determined in numerous other normal and cancer cells lines, including: HAEC (normal human aortic endothelial cells), MCF-7 (breast cancer), HepG2 (liver cancer) and highly metastatic PC-3 (prostate cancer) cell lines. In all of the cell lines tested, exposure to CoQ10 in the absence and/or presence of stressors (e.g., hyperglycemia, hypoxia, lactic acid) was associated with a shift in OCR and ECAR values representative of values observed in a normal cells under normal physiological conditions. Thus, the overall effect of CoQ10 in the treatment of cancer, including cell death, is an downstream effect of its collective influence on proteomic, genomic, metabolomic outcomes in concert with shifting of the cellular bioenergetics from glycolysis to mitochondrial OXPHOS.

Example 44

Building Block Molecules for the Biosynthesis of CoQ10

This example demonstrates that certain precursors of CoQ10 biosynthesis, such as those for the biosynthesis of the benzoquinone ring, and those for the biosynthesis of the isoprenoid repeats and their attachment to the benzoquinone ring ("building block components"), can be individually administered or administered in combination to target cells, and effect down-regulation of the apoptosis inhibitor Bcl-2, and/or up-regulation of the apoptosis promoter Caspase-3. Certain precursors or combinations thereof may also inhibit cell proliferation. The data suggests that such CoQ10 precursors may be used in place of CoQ10 to achieve substantially the same results as CoQ10 administration.

Certain exemplary experimental conditions used in the experiments are listed below.

Skmel-28 melanoma cells were cultured in DMEM/F12 supplemented with 5% Fetal Bovine Serum (FBS) and 1× final concentration of Antibiotics. The cells were grown to 85% confluency and treated with building block components for 3, 6, 12 and 24 hours. The cells were then pelleted and a Western blot analysis was performed.

The test building block components included L-Phenylalanine, DL-Phenylalanine, D-Phenlylalanine, L-Tyrosine, DL-Tyrosine, D-Tyrosine, 4-Hydroxy-phenylpyruvate, phenylacetate, 3-methoxy-4-hydroxymandelate (vanillylmandelate or VMA), vanillic acid, 4-hydroxy-benzoate, pyridoxine, panthenol, mevalonic acid, Acetylglycine, Acetyl-CoA, Farnesyl, and 2,3-Dimethoxy-5-methyl-p-benzoquinone.

In the Western Blot Analysis, the cells were pelleted in cold PBS, lysed, and the protein levels were quantified using a BCA protein assay. The whole cell lysate was loaded in a 4% loading 12% running Tris-HCl gel. The proteins were then transferred to a nitrocellulose paper then blocked with a 5% milk Tris-buffered solution for 1 hour. The proteins were then exposed to primary antibodies (Bcl-2 and Caspase-3) overnight. The nitrocellulose paper was then exposed to Pico Chemilluminescent for 5 min and the protein expression was recorded. After exposure, actin was quantified using the same method. Using ImageJ the levels of protein expression were quantified. A t-Test was used to analyze for statistical significance.

Illustrative results of the experiments are summarized below.

Western Blot Analysis of Building Block component L-Phenylalanine: Before proceeding to the synthesis pathway for the quinone ring structure, L-Phenylalanine is converted to tyrosine. A western blot analysis was performed to quantify any changes in the expression of the apoptotic proteins in the melanoma cells. The concentrations tested were 5 µM, 25 µM, and 100 µM. Initial studies added L-Phenylalanine to DMEM/F12 medium which contained a concentration of 0.4 M phenylalanine. For the 5 µM, 25 µM, and 100 µM the final concentration of the L-Phenylalanine in the medium was 0.405 M, 0.425 M, and 0.500 M, respectively. These final concentrations were tested on the Skmel-28 cells for incubation periods of 3,6, 12 and 24 hours. The cells were grown to 80% confluency before adding the treatment medium and harvested using the western blot analysis procedure as described above. A statistically significant decrease in Bcl-2 was observed for the 100 µM L-Phenylalanine after 3 hours and 12 hours incubation. Fr the 5 µM L-phenylalanine, a statistically significant decrease in Bcl-2 was observed after 6 hours of incubation. For the 25 µM L-phenylalanine, a statistically significant decrease in Bcl-2 and a statistically significant increase in Caspase-3 were observed after 12 hours of incubation. A statistically significant decrease in Bcl-2 indicates a change in the apoptotic potential and a statistically significant increase in Caspase-3 confirms the cells are undergoing apoptosis. There was a constant trend for the decrease in Bcl-2 compared to the control even though, due to sample size and standard deviation, these time points were not statistically significant in this experiment.

Western Blot Analysis of Building Block component D-Phenylalanine: D-Phenylalanine, a chemically synthetic form of the bioactive L-Phenylalanine, was tested for comparison to L-phenylalanine. For all three concentrations (5 µM, 25 µM, and 10 µM of D-Phenylalanine, there was a significant reduction in Bcl-2 expression after 6 hours of incubation. In addition, for the 5 µM and 25 µM, there was a significant reduction after 3 hours of incubation. For the 5 µM and 100 µM concentrations, a significant increase in Caspase-3 expression was observed after 6 hours of incubation.

Western Blot Analysis of Building Block component DL-Phenylalanine: DL-Phenylalanine was also tested for comparison to L-Phenylalanine. Again, concentrations of 5 µM, 25 µM, and 100 µM were tested on Skmel-28 cells. The incubation periods were 3, 6, 12 and 24 hours. A statistically significant increase in Caspase-3 was observed after 3 hours of incubation. A statistically significant decrease in Bcl-2 was observed after 24 hours of incubation. Although a decreasing Bcl-2 and increasing Caspase-3 trend at all other concentrations and incubation time points, they were not statistically significant in this experiment.

Western Blot Analysis of Building Block component L-Tyrosine: L-Tyrosine is a building block component for the synthesis of quinone ring structure of CoQ10. Initial testing of L-Tyrosine did not result in a high enough protein concentration for western blot analysis. From this study concentrations under 25 µM were tested for Western Blot Analysis. The DMEM/F12 medium used contained L-Tyrosine disodium salt concentration of 0.398467 M. The initial concentration was increased by 500 nM, 5 µM, and 15 µM. A statistically significant increase in Caspase-3 was observed for the 500 nM concentration after 12 hours of incubation. A statistically significant increase in Caspase-3 was also observed for the 5A statistically significant decrease in Bcl-2 was observed for the 5 µM concentration after 24 hours of incubation. A statistically significant decrease in Bcl-2 was observed for the 500 µM and 5 µM concentrations after 24 hours of incubation.

Western Blot Analysis of Building Block component D-Tyrosine: D-Tyrosine, a synthetic form of L-Tyrosine, was tested for comparison against the L-Tyrosine apoptotic effect on the melanonal cells. Based on initial studies with L-Tyrosine, concentrations below 25 µM were chosen for the western blot analysis. The concentrations tested were 1 µm, 5 µM, and 15 µM. D-Tyrosine showed a reduction in Bcl-2 expression for the 5 µM and 15 µM concentrations for 12 and 24 hour time periods. Caspase-3 was significantly increased for the concentration of 5 µM for 3, 12 and 24 time periods. Also there was an increase in Caspase-3 expression for the 1 µM for 12 and 24 hour time period. In addition there is an increase in Caspase-3 expression for 5 µM for the 12 hour time period.

Western Blot Analysis of Building Block component DL-Tyrosine: DL-Tyrosine, a synthetic form of L-Tyrosine, was also tested for comparison against L-Tyrosine's apoptotic effect on the cells. There is a statistical decrease in Bcl-2 expression seen in the 1 µM and 15 µM concentrations after 12 hours incubation and for the 5 µM after 24 hour of incubation. An increase in Caspase-3 expression was also observed for the 5 µM and 15 µM after 12 hours of incubation.

Western Blot Analysis of Building Block component 4-Hydroxy-Phenylpyruvate: 4-Hydroxy-phenylpyruvate is derived from Tyrosine and Phenylalanine amino acids and may play a role in the synthesis of the ring structure. The concentration of 1 µM, 5 µM, and 15 µM were tested for Bcl-2 and Caspase-3 expression. For the 5 µM and 15 µM concentrations there is a significant reduction in Bcl-2 expression after 24 hours of incubation and a significant increase in Caspase-3 expression after 12 hours of incubation.

Western Blot Analysis of Building Block component Phenylacetate: Phenylacetate has the potential to be converted to 4-Hydroxy-benzoate, which plays a role in the attachment of the side chain to the ring structure. The concentration tested were 1 µM, 5 µM, and 15 µM. For phenylacetate there was a decrease in Bcl-2 expression for the concentration of 5 µM and 15 µM after 12 hours and 24 hours of incubation. An increase in Caspase-3 expression was observed for the concentration of 5 µM and 15 µM after 12 hours and 24 hours of incubation.

Western Blot Analysis of Building Block component 3-Methoxy-4-Hydroxymandelate (vanillylmandelate or VMA): VMA is an additional component for the synthesis of the CoQ10 quinone ring structure. The concentrations tested were 100 nM, 250 nM, 500 nM, 1 µM, 25 µM, 50 µM, and 100 µM. Though no statistically significant apoptotic effect was observed in this experiment, the data indicated a downward trend of Bcl-2 expression.

Western Blot Analysis of Building Block component Vanillic Acid: Vanillic is a precursor for the synthesis of the quinone ring and was tested at a concentration of 500 nm, 5 µM, and 15 µM. A western blot analysis measured Bcl-2 and Caspase-3 expression. Vanillic Acid was shown to significantly reduce Bcl-2 expression for the concentrations of 500 nM and 5 µM at the 24 hour incubation time point. For the 15 µM concentration there is a reduction in Bcl-2 expression after 3 hours of incubation. For the cells incubated with 15 µM for 24 hours there was a significant increase in Caspase-3 expression.

Western Blot Analysis of Building Block component 4-Hydroxybenzoate: 4-Hydroxybenzoate acid plays a role in the attachment of the isoprenoid side chain to the ring structure. The concentrations tested were 500 nM, 1 µM, and 50 µM. There was a significant reduction in Bcl-2 expression for the 15 µM concentration after 24 hours of incubation.

Western Blot Analysis of Building Block component 4-Pyridoxine: Pyridoxine is another precursor building block for the synthesis of the quinone ring structure of CoQ10. The concentrations tested for this compound are 5 µM, 25 µM, and 100 µM. The cells were assayed for their levels of Bcl-2 and Caspase-3. Pyridoxine showed a significant reduction in Bcl-2 after 24 hours of incubation in melanoma cells.

Western Blot Analysis of Building Block component Panthenol: Panthenol plays a role in the synthesis of the quinone ring structure of CoQ10. The concentrations tested on melanoma cells were 5 µM, 25 µM, and 100 µM. This compound showed a significant reduction in Bcl-2 expression for the 25 µM concentration.

Western Blot Analysis of Building Block component Mevalonic: Mevalonic Acid is one of the main components for the synthesis of CoQ10. This compound was tested at the concentrations of 500 nM, 1 µM, 25 µm, and 50 µM. There was no significant reduction in Bcl-2 expression or an increase in Caspase-3 expression in this experiment.

Western Blot Analysis of Building Block component Acetylglycine: Another route for the synthesis of CoQ10 is the isoprenoid (side chain) synthesis. The addition of Acetylglycine converts Coenzyme A to Acetyl-CoA which enters the mevalonic pathway for the synthesis of the isoprenoid synthesis. The concentrations tested were 5 µM, 25 µM, and 100 µM. The testing of Acetylglycine showed significant decrease in Bcl-2 expression after 12 hours of incubation for the concentration of 5 µM and 25 µM. A significant decrease in Bcl-2 was recorded for the 10 µM concentration at the 24 hour incubation time point.

Western Blot Analysis of Building Block component Acetyl-CoA: Acetyl-CoA is a precursor for the mevalonic pathway for the synthesis of CoQ10. The concentrations tested were 500 nm, 1 µM, 25 µM, and 5 µM. There was no significant observed reduction in Bcl-2 or increase in Caspase-3 expression for the time points and concentrations tested.

Western Blot Analysis of Building Block component L-Tyrosine in combination with farnesyl: L-Tyrosine is one of the precursors for the synthesis of the quinone ring structure for CoQ10. Previous experiment tested the reaction of L-Tyrosine in medium with L-Phenylalanine and L-Tyrosine. In this study L-Tyrosine was examined in medium without the addition of L-Phenylalanine and L-Tyrosine. In this study the final concentrations of L-Tyrosine tested were 500 nM, 5 µM, and 1 µM. Farnesyl was tested at a concentration of 5 µM. There was no observed significant response for the 3 and 6 hour time points.

Western Blot Analysis of Building Block component L-Phenylalanine in combination with Farnesyl: L-Phenylalanine, a precursor for the synthesis of the quinone ring structure, was examine in combination with farnesyl in medium free of L-Tyrosine and L-Phenylalanine. A western blot analysis was performed to assay the expression of Bcl-2 and Caspase-3. The final concentrations of L-Phenylalanine were: 5 µM, 25 µM, and 100 µM. Farnesyl was added at a concentration of 50 µM. This study showed a decrease in Bcl-2 expression for most of the concentrations and combinations tested as depicted in the table below.

TABLE 130

| L-Phenylalanine | 3 hr | | 6 hr | | 12 hr | | 24 hr | |
|---|---|---|---|---|---|---|---|---|
| | Bcl-2 | Cas-3 | Bcl-2 | Cas-3 | Bcl-2 | Cas-3 | Bcl-2 | Cas-3 |
| 5 µM | X | | | | | | | |
| 5 µM w/ Farnesyl | | | | | | | X | X |
| 25 µM | X | | X | | | | | |
| 25 µM w/ Farnesyl | X | | | | | | X | |
| 100 µM | X | | X | | | | X | |
| 100 µM w/ Farnesyl | | | | X | | | | |

Cell Proliferation Assay of the Combination of 4-Hydroxy-Benzoate with Benzoquinone: This set of experiments used a cell proliferation assay to assess the effect of combining different building block molecules on cell proliferation.

The first study examined the effect of combining 4-Hydroxy-Benzoate with Benzoquinone. Cells were incubated for 48 hours, after which a cell count was performed for the live cells. Each test group was compared to the control, and each combination groups were compared to Benzoquinone control. The compounds were statistically analyzed for the addition of Benzoquinone. The following table summarizes the cell count results wherein the X mark indicates a statistical decrease in cell number.

TABLE 131

| 4-Hydroxy | Compared to Ctrl | Compared to 4-Hydroxy to compound w/o Benzoquinone | Compared to Benzoquinone Control |
|---|---|---|---|
| 500 nm | X | | |
| 500 nm w/ Benzo (35 µM) | X | X | |
| 500 nm w/ Benzo (70 µM) | X | X | |
| 1 µm | X | | |
| 1 µm w/ Benzo (35 µM) | X | X | |
| 1 µm w/ Benzo (70 µM) | X | X | |
| 50 µm | X | | |
| 50 µm w/ Benzo (35 µM) | X | | |
| 50 µm w/ Benzo (70 µM) | X | X | X |

There is a significant decrease in cell number for the cells incubated with 4-Hydroxybenzoic and benzoquinone and in combination. For the combination of 50 µM 4-Hydroxybenzoate in combination with 70 µM Benzoquinone there is significant reduction in cell number compared to the Benzoquinone control. This suggests a synergistic effect for this molar ratio.

Additional studies were performed testing additional molar ratios. For the first test 4-Hydroxybenzoic were tested at concentrations of 500 nM, 1 µM, and 50 µM. These concentrations were tested in combination with 2,3-Dimethoxy-5-methyl-p-benzoquinone (Benzo). The concentration of Benzo tested were 25 µM, 50 µM, and 100 10 µM. Melanoma cells were grown to 80% confluency and seeded in 6 well plates at a concentration of 40K cells per well. The cells were treated with CoQ10, 4-Hydroxybenzoate, Benzo, and a combination of 4-Hydroxybenzoate/Benzo.

A T-test was performed with $p<0.05$ as statistically significant. An X signifies a statistical decrease in cell number.

TABLE 132

| | |
|---|---|
| Ctrl vs Benzo 25 µM | X |
| Ctrl vs Benzo (B) 50 µM | |
| Ctrl vs Benzo (B) 100 uM | X |
| Ctrl vs 4-Hydroxybenzoate (HB) 500 nm | X |
| Ctrl vs HB 1 µM | X |
| Ctrl vs HB 50 µM | X |
| 500 nM HB vs 500 nM HB w/ 25 B | X |
| 500 nM HB vs 500 nM HB w/ 50 B | X |
| 500 nM HB vs 500 nM HB w/ 100 B | X |
| 1 uM HB vs 1 µM HB w/ 25 B | X |
| 1 uM HB vs 1 µM HB w/ 50 B | X |
| 1 uM HB vs 1 µM HB w/ 100 B | |
| 50 uM HB vs 50 µM HB w/ 25 B | X |
| 50 uM HB vs 50 µM HB w/ 50 B | X |
| 50 uM HB vs 50 µM HB w/ 100 B | |
| 500 nM HB w/ 25 B vs 25 B | X |
| 500 nM HB w/ 50 B vs 50 B | X |
| 500 nM HB w/ 100 B vs 100 B | X |
| 1 µM HB w/ 25 B vs 25 B | X |
| 1 µM HB w/ 50 B vs 50 B | X |
| 1 µM HB w/ 100 B vs 100 B | |
| 50 µM HB w/ 25 B vs 25 B | X |
| 50 µM HB w/ 50 B vs 50 B | X |
| 50 µM HB w/ 100 B vs 100 B | |

There is a significant decrease in cell proliferation for the treatment medium containing HB. Moreover the combination of the HB with benzoquinone showed a significant reduction in cell number compare to the cells incubated with the corresponding benzoquinone concentrations.

A cell proliferation assay was also performed on neonatal fibroblast cells. The concentrations of HB tested were 500 nM, 5 µM, and 25 µM. HB was also tested in combination with benzoquinone at a concentrations of 25 µM, 50 µM, and 100 µM. Melanoma cells were seeded at 40 k cells per well and were treated for 24 hours. The cells were trypsinized and quantified using a coulter counter.

Statistical analysis did not show a significant reduction in fibroblast cells. This indicates minimal to no toxicity in normal cells.

Cell Proliferation Assay of the Combination of phenylacetate and benzoquinone: Phenyl acetate is a precursor for the synthesis of 4-Hydroxybenzoic acid (facilitates the attachment of the ring structure. A cell proliferation assay was performed to assay the effect of incubating phenylacetate in combination with CoQ10 and Benzoquinone.

TABLE 133

| | |
|---|---|
| Ctrl and 25/25 µM Ben | X |
| Ctrl and 25/50 µM Ben | X |
| Ctrl and 25/100 µM Ben | X |
| Ctrl and 25/25 µM Q-10 | X |
| Ctrl and 25/25 µM Q-10 | X |
| Ctrl and 25/50 µM Q-10 | X |
| Ctrl and 25/100 µM Q-10 | X |
| Ctrl and Ben 25 | X |
| Ctrl and Ben 50 | X |
| Ctrl and Ben 100 | X |
| Ctrl and Q-10 25 | |
| Ctrl and Q-10 50 | |
| Ctrl and Q-10 100 | X |
| Ben 25 µM and 500 nM/25 µM Ben | X |
| Ben 25 µM and 5 nM/25 µM Ben | X |
| Ben 25 µM and 25 nM/25 µM Ben | X |
| Ben 50 µM and 500 nM/50 µM Ben | X |
| Ben 50 µM and 5 nM/50 µM Ben | X |

TABLE 133-continued

| | |
|---|---|
| Ben 50 µM and 25 nM/50 µM Ben | X |
| Ben 100 µM and 500 nM/100 µM Ben | |
| Ben 100 µM and 5 nM/100 µM Ben | |
| Ben 100 µM and 25 nM/100 µM Ben | |
| Q-10 25 µM and 500 nM/25 µM Q-10 | X |
| Q-10 25 µM and 5 nM/25 µM Q-10 | X |
| Q-10 25 µM and 25 nM/25 µM Q-10 | X |
| Q-10 50 µM and 500 nM/50 µM Q-10 | X |
| Q-10 50 µM and 5 nM/50 µM Q-10 | X |
| Q-10 50 µM and 25 nM/50 µM Q-10 | X |
| Q-10 100 µM and 500 nM/100 µM Q-10 | X |
| Q-10 100 µM and 5 nM/100 µM Q-10 | X |
| Q-10 100 µM and 25 nM/100 µM Q-10 | X |

The data indicates the addition of phenylacetate in combination with benzoquinone significantly decreases the cellular proliferation. The combination with CoQ10 and phenylacetate significantly decrease the cell number compared to incubation with CoQ10 and benzoquinone alone.

Cell Proliferation Assay of the Combination of 4-Hydroxy-Benzoate with Farnesyl: 4-Hydroxy-Benzoate was incubated in combination with Farnesyl. The summary of the results are listed below. 4-Hydroxybenzoate groups were compared to the control and Farnesyl control groups. The X signifies a statistical decrease in cell number.

TABLE 134

| 4-Hydroxy-Benzoate | Compared to Ctrl | Compared to 4-Hydroxy to compound w/o Farnesyl | Compared to Farnesyl Control |
|---|---|---|---|
| 500 nm | X | | |
| 500 nm w/ Farnesyl (35 µM) | X | | |
| 500 nm w/ Farnesyl (70 µM) | X | | |
| 1 µm | Error | | |
| 1 µm w/ Farnesyl (35 µM) | Error | | |
| 1 µm w/ Farnesyl (70 µM) | Error | | |
| 50 µm | X | | |
| 50 µm w/ Farnesyl (35 µM) | X | | |
| 50 µm w/ Farnesyl (70 µM) | X | | |

Cell Proliferation Assay of the Combination of L-Phenylalanine with Benzoquinone: A cell proliferation assay was performed to test the combination of L-Phenylalanine combined with Benzoquinone. Below is a summary of the results of L-Phenylalanine compared to the control and Benzoquinone control. The X signifies a statistical decrease.

TABLE 135

| L-Phenylalanine | Compared to Ctrl | Compared to L-Phenylalanine to compound w/o Benzoquinone | Compared to Benzoquinone Control |
|---|---|---|---|
| 5 µM | | | |
| 5 µm w/ Benzo (50 µM) | | X | |
| 5 µm w/ Benzo (100 µM) | | X | |
| 25 µm | | | |
| 25 µm w/ Benzo (50 µM) | | X | |

TABLE 135-continued

| L-Phenylalanine | Compared to Ctrl | Compared to L-Phenylalanine to compound w/o Benzoquinone | Compared to Benzoquinone Control |
|---|---|---|---|
| 25 µm w/ Benzo (100 µM) | | X | |
| 100 µm | | | |
| 100 µm w/ Benzo (50 µM) | X | X | X |
| 100 µm w/ Benzo (100 µM) | X | X | X |

A similar synergistic role is seen for the L-Phenylalanine combined with Benzoquinone.

Cell Proliferation Assay of the Combination of L-Phenylalanine with Farnesyl: Preliminary results for combination cell proliferation study of L-Phenylalanine incubated in combination with Farnesyl. The L-Phenylalanine were compared to the control and Farnesyl control group. An X signifies a statistical decrease in cell number.

TABLE 136

| L-Phenylalanine | Compared to Ctrl | Compared to L-Phenylalanine to compound w/o Farnesyl | Compared to Farnesyl Control |
|---|---|---|---|
| 5 µM | | | |
| 5 µm w/ Farnesyl (50 µM) | | | |
| 5 µm w/ Farnesyl (100 µM) | | | |
| 25 µm | X | | |
| 25 µm w/ Farnesyl (50 µM) | X | X | X |
| 25 µm w/ Farnesyl (100 µM) | X | X | X |
| 100 µm | X | | |
| 100 µm w/ Farnesyl (50 µM) | X | | X |
| 100 µm w/ Farnesyl (100 µM) | X | | |

Cell Proliferation Assay of the Combination of L-Tyrosine with Benzoquinone: L-Tyrosine was incubated in combination with Benzoquinone after which a cell count was performed. The groups were compared the control groups and Benzoquinone control group.

TABLE 137

| L-Tyrosine | Compared to Ctrl | Compared to L-Tyrosine to compound w/o Benzoquinone | Compared to Benzoquinone Control |
|---|---|---|---|
| 500 nm | | | |
| 500 nm w/ Benzo (50 µM) | | | |
| 500 nm w/ Benzo (100 µM) | | | |
| 5 µm | X | | |
| 5 µm w/ Benzo (50 µM) | X | | |
| 5 µm w/ Benzo (100 µM) | X | | |
| 15 µm | X | | |

TABLE 137-continued

| L-Tyrosine | Compared to Ctrl | Compared to L-Tyrosine to compound w/o Benzoquinone | Compared to Benzoquinone Control |
|---|---|---|---|
| 15 µm w/ Benzo (50 µM) | X | | |
| 15 µm w/ Benzo (100 µM) | x | | |

The addition of Benzoquinone did not amplify the effect of L-Tyrosine on the cell number.

Cell Proliferation Assay of the Combination of L-Tyrosine with Benzoquinone: This study examined the combination of L-Tyrosine with Farnesyl. The groups were compared to control and Farnesyl control groups.

TABLE 138

| L-Tyrosine | Compared to Ctrl | Compared to L-Tyrosine to compound w/o Farnesyl | Compared to Farnesyl Control |
|---|---|---|---|
| 500 nm | | | |
| 500 nm w/ Farnesyl (50 µM) | | | |
| 500 nm w/ Farnesyl (50 µM) | | | |
| 5 µm | X | | |
| 5 µm w/ Farnesyl (50 µM) | X | | |
| 5 µm w/ Farnesyl (100 µM) | X | | |
| 15 µm | X | | |
| 15 µm w/ Farnesyl (50 µM) | X | | |
| 15 µm w/ Farnesyl (100 µM) | X | | |

Combining L-Tyrosine and Farnesyl does not appear to have a synergistic effect on reducing the cell number in this experiment.

The synthesis of the CoQ10 is divided into two main parts, which consist of the synthesis of the ring structure and synthesis of the side chain structure. Here, oncogenic cells were supplemented with compounds which are precursors for the synthesis of the side chain and the ring structure components. Our results have focused the study to 3 main components involved in the synthesis of the ring structure and two compounds that play a role in the attachment of the ring structure to the side chain structure. The three compounds that have shown a significant reduction in Bcl-2 and increase in Caspase-3 expression are: 1) L-Phenylalanine, 2) L-Tyrosine and 3) 4-Hydroxyphenylpyruvate. The two compounds involved with the attachment of the side chain to the ring structure are: 1) 4-hydroxy benzoate and 2) Phenylacetate.

Our results also showed that exogenous delivery of these compounds in combination with 2,3 Dimethoxy-5-methyl-p-benzoquinone (benzoquinone) significantly inhibits cell proliferation. This indicates a supplementation of the ring structure with compounds for the attachment of the side chain to the benzoquinone ring may supplement an impaired CoQ10 synthesis mechanism. This may also assist in the stabilization of the molecule to maintain the functional properties required by cellular processes. Phenylacetate is a precursor for the synthesis of 4-Hydroxybenzoate, which exogenous delivery in combination with benzoquinone has a similar effect in oncogenic cells.

Example 45

In Vivo Effects of Coenzyme Q10 Administration on Pancreatic Cancer

An intravenously administered formulation of coenzyme Q10 was evaluated for treating pancreatic cancer in an animal model. Rats with induced pancreatic cancer were randomized into groups and received one of the following 9 treatments:
  Group A: control
  Group B: saline solution
  Group C: vehicle
  Group D: 5 mg/kg coenzyme Q10
  Group E: 10 mg/kg coenzyme Q10
  Group F: 25 mg/kg coenzyme Q10
  Group G: 50 mg/kg coenzyme Q10
  Group H: 5 mg/kg Doxorubicin
  Group I: 50 mg/kg coenzyme Q10 and 5 mg/kg Doxorubicin After 28 days, all animals in Groups A and B and the majority of the animals in Group C had died. In contrast, most of the animals in Groups D, E and F remained alive, with those animals receiving the higher dose of coenzyme Q10 remaining alive longer. Indeed, all of the animals receiving the highest dose of coenzyme Q10 (Group G) remained alive at 28 days. These data demonstrate an overall dose response curve in which those animals receiving higher doses had a higher survival rate.

To evaluate the effectiveness of coenzyme Q10 in treating pancreatic cancer in combination with Doxorubicin, Group H was administered Doxorubicin alone, while Group I was administered the combination of Doxorubicin and coenzyme Q10. After 28 days, a significant number of the animals in Group H had died due to the toxicity of Doxorubicin, while those animals in Group I had an increased survival rate. These data suggest that, in addition to increasing the survival rate associated with pancreatic cancer, coenzyme Q10 can also mitigate the toxic side effects of a chemotherapeutic regimen.

Equivalents:

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A method for treating pancreatic cancer in a human, comprising: intravenously administering Coenzyme Q10 (CoQ10) to the human at a dose of at least 5 mg/kg such that treatment occurs, wherein the CoQ10 is in its oxidized form and has a purity between 95% and 100%, and wherein administration of the CoQ10 to the human results in an increase of CoQ10 in the oxidized form in the human.

2. The method of claim 1, wherein the treatment occurs via an interaction of Coenzyme Q10 with a protein selected from the group consisting of HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex I, complex II, complex III, complex IV, Foxo 3a, DJ-1, IDH-1, Cpt1C, and Cam Kinase II and any one or more of genes listed in Tables 2-4 & 6-28.

3. The method of claim 1, further comprising a treatment regimen selected from the group consisting of surgery, radiation, hormone therapy, antibody therapy, therapy with growth factors, cytokines, and chemotherapy.

4. The method of claim 1, wherein the Coenzyme Q10 is administered with an additional therapeutic agent.

5. The method of claim 4, wherein the Coenzyme Q10 is administered concurrently with the additional therapeutic agent.

6. The method of claim 4, wherein the Coenzyme Q10 is administered prior to administration of the additional therapeutic agent.

7. The method of claim 4, wherein the Coenzyme Q10 is administered subsequent to administration of the additional therapeutic agent.

8. The method of claim 4, wherein the additional therapeutic agent is a chemotherapeutic agent.

9. The method of claim 8, wherein the chemotherapeutic agent is gemcitabine.

* * * * *